(12) United States Patent
Fox et al.

(10) Patent No.: US 11,993,635 B2
(45) Date of Patent: May 28, 2024

(54) GENETICALLY ENCODED SYSTEM FOR CONSTRUCTING AND DETECTING BIOLOGICALLY ACTIVE AGENTS

(71) Applicant: The Regents of the University of Colorado, a Body Corporate, Denver, CO (US)

(72) Inventors: Jerome Fox, Boulder, CO (US); Ankur Sarkar, Boulder, CO (US); Akarawin Hongdusit, Boulder, CO (US); Edward Kim, Oakland, CA (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 45 days.

(21) Appl. No.: 17/816,937

(22) Filed: Aug. 2, 2022

(65) Prior Publication Data
US 2023/0151062 A1 May 18, 2023

Related U.S. Application Data

(60) Division of application No. 17/141,321, filed on Jan. 5, 2021, now Pat. No. 11,472,847, which is a continuation of application No. PCT/US2019/040896, filed on Jul. 8, 2019.

(60) Provisional application No. 62/694,838, filed on Jul. 6, 2018.

(51) Int. Cl.
| | | |
|---|---|---|
| C12N 1/20 | (2006.01) | |
| C07K 14/005 | (2006.01) | |
| C07K 14/47 | (2006.01) | |

(52) U.S. Cl.
CPC ............ *C07K 14/005* (2013.01); *C07K 14/47* (2013.01); *C12N 1/20* (2013.01); *C07K 2319/80* (2013.01); *C12Y 205/01001* (2013.01); *C12Y 205/0101* (2013.01); *C12Y 207/01036* (2013.01); *C12Y 207/04002* (2013.01); *C12Y 301/01048* (2013.01); *C12Y 401/01033* (2013.01); *C12Y 402/03017* (2013.01); *C12Y 402/03018* (2013.01); *C12Y 402/03024* (2013.01); *C12Y 402/03056* (2013.01); *C12Y 503/03002* (2013.01)

(58) Field of Classification Search
CPC ........ C07K 14/47; C07K 14/005; C12N 1/20; C12N 9/16
See application file for complete search history.

(56) References Cited

U.S. PATENT DOCUMENTS

| | | |
|---|---|---|
| 5,925,523 A | 7/1999 | Dove et al. |
| 6,200,759 B1 | 3/2001 | Dove et al. |
| 6,303,319 B1 | 10/2001 | Rickles |
| 6,428,951 B1 | 8/2002 | Michnick et al. |
| 7,927,794 B2 | 4/2011 | Keasling et al. |
| 8,586,725 B2 | 11/2013 | Cummins et al. |
| 8,716,460 B2 | 5/2014 | Alfano et al. |
| 8,859,232 B2 | 10/2014 | Hahn et al. |
| 10,385,332 B2 | 8/2019 | Hill et al. |
| 11,020,429 B2 | 6/2021 | Thompson |
| 11,472,847 B2 * | 10/2022 | Fox ........................ C07K 14/47 |
| 2002/0120947 A1 | 8/2002 | Roch et al. |
| 2002/0164587 A1 | 11/2002 | Camonis et al. |
| 2003/0170855 A1 | 9/2003 | Zhang et al. |
| 2003/0203471 A1 | 10/2003 | Althoff et al. |
| 2005/0040550 A1 | 2/2005 | Short et al. |
| 2005/0227357 A1 | 10/2005 | Bohlmann et al. |
| 2006/0292155 A1 | 12/2006 | Golz et al. |
| 2011/0046018 A1 | 2/2011 | Chen et al. |
| 2014/0315214 A1 | 10/2014 | Taipale et al. |
| 2018/0057545 A9 | 3/2018 | Liu et al. |
| 2018/0111929 A1 | 4/2018 | Ibrahim et al. |
| 2018/0230449 A1 | 8/2018 | Niesert et al. |

(Continued)

FOREIGN PATENT DOCUMENTS

| | | |
|---|---|---|
| CN | 103160570 A | 6/2013 |
| EP | 2116263 A1 | 11/2009 |

(Continued)

OTHER PUBLICATIONS

Abraham et al., GROMACS: High performance molecular simulations through multi-level parallelism from laptops to supercomputers. SoftwareX. 1-2: 19-25 (2015).
Abu Bakar et al., Nonstructural proteins of alphavirus-potential targets for drug development. Viruses. 10(2):71 (2018).
Adams et al., Potent and selective inhibitors of the proteasome: dipeptidyl boronic acids. Bioorg Med Chem Lett. 8(4):333-338 (1998).
Aerts et al., Are public-private partnerships the solution to tackle neglected tropical diseases? A systematic review of the literature. Health Policy. 121(7):745-754 (2017).

(Continued)

*Primary Examiner* — Tekchand Saidha
(74) *Attorney, Agent, or Firm* — Wilson Sonsini Goodrich & Rosati

(57) ABSTRACT

This invention relates to the field of genetic engineering. Specifically, the invention relates to the construction of operons to produce biologically active agents. For example, operons may be constructed to produce agents that control the function of biochemical pathway proteins (e.g., protein phosphatases, kinases and/or proteases). Such agents may include inhibitors and modulators that may be used in studying or controlling phosphatase function associated with abnormalities in a phosphatase pathway or expression level. Fusion proteins, such as light activated protein phosphatases, may be genetically encoded and expressed as photoswitchable phosphatases. Systems are provided for use in controlling phosphatase function within living cells or in identifying small molecule inhibitors/activator/modulator molecules of protein phosphatases associated with cell signaling.

20 Claims, 52 Drawing Sheets

Specification includes a Sequence Listing.

(56) References Cited

U.S. PATENT DOCUMENTS

| | | |
|---|---|---|
| 2020/0181598 A1 | 6/2020 | Bode et al. |
| 2020/0347428 A1 | 11/2020 | Bode et al. |

FOREIGN PATENT DOCUMENTS

| | | |
|---|---|---|
| WO | WO-2004003550 A2 | 1/2004 |
| WO | WO-2004048549 A2 | 6/2004 |
| WO | WO-2008115420 A2 | 9/2008 |
| WO | WO-2011002977 A2 | 1/2011 |
| WO | WO-2011133493 A2 | 10/2011 |
| WO | WO-2012111772 A1 | 8/2012 |
| WO | WO-2012154858 A1 | 11/2012 |
| WO | WO-2013016693 A2 | 1/2013 |
| WO | WO-2014022434 A1 | 2/2014 |
| WO | WO-2015040197 A1 | 3/2015 |
| WO | WO-2015187792 A1 | 12/2015 |
| WO | WO-2015189428 A1 | 12/2015 |
| WO | WO-2018096150 A1 | 5/2018 |
| WO | WO-2019032628 A1 | 2/2019 |
| WO | WO-2019232025 A2 | 12/2019 |
| WO | WO-2020010364 A1 | 1/2020 |
| WO | WO-2021142207 A1 | 7/2021 |

OTHER PUBLICATIONS

Afonine et al. Towards automated crystallographic structure refinement with phenix.refine. Acta Crystallogr D Biol Crystallogr. 68(Pt 4):352-367 (2012).

Ajikumar et al. Isoprenoid pathway optimization for Taxol precursor overproduction in Escherichia coli. Science. 330(6000):70-74 (2010).

Akutsu et al., Molecular basis for ubiquitin and ISG15 cross-reactivity in viral ovarian tumor domains. Proc Natl Acad Sci USA. 108(6):2228-2233 (2011).

Aleshin et al., Activity, specificity, and probe design for the smallpox virus protease K7L. J Biol Chem. 287(47):39470-39479 (2012).

Aleshin et al., Structural evidence for regulation and specificity of flaviviral proteases and evolution of the Flaviviridae fold. Protein Sci. 16(5):795-806 (2007).

Alonso et al., Protein tyrosine phosphatases in the human genome. Cell. 117(6):699-711 (2004 ).

Amamuddy et al. Integrated computational approaches and tools for allosteric drug discovery. Int J Mol Sci. 21(3):847 (2020).

Anderie et al., Characterization of the C-terminal ER membrane anchor of PTP1B. Exp Cell Res. 313(15):3189-3197 (2007).

Antosch et al., Heterologous Reconstitution of Ikarugamycin Biosynthesis in E. coli. Angew Chem Int Ed Engl. 53(11):3011-3014 (2014).

Aramini et al., The RAS-binding domain of human BRAF protein serine/threonine kinase exhibits allosteric conformational changes upon binding HRAS. Structure. 23(8):1382-1393 (2015).

Arregui et al., Protein tyrosine phosphatase PTP1B in cell adhesion and migration. Cell Adh Migr. 7(5): 418-423 (2013).

Atanasov et al., Discovery and resupply of pharmacologically active plant-derived natural products: A review. Biotechnol Adv. 33(8):1582-1614 (2015).

Atanasov et al., Natural products in drug discovery: Advances and opportunities. Nat Rev Drug Discov. 20(3):200-216 (2021).

Attia et al., Molecular cloning and characterization of (+)-epi-α-bisabolol synthase, catalyzing the first step in the biosynthesis of the natural sweetener, hernandulcin, in Lippia dulcis. Arch Biochem Biophys. 527(1):37-44 (2012).

Auffinger et al., Halogen bonds in biological molecules. Proc Natl Acad Sci. USA. 101(48):16789-16794 (2004).

Auldridge et al., Bacterial phytochromes: more than meets the light. Crit Rev Biochem Mol Biol. 46(1):67-88 (2011).

Badran et al., Continuous evolution of Bacillus thuringiensis toxins overcomes insect resistance. Nature. 533(7601):58-63 (2016).

Banno et al., PTP1B and SHP2 in POMC neurons reciprocally regulate energy balance in mice. J Clin Invest. 120(3):120, 720-734 (2010).

Barr et al., Large-scale structural analysis of the classical human protein tyrosine phosphatome. Cell. 136(2):352-363 (2009).

Bence et al., Neuronal PTP1B regulates body weight, adiposity and leptin action. Nat Med. 12(8):917-924 (2006).

Benkert et al., Toward the estimation of the absolute quality of individual protein structure models. Bioinformatics. 27(3):343-350 (2011).

Bentires-Alj et al., Protein-tyrosine phosphatase 1B is required for HER2/Neu-induced breast cancer. Cancer Res. 67(6):2420-2424 (2007).

Bergmann et al., The refined crystal structure of the 3C gene product from hepatitis A virus: specific proteinase activity and RNA recognition. J Virol. 71(3): 2436-2448 (1997).

Bernhardt, Cytochromes P450 as versatile biocatalysts. J Biotechnol. 124(1):128-145 (2006).

Bohlmann et al., Terpenoid-based defenses in conifers: cDNA cloning, characterization, and functional expression of wound-inducible (E)-alpha-bisabolene synthase from grand fir (Abies grandis). 95(12): 6756-6761 (1998).

Boras et al., Preclinical characterization of an intravenous coronavirus 3CL protease inhibitor for the potential treatment of COVID19. Nat Commun. 12(1): 6055, 17pages (2021).

Boulware et al., Protease specificity determination by using cellular libraries of peptide substrates (CLiPS). Proc Natl Acad Sci USA. 103(20):7583-7588 (2006).

Bozhüyük et al., Modification and de novo design of non-ribosomal peptide synthetases using specific assembly points within condensation domains. Nat Chem. 11(7), 653-661 (2019).

Braun et al., MuteinDB: the mutein database linking substrates, products and enzymatic reactions directly with genetic variants of enzymes. Database (Oxford). 2012: bas028,1-9 (2012).

Brown et al., Halogenase engineering for the generation of new natural product analogues. Chembiochem. 16(15): 2129-2135 (2015).

Bullock et al., Assessing helical protein interfaces for inhibitor design J Am Chem Soc. 133(36):14220-14223 (2011).

Burnham, K. P. & Anderson, D. R. Model Selection and Multimodel Inference: a Practical Information-theoretic Approach, 2nd edn. Springer-Verlag, New York. (2002).

Bussi et al., Canonical sampling through velocity rescaling. J Chem Phys. 126(1):014101 (2007).

Butler et al., Key mutations alter the cytochrome P450 BM3 conformational landscape and remove inherent substrate bias. J Biol Chem. 288(35):25387-25399 (2013).

Calla et al., Cytochrome P450 diversification and hostplant utilization patterns in specialist and generalist moths: Birth, death and adaptation. Mol Ecol. 26(21):6021-6035 (2017).

Camuesco et al., The intestinal anti-inflammatory effect of quercitrin is associated with an inhibition in iNOS expression. Br J Pharmacol. 143(7):908-918 (2004).

Carlson et al., Negative selection and stringency modulation in phage-assisted continuous evolution. Nat Chem Biol. 10(3):216-222 (2014).

Carter et al., Enthalpy-entropy compensation in biomolecular halogen bonds measured in DNA junctions. Biochemistry. 52(29):4891-4903 (2013).

Carter-Franklin et al., Vanadium haloperoxidase-catalyzed bromination and cyclization of terpenes. J Am Chem Soc. 125(13):3688-3689 (2003).

Chandramouli et al., Serotype-specific structural differences in the protease-cofactor complexes of the dengue virus family. J Virol. 84(6):3059-3067 (2010).

Chang et al., Production of isoprenoid pharmaceuticals by engineered microbes. Nat Chem Biol. 2(12):674-681 (2006).

Chang et al., Engineering Escherichia coli for production of functionalized terpenoids using plant P450s. Nat Chem Biol. 3(5):274-277 (2007).

Chatzivasileiou et al., Two-step pathway for isoprenoid synthesis. Proc Natl Acad Sci USA. 116(2):506-511 (2019).

(56) References Cited

OTHER PUBLICATIONS

Chaudhury et al., Identification of structural mechanisms of HIV-1 protease specificity using computational peptide docking: implications for drug resistance. Structure. 17(12):1636-1648 (2009).
Cheesman et al., Soluble and membrane-bound Drosophila melanogaster CYP6G1 expressed in *Escherichia coli*: purification, activity, and binding properties toward multiple pesticides. Insect Biochem Mol Biol. 43(5):455-465 (2013).
Chen et al., Allosteric inhibition of SHP2 phosphatase inhibits cancers driven by receptor tyrosine kinases. Nature. 535(7610):148-152 (2016).
Chen et al., Mechanisms of activation and inhibition of Zika virus NS2B-NS3 protease. Cell Res. 26(11):1260-1263 (2016).
Chen et al., Genomics and evolution of protein phosphatases. Sci Signal. 10(474):eaag1796. (2017).
Chen et al., A predictably selective aliphatic C-H oxidation reaction for complex molecule synthesis. Science. 318(5851):783-787 (2007).
Chen, X. et al., Statistical experimental design guided optimization of a one-pot biphasic multienzyme total synthesis of amorpha-4,11-diene. PLoS One. 8(11):e79650. (2013).
Chen, Y. et al., Emerging coronaviruses: Genome structure, replication, and pathogenesis. J Med Virol. 92(10):2249 (2020).
Cheng, Y. et al., Kidney disease is associated with in-hospital death of patients with COVID-19. Kidney Int. 97(5):829-838 (2020).
Cho, I. et al., Site-selective enzymatic C-H amidation for synthesis of diverse lactams. Science. 364(6440):575-578 (2019). Retraction (2020).
Choi, E. et al., Mitotic regulators and the SHP2-MAPK pathway promote IR endocytosis and feedback regulation of insulin signaling. Nat Commun. 10(1):1473 (2019).
Choi et al., Improvements to the ABSINTH force field for proteins based on experimentally derived amino acid specific backbone conformational statistics. J Chem Theory Comput. 15(2):1367-1382 (2019).
Choi, O. et al. Biosynthesis of plant-specific phenylpropanoids by construction of an artificial biosynthetic pathway in *Escherichia coli*. J Ind Microbiol Biotechnol. 38(10): 1657-1665 (2011).
Choy et al., Conformational rigidity and protein dynamics at distinct timescales regulate PTP1B activity and allostery. Mol Cell 65(4):644-658 (2017).
Christianson, Structural biology and chemistry of the terpenoid cyclases. Chem Rev. 106(8):3412-3442 (2006).
Cortesio et al., Calpain 2 and PTP1B function in a novel pathway with Src to regulate invadopodia dynamics and breast cancer cell invasion. J Cell Biol. 180(5):957-971 (2008).
Cosentino et al., Engineering of a light-gated potassium channel. Science. 348(6235):707-710 (2015).
Cragg et al., Natural products: A continuing source of novel drug leads. Biochim Biophys Acta—Gen Subj. 1830(6):3670-3695 (2013).
Criswell et al., A single residue change leads to a hydroxylated product from the class II diterpene cyclization catalyzed by abietadiene synthase. Org Lett. 14(23):5828-5831 (2012).
Cui et al., A map of human cancer signaling. Mol Syst Biol. 3:152 (2007).
Culp et al., Evolution-guided discovery of antibiotics that inhibit peptidoglycan remodelling. Nature. 578(7796):582-587 (2020).
Cutler et al., The COVID-19 pandemic and the $16 trillion virus. Jama 324(15):1495-1496 (2020).
Dagliyan et al., Engineering extrinsic disorder to control protein activity in living cells. Science. 354(6318):1441-1444 (2016).
Danial et al., Cell death: critical control points. Cell. 116(2):205-219 (2004).
D'Arcy et al., Purification and crystallization of dengue and West Nile virus NS2B-NS3 complexes. Acta Crystallogr Sect F Struct Biol Cryst Commun. 62(Pt 2):157-162 (2006).
Darden et al., Particle mesh Ewald: An N•log(N) method for Ewald sums in large systems. J Chem Phys. 98:10089 (1993).
Davis et al., Directing evolution: The next revolution in drug discovery? Nat Rev Drug Discov. 16(10):681-698 (2017).

Davis, et al. Design, construction and characterization of a set of insulated bacterial promoters. Nucleic Acids Res. 39(3):1131-1141(2011).
De Sousa et al., Flavonoids as noncompetitive inhibitors of Dengue virus NS2B-NS3 protease: inhibition kinetics and docking studies. Bioorg Med Chem. 23(3):466-470 (2015).
Dempke et al., Targeting SHP-1, 2 and SHIP Pathways: A Novel Strategy for Cancer Treatment? Oncology. 95(5):257-269 (2018).
Dias et al., A Historical overview of natural products in drug discovery. Metabolites. 2(2):303-36 (2012).
Dietrich et al., A novel semi-biosynthetic route for artemisinin production using engineered substrate-promiscuous P450(BM3). ACS Chem Biol. 4(4):261-267 (2009).
Dietrich et al., High-throughput metabolic engineering: advances in small-molecule screening and selection. Annu Rev Biochem. 79:563-590 (2010).
Dong et al.; An interactive web-based dashboard to track COVID-19 in real time. Lancet Infect Dis. 20(5):533-534 (2020).
Douangamath et al., Crystallographic and electrophilic fragment screening of the SARS-CoV-2 main protease. Nat Commun. 11(1):5047 (2020).
Douzery et al., The timing of eukaryotic evolution: does a relaxed molecular clock reconcile proteins and fossils? Proc Natl Acad Sci. USA. 101(43):15386-15391 (2004).
Dove et al., Conversion of the ω subunit of *Escherichia coli* RNA polymerase into a transcriptional activator or an activation target. Genes Dev. 12(5):745-754 (1998).
Dove et al., Activation of prokaryotic transcription through arbitrary protein-protein contacts. Nature. 386(6625):627-630 (1997).
Dube et al., Genetic ablation of protein tyrosine phosphatase 1B accelerates lymphomagenesis of p53-null mice through the regulation of B-cell development. Cancer Res. 65(21):10088-10095 (2005).
Dubois et al., The SHP-1 protein tyrosine phosphatase negatively modulates glucose homeostasis. Nat Med. 12(5):549-556 (2006).
Dye, Flow cytometric analysis of CFP-YFP FRET as a marker for in vivo protein-protein interaction. Clin. Appl. Immunol. Rev. 5: 307-324 (2005).
Eche et al., Recombinant expression of HIV-1 protease using soluble fusion tags in *Escherichia coli*: A vital tool for functional characterization of HIV-1 protease. Virus Res. 295:198289 (2021).
Eden et al., Membrane contacts between endosomes and ER provide sites for PTP1B-epidermal growth factor receptor interaction. Nat Cell Biol. 12(3):267-72 (2010).
Edgar et al., Mechanistic insights into taxadiene epoxidation by taxadiene-5α-hydroxylase. ACS Chem. Biol. 11(2):460-469 (2016).
Emanuel et al., Fair allocation of scarce medical resources in the time of Covid-19. N Engl J Med. 382(21):2049-2055 (2020).
Emsley et al. Coot: model-building tools for molecular graphics. Acta Crystallogr D Biol Crystallogr. 60(Pt 12 Pt 1):2126-2132 (2004).
Erbel et al., Structural basis for the activation of flaviviral NS3 proteases from dengue and West Nile virus. Nat Struct Mol Biol. 13(4):372-373 (2006).
Esvelt et al., A system for the continuous directed evolution of biomolecules. Nature. 472(7344):499-503 (2011).
Faeder et al., Rule-based modeling of biochemical systems with BioNetGen. Methods Mol Biol. 500:113-167 (2009).
Fan et al., Optical control of biological processes by light-switchable proteins. Wiley Interdiscip Rev Dev Biol 4(5):545-554 (2015).
Fan et al., Protein-tyrosine phosphatase 1B antagonized signaling by insulin-like growth factor-1 receptor and kinase BRK/PTK6 in ovarian cancer cells. J Biol Chem. 288(34):24923-34 (2013).
Fasan, Tuning P450 enzymes as oxidation catalysts. ACS Catal. 2(4):647-666 (2012).
FDA Food and Drug Administration. Coronavirus (COVID-19) Drugs. at https://www.fda.gov/drugs/emergency-preparedness-drugs/coronavirus-covid-19-drugs (2022).
FDA Food and Drug Administration. Emergency Use Authorization. https://www.fda.gov/emergency-preparedness-and-response/mcm-legal-regulatory-and-policy-framework/emergency-use-authorization#coviddrugs (2022).

(56) References Cited

OTHER PUBLICATIONS

Fehr et al., In vivo imaging of the dynamics of glucose uptake in the cytosol of COS-7 cells by fluorescent nanosensors. J. Biol. Chem. 278: 19127-19133 (2003).
Felgner et al., Lipofection: a highly efficient, lipid-mediated DNA-transfection procedure. Proc Natl Acad Sci USA. 84(21):7413-7417 (1987).
Feiler et al., Directed evolution of mycobacterium tuberculosis β-lactamase reveals gatekeeper residue that regulates antibiotic resistance and catalytic efficiency. PLoS One. 8(9):e73123 (2013).
Ferguson et al., Kinase inhibitors: The road ahead. Nat Rev Drug Discov. 17(5):353-377 (2018).
Ferreira et al., Molecular docking and structure-based drug design strategies. Molecules. 20(7): 13384-13421 (2015).
Fox et al., Interactions between Hofmeister anions and the binding pocket of a protein. J Am Chem Soc. 137(11):3859-3866 (2015).
Fox et al., Water-restructuring mutations can reverse the thermodynamic signature of ligand binding to human carbonic anhydrase. Angew Chem Int Ed Engl. 56(14):3833-3837 (2017).
Fox et al., The molecular origin of enthalpy/entropy compensation in biomolecular recognition. Annu Rev Biophys. 47:223-250 (2018).
Fürstenberg-Hägg et al., Plant defense against insect herbivores. Int J Mol Sci. 14(5):10242-10297 (2013).
Fujimori et al., What's new in enzymatic halogenations. Curr Opin Chem Biol. 11(5):553-560 (2007).
Fujisawa et al., Cloning and characterization of a novel gene that encodes (S)-β-bisabolene synthase from ginger, Zingiber officinale. Planta 232(1):121-130 (2010).
Galanie et al., Complete biosynthesis of opioids in yeast. Science. 349(6252):1095-1100 (2015).
Gallagher, COVID19 therapeutics: Expanding the antiviral arsenal. EBioMedicine. 66:103289 (2021).
Gao et al., Structure of the RNA-dependent RNA polymerase from COVID-19 virus. Science. 368(6492):779-782 (2020).
Gautier et al., How to control proteins with light in living systems. Nat. Chem. Biol. 10: 533-41 (2014).
Gavory et al., Discovery and characterization of highly potent and selective allosteric USP7 inhibitors. Nat Chem Biol.14(2):118-125 (2018).
George et al., Isoprenoid drugs, biofuels, and chemicals—artemisinin, farnesene, and beyond. Adv Biochem Eng Biotechnol. 148: 355-389 (2015).
Gershenzon et al., The function of terpene natural products in the natural world. Nat Chem Biol. 3(7):408-414 (2007).
Gibbs et al., Inhibitor bound dengue NS2B-NS3pro reveals multiple dynamic binding modes. Biochemistry 57(10):1591-1602 (2018).
Gil-Parrado et al., Ionomycin-activated calpain triggers apoptosis. A probable role for Bcl-2 family members. J Biol Chem. 277(30): 27217-27226 (2002).
Goldstein et al., Tyrosine dephosphorylation and deactivation of insulin receptor substrate-1 by protein-tyrosine phosphatase 1B. Possible facilitation by the formation of a ternary complex with the GRB2 adaptor protein. J Biol Chem. 275(6):4283-4289 (2000).
Gorbalenya et al., The species Severe acute respiratory syndrome-related coronavirus: classifying 2019-nCOV and naming it SARS-COV-2. Nature Microbiology 5(4):536-544 (2020).
Gordon et al., A SARS-CoV-2-Human protein-protein interaction map reveals drug targets and potential drug-repurposing. Nature. 583(7816):459-468 (2020).
Govindarajan et al., Estimating the total number of protein folds. Proteins 35(4): 408-414 (1999).
Grangeasse et al., Bacterial tyrosine kinases: Evolution, biological function and structural insights. Philos Trans R Soc B Biol Sci. 367(1602):2640-2655 (2012).
Gruet et al., One-step generation of error-prone PCR libraries using Gateway® technology. Microb Cell Fact. 11:14 (2012).
Gu et al., COVID-19: gastrointestinal manifestations and potential fecal-oral transmission. Gastroenterology. 158(6):1518-1519 (2020).
Guex et al., Automated comparative protein structure modeling with SWISS-MODEL and Swiss-PdbViewer: a historical perspective. Electrophoresis. 30(Suppl 1):S162-S173 (2009).
Gunst et al., Efficacy of the TMPRSS2 inhibitor camostat mesilate in patients hospitalized with Covid-19-a double-blind randomized controlled trial. EClinicalMedicine. 35:100849 (2021).
Guo et al., Bisphosphonates target multiple sites in both cis- and trans-prenyltransferases. Proc Natl Acad Sci USA. 104(24):10022-10027(2007).
Guo et al., Discovery of reactive microbiota-derived metabolites that inhibit host proteases. Cell. 168(3):517-526.e18 (2017).
Haj et al., Imaging sites of receptor dephosphorylation by PTP1B on the surface of the endoplasmic reticulum. Science. 295(5560):1708-1711 (2002).
Haj et al., Regulation of signaling at regions of cell-cell contact by endoplasmic reticulum-bound protein-tyrosine phosphatase 1B. PLoS One. 7(5):e36633 (2012).
Halavaty et al., N- and C-terminal flanking regions modulate light-induced signal transduction in the LOV2 domain of the blue light sensor phototropin 1 from Avena sativa. Biochemistry. 46(49):14001-14009 (2007).
Hamberger et al., Evolution of diterpene metabolism: Sitka spruce CYP720B4 catalyzes multiple oxidations in resin acid biosynthesis of conifer defense against insects. Plant Physiol. 157(4): 1677-1695 (2011).
Hammamy et al., Development and Characterization of new peptidomimetic inhibitors of the West Nile Virus NS2B-NS3 Protease. ChemMedChem 8(2):231-241 (2013).
Hartenfeller et al., De novo drug design. Chemoinformatics and Computational Chemical Biology (ed. Bajorath, J.). 672: 299-323 (2010).
Harvey et al., The re-emergence of natural products for drug discovery in the genomics era. Nature reviews drug discovery 14(2):111-129 (2015).
Harvey, Natural products in drug discovery. Drug Discov. 13(19-20):894-901 (2008).
He et al., Protein tyrosine phosphatases as potential therapeutic targets. Acta Pharmacol Sin. 35(10):1227-1246 (2014).
Henrich et al., Matching the power of high throughput screening to the chemical diversity of natural products. Nat Prod Rep. 30(10):1284-1298 (2013).
Hert et al., Quantifying biogenic bias in screening libraries. Nat Chem Biol. 5(7): 479-483 (2009).
Hess et al., LINCS: A linear constraint solver for molecular simulations. J Comput Chem. 18:1463-1472 (1997).
Hjortness et al., Abietane-type diterpenoids inhibit protein tyrosine phosphatases by stabilizing an inactive enzyme conformation. Biochemistry 57(40):5886-5896 (2018).
Hjortness et al., Evolutionarily Conserved Allosteric Communication in Protein Tyrosine Phosphatases. Biochemistry. 57(45):6443-6451 (2018).
Ho et al., Critical assessment of the important residues involved in the dimerization and catalysis of MERS coronavirus main protease. PLoS One 10(12):e0144865 (2015).
Hoffman et al., SARS-CoV-2 cell entry depends on ACE2 and TMPRSS2 and is blocked by a clinically proven protease inhibitor. Cell. 181(2):271-280 (2020).
Hu et al., Kinetic, mutational, and structural studies of the Venezuelan equine encephalitis virus nonstructural protein 2 cysteine protease. Biochemistry 55(21):3007-3019 (2016).
Huang et al., Sesquiterpenes produced by truncated taxadiene synthase. Tetrahedron Lett. 41(50): 9701-9704 (2000).
Huang et al., CHARMM36m: An improved force field for folded and intrinsically disordered proteins. Nat Methods. 14(1): 71-73 (2017).
Huang et al., Understanding HIV-1 protease autoprocessing for novel therapeutic development. Future Med Chem. 5(11):1215-1229 (2013).
Hubbard et al., Protein tyrosine kinase structure and function. Annu Rev Biochem. 69:373-398 (2000).
Hubert et al., Dereplication strategies in natural product research: How many tools and methodologies behind the same concept? Phytochem Rev.16(1):55-95 (2017).

(56) References Cited

OTHER PUBLICATIONS

Hughes et al., Principles of early drug discovery. Br J Pharmacol. 162(6):1239-1249 (2011).
Ito et al., PTK6 inhibition suppresses metastases of triple-negative breast cancer via SNAIL-dependent E-cadherin regulation. Cancer Res. 76(15):4406-4417 (2016).
Jantan et al., Plant-derived immunomodulators: an insight on their preclinical evaluation and clinical trials. Front Plant Sci. 6:655 (2015).
Jendresen et al., Highly active and specific tyrosine ammonia-lyases from diverse origins enable enhanced production of aromatic compounds in bacteria and Saccharomyces cerevisiae. Appl Environ Microbiol. 81(13):4458-4476 (2015).
Jensen et al., Challenges and triumphs to genomics-based natural product discovery. J Ind Microbiol Biotechnol. 41(2):203-209 (2014).
Jensen, Natural products and the gene cluster revolution. Trends Microbiol. 24(12):968-977 (2016).
Jewell et al., Hepatitis A virus 3C proteinase substrate specificity. Biochemistry 31(34): 7862-7869 (1992).
Jia et al., Extreme promiscuity of a bacterial and a plant diterpene synthase enables combinatorial biosynthesis. Metab Eng. 37: 24-34 (2016).
Jia et al., Combinatorial biosynthesis and the basis for substrate promiscuity in class I diterpene synthases. Metabolic Eng. 55:44-58 (2019).
Jiang et al., Natural products possessing protein tyrosine phosphatase 1B (PTP1B) inhibitory activity found in the last decades. Acta Pharmacol Sin. 33(10):1217-1245 (2012). doi:10.1038/aps.2012.90.
Jin et al., Structure of Mpro from SARS-CoV-2 and discovery of its inhibitors. Nature. 582(7811):289-293 (2020).
Johnson et al., Protein tyrosine phosphatase IB inhibitors for diabetes. Nat Rev Drug Discov. 1(9):696-709 (2002).
Johnston et al., Continuous bioactivity-dependent evolution of an antibiotic biosynthetic pathway. Nat. Commun. 11(1):4202 (2020).
Joosten et al., The PDB_REDO server for macromolecular structure model optimization. IUCrJ 1(Pt 4):213-220 (2014).
Jung et al., Cytochrome P450: taming a wild type enzyme. Curr Opin Biotechnol. 22(6):809-817 (2011).
Kaberniuk et al., A bacterial phytochrome-based optogenetic system controllable with near-infrared light. Nat Methods. 13(7):591-7 (2016).
Kachroo et al., Systematic humanization of yeast genes reveals conserved functions and genetic modularity. Science. 348(6237):921-925 (2015).
Kampranis et al., Rational conversion of substrate and product specificity in a Salvia monoterpene synthase: structural insights into the evolution of terpene synthase function. Plant Cell. 19(6):1994-2005 (2007).
Kaneko et al. Superbinder SH2 domains act as antagonists of cell signaling. Sci Signal. 5(243):ra68 (2012).
Karunarathne et al., Subcellular optogenetics—controlling signaling and single-cell behavior. J Cell Sci. 128(1):15-25 (2015).
Keedy et al., An expanded allosteric network in PTP1B by multitemperature crystallography, fragment screening, and covalent tethering. Elife. 7:e36307 (2018).
Kennedy, Signal-Processing Machines at the Postsynaptic Density. Science. 290(5492):750-754 (2000).
Kennedy, Managing the drug discovery/development interface. Drug Discov Today. 2(10):436-444 (1997).
Khaerunnisa et al., Potential Inhibitor of COVID-19 Main Protease (Mpro) from Several Medicinal Plant Compounds by Molecular Docking Study. Preprints. 14 pages (2020). doi:10.20944/preprints202003.0226.v1.
Khrimian et al., Absolute configurations of stink bug- and plant-produced sesquipiperitols via synthesis of all stereoisomers. J Nat Prod. 83(7)2281-2286 (2020).
Kitaoka et al., Optimization of recombinant expression enables discovery of novel cytochrome P450 activity in rice diterpenoid biosynthesis. Appl Microbiol Biotechnol. 99(18):7549-7558 (2015).
Klebe, Applying thermodynamic profiling in lead finding and optimization. Nat Rev Drug Discov. 14(2):95-110 (2015).
Koehn et al., The evolving role of natural products in drug discovery. Nat Rev Drug Discov. 4(3):206-220 (2005).
Koh et al., Current trends in modem pharmaceutical analysis for drug discovery. Drug Discov Today. 8(19): 889-897 (2003).
Konc et al., ProBiS-CHARMMing: web interface for prediction and optimization of ligands in protein binding sites. J Chem Inf Model. 55(11):2308-2314 (2015).
Kondo et al., Yellow fever virus NS2B/NS3 protease: hydrolytic properties and substrate specificity. Biochem Biophys Res Commun. 407(4):640-644 (2011).
Koren et al., Inhibition of the protein tyrosine phosphatase PTP1B: potential therapy for obesity, insulin resistance and type-2 diabetes mellitus. Best Pract Res Clin Endocrinol Metab. Metab. 21(4):621-640 (2007).
Krauss et al., LOVely enzymes—towards engineering light-controllable biocatalysts. Microb Biotechnol. 3(1):15-23 (2010).
Krimmer et al., Methyl, ethyl, propyl, butyl: futile but not for water, as the correlation of structure and thermodynamic signature shows in a congeneric series of thermolysin inhibitors. ChemMedChem 9(4):833-846 (2014).
Krishnan et al., Anxious moments for the protein tyrosine phosphatase PTP1B. Trends Neurosci. 38(8):462-465 (2015).
Krishnan et al., Targeting the disordered C terminus of PTP1B with an allosteric inhibitor. Nat Chem Biol. 10(7): 558-566 (2014).
Krishnan et al. PTP1B inhibition suggests a therapeutic strategy for Rett syndrome. J Clin Invest. 125(8):3163-3177 (2015).
Lancaster, J et al., An IDS-type sesquiterpene synthase produces the pheromone precursor (Z)-α-bisabolene in Nezara viridula. J Chem Ecol. 45(2):187-197 (2019).
Lange et al., Enzymology of monoterpene functionalization in glandular trichomes. J Exp Bot. 70(4):1095-1108 (2019).
Lauchli et al., High-throughput screening for terpene-synthase-cyclization activity and directed evolution of a terpene synthase. Angew Chem Int Ed Engl. 52(21):5571-5574 (2013).
Lee et al., Identification of novel small molecule inhibitors against NS2B/NS3 serine protease from Zika virus. Antiviral Res. 139, 49-58 (2017).
Lee et al., Phosphorylation of the AMPA receptor GluR1 subunit is required for synaptic plasticity and retention of spatial memory. Cell. 112(5):631-643 (2003).
Lee et al. Proteasome inhibitors: valuable new tools for cell biologists. Trends Cell Biol. 8(10):397-403 (1998).
Lee et al., Surface sites for engineering allosteric control in proteins. Science. 322(5900):438-442 (2008).
Lehmann et al., Identification of human triple-negative breast cancer subtypes and preclinical models for selection of targeted therapies. J Clin Invest. 121(7):2750-2767 (2011).
Lei et al., Crystal structure of the papain-like protease of MERS coronavirus reveals unusual, potentially druggable active-site features. Antiviral Res. 109:72-82 (2014).
Lei et al., Crystal structure of Zika virus NS2B-NS3 protease in complex with a boronate inhibitor. Science. 353(6298):503-505 (2016).
Leonard et al., Combining metabolic and protein engineering of a terpenoid biosynthetic pathway for overproduction and selectivity control. Proc Natl Acad Sci USA. 107(31):13654-13659 (2010).
Lessard et al., PTP1B is an androgen receptor-regulated phosphatase that promotes the progression of prostate cancer. Cancer Res. 72(6):1529-1537 (2012).
Lessard et al., The two faces of PTP1B in cancer. Biochim Biophys Acta. 1804(3):613-619 (2010).
Lewis et al., Combinatorial alanine substitution enables rapid optimization of cytochrome P450BM3 for selective hydroxylation of large substrates. Chembiochem 11(18):2502-2505 (2010).
Li et al., Reprogramming the chemodiversity of terpenoid cyclization by remolding the active site contour of epi-isozizaene synthase. Biochemistry. 53(7):1155-1168 (2014).
Li et al., Therapeutic options for the 2019 novel coronavirus (2019-nCoV). Nat Rev Drug Discov. 19(3):149-150 (2020).
Li et al., Crystal Structure and Substrate Specificity of PTPN12. Cell Rep. 15(6):1345-1358 (2016).

(56) References Cited

OTHER PUBLICATIONS

Li et al., Production of plant-specific flavones baicalein and scutellarein in an engineered *E. coli* from available phenylalanine and tyrosine. Metab Eng. 52:124-133 (2019).
Li et al., Drug discovery and natural products: end of an era or an endless frontier? Science. 10;325(5937):161-165 (2009).
Li et al., Complete biosynthesis of noscapine and halogenated alkaloids in yeast. Proc Natl Acad Sci USA. 115(17):E3922-E3931 (2018).
Lim et al., (-)-α-Bisabolol production in engineered *Escherichia coli* expressing a novel (-)-α- Bisabolol synthase from the globe artichoke Cynara cardunculus var. scolymus. J Agric Food Chem. 69 (30):8492-8503 (2021).
Lim et al., Human coronaviruses: A review of virus-host interactions. Diseases. 4(3):26 (2016).
Lindner et al., The papain-like protease from the severe acute respiratory syndrome coronavirus is a deubiquitinating enzyme. J Virol. 79(24):15199-15208 (2005).
Ling et al., Cytostatic and cytotoxic natural products against cancer cell models. Molecules. 24(10):2012 (2019).
Liu et al., PTP1B promotes cell proliferation and metastasis through activating src and ERK1/2 in non-small cell lung cancer. Cancer Lett. 359(2):218-225 (2015).
Loehr et al., Yellow fever virus NS3 protease: peptide-inhibition studies. J Gen Virol. 88(Pt 8):2223-2227 (2007).
Lu et al., Co-expression of P450 BM3 and glucose dehydrogenase by recombinant *Escherichia coli* and its application in an NADPH-dependent indigo production system. J Ind Microbiol Biotechnol. 34(3):247-253 (2007).
Lukyanov et al., Innovation: Photoactivatable fluorescent proteins. Nat Rev Mol Cell Biol. 6(11):885-891 (2005).
Luo et al., Crystal structure of the NS3 protease-helicase from dengue virus. J Virol 82(1):173-183 (2008).
Luo et al., Flexibility between the protease and helicase domains of the dengue virus NS3 protein conferred by the linker region and its functional implications. J Biol Chem. 285(24):18817-18827 (2010).
Luo et al., Complete biosynthesis of cannabinoids and their unnatural analogues in yeast. Nature. 567(7746):123-126 (2019).
Lv et al., HIV protease inhibitors: a review of molecular selectivity and toxicity. HIV AIDS (Auckl). 7:95-104. (2015).
Mackerell et al., All-atom empirical potential for molecular modeling and dynamics studies of proteins. J Phys Chem B. 102(18):3586-3616 (1998).
Mafu et al., Probing the promiscuity of ent -kaurene oxidases via combinatorial biosynthesis. Proc Natl Acad Sci USA. 113(9):2526-2531 (2016).
Maier, Design and synthesis of analogues of natural products. Org Biomol Chem. 13(19):5302-5343 (2015).
Malcolm et al., Expression and characterization of recombinant hepatitis A virus 3C proteinase. Biochemistry. 31(13):3358-3363 (1992).
Manguso et al. In vivo CRISPR screening identifies Ptpn2 as a cancer immunotherapy target. Nature. 547(7664):413-418 (2017).
Mao et al., Neurologic manifestations of hospitalized patients with coronavirus disease 2019 in Wuhan, China. JAMA Neurol. 77(6):683-690 (2020).
Martin et al., Engineering a mevalonate pathway in *Escherichia coli* for production of terpenoids. Nat Biotechnol. 21(7):796-802 (2003).
Martins et al., Marketed marine natural products in the pharmaceutical and cosmeceutical industries: tips for success. Mar drugs. 12(2):1066-1101 (2014).
Matulka et al., PTP1B is an effector of activin signaling and regulates neural specification of embryonic stem cells. Cell Stem Cell. 13(6):706-719 (2013).
McAndrew et al., Structure of a three-domain sesquiterpene synthase: A prospective target for advanced biofuels production. Structure. 19(12):1876-1884 (2011).
McKibbin et al., The Global Macroeconomic Impacts of COVID-19: Seven Scenarios. SSRN Electronic Journal. CAMA Working Paper No. 19/2020: 45 pages (2020).
Medema et al., antiSMASH: rapid identification, annotation and analysis of secondary metabolite biosynthesis gene clusters in bacterial and fungal genome sequences. Nucleic Acids Res. 39(Web Server issue): W339-46 (2011).
Mehla et al., A comparison of two-hybrid approaches for detecting protein-protein interactions. Methods Enzymol. 586:333-358 (2017).
Mellott et al., A clinical-stage cysteine protease inhibitor blocks SARS-CoV-2 infection of human and monkey cells. ACS Chem Biol. 16(4):642-650 (2021).
Mendoza et al., Two detailed plaque assay protocols for the quantification of infectious SARS-CoV-2. Curr Protoc Microbiol. 57(1):ecpmc105 (2020).
Menon et al., RadH: A versatile halogenase for integration into synthetic pathways. Angew Chem Int Ed Engl. 56(39):11841-11845 (2017).
Merck. Merck and Ridgeback Biotherapeutics Provide Update on Results from MOVe-OUT Study of Molnupiravir, an Investigational Oral Antiviral Medicine, in at Risk Adults With Mild-to-Moderate COVID-19. at https://www.merck.com/news/merck-and-ridgeback-biotherapeutics-provide-update-on-results-from-move-out-study-of-molnupiravir-an-investigational-oral-antiviral-medicine-in-at-risk-adults-with-mild-to-moderate-covid-19/ (2021).
Merck. Merck and Ridgeback's Investigational Oral Antiviral Molnupiravir Reduced the Risk of Hospitalization or Death by Approximately 50 Percent Compared to Placebo for Patients with Mild or Moderate COVID-19 in Positive Interim Analysis of Phase 3 Study. at https://www.merck.com/news/merck-and-ridgebacks-investigational-oral-antiviral-molnupiravir-reduced-the-risk-of-hospitalization-or-death-by-approximately-50-percent-compared-to-placebo-for-patients-with-mild-or-moderat/ (2021).
Mobley et al., Predicting binding free energies: frontiers and benchmarks. Annu. Rev. Biophys. 46:531-558 (2017).
Montalibet et al., Using yeast to screen for inhibitors of protein tyrosine phosphatase 1B. Biochem Pharmacol. 68(9):1807-1814 (2004).
Montalibet et al. Residues distant from the active site influence protein-tyrosine phosphatase 1B inhibitor binding. J Biol Chem. 281(8):5258-5266 (2006).
Morrone et al., Increasing diterpene yield with a modular metabolic engineering system in *E. coli*: Comparison of MEV and MEP isoprenoid precursor pathway engineering. Appl Microbial Biotechnol. 85(6):1893-1906 (2010).
Muangphrom et al., Identification and characterization of a novel sesquiterpene synthase, 4-amorphen-11-ol synthase, from artemisia maritima. Plant Biotechnol. 35(2):113-121 (2018).
Muangphrom et al. Functional analysis of amorpha-4,11-diene synthase (ADS) homologs from non-artemisinin-producing artemisia species: The discovery of novel koidzumiol and (+)-α-Bisabolol synthases. Plant Cell Physiol. 57(8):1678-1688 (2016).
Murphy et al., WScore: A flexible and accurate treatment of explicit water molecules in ligand-receptor docking. J Med Chem. 59(9):4364-4384 (2016).
Muzzarelli et al., Structural and antiviral studies of the human norovirus GII.4 protease. Biochemistry. 58(7):900-907 (2019).
Nakagawa et al., A bacterial platform for fermentative production of plant alkaloids. Nat Commun. 2:326 (2011).
Nakamura et al., A norovirus protease structure provides insights into active and substrate binding site integrity. J Virol. 79(21):13685-13693 (2005).
Nalam et al., Evaluating the substrate-envelope hypothesis: structural analysis of novel HIV-1 protease inhibitors designed to be robust against drug resistance. J Virol. 84(10):5368-5378 (2010).
Namchuk, Early returns on small molecule therapeutics for SARS-CoV-2. Acs Infect Dis. 7(6):1298-1302 (2021).
Narwal et al., Crystal structure of chikungunya virus nsP2 cysteine protease reveals a putative flexible loop blocking its active site. Int J Biol Macromol. 116:451-462 (2018).
Needle et al., Structures of the middle east respiratory syndrome coronavirus 3C-like protease reveal insights into substrate specificity. Acta Crystallogr D Biol Crystallogr. 71(Pt 5):1102-1111 (2015).
Newman et al., Natural products as sources of new drugs from 1981 to 2014. Journal of Natural Products. 79(3):629-661 (2016).

(56) References Cited

OTHER PUBLICATIONS

Next Generation Sequencing: Amplicon-EZ. at https://www.genewiz.com/en/Public/Services/Next-Generation-Sequencing/Amplicon-Sequencing-Services/Amplicon-EZ (2022).
NIAID National Institute of Allergy and Infectious Diseases. Emerging Infectious Diseases/Pathogens. at https://www.niaid.nih.gov/research/emerging-infectious-diseases-pathogens (2018).
Nitsche et al., Peptide-boronic acid inhibitors of flaviviral proteases: medicinal chemistry and structural biology. J Med Chem. 60(1):511-516 (2017).
Nitsche, Proteases from dengue, West Nile and Zika viruses as drug targets. Biophys Rev. 11(2):157-165 (2019).
Noble et al., Ligand-bound structures of the dengue virus protease reveal the active conformation. J Virol. 86(1):438-446 (2012).
Noske et al., Structural characterization and polymorphism analysis of the NS2B-NS3 protease from the 2017 Brazilian circulating strain of Yellow Fever virus. Biochimica et Biophysica Acta (BBA)-General Subjects 1864(4):129521 (2020).
O'Brien et al., Inparanoid: A comprehensive database of eukaryotic orthologs. Nucleic Acids Res. 33(Database issue):D476-D480 (2005).
Oleinikovas et al., Understanding cryptic pocket formation in protein targets by enhanced sampling simulations. J Am Chem Soc. 138(43):14257-14263 (2016).
Olsson et al., The thermodynamics of protein-ligand interaction and solvation: insights for ligand design. J Mol Biol. 384(4):1002-1017 (2008).
O'Maille et al., Quantitative exploration of the catalytic landscape separating divergent plant sesquiterpene synthases. Nat Chem Biol. 4(10):617-623 (2008).
Otto et al., Cysteine proteases and their inhibitors. Chem Rev. 97(1):133-172 (1997).
Ouyang et al., Determination of hierarchical relationship of Src and Rac at subcellular locations with FRET biosensors. Proc Natl Acad Sci USA. 105(38):14353-14358 (2008).
Packer et al., Methods for the directed evolution of proteins. Nat Rev Genet. 16(7):379-394 (2015).
Paddon et al., Semi-synthetic artemisinin: a model for the use of synthetic biology in pharmaceutical development. Nat Rev Microbiol. 12(5):355-367 (2014).
Palazón-Riquelme et al., USP7 and USP47 deubiquitinases regulate NLRP3 inflammasome activation. EMBO Rep. 19(10):e44766 (2018).
Paling et al., Role of the protein tyrosine phosphatase SHP-1 (Src homology phosphatase-1) in the regulation of interleukin-3-induced survival, proliferation and signalling. Biochem. J. 368(Pt 3):885-894 (2002).
Pallesen et al., Immunogenicity and structures of a rationally designed prefusion MERS-CoV spike antigen. Proc Natl Acad Sci USA. 114(35):E7348-E7357 (2017).
Park et al., Whole-cell biocatalysis using cytochrome P450 monooxygenases for biotransformation of sustainable bioresources (fatty acids, fatty alkanes, and aromatic amino acids). Biotechnol Adv. 40:107504 (2020).
Parrinello, Polymorphic transitions in single crystals: A new molecular dynamics method. J Appl Phys. 52(12):7182 (1981).
Pastorino et al., Expression and biochemical characterization of nsP2 cysteine protease of Chikungunya virus. Virus Res.131(2):293-298 (2008).
Pastorino et al., Improvement of the purification of Saint Louis encephalitis virus NS2B-NS3 recombinant protease expressed in *Escherichia coli*. J Chromatogr B Analyt Technol Biomed Life Sci. 868(1-2):58-63 (2008).
Pathan et al., Basic opioid pharmacology: an update. Br J Pain. 6(1):11-16 (2012).
Paul et al., Tyrosine kinase—role and significance in Cancer. Int J Med Sci. 1(2):101-115 (2004).
Paul et al., How to improve R&D productivity: The pharmaceutical industry's grand challenge. Nat Rev Drug Discov. 9(3):203-214 (2010).
PCT/US2019/040896 International Preliminary Report on Patentability dated Jan. 12, 2021.
PCT/US2019/040896 International Search Report and Written Opinion dated Nov. 8, 2019.
PCT/US2021/012621 International Search Report and Written Opinion dated Apr. 6, 2021.
Pelander et al., In silico methods for predicting metabolism and mass fragmentation applied to quetiapine in liquid chromatography/time-of-flight mass spectrometry urine drug screening. Rapid Commun Mass Spectrom. 23(4):506-514 (2009).
Peralta-Yahya et al. Identification and microbial production of a terpene-based advanced biofuel. Nat Commun. 2:483 (2011).
Peter et al., Mechanism of signal transduction of the LOV2-Jα photosensor from Avena sativa. Nat Commun. 1:122 (2010).
Peters et al., Abietadiene synthase catalysis: mutational analysis of a prenyl diphosphate ionization-initiated cyclization and rearrangement. Proc Natl Acad Sci USA. 99(2):580-584 (2002).
Peters et al., Abietadiene synthase from grand fir (Abies grandis): Characterization and mechanism of action of the "pseudomature" recombinant enzyme. Biochemistry 39(50):15592-15602 (2000).
Pfeifer et al., Biosynthesis of Yersiniabactin, a complex polyketide-nonribosomal peptide, using *Escherichia coli* as a heterologous host. Appl Environ Microbiol. 69(11):6698-6702 (2003).
Pfizer. Pfizer Seeks Emergency Use Authorization for Novel COVID-19 Oral Antiviral Candidate. at https://www.pfizer.com/news/press-release/press-release-detail/pfizer-seeks-emergency-use-authorization-novel-covid-19 (2021).
PHE Public Health Emergency. Pause in the Distribution of Bamlanivimab/Etesevimab. at https://www.phe.gov/emergency/events/COVID19/investigation-MCM/Bamlanivimab-etesevimab/Pages/bamlanivimab-etesevimab-distribution-pause.aspx (2021).
Phoo et al., Structures of Zika virus NS2B-NS3 protease in complex with peptidomimetic inhibitors. Antiviral Res. 160:17-24 (2018).
Pike et al., Protein tyrosine phosphatase 1B is a regulator of the interleukin-10-induced transcriptional program in macrophages. Sci Signal. 7(324):ra43 (2014).
Piserchio et al., Expression and purification of Src-family kinases for solution NMR studies. Methods Mol Biol. 831:111-131 (2012).
Porter et al., Cooperative changes in solvent exposure identify cryptic pockets, switches, and allosteric coupling. Biophys J. 116(5):818-830 (2019).
Price et al., FastTree 2—approximately maximum-likelihood trees for large alignments. PLoS One 5(3):e9490 (2010).
Qin et al., Chronic stress induces anxiety via an amygdalar intracellular cascade that impairs endocannabinoid signaling. Neuron. 85(6):1319-1331 (2015).
Rani et al., Drug development post COVID-19 pandemic: toward a better system to meet current and future global health challenges. Expert Opin Drug Discov. 16(4):365-371 (2021).
Ratia et al., Severe acute respiratory syndrome coronavirus papain-like protease: structure of a viral deubiquitinating enzyme. Proc Natl Acad Sci USA.103(15):5717-5722 (2006).
Repina et al., At light speed: Advances in optogenetic systems for regulating cell signaling and behavior. Annu Rev Chem Biomol Eng. 8:13-39 (2017).
Rhee et al., Protein tyrosine phosphatases in lymphocyte activation and autoimmunity. Nat Immunol. 13(5): 439-447 (2012).
Rinkel et al., Stereochemical investigations on the biosynthesis of achiral (Z)-γ-bisabolene in Cryptosporangium arvum. Beilstein J Org Chem. 15:789-794 (2019).
Rizzuti et al., Sub-micromolar inhibition of SARS-CoV-2 3CLpro by natural compounds. Pharmaceuticals (Basel) 14(9):892 (2021).
Ro et al., Production of the antimalarial drug precursor artemisinic acid in engineered yeast. Nature. 440(7086):940-943 (2006).
Robin et al., Structure of West Nile virus NS3 protease: ligand stabilization of the catalytic conformation. J Mol Biol. 385(5):1568-1577 (2009).
Robinson et al., Differential water thermodynamics determine PI3K-Beta/Delta selectivity for solvent-exposed ligand modifications. J Chem Inf Model. 56(5):886-894 (2016).
Rodrigues et al., Counting on natural products for drug design. Nature chemistry 8(6):531-541 (2016).
Rodriguez et al., The growing and glowing toolbox of fluorescent and photoactive proteins. Trends Biochem. Sci. 42(2):111-129 (2017).

(56) References Cited

OTHER PUBLICATIONS

Romsicki et al., Protein tyrosine phosphatase-1B dephosphorylation of the insulin receptor occurs in a perinuclear endosome compartment in human embryonic kidney 293 cells. J Biol Chem. 279(13): 12868-12875 (2004).
Rougé et al., Molecular understanding of USP7 substrate recognition and C-terminal activation. Structure. 24(8): 1335-1345 (2016).
Rowland et al., ER contact sites define the position and timing of endosome fission. Cell 159(5):1027-1041 (2014).
Russo et al., The crystal structure of the Venezuelan equine encephalitis alphavirus nsP2 protease. Structure 14(9):1449-1458 (2006).
Rut et al., Profiling of flaviviral NS2B-NS3 protease specificity provides a structural basis for the development of selective chemical tools that differentiate Dengue from Zika and West Nile viruses. Antiviral Research 175:104731 (2020).
Rutledge et al. Discovery of microbial natural products by activation of silent biosynthetic gene clusters. Nat Rev Microbiol. 13(8):509-523 (2015).
Ruttkies et al., MetFrag relaunched: Incorporating strategies beyond in silica fragmentation. J Cheminform. 8:3 (2016).
Salis, The ribosome binding site calculator. Methods Enzymol. 498:19-42 (2011).
Sangster et al., New trends and future opportunities in the enzymatic formation of C-C, C-N, and C-O bonds. Chembiochem 23(6):e202100464. (2021).
Sarkar et al., Microbially guided discovery and biosynthesis of biologically active natural products. ACS Synth Biol 10(6):1505-1519 (2021).
Sarkar et al., Evolution-guided biosynthesis of terpenoid Inhibitors. ACS Synth Biol. 11(9):3015-3027 (2022).
Sarrade-Loucheur et al., Synthetic derivatives of (+)-epi-α-bisabolol are formed by mammalian cytochromes P450 expressed in a yeast reconstituted pathway. ACS Synth Biol. 9(2):368-380 (2020).
Sato et al., Fluorescent indicators for imaging protein phosphorylation in single living cells. Nat Biotechnol. 20(3):287-294 (2002).
Scott et al., Targeting protein tyrosine phosphatases for anticancer drug discovery. Curr Pharm Des. 16(16):1843-1862 (2010).
Seifert et al., Rational design of a minimal and highly enriched CYP102AI mutant library with improved regio-, stereo- and chemoselectivity. Chembiochem 10(5):853-861 (2009).
Shang et al., Biochemical characterization of recombinant enterovirus 71 3C protease with fluorogenic model peptide substrates and development of a biochemical assay. Antimicrob Agents Chemother. 59(4):1827-1836 (2015).
Shchelkunov et al., Analysis of the monkeypox virus genome. Virology. 297(2):172-194 (2002).
Shepherd et al., A structure-guided switch in the regioselectivity of a tryptophan halogenase. Chembiochem 17(9):821-824 (2016).
Shi et al., Discovery and biosynthesis of guanipiperazine from a NRPS-like pathway. Chem Sci. 12(8):2925-2930 (2021).
Shimada et al., Selectivity of polycyclic inhibitors for human cytochrome P450s 1A1, 1A2, and 1B1. Chem. Res. Toxicol. 11(9):1048-1056 (1998).
Shin et al., Papain-like protease regulates SARS-CoV-2 viral spread and innate immunity. Nature. 587(7835):657-662 (2020).
Smanski et al., Synthetic biology to access and expand nature's chemical diversity. Nat Rev Microbiol. 14(3):135-149 (2016).
Snyder et al., Is it the shape of the cavity, or the shape of the water in the cavity? Eur Phys J. Special Topics. 223: 853-891 (2014).
Soysal et al., PTP1B expression is an independent positive prognostic factor for human breast cancer. Breast Cancer Res Treat. 137(2):637-644 (2013).
Stanford et al., Targeting tyrosine phosphatases: Time to end the stigma. Trends Pharmacol Sci. 38(6):524-540 (2017).
Steele et al., Sesquiterpene synthases from grand fir (Abies grandis). Comparison of constitutive and wound-induced activities, and cDNA isolation, characterization, and bacterial expression of delta-selinene synthase and gamma-humulene synthase J. Biol. Chem. 273(4):2078-2089 (1998).
Strickland et al., Rationally improving LOV domain-based photoswitches. Nat. Methods. 7(8):623-6 (2010).
Su et al., Anti-SARS-CoV-2 activities in vitro of Shuanghuanglian preparations and bioactive ingredients. Acta Pharmacol Sinica 41(9):1167-1177 (2020).
Su et al., Identification of pyrogallol as a warhead in design of covalent inhibitors for the SARS-CoV-2 3CL protease. Nat Commun. 12(1):3623 (2021).
Sun et al., Crystal structure of PTP1B complexed with a potent and selective bidentate inhibitor. J Biol Chem. 278(14):12406-12414 (2003).
Sun et al., Activity based fingerprinting of proteases using FRET peptides. 88(2):141-149 (2007).
Sycz et al., LOV Histidine kinase modulates the general stress response system and affects the virB operon expression in *Brucella abortus*. PLoS One. 10(5): e0124058 (2015).
Tachibana et al., Novel prenyltransferase gene encoding farnesylgeranyl diphosphate synthase from a hyperthermophilic archaeon, Aeropyrum pernix. Molecular evolution with alteration in product specificity. Eur J Biochem. 267(2):321-328 (2000).
Tan et al., 3C protease of enterovirus 68: structure-based design of Michael acceptor inhibitors and their broad-spectrum antiviral effects against picornaviruses. J Virol. 87(8):4339-4351 (2013).
Tautz et al., Targeting the PTPome in human disease. Expert Opin Ther Targets 10(1):157-177 (2006).
Teng et al., Structures, mechanisms and inhibitors of undecaprenyl diphosphate synthase: a cis-prenyltransferase for bacterial peptidoglycan biosynthesis. Bioorg Chem. 43:51-57 (2012).
Tholl, Biosynthesis and biological functions of terpenoids in plants. Adv Biochem Eng Biotechnol. 148:63-106 (2015).
Tian et al., Circular polymerase extension cloning of complex gene libraries and pathways. PLoS One. 4(7): e6441 (2009).
Tiganis et al., Epidermal growth factor receptor and the adaptor protein p52Shc are specific substrates of T-cell protein tyrosine phosphatase. Mol Cell Biol. 18(3):1622-1634 (1998).
Ting et al., Genetically encoded fluorescent reporters of protein tyrosine kinase activities in living cells. Proc Natl Acad Sci USA. 98(26):15003-15008 (2001).
Tonks et al., A brake becomes an accelerator: PTP1B—a new therapeutic target for breast cancer. Cancer Cell 11(3):214-216 (2007).
Tonks, Protein tyrosine phosphatases—from housekeeping enzymes to master regulators of signal transduction. FEBS J. 280(2):346-378 (2013).
Tonks, Protein tyrosine phosphatases: from genes, to function, to disease. Nat Rev Mol Cell Biol. 7(11):833-846 (2006).
Traves et al., Pivotal role of protein tyrosine phosphatase 1B (PTP1B) in the macrophage response to proinflammatory and anti-inflammatory challenge. Cell Death Dis. 5(3): e1125 (2014).
Traylor et al., Recombinant expression and characterization of Lucilia cuprina CYP6G3: Activity and binding properties toward multiple pesticides. Insect Biochem Mol Biol. 90:14-22 (2017).
Trouiller et al., Drug development for neglected diseases: a deficient market and a public-health policy failure. Lancet. 359(9324):2188-2194 (2002).
Tzeng et al., Protein activity regulation by conformational entropy. Nature. 488(7410):236-240 (2012).
Urlacher et.al.; Cytochrome P450 monooxygenases in biotechnology and synthetic biology. Trends Biotechnol. 37(8): 882-897 (2019).
Ursu et al., Understanding drug-likeness. Wiley Interdisciplinary Reviews: Computational Molecular Science 1, 760-781 (2011).
Vajda et al., Cryptic binding sites on proteins: definition, detection, and druggability. Curr Opin Chem Biol. 44:1-8 (2018).
Vallurupalli et al., Studying "invisible" excited protein states in slow exchange with a major state conformation. J. Am. Chem. Soc. 134(19):8148-8161 (2012).
Van Stokkum et al., The primary photophysics of the Avena sativa phototropin 1 LOV2 domain observed with time-resolved emission spectroscopy. Photochem Photobiol. 87(3): 534-541 (2011).
Van Vliet et al., Selective regulation of tumor necrosis factor-induced Erk signaling by Src family kinases and the T cell protein tyrosine phosphatase. Nat Immunol. 6(3):253-260 (2005).

(56) References Cited

OTHER PUBLICATIONS

Vanommeslaeghe, K. et al. CHARMM general force field: A force field for drug-like molecules compatible with the CHARMM all-atom additive biological force fields. J Comput Chem. 31(4): 671-690 (2010).
Varone et al., Shp1 in solid cancers and their therapy. Front Oncol. 10:935 (2020).
Varshavsky, N-degron and C-degron pathways of protein degradation. Proc Natl Acad Sci. USA. 116(2):358-366 (2019).
Veening et al., Phosphatases modulate the bistable sporulation gene expression pattern in *Bacillus subtilis*. Mol Microbiol. 56(6):1481-1494 (2005).
Vereb et al., Flow cytometric FRET analysis of protein interaction. Methods Mol Biol. 699:371-392 (2011).
Vidal et al., Library-based discovery and characterization of daphnane diterpenes as potent and selective HIV inhibitors in Daphne gnidium. J Nat Prod. 75(3):414-419 (2012).
Villamagna et al., The need for antiviral drugs for pandemic coronaviruses from a global health perspective. Front Med (Lausanne). 7:596587 (2020).
Viskovska et al., GII.4 norovirus protease shows pH-sensitive proteolysis with a unique Arg-His pairing in the catalytic site. J Virol. 93(6):e01479-18 (2019).
Vistoli et al., Assessing drug-likeness—what are we missing? Drug Discov Today. 13(7-8):285-294 (2008).
Vitalis et al., Absinth: A new continuum solvation model for simulations of polypeptides in aqueous solutions. J Comput Chem. 30(5):673-699 (2009).
Vitalis et al., Methods for Monte Carlo simulations of biomacromolecules. Annu Rep Comput Chem. 5:49-76 (2009).
Volinksy et al., Complexity of receptor tyrosine kinase signal processing. Cold Spring Harb Perspect Biol. 5(8): a009043 (2013).
Wang et al., Metabolic engineering of *Escherichia coli* for the biosynthesis of various phenylpropanoid derivatives. Metab Eng. 29:153-159 (2015).
Wang et al., Metabolic engineering of flavonoids in plants and microorganisms. Applied Microbiol Biotechnol. 91(4):949-956 (2011).
Wang et al., Structure of the Enterovirus 71 3C protease in complex with NK-1.8k and indications for the development of antienterovirus protease inhibitor. Antimicrob Agents Chemother. 61(7): e00298-17 (2017).
Waterhouse et al., SWISS-MODEL: Homology modelling of protein structures and complexes. Nucleic Acids Res. 46(W1):W296-W303 (2018).
Weaver, How Taxol/paclitaxel kills cancer cells. Mol Biol Cell. 25(18):2677-2681 (2014).
Weaver, Invadopodia: Specialized cell structures for cancer invasion. Clin Exp Metastasis. 23(2):97-105 (2006).
Weinert et al., Fast native-SAD phasing for routine macromolecular structure determination. Nature Methods. 12(2):131-133 (2015).
Welsch et al., Privileged scaffolds for library design and drug discovery. Curr Opin Chem Biol. 14(3):347-361 (2010).
Whitesides et al., Designing ligands to bind proteins. Q Rev Biophys. 38(4): 385-395 (2005).
WHO World Health Organization. Coronavirus disease 2019 (COVID-19): Situation Report—87. (2020).
WHO World Health Organization. Prioritizing diseases for research and development in emergency contexts. at https://www.who.int/activities/prioritizing-diseases-for-research-and-development-in-emergency-contexts (2022).
Wiesmann et al., Allosteric inhibition of protein tyrosine phosphatase 1B. Nat Struct Mol Biol. 11(8):730-737 (2004).
Wilderman et al., A single residue switch converts abietadiene synthase into a pimaradiene specific cyclase. J Am Chem Soc. 129(51):15736-15737 (2007).
Williams et al., Heterologous expression and characterization of a "pseudomature" form of taxadiene synthase involved in paclitaxel (Taxol) biosynthesis and evaluation of a potential intermediate and inhibitors of the multistep diterpene cyclization reaction. Arch Biochem Biophys. 379(1):137-146 (2000).
Winter, Xia2: An expert system for macromolecular crystallography data reduction. J Appl Cryst. 43:186-190 (2010).
Wrapp et al., Cryo-EM structure of the 2019-nCoV spike in the prefusion conformation. Science. 367(6483):1260-1263 (2020).
Wray et al., Inhibition of glycogen synthase kinase-3 alleviates Tcf3 repression of the pluripotency network and increases embryonic stem cell resistance to differentiation. Nat Cell Biol. 13(7):838-845 (2011).
Wu et al., A genetically encoded photoactivatable Rac controls the motility of living cells. Nature. 461(7260):104-108 (2009).
Wu et al., FDA-approved small-molecule kinase inhibitors. Trends Pharmacol Sci. 36(7):422-439 (2015).
Wu et al., Protein tyrosine phosphatase PTP1B is involved in neuroendocrine differentiation of prostate cancer. Prostate. 66(11):1125-1135 (2006).
Xue et al., Production of authentic SARS-CoV M(pro) with enhanced activity: application as a novel Tag-cleavage endopeptidase for protein overproduction. J Mol Biol. 366(3):965-975 (2007).
Yan et al., Resistance-gene-directed discovery of a natural-product herbicide with a new mode of action. Nature. 559(7714):415-418 (2018).
Yang et al., Targeting protein tyrosine phosphatase PTP-PEST (PTPN12) for therapeutic intervention in acute myocardial infarction. Cardiovasc Res. 116(5):1032-1046 (2020).
Yang et al., The crystal structures of severe acute respiratory syndrome virus main protease and its complex with an inhibitor. Proc Natl Acad Sci USA. 100(23):13190-13195 (2003).
Yang et al., Biological synthesis of coumarins in *Escherichia coli*. Microb Cell Fact. 14:65 (2015).
Yao et al., Discovery, X-ray crystallography and antiviral activity of allosteric inhibitors of flavivirus NS2B-NS3 protease. J Am Chem Soc. 141(17):6832-6836 (2019).
Yao et al., Estimation of the available free energy in a LOV2-Jα photoswitch. Nat Chem Biol. 4(8):491-497 (2008).
Yesudhas et al., COVID-19 outbreak: history, mechanism, transmission, structural studies and therapeutics. Infection. 49(2):199-213 (2021).
Yildiz et al., Allosteric inhibition of the NS2B-NS3 protease from dengue virus. ACS Chem Biol. 8(12):2744-2752 (2013).
Yoshikuni et al., Designed divergent evolution of enzyme function. Nature. 440(7087):1078-1082 (2006).
Yu et al., GGTREE: an R package for visualization and annotation of phylogenetic trees with their covariates and other associated data. Methods Ecol. Evol. 8(1), 28-36 (2017).
Yu et al., Extension of the CHARMM general force field to sulfonyl-containing compounds and its utility in biomolecular simulations. J Comput Chem. 33(31):2451-2468 (2012).
Zabolotny et al., Protein-tyrosine phosphatase 1B expression is induced by inflammation in vivo. J Biol Chem. 283(21):14230-14241 (2008).
Zayner et al., The amino-terminal helix modulates light-activated conformational changes in AsLOV2. J Mol Biol. 419(1-2):61-74 (2012).
Zegzouti et al., ADP-Glo: A bioluminescent and homogeneous ADP monitoring assay for kinases. Assay Drug Dev Technol. 7(6):560-572 (2009).
Zhabinskii et al., Steroid plant hormones: Effects outside plant kingdom. Steroids. 97:87-97 (2015).
Zhang et al., Efflux transporter engineering markedly improves amorphadiene production in *Escherichia coli*. Biotechnol Bioeng. 113(8):1755-1763 (2016).
Zhang et al., Multidimensional heuristic process for high-yield production of astaxanthin and fragrance molecules in *Escherichia coli*. Nat Commun. 9(1):1858 (2018).
Zhang et al., Biosensors and their applications in microbial metabolic engineering. Trends Microbiol. 19(7):323-329 (2011).
Zhang et al., Crystal structure of SARS-CoV-2 main protease provides a basis for design of improved α-ketoamide inhibitors. Science, 368(6489):409-412 (2020).
Zhang et al., Genetic reduction of striatal-enriched tyrosine phosphatase (STEP) reverses cognitive and cellular deficits in an Alzheimer's disease mouse model. Proc Natl Acad Sci. 107(44):19014-19019 (2010).

(56) References Cited

OTHER PUBLICATIONS

Zhang et al., P450 fingerprinting method for rapid discovery of terpene hydroxylating P450 catalysts with diversified regioselectivity. J Am Chem Soc. 133(10):3242-3245 (2011).

Zhang et al., Complete biosynthesis of erythromycin A and designed analogs using *E. coli* as a heterologous host. Chem Biol. 17(11):1232-1240 (2010).

Zhang et al., Enzymatic assembly of carbon-carbon bonds via iron-catalysed sp3 C-H functionalization. Nature. 565(7737):67-72 (2019).

Zhang et al., PTP1B as a drug target: recent developments in PTP1B inhibitor discovery. Drug Discov Today. 12(9-10):373-381 (2007).

Zhang et al., Crystal structure of unlinked NS2B-NS3 protease from Zika virus. Science. 354(6319):1597-1600 (2016).

Zhao et al., Norovirus protease structure and antivirals development. Viruses. 13(10):2069 (2021).

Zhou et al., A pneumonia outbreak associated with a new coronavirus of probable bat origin. Nature. 579(7798):270-273 (2020).

Zhou et al., Optical control of cell signaling by single-chain photoswitchable kinases. Science. 355(6327):836-842 (2017).

Zhu et al., Antibacterial drug leads targeting isoprenoid biosynthesis. Proc Natl Acad Sci USA. 110(1):123-128 (2013).

Zhu et al., PTP1B contributes to the oncogenic properties of colon cancer cells through Src activation. Cancer Res. 67(21): 10129-10137 (2007).

EP 23182468.1 European search report and opinion dated Jan. 18, 2024.

Hajj Chehade et al., A soluble metabolon synthesizes the isoprenoid lipid Ubiquinone. Cell Chem Biol. 26(4):482-492.e7 (2019).

Kuranda et al., The YTA7 gene is involved in the regulation of the isoprenoid pathway in the yeast Saccharomyces cerevisiae. FEMS Yeast Research. 9(3):381-390 (2009).

Zhou et al., Engineering bacterial transcription regulation to create a synthetic in vitro two-hybrid system for protein interaction. Assays J Am Chem Soc. 136(40): 14031-14038 (2014).

\* cited by examiner

Fig. 21C                    Fig. 21D

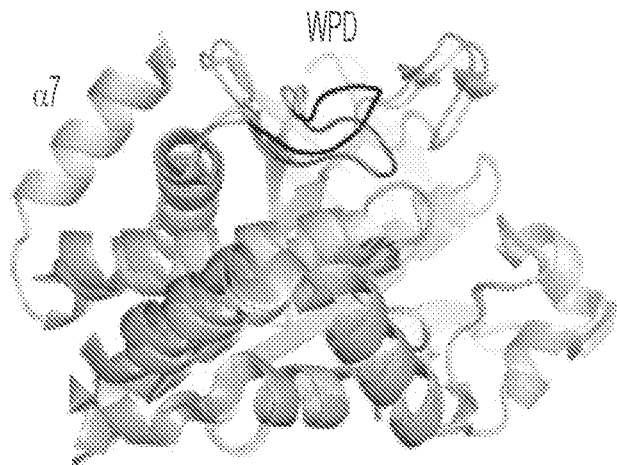
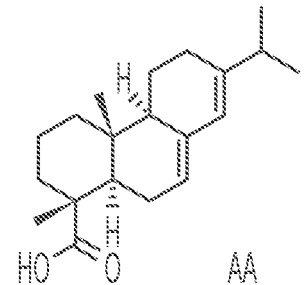
Fig. 22B
Fig. 22A
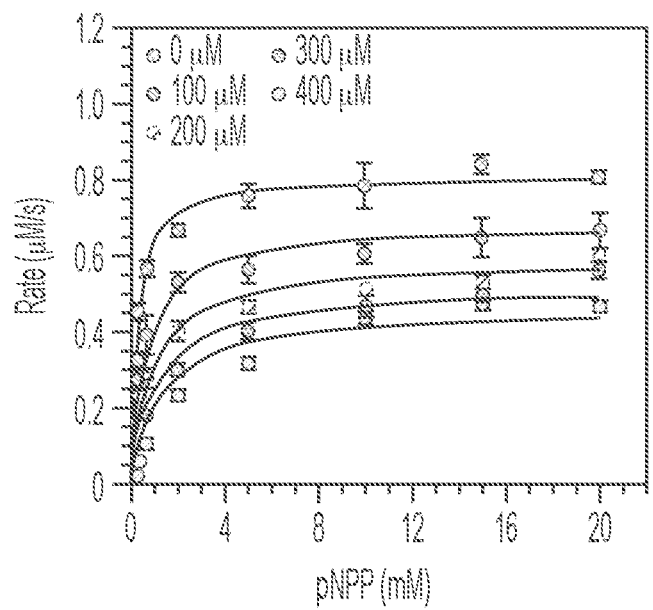
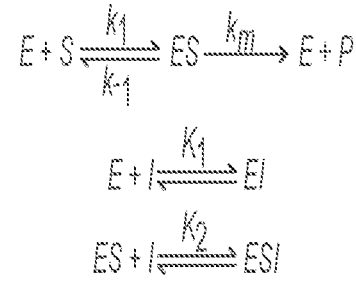
Fig. 22D
Fig. 22C

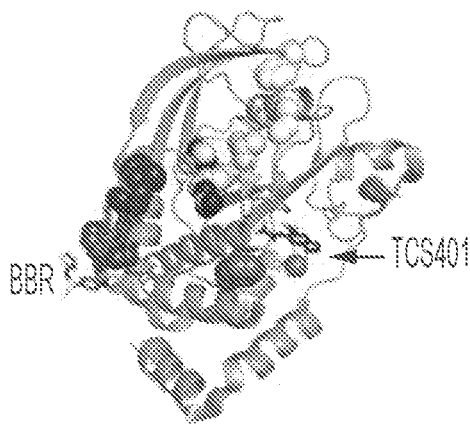
Fig. 24A
| Site | Mutation | Site | Mutation |
|---|---|---|---|
| Active | F182Y | Site 2 | A122F |
| Active | G259S | Site 2 | F135Y |
| Site 1 | R112A | Allosteric | A189S |
| Site 1 | V113T | Allosteric | F196Y |
| Site 1 | H175A | Allosteric | F280Y |
| Site 2 | C92A | L11 | YAYA |
| Site 2 | A122S | | |
Fig. 24B
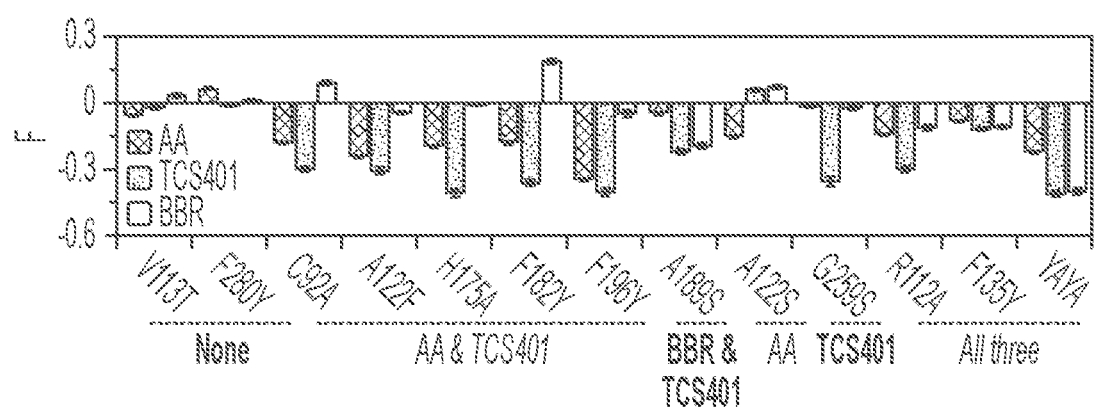
Fig. 24C

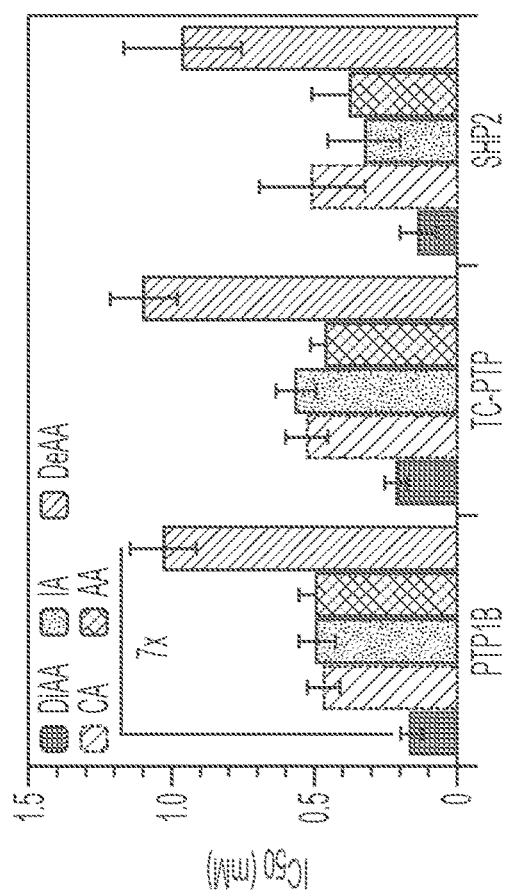
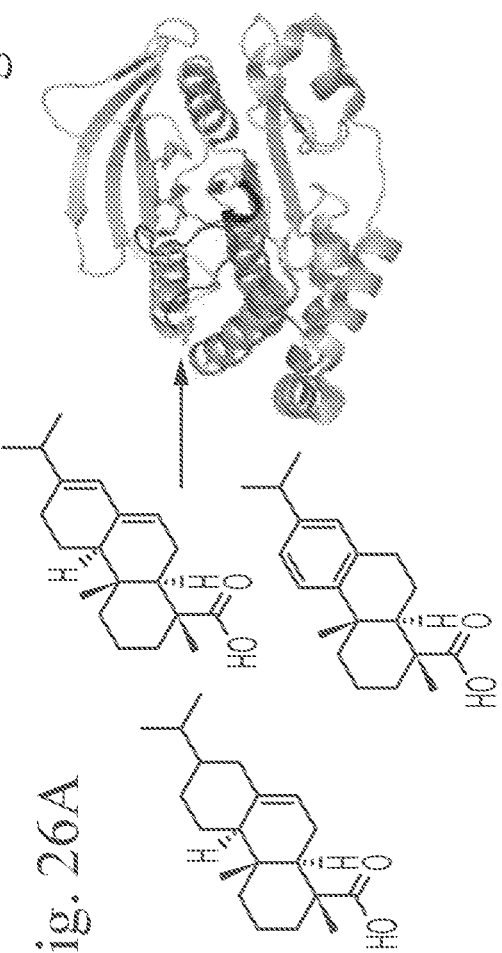
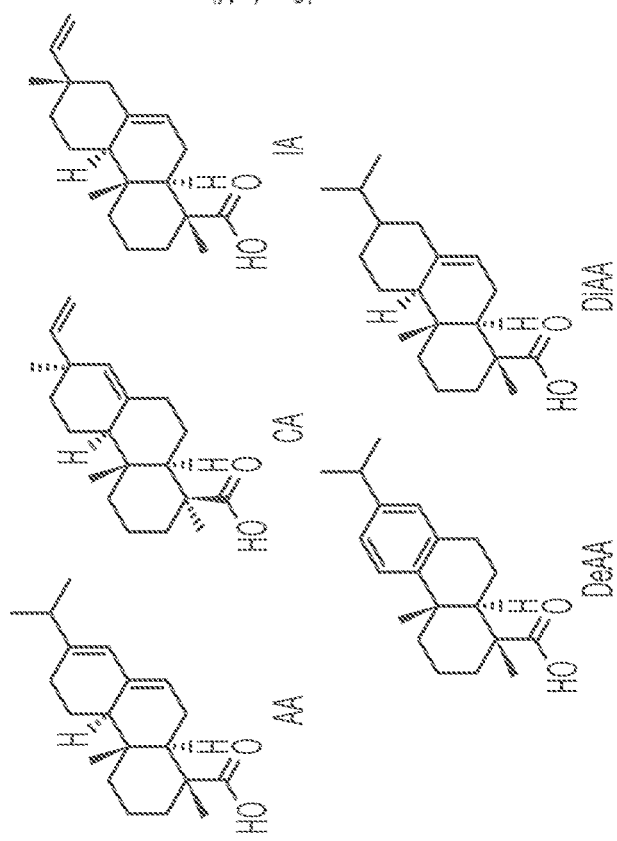
Fig. 26A
Fig. 26B
Fig. 26C

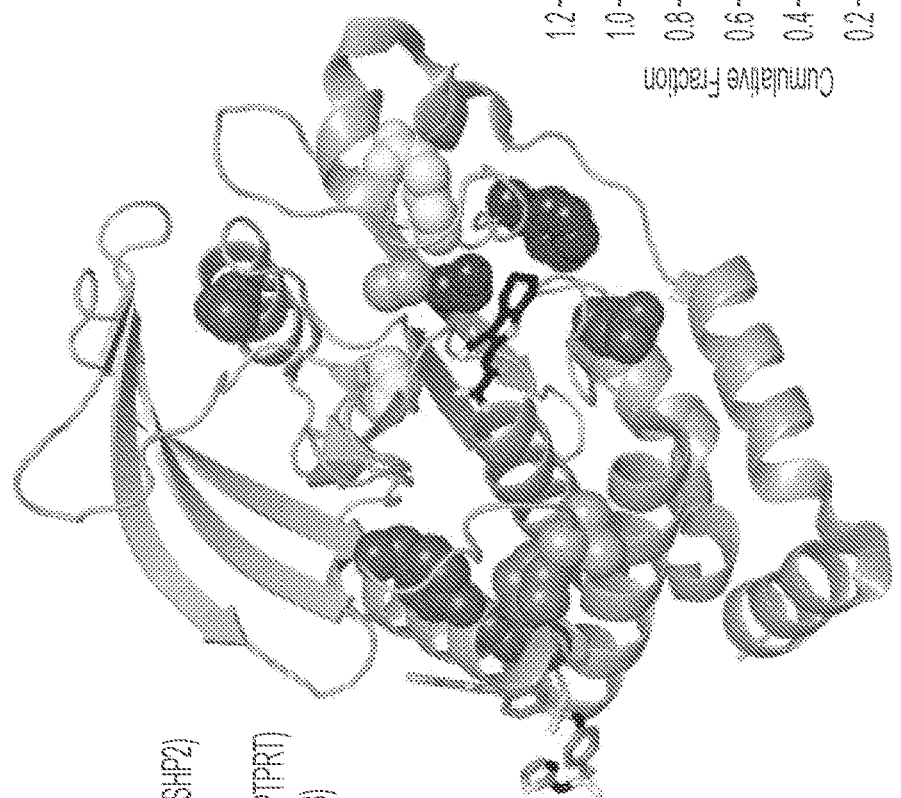
Fig. 27B
Fig. 27C
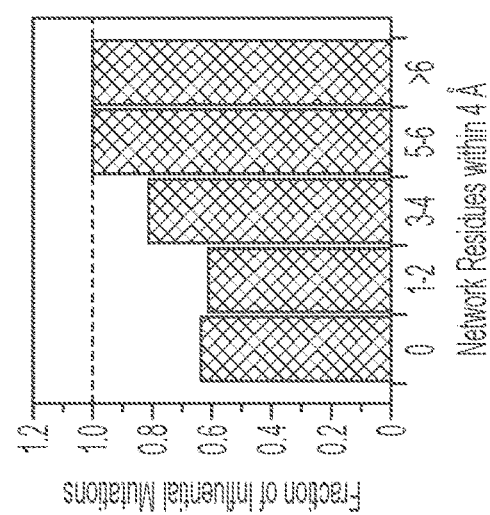
Fig. 27A

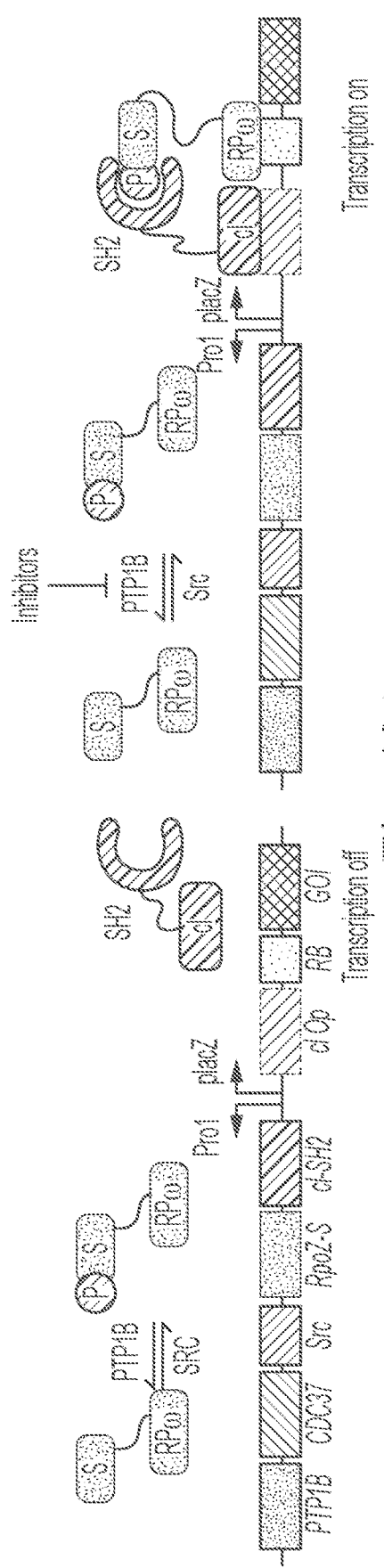
Fig. 40A
Fig. 40B
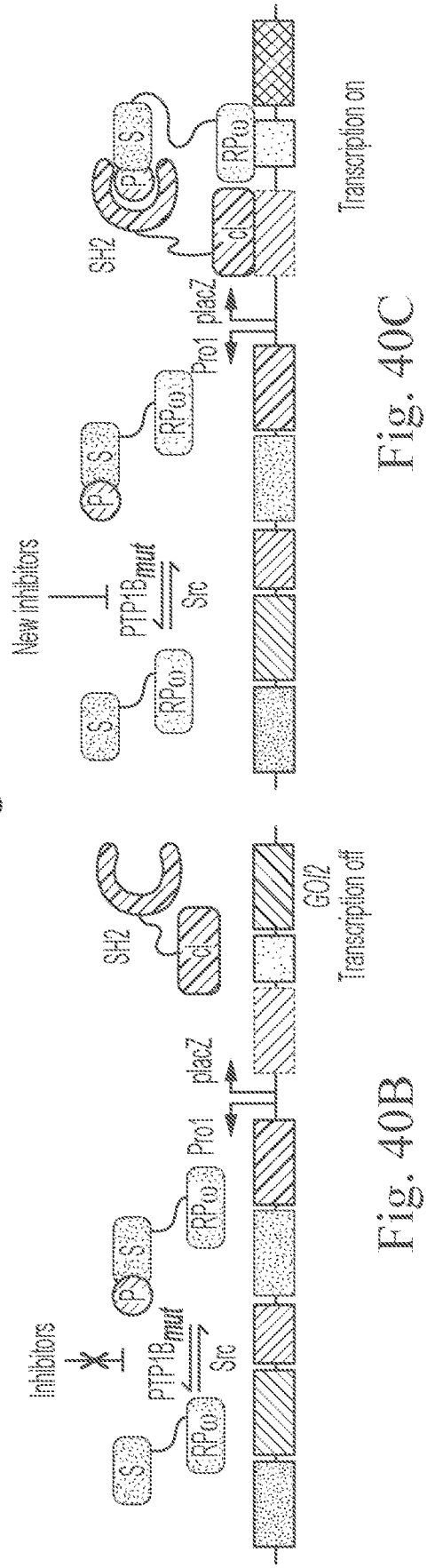
Fig. 40C

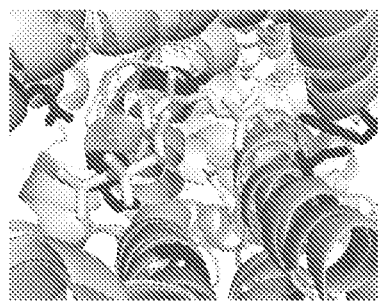 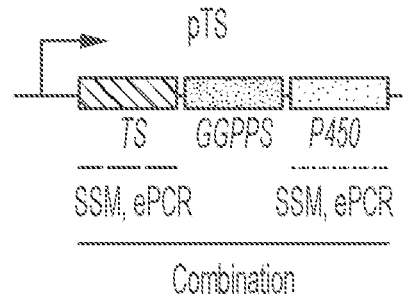
Fig. 41A  Fig. 41B
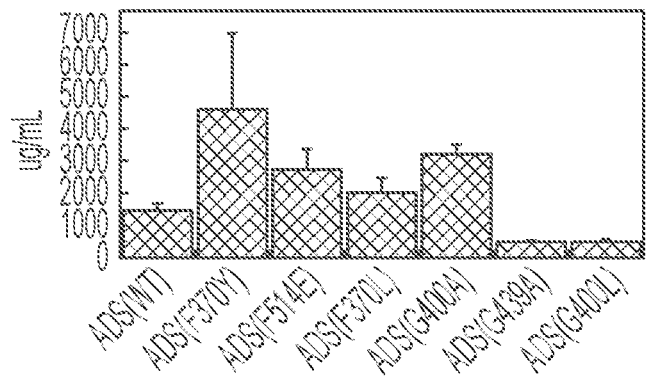
Fig. 41C
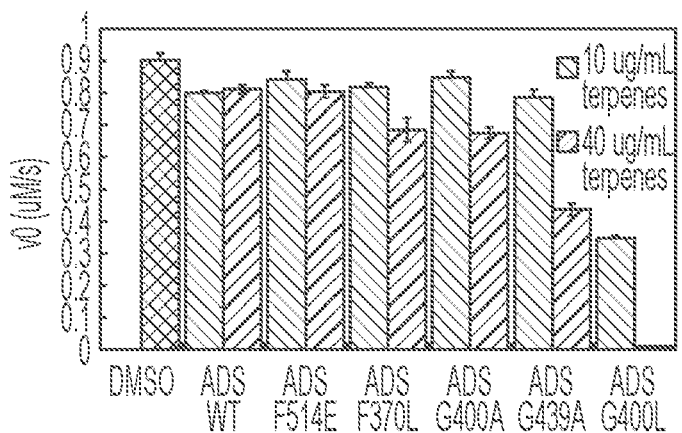
Fig. 41D

| PTPN6 | Resolution (Å) | Align w/ 3A5J (Å) | Align w/ 2F71 (Å) |
|---|---|---|---|
| 3A5J | 1.7 | - | 0.409 |
| 2F71 | 1.55 | 0.409 | - |
| 4HJP | 1.4 | 0.746 | 0.922 |
| 4HJQ | 1.8 | 0.76 | 0.776 |
| 4GRY | 1.7 | 0.761 | 0.922 |
| 4GRZ | 1.37 | 0.841 | 0.81 |
| 4GS0 | 1.8 | 0.842 | 0.892 |
| 3PS5 | 3.1 | 0.874 | 0.894 |
| 2B3O | 2.8 | 0.931 | 0.943 |
| | Maximum | 0.931 | 0.943 |

```
EMBOSS_001  PTP1B    1 MEMEKEFEQID---KSGSWAAIYQDIRHEASDFPCRV-AKLPKNKNRNRYR  47
                       :|.|.:.|..|   |:|.|.........|.:.....|:  .:.:||.|:||||:
EMBOSS_001  PTPN6    1 LEINKKQESEDTAKAGFWEEFESLQKQEVKNLHQRLEGQRPENKGKNRYK  50

EMBOSS_001         48 DVSPFDHSRIKLHQED------NDYINASLIK------MEEAQRSYILTQGP  87
                       :.:|||||||:..|.   :|||||..|    ..:...:||..:||.
EMBOSS_001         51 NILPFDHSRVILQGRDSNIPGSDYINANYIKNQLLGPDENAKTYIASQGC  100

EMBOSS_001         88 LPNTCGHFWEMVWEQKSRGVVMLNRVMEKGSLKCAQYWPQKEEKEMI--F  135
                       |..|...||:|.|:.||.|..|.||.|..||.|.|..|..|......:
EMBOSS_001        101 LEATVNDFWQMAWQENSRVIVMTTREVEKGRNKCVPYWPEVGMQRAYGPY  150

EMBOSS_001        136 EDTNLKLTLISEDIKSYYTVRQLELENLTTQE-TREILHFHYTTWPDFGV  184
                       :||      ..:....:.|.|.:|..:...| .|||.|:..:|||.||
EMBOSS_001        151 SVTN-----CGEHDTTEYKLRTLQVSPLDNGDLIREIWHQYLSWPDHGV  195

EMBOSS_001        185 PESPASFLNFLFKVRESGSLSPEHGPVVHCSAGIGRSGTFCLADTCLLL  234
                       |..|..:||:.:..........||:|||||||||:||:.:..|.:..
EMBOSS_001        196 PSEPGGVLSFLDQINQRQESLPHAGPIIVHCSAGIGRTGTIIVIDMLMEN  245

EMBOSS_001        235 MDKRKDPSSVDIKKVLLEMRKFRMGLIQTADQLRFSYLAVIEGAKFIMGD  284
                       :...:....:|.|::.|:..:.::.|.||.|.:|.:|||  |:||
EMBOSS_001        246 ISTKGLDCDIDIQKTIQMVRAQRSGMVQTEAQYKFIYVAI---AQFT---  289

EMBOSS_001        285 SSVQDQWKELSHED     298
                       .:.:.:.|.|:.
EMBOSS_001        290 ETTKKKLEVLQSQK     303
```

Fig. 44C

| Property | Value |
|---|---|
| Length | 314 |
| Identity | 107/314 (34.1%) |
| Similarity | 168/314 (53.5%) |
| Gaps | 27/314 (8.6%) |
| Score | 473.0 |
| Matrix | EBLOSUM62 |
| Gap Penalty | 10.0 |
| Extend Penalty | 0.5 |

Fig. 44D

```
                          SEQUENCE LISTING

Sequence total quantity: 104
SEQ ID NO: 1            moltype = AA  length = 27
FEATURE                 Location/Qualifiers
REGION                  1..27
                        note = Synthetic Polypeptide
source                  1..27
                        mol_type = protein
                        organism = synthetic construct
SEQUENCE: 1
MGDSSVQDQW KELSHEDLEP PPEHIPP                                       27

SEQ ID NO: 2            moltype = AA  length = 27
FEATURE                 Location/Qualifiers
REGION                  1..27
                        note = Synthetic Polypeptide
source                  1..27
                        mol_type = protein
                        organism = synthetic construct
SEQUENCE: 2
ESFDDELRRK EMRRGIDLAT TLERIEK                                       27

SEQ ID NO: 3            moltype = AA  length = 298
FEATURE                 Location/Qualifiers
REGION                  1..298
                        note = Synthetic Polypeptide
source                  1..298
                        mol_type = protein
                        organism = synthetic construct
SEQUENCE: 3
MEMEKEFEQI DKSGSWAAIY QDIRHEASDF PCRVAKLPKN KNRNRYRDVS PFDHSRIKLH   60
QEDNDYINAS LIKMEEAQRS YILTQGPLPN TCGHFWEMVW EQKSRGVVML NRVMEKGSLK   120
CAQYWPQKEE KEMIFEDTNL KLTLISEDIK SYYTVRQLEL ENLTTQETRE ILHFHYTTWP   180
DFGVPESPAS FLNFLFKVRE SGSLSPEHGP VVVHCSAGIG RSGTFCLADT CLLLMDKRKD   240
PSSVDIKKVL LEMRKFRMGL IQTADQLRFS YLAVIEGAKF IMGDSSVQDQ WKELSHED    298

SEQ ID NO: 4            moltype = AA  length = 303
FEATURE                 Location/Qualifiers
REGION                  1..303
                        note = Synthetic Polypeptide
source                  1..303
                        mol_type = protein
                        organism = synthetic construct
SEQUENCE: 4
LELNKKQESE DTAKAGFWEE FESLQKQEVK NLHQRLEGQR PENKGKNRYK NILPFDHSRV   60
ILQGRDSNIP GSDYINANYI KNQLLGPDEN AKTYIASQGC LEATVNDFWQ MAWQENSRVI   120
VMTTREVEKG RNKCVPYWPE VGMQRAYGPY SVTNCGEHDT TEYKLRTLQV SPLDNGDLIR   180
EIWHYQYLSW PDHGVPSEPG GVLSFLDQIN QRQESLPHAG PIIVHCSAGI GRTGTIIVID   240
MLMENISTKG LDCDIDIQKT IQMVRAQRSG MVQTEAQYKF IYVAIAQFIE TTKKKLEVLQ   300
SQK                                                                303

SEQ ID NO: 5            moltype = AA  length = 10
FEATURE                 Location/Qualifiers
REGION                  1..10
                        note = Synthetic Polypeptide
source                  1..10
                        mol_type = protein
                        organism = synthetic construct
SEQUENCE: 5
LSHEDLATTL                                                          10

SEQ ID NO: 6            moltype = AA  length = 5
```

```
FEATURE                 Location/Qualifiers
REGION                  1..5
                        note = Synthetic Polypeptide
source                  1..5
                        mol_type = protein
                        organism = synthetic construct
SEQUENCE: 6
LSHED                                                                    5

SEQ ID NO: 7            moltype = AA  length = 5
FEATURE                 Location/Qualifiers
REGION                  1..5
                        note = Synthetic Polypeptide
source                  1..5
                        mol_type = protein
                        organism = synthetic construct
SEQUENCE: 7
LATTL                                                                    5

SEQ ID NO: 8            moltype = AA  length = 9
FEATURE                 Location/Qualifiers
REGION                  1..9
                        note = Synthetic Polypeptide
source                  1..9
                        mol_type = protein
                        organism = synthetic construct
SEQUENCE: 8
LSHEDATTL                                                                9

SEQ ID NO: 9            moltype = AA  length = 8
FEATURE                 Location/Qualifiers
REGION                  1..8
                        note = Synthetic Polypeptide
source                  1..8
                        mol_type = protein
                        organism = synthetic construct
SEQUENCE: 9
LSHEDTTL                                                                 8

SEQ ID NO: 10           moltype = AA  length = 13
FEATURE                 Location/Qualifiers
REGION                  1..13
                        note = Synthetic Polypeptide
MOD_RES                 7
                        note = phosphorylated
source                  1..13
                        mol_type = protein
                        organism = synthetic construct
SEQUENCE: 10
ETGTEEYMKM DLG                                                          13

SEQ ID NO: 11           moltype = AA  length = 13
FEATURE                 Location/Qualifiers
REGION                  1..13
                        note = Synthetic Polypeptide
MOD_RES                 9
                        note = phosphorylated
source                  1..13
                        mol_type = protein
                        organism = synthetic construct
SEQUENCE: 11
RRLIEDAEYA ARG                                                          13

SEQ ID NO: 12           moltype = DNA  length = 1347
FEATURE                 Location/Qualifiers
misc_feature            1..1347
                        note = Synthetic Polynucleotide
source                  1..1347
                        mol_type = other DNA
                        organism = synthetic construct
SEQUENCE: 12
atggagatgg aaaaggagtt cgagcagatc gacaagtccg ggagctgggc ggccatttac        60
caggatatcc gacatgaagc cagtgacttc ccatgtagag tggccaagct tcctaagaac       120
aaaaaccgaa ataggtacag agacgtcagt cccttttgacc atagtcggat taaactacat      180
caagaagata atgactatat caacgctagt ttgataaaaa tggaagaagc ccaaggagt        240
tacattctta cccagggccc tttgcctaac acatgcggtc actttttggga gatggtgtgg     300
gagcagaaaa gcagggggtgt cgtcatgctc aacagagtga tggagaaagg ttcgttaaaa      360
tgcgcacaat actggcccaca aaaagaagaa aaagagatga tctttgaaga cacaaatttg      420
aaattaacat tgatctctga agatatcaag tcatattata cagtgcgaca gctagaattg      480
```

-continued

```
gaaaaccctta caacccaaga aactcgagag atcttacatt tccactatac cacatggcct    540
gactttggag tccctgaatc accagcctca ttcttgaact ttcttttcaa agtccgagag    600
tcagggtcac tcagcccgga gcacgggccc gttgtggtgc actgcagtgc aggcatcggc    660
aggtctggaa ccttctgtct ggctgatacc tgcctcttgc tgatggacaa gaggaaagac    720
ccttcttccg ttgatatcaa gaaagtgctg ttagaaatga ggaagtttcg gatggggctg    780
atccagacag ccgaccagct gcgcttctcc tacctggctg tgatcgaagg tgccaaattc    840
atcatggggg actcttccgt gcaggatcag tggaaggagc tttcccacga ggacgctgct    900
acacttgaac gtattgagaa gaactttgtc attactgacc caaggttgcc agataatccc    960
attatattcg cgtccgatag tttcttgcag ttgacagaat atagccgtga agaaatttg   1020
ggaagaaact gcaggtttct acaaggtcct gaaactgatc gcgcgacagt gagaaaaatt   1080
agagatgcca tagataacca aacagaggtc actgttcagc tgattaatta tacaaagagt   1140
ggtaaaaagt tctggaacct ctttcacttg cagcctatgc gagatcagaa gggagatgtc   1200
cagtacttta ttggggttca gttggatgga actgagcatg tccgagatgc tgccgagaga   1260
gagggagtca tgctgattaa gaaaactgca gaaaatattg atgaggcggc aaaagaactt   1320
ctcgagcacc accaccacca ccactga                                      1347
```

```
SEQ ID NO: 13           moltype = AA   length = 448
FEATURE                 Location/Qualifiers
REGION                  1..448
                        note = Synthetic Polypeptide
source                  1..448
                        mol_type = protein
                        organism = synthetic construct
SEQUENCE: 13
MEMEKEFEQI DKSGSWAAIY QDIRHEASDF PCRVAKLPKN KNRNRYRDVS PFDHSRIKLH     60
QEDNDYINAS LIKMEEAQRS YILTQGPLPN TCGHFWEMVW EQKSRGVVML NRVMEKGSLK    120
CAQYWPQKEE KEMIFEDTNL KLTLISEDIK SYYTVRQLEL ENLTTQETRE ILHFHYTTWP    180
DFGVPESPAS FLNFLFKVRE SGSLSPEHGP VVVHCSAGIG RSGTFCLADT CLLLMDKRKD    240
PSSVDIKKVL LEMRKFRMGL IQTADQLRFS YLAVIEGAKF IMGDSSVQDQ WKELSHEDAA    300
TLERIEKNFV ITDPRLPDNP IIFASDSFLQ LTEYSREEIL GRNCRFLQGP ETDRATVRKI    360
RDAIDNQTEV TVQLINYTKS GKKFWNLFHL QPMRDQKGDV QYFIGVQLDG TEHVRDAAER    420
EGVMLIKKTA ENIDEAAKEL LEHHHHHH                                      448
```

```
SEQ ID NO: 14           moltype = DNA   length = 1347
FEATURE                 Location/Qualifiers
misc_feature            1..1347
                        note = Synthetic Polynucleotide
source                  1..1347
                        mol_type = other DNA
                        organism = synthetic construct
SEQUENCE: 14
atggagatgg aaaaggagtt cgagcagatc gacaagtccg ggagctgggc ggccatttac     60
caggatatcc gacatgaagc cagtgacttc ccatgtaggg tggccaagct tcctaagaac    120
aaaaaccgaa ataggtacag agacgtcagt ccctttgacc atagtcggat taaactacat    180
caagaagata atgactatat caacgctagt ttgataaaaa tggaagaagc ccaaaggagt    240
tacattctta cccagggccc tttgcctaac acatgcggtc acttttggga gatggtgtgg    300
gagcagaaaa gcaggggtgt cgtcatgctc aacagagtga tggagaaagg ttcgttaaaa    360
tgcgcacaat actggccaca aaaagaagaa aaagagatga tctttgaaga cacaaatttg    420
aaattaacat tgatctctga agatatcaag tcatattata cagtgcgaca gctagaattg    480
gaaaacctta caccccaaga aactcgagag atcttacatt tccactatac cacatggcct    540
gactttggag tccctgaatc accagcctca ttcttgaact ttcttttcaa agtccgagag    600
tcagggtcac tcagcccgga gcacgggccc gttgtggtgc actgcagtgc aggcatcggc    660
aggtctggaa ccttctgtct ggctgatacc tgcctcttgc tgatggacaa gaggaaagac    720
ccttcttccg ttgatatcaa gaaagtgctg ttagaaatga ggaagtttcg gatggggctg    780
atccagacag ccgaccagct gcgcttctcc tacctggctg tgatcgaagg tgccaaattc    840
atcatggggg actctgccgt gcaggatcag tggaaggagc tttcccacga ggacgctact    900
acacttgaac gtattgagaa gaactttgtc attactgacc caaggttgcc agataatccc    960
attatattcg cgtccgatag tttcttgcag ttgacagaat atagccgtga agaaatttg   1020
ggaagaaact gcaggtttct acaaggtcct gaaactgatc gcgcgacagt gagaaaaatt   1080
agagatgcca tagataacca aacagaggtc actgttcagc tgattaatta tacaaagagt   1140
ggtaaaaagt tctggaacct ctttcacttg cagcctatgc gagatcagaa gggagatgtc   1200
cagtacttta ttggggttca gttggatgga actgagcatg tccgagatgc tgccgagaga   1260
gagggagtca tgctgattaa gaaaactgca gaaaatattg atgaggcggc aaaagaactt   1320
ctcgagcacc accaccacca ccactga                                      1347
```

```
SEQ ID NO: 15           moltype = AA   length = 448
FEATURE                 Location/Qualifiers
REGION                  1..448
                        note = Synthetic Polypeptide
source                  1..448
                        mol_type = protein
                        organism = synthetic construct
SEQUENCE: 15
MEMEKEFEQI DKSGSWAAIY QDIRHEASDF PCRVAKLPKN KNRNRYRDVS PFDHSRIKLH     60
QEDNDYINAS LIKMEEAQRS YILTQGPLPN TCGHFWEMVW EQKSRGVVML NRVMEKGSLK    120
CAQYWPQKEE KEMIFEDTNL KLTLISEDIK SYYTVRQLEL ENLTTQETRE ILHFHYTTWP    180
DFGVPESPAS FLNFLFKVRE SGSLSPEHGP VVVHCSAGIG RSGTFCLADT CLLLMDKRKD    240
PSSVDIKKVL LEMRKFRMGL IQTADQLRFS YLAVIEGAKF IMGDSAVQDQ WKELSHEDAT    300
TLERIEKNFV ITDPRLPDNP IIFASDSFLQ LTEYSREEIL GRNCRFLQGP ETDRATVRKI    360
```

```
RDAIDNQTEV TVQLINYTKS GKKFWNLFHL QPMRDQKGDV QYFIGVQLDG TEHVRDAAER    420
EGVMLIKKTA ENIDEAAKEL LEHHHHHH                                      448

SEQ ID NO: 16           moltype = DNA  length = 1350
FEATURE                 Location/Qualifiers
misc_feature            1..1350
                        note = Synthetic Polynucleotide
source                  1..1350
                        mol_type = other DNA
                        organism = synthetic construct
SEQUENCE: 16
atgcccacca ccatcgagcg ggagttcgaa gagttggata tcagcgtcg  ctggcagccg    60
ctgtacttgg aaattcgaaa tgagtccat  gactatcctc atagagtggc caagtttcca   120
gaaacagaa  atcgaaacag atacagagat gtaagcccat atgatcacag tcgtgttaaa   180
ctgcaaaatg ctgagaatga ttatattaat gccagtttag ttgacataga agaggcacaa   240
aggagttaca tcttaacaca gggtccactt cctaacacat gctgccattt ctggcttatg   300
gtttggcagc agaagaccaa agcagttgtc atgctgaacc gcgtgatgga gaaaggttcg   360
ttaaaatgtg cacagtactg gccaacagat gaccaagaga tgctgtttaa agaaacagga   420
ttcagtgtga agctcttgtc agaagatgtg aagtcgtatt atacagtaca tctactacaa   480
ttagaaaata tcaatagtgg tgaaaccaga acaatatctc actttcatta tactacctgg   540
ccagattttg gagtccctga atcaccagct tcatttctca atttcttgtt taaagtgaga   600
gaatctggct ccttgaaccc tgaccatggg cctgcggtga tccactgtag tgcaggcatt   660
gggcgctctg gcaccttctc tctggtagac acttgtcttt tgctgatgga caagaggaaa   720
gaccccttctt ccgttgatat caagaaagtg ctgttagaaa tgaggaagtt tcggatgggg   780
ctgatccaga cagccgacca gctgcgcttc tcctacctgg ctgtgatcga aggtgccaaa   840
ttcatcatgg gggactcttc cgtgcaggat cagtggaagg agctttccca cgaggacgct   900
gctacacttg aacgtattga agaactttt  gtcattactg acccaaggtt gccagataat   960
cccattatat tcgcgtccga tagttcttt  cagttgacag aatatagccg tgaagaaatt  1020
ttgggaagaa actgcaggtt tctacaaggt cctgaaactg atcgcgcgac agtgagaaaa  1080
attagagatg ccatagataa ccaaacagag gtcactgttc agctgattaa ttatacaaag  1140
agtggtaaaa agttctggaa cctctttcac ttgcagccta tgcgagatca aagggagat   1200
gtccagtact ttattggggt tcagttggat ggaactgagc atgtccgaga tgctgccgag  1260
agagagggag tcatgctgat taagaaaact gcagaaaata ttgatgaggc ggcaaaagaa  1320
cttctcgagc accaccacca ccaccactga                                   1350

SEQ ID NO: 17           moltype = AA  length = 449
FEATURE                 Location/Qualifiers
REGION                  1..449
                        note = Synthetic Polypeptide
source                  1..449
                        mol_type = protein
                        organism = synthetic construct
SEQUENCE: 17
MPTTIEREFE ELDTQRRWQP LYLEIRNESH DYPHRVAKFP ENRNRNRYRD VSPYDHSRVK     60
LQNAENDYIN ASLVDIEEAQ RSYILTQGPL PNTCCHFWLM VWQQKTKAVV MLNRVMEKGS   120
LKCAQYWPTD DQEMLFKETG FSVKLLSEDV KSYYTVHLLQ LENINSGETR TISHFHYTTW   180
PDFGVPESPA SFLNFLFKVR ESGSLNPDHG PAVIHCSAGI GRSGTFSLVD TCLLLMDKRK   240
DPSSVDIKKV LLEMRKFRMG LIQTADQLRF SYLAVIEGAK FIMGDSSVQD QWKELSHEDA   300
ATLERIEKNF VITDRKPLPDN PIIFASDSFL QLTEYSREEI LGRNCRFLQG PETDRATVRK   360
IRDAIDNQTE VTVQLINYTK SGKKFWNLFH LQPMRDQKGD VQYFIGVQLD GTEHVRDAAE   420
REGVMLIKKT AENIDEAAKE LLEHHHHHH                                    449

SEQ ID NO: 18           moltype = DNA  length = 1350
FEATURE                 Location/Qualifiers
misc_feature            1..1350
                        note = Synthetic Polynucleotide
source                  1..1350
                        mol_type = other DNA
                        organism = synthetic construct
SEQUENCE: 18
atgcccacca ccatcgagcg ggagttcgaa gagttggata tcagcgtcg  ctggcagccg    60
ctgtacttgg aaattcgaaa tgagtccat  gactatcctc atagagtggc caagtttcca   120
gaaacagaa  atcgaaacag atacagagat gtaagcccat atgatcacag tcgtgttaaa   180
ctgcaaaatg ctgagaatga ttatattaat gccagtttag ttgacataga agaggcacaa   240
aggagttaca tcttaacaca gggtccactt cctaacacat gctgccattt ctggcttatg   300
gtttggcagc agaagaccaa agcagttgtc atgctgaacc gcattgtgga gaaagaatcg   360
gttaaatgtg cacagtactg gccaacagat gaccaagaga tgctgtttaa agaaacagga   420
ttcagtgtga agctcttgtc agaagatgtg aagtcgtatt atacagtaca tctactacaa   480
ttagaaaata tcaatagtgg tgaaaccaga acaatatctc actttcatta tactacctgg   540
ccagattttg gagtccctga atcaccagct tcatttctca atttcttgtt taaagtgaga   600
gaatctggct ccttgaaccc tgaccatggg cctgcggtga tccactgtag tgcaggcatt   660
gggcgctctg gcaccttctc tctggtagac acttgtcttt tgctgatgga caagaggaaa   720
gaccccttctt ccgttgatat caagaaagtg ctgttagaaa tgaggaagtt tcggatgggg   780
ctgatccaga cagccgacca gctgcgcttc tcctacctgg ctgtgatcga aggtgccaaa   840
ttcatcatgg gggactcttc cgtgcaggat cagtggaagg agctttccca cgaggacgct   900
gctacacttg aacgtattga agaactttt  gtcattactg acccaaggtt gccagataat   960
cccattatat tcgcgtccga tagttcttt  cagttgacag aatatagccg tgaagaaatt  1020
ttgggaagaa actgcaggtt tctacaaggt cctgaaactg atcgcgcgac agtgagaaaa  1080
attagagatg ccatagataa ccaaacagag gtcactgttc agctgattaa ttatacaaag  1140
```

```
agtggtaaaa agttctggaa cctctttcac ttgcagccta tgcgagatca aagggagat  1200
gtccagtact ttattggggt tcagttggat ggaactgagc atgtccgaga tgctgccgag  1260
agagagggag tcatgctgat taagaaaact gcagaaaata ttgatgaggc ggcaaaagaa  1320
cttctcgagc accaccacca ccaccactga                                  1350
```

```
SEQ ID NO: 19          moltype = AA   length = 449
FEATURE                Location/Qualifiers
REGION                 1..449
                       note = Synthetic Polypeptide
source                 1..449
                       mol_type = protein
                       organism = synthetic construct
SEQUENCE: 19
MPTTIEREFE ELDTQRRWQP LYLEIRNESH DYPHRVAKFP ENRNRNRYRD VSPYDHSRVK   60
LQNAENDYIN ASLVDIEEAQ RSYILTQGPL PNTCCHFWLM VWQQKTKAVV MLNRIVEKES  120
VKCAQYWPTD DQEMLFKETG FSVKLLSEDV KSYYTVHLLQ LENINSGETR TISHFHYTTW  180
PDFGVPESPA SFLNFLFKVR ESGSLNPDHG PAVIHCSAGI GRSGTFSLVD TCLLLMDKRK  240
DPSSVDIKKV LLEMRKFRMG LIQTADQLRF SYLAVIEGAK FIMGDSSVQD QWKELSHEDA  300
ATLERIEKNF VITDPRLPDN PIIFASDSFL QLTEYSREEI LGRNCRFLQG PETDRATVRK  360
IRDAIDNQTE VTVQLINYTK SGKKFWNLFH LQPMRDQKGD VQYFIGVQLD GTEHVRDAAE  420
REGVMLIKKT AENIDEAAKE LLEHHHHHH                                   449

SEQ ID NO: 20          moltype = DNA   length = 1827
FEATURE                Location/Qualifiers
misc_feature           1..1827
                       note = Synthetic Polynucleotide
source                 1..1827
                       mol_type = other DNA
                       organism = synthetic construct
SEQUENCE: 20
atgcatcatc atcatcatca tgtgagcaag ggcgaggagc tgttcaccgg ggtggtgccc   60
atcctggtcg agctggacgg cgacgtaaac ggccacaagt tcagcgtccg cggcgagggc  120
gagggcgatg ccaccaacgg caagctgacc ctgaagttca tctgcaccac cggcaagctg  180
cccgtgccct ggcccaccct cgtgaccacc ttcggctacg gcgtggcctg cttcagccgc  240
taccccgacc acatgaagca gcacgacttc ttcaagtccg ccatgcccga aggctacgtc  300
caggagcgca ccatctcttt caaggacgac ggtacctaca agacccgcgc cgaggtgaag  360
ttcgagggcg acaccctggt gaaccgcatc gagctgaagg gcatcgactt caaggaggac  420
ggcaacatcc tggggcacaa gctggagtac aacttcaaca gccactacgt ctatatcacg  480
gccgacaagc agaagaactg catcaaggct aacttcaaga tccgccacaa cgttgaggac  540
ggcagcgtgc agctcgccga ccactaccag cagaacaccc ccatcggcga cggccccgtg  600
ctgctgcccg acaaccacta cctgagccat cagtccaagc tgagcaaaga ccccaacgag  660
aagcgcgatc acatggtcct gctggagttc gtgaccgccg ccgggattac acatggcatg  720
gacgagctgt acaagtggta ttttgggaag atcactcgtc ggagtccgga cgggctgctg  780
ctcaaccccg aaaaccccg gggaaccttc ttggtccggg agagcgagac gacaaaaggt  840
gcctattgcc tctccgtttc tgactttgac aacgccaagg ggctcaatgt gaagcactac  900
aagatccgca agctggacag cggcggcttc tacatcacct cacgcacaca gttcagcagc  960
ctgcagcagc tggtggccta ctactccaaa catgctgatg gcttgtgcca ccgcctgact  1020
aacgtctgtg ggtctacatc tggatctggg aagcccggtt ctggtgaggg ttcttggatg  1080
gaggactatg actacgtcca cctacagggg gagctcgtgt ctaagggcga agagtcgatc  1140
aaggaaaata tgcgtatgaa ggtggtcatg gaaggttcgg tcaacggcca ccaattcaaa  1200
tgcacaggtg aaggagaagg cagaccgtac gagggaactc aaaccatgag gatcaaagtc  1260
atcgagggag acccctgcc atttgccttt gacattcttg ccacgtcgtt catgtatggc  1320
agccgtactt tatcaagta cccggccgac atccctgatt tctttaaaca gtcctttcct  1380
gagggtttta cttgggaaag agttacgaga tacgaagatg gtggagtcgt caccgtcacg  1440
caggacacca gccttgagga tggcgagctc gtctacaacg tcaaggtcag aggggtaaac  1500
tttcctcca atggtcccgt gatgcagaag aagaccaagg gttgggagcc taatacagag  1560
atgatgtatc cagcagatgg tggtctgaga ggatacactg acatcgcact gaaagttgat  1620
ggtggtggcc atctgcactg caacttcgtg acaacttaca ggtcaaaaaa gaccgtcggg  1680
aacatcaaga tgcccggtgt ccatgccgtt gatcaccgcc tggaaaggat cgaggagagt  1740
gacaatgaaa cctacgtagt gcaacgcgaa gtggcagttg ccaaatacag caaccttggt  1800
ggtggcatgg acgagctgta caagtaa                                     1827

SEQ ID NO: 21          moltype = AA   length = 608
FEATURE                Location/Qualifiers
REGION                 1..608
                       note = Synthetic Polypeptide
source                 1..608
                       mol_type = protein
                       organism = synthetic construct
SEQUENCE: 21
MHHHHHHVSK GEELFTGVVP ILVELDGDVN GHKFSVRGEG EGDATNGKLT LKFICTTGKL   60
PVPWPTLVTT FGYGVACFSR YPDHMKQHDF FKSAMPEGYV QERTISFKDD GTYKTRAEVK  120
FEGDTLVNRI ELKGIDFKED GNILGHKLEY NFNSHYVYIT ADKQKNCIKA NFKIRHNVED  180
GSVQLADHYQ QNTPIGDGPV LLPDNHYLSH QSKLSKDPNE KRDHMVLLEF VTAAGITHGM  240
DELYKWYFGK ITRRESERLL LNPENPRGTF LVRESETTKG AYCLSVSDFD NAKGLNVKHY  300
KIRKLDSGGF YITSRTQFSS LQQLVAYYSK HADGLCHRLT NVCGSTSGSG KPGSEGSWM  360
EDYDYVHLQG ELVSKGEELI KENMRMKVVM EGSVNGHQFK CTGEGEGRPY EGTQTMRIKV  420
IEGGPLPFAF DILATSFMYG SRTFIKYPAD IPDFFKQSFP EGFTWERVTR YEDGGVVTVT  480
QDTSLEDGEL VYNVKVRGVN FPSNGPVMQK KTKGWEPNTE MMYPADGGLR GYTDIALKVD  540
```

```
GGGHLHCNFV TTYRSKKTVG NIKMPGVHAV DHRLERIEES DNETYVVQRE VAVAKYSNLG    600
GGMDELYK                                                            608

SEQ ID NO: 22           moltype = DNA  length = 70
FEATURE                 Location/Qualifiers
misc_feature            1..70
                        note = Synthetic Polynucleotide
source                  1..70
                        mol_type = other DNA
                        organism = synthetic construct
SEQUENCE: 22
gcaaatgggc ggtaggcgtg tacggtggga ggtctatata agcagagctg gtttagtgaa    60
ccgtcagatc                                                          70

SEQ ID NO: 23           moltype = DNA  length = 66
FEATURE                 Location/Qualifiers
misc_feature            1..66
                        note = Synthetic Polynucleotide
source                  1..66
                        mol_type = other DNA
                        organism = synthetic construct
SEQUENCE: 23
ggcagcggcg ccaccaactt ctccctgctg aagcaggccg gcgacgtgga ggagaaccc     60
ggcccc                                                              66

SEQ ID NO: 24           moltype = AA   length = 22
FEATURE                 Location/Qualifiers
REGION                  1..22
                        note = Synthetic Polypeptide
source                  1..22
                        mol_type = protein
                        organism = synthetic construct
SEQUENCE: 24
GSGATNFSLL KQAGDVEENP GP                                            22

SEQ ID NO: 25           moltype = DNA  length = 160
FEATURE                 Location/Qualifiers
misc_feature            1..160
                        note = Synthetic Polynucleotide
source                  1..160
                        mol_type = other DNA
                        organism = synthetic construct
SEQUENCE: 25
ttctagagca cagctaacac cacgtcgtcc ctatctgctg ccctaggtct atgagtggtt    60
gctggataac tttacgggca tgcataaggc tcggtatcta tattcaggga gaccacaacg   120
gtttccctct acaaataatt ttgtttaact tttactagag                         160

SEQ ID NO: 26           moltype = DNA  length = 153
FEATURE                 Location/Qualifiers
misc_feature            1..153
                        note = Synthetic Polynucleotide
source                  1..153
                        mol_type = other DNA
                        organism = synthetic construct
SEQUENCE: 26
gcacagctaa caccacgtcg tccctatctg ctgccctagg tctatgagtg gttgctggat    60
aactttacgg gcatgcataa ggctcgtata atatattcag ggagaccaca acggtttccc   120
tctacaaata attttgttta acttttacta gag                                153

SEQ ID NO: 27           moltype = DNA  length = 304
FEATURE                 Location/Qualifiers
misc_feature            1..304
                        note = Synthetic Polynucleotide
source                  1..304
                        mol_type = other DNA
                        organism = synthetic construct
SEQUENCE: 27
agaaaccaat tgtccatatt gcatcagaca ttgccgtcac tgcgtctttt actggctctt    60
ctcgctaacc aaaccggtaa ccccgcttat taaaagcatt ctgtaacaaa gcgggaccaa   120
agccatgaca aaaacgcgta acaaaagtgt ctataatcac ggcagaaaag tccacattga   180
ttatttgcac ggcgtcacac tttgctatgc catagcattt ttatccataa gattagcgga   240
tcctacctga cgctttttat cgcaactctc tactgtttct ccatacccgt ttttttgggc   300
tagc                                                                304

SEQ ID NO: 28           moltype = DNA  length = 72
FEATURE                 Location/Qualifiers
misc_feature            1..72
                        note = Synthetic Polynucleotide
source                  1..72
```

```
                                mol_type = other DNA
                                organism = synthetic construct
SEQUENCE: 28
acaagaaagt tgttcatta ggcaccccgg gctttactcg taaagcttcc ggcgcgtatg    60
ttgtgtcgac cg                                                      72

SEQ ID NO: 29                   moltype = DNA   length = 246
FEATURE                         Location/Qualifiers
misc_feature                    1..246
                                note = Synthetic Polynucleotide
source                          1..246
                                mol_type = other DNA
                                organism = synthetic construct
SEQUENCE: 29
cgactgcacg gtgcaccaat gcttctggcg tcaggcagcc atcggaagct gtggtatggc    60
tgtgcaggtc gtaaatcact gcataattcg tgtcgctcaa ggcgcactcc cgttctggat   120
aatgtttttt gcgccgacat cataacggtt ctggcaaata ttctgaaatg agctgttgac   180
aattaatcat ccggctcgta taatgtgtgg aattgtgagc ggataacaat ttcacacagg   240
aaacag                                                             246

SEQ ID NO: 30                   moltype = DNA   length = 19
FEATURE                         Location/Qualifiers
misc_feature                    1..19
                                note = Synthetic Polynucleotide
source                          1..19
                                mol_type = other DNA
                                organism = synthetic construct
SEQUENCE: 30
cctatagtga gtcgtatta                                                19

SEQ ID NO: 31                   moltype = DNA   length = 18
FEATURE                         Location/Qualifiers
misc_feature                    1..18
                                note = Synthetic Polynucleotide
source                          1..18
                                mol_type = other DNA
                                organism = synthetic construct
SEQUENCE: 31
ttaaagagga gaaaggtc                                                 18

SEQ ID NO: 32                   moltype = DNA   length = 24
FEATURE                         Location/Qualifiers
misc_feature                    1..24
                                note = Synthetic Polynucleotide
source                          1..24
                                mol_type = other DNA
                                organism = synthetic construct
SEQUENCE: 32
cgaaaaaaag taaggcggta atcc                                          24

SEQ ID NO: 33                   moltype = DNA   length = 23
FEATURE                         Location/Qualifiers
misc_feature                    1..23
                                note = Synthetic Polynucleotide
source                          1..23
                                mol_type = other DNA
                                organism = synthetic construct
SEQUENCE: 33
tgcagaaaga ggagaaatac tag                                           23

SEQ ID NO: 34                   moltype = DNA   length = 21
FEATURE                         Location/Qualifiers
misc_feature                    1..21
                                note = Synthetic Polynucleotide
source                          1..21
                                mol_type = other DNA
                                organism = synthetic construct
SEQUENCE: 34
attaaagagg agaaatacta g                                             21

SEQ ID NO: 35                   moltype = DNA   length = 22
FEATURE                         Location/Qualifiers
misc_feature                    1..22
                                note = Synthetic Polynucleotide
source                          1..22
                                mol_type = other DNA
                                organism = synthetic construct
SEQUENCE: 35
gtgcagtaag gaggaaaaaa aa                                            22
```

```
SEQ ID NO: 36              moltype = DNA  length = 25
FEATURE                    Location/Qualifiers
misc_feature               1..25
                           note = Synthetic Polynucleotide
source                     1..25
                           mol_type = other DNA
                           organism = synthetic construct
SEQUENCE: 36
gctagcttta agaaggagat atacc                                         25

SEQ ID NO: 37              moltype = AA  length = 94
FEATURE                    Location/Qualifiers
REGION                     1..94
                           note = Synthetic Polypeptide
source                     1..94
                           mol_type = protein
                           organism = synthetic construct
SEQUENCE: 37
MARVTVQDAV EKIGNRFDLV LVAARRARQM QVGGKDPLVP EENDKTTVIA LREIEEGLIN   60
NQILDVRERQ EQQEQEAAEL QAVTAIAEGR RAAA                               94

SEQ ID NO: 38              moltype = AA  length = 218
FEATURE                    Location/Qualifiers
REGION                     1..218
                           note = Synthetic Polypeptide
source                     1..218
                           mol_type = protein
                           organism = synthetic construct
SEQUENCE: 38
MSISSRVKSK RIQLGLNQAE LAQKVGTTQQ SIEQLENGKT KRPRFLPELA SALGVSVDWL   60
LNGTSDSNVR FVGHVEPKGK YPLISMVRAR SWCEACEPYD IKDIDEWYDS DVNLLGNGFW  120
LKVEGDSMTS PVGQSIPEGH MVLVDTGREP VNGSLVVAKL TDANEATFKK LVIDGGQYL  180
KGLNPSWPMT PINGNCKIIG VVVEARVKFV DYKDDDDK                          218

SEQ ID NO: 39              moltype = AA  length = 98
FEATURE                    Location/Qualifiers
REGION                     1..98
                           note = Synthetic Polypeptide
source                     1..98
                           mol_type = protein
                           organism = synthetic construct
SEQUENCE: 39
WYFGKITRRE SERLLLNPEN PRGTFLVRES ETVKGAYALS VSDFDNAKGL NVKHYLIRKL   60
DSGGFYITSR TQFSSLQQLV AYYSKHADGL CHRLTNVC                          98

SEQ ID NO: 40              moltype = AA  length = 12
FEATURE                    Location/Qualifiers
REGION                     1..12
                           note = Synthetic Polypeptide
source                     1..12
                           mol_type = protein
                           organism = synthetic construct
SEQUENCE: 40
WMEDYDYVHL QG                                                       12

SEQ ID NO: 41              moltype = AA  length = 11
FEATURE                    Location/Qualifiers
REGION                     1..11
                           note = Synthetic Polypeptide
source                     1..11
                           mol_type = protein
                           organism = synthetic construct
SEQUENCE: 41
EPQYEEIPIY L                                                        11

SEQ ID NO: 42              moltype = AA  length = 10
FEATURE                    Location/Qualifiers
REGION                     1..10
                           note = Synthetic Polypeptide
source                     1..10
                           mol_type = protein
                           organism = synthetic construct
SEQUENCE: 42
DHQYYNDFPG                                                          10

SEQ ID NO: 43              moltype = AA  length = 10
FEATURE                    Location/Qualifiers
REGION                     1..10
```

|   |   |   |
|---|---|---|
| source | 1..10<br>mol_type = protein<br>organism = synthetic construct | note = Synthetic Polypeptide |

SEQUENCE: 43
PQRYLVIQGD                                                                10

| SEQ ID NO: 44 | moltype = AA  length = 287 |
|---|---|
| FEATURE | Location/Qualifiers |
| REGION | 1..287 |
|  | note = Synthetic Polypeptide |
| source | 1..287 |
|  | mol_type = protein |
|  | organism = synthetic construct |

SEQUENCE: 44
MSKPQTQGLA KDAWEIPRES LRLEVKLGQG CFGEVWMGTW NGTTRVAIKT LKPGTMSPEA  60
FLQEAQVMKK LRHEKLVQLY AVVSEEPIYI VTEYMSKGSL LDFLKGETGK YLRLPQLVDM 120
AAQIASGMAY VERMNYVHRD LRAANILVGE NLVCKVADFG LARLIEDNEY TARQGAKFPI 180
KWTAPEAALY GRFTIKSDVW SFGILLTELT TKGRVPYPGM VNREVLDQVE RGYRMPCPPE 240
CPESLHDLMC QCWRKEPEER PTFEYLQAFL EDYFTSTEPQ YQPGENL                287

| SEQ ID NO: 45 | moltype = AA  length = 378 |
|---|---|
| FEATURE | Location/Qualifiers |
| REGION | 1..378 |
|  | note = Synthetic Polypeptide |
| source | 1..378 |
|  | mol_type = protein |
|  | organism = synthetic construct |

SEQUENCE: 45
MVDYSVWDHI EVSDDEDETH PNIDTASLFR WRHQARVERM EQFQKEKEEL DRGCRECKRK  60
VAECQRKLKE LEVAEGGKAE LERLQAEAQQ LRKEERSWEQ KLEEMRKKEK SMPWNVDTLS 120
KDGFSKSMVN TKPEKTEEDS EEVREQKHKT FVEKYEKQIK HFGMLRRWDD SQKYLSDNVH 180
LVCEETANYL VIWCIDLEVE EKCALMEQVA HQTIVMQFIL ELAKSLKVDP RACFRQFFTK 240
IKTADRQYME GFNDELEAFK ERVRGRAKLR IEKAMKEYEE EERKKRLGPG GLDPVEVYES 300
LPEELQKCFD VKDVQMLQDA ISKMDPTDAK YHMQRCIDSG LWVPNSKASE AKEGEEAGPG 360
DPLLEAVPKT GDEKDVSV                                               378

| SEQ ID NO: 46 | moltype = AA  length = 321 |
|---|---|
| FEATURE | Location/Qualifiers |
| REGION | 1..321 |
|  | note = Synthetic Polypeptide |
| source | 1..321 |
|  | mol_type = protein |
|  | organism = synthetic construct |

SEQUENCE: 46
MEMEKEFEQI DKSGSWAAIY QDIRHEASDF PCRVAKLPKN KNRNRYRDVS PFDHSRIKLH  60
QEDNDYINAS LIKMEEAQRS YILTQGPLPN TCGHFWEMVW EQKSRGVVML NRVMEKGSLK 120
CAQYWPQKEE KEMIFEDTNL KLTLISEDIK SYYTVRQLEL ENLTTQETRE ILHFYTTWP 180
DFGVPESPAS FLNFLFKVRE SGSLSPEHGP VVVHSSAGIG RSGTFCLADT CLLLMDKRKD 240
PSSVDIKKVL LEMRKFRMGL IQTADQLRFS YLAVIEGAKF IMGDSSVQDQ WKELSHEDLE 300
PPPEHIPPPP RPPKRILEPH N                                           321

| SEQ ID NO: 47 | moltype = AA  length = 371 |
|---|---|
| FEATURE | Location/Qualifiers |
| REGION | 1..371 |
|  | note = Synthetic Polypeptide |
| source | 1..371 |
|  | mol_type = protein |
|  | organism = synthetic construct |

SEQUENCE: 47
MKIEEGKLVI WINGDKGYNG LAEVGKKFEK DTGIKVTVEH PDKLEEKFPQ VAATGDGPDI  60
IFWAHDRFGG YAQSGLLAEI TPDKAFQDKL YPFTWDAVRY NGKLIAYPIA VEALSLIYNK 120
DLLPNPPKTW EEIPALDKEL KAKGKSALMF NLQEPYFTWP LIAADGGYAF KYENGKYDIK 180
DVGVDNAGAK AGLTFLVDLI KNKHMNADTD YSIAEAAFNK GETAMTINGP WAWSNIDTSK 240
VNYGVTVLPT FKGQPSKPFV GVLSAGINAA SPNKELAKEF LENYLLTDEG LEAVNKDKPL 300
GAVALKSYEE ELAKDPRIAA TMENAQKGEI MPNIPQMSAF WYAVRTAVIN AASGRQTVDE 360
ALKDAQTRIT K                                                      371

| SEQ ID NO: 48 | moltype = AA  length = 707 |
|---|---|
| FEATURE | Location/Qualifiers |
| REGION | 1..707 |
|  | note = Synthetic Polypeptide |
| source | 1..707 |
|  | mol_type = protein |
|  | organism = synthetic construct |

SEQUENCE: 48
MKFGNFLLTY QPPQFSQTEV MKRLVKLGRI SEECGFDTVW LLEHHFTEFG LLGNPYVAAA  60
YLLGATKKLN VGTAAIVLPT AHPVRQLEDV NLLDQMSKGR FRFGICRGLY NKDFRVFGTD 120
MNNSRALAEC WYGLIKNGMT EGYMEADNEH IKFHKVKVNP AAYSRGGAPV YVVAESASTT 180

```
EWAAQFGLPM ILSWIINTNE KKAQLELYNE VAQEYGHDIH NIDHCLSYIT SVDHDSIKAK    240
EICRKFLGHW YDSYVNATTI FDDSDQTRGY DFNKGQWRDF VLKGHKDTNR RIDYSYEINP    300
VGTPQECIDI IQKDIDATGI SNICCGFEAN GTVDEIIASM KLFQSDVMPF LKEKQRSLLY    360
YGGGGSGGGG SGGGGSGGGG SKFGLFFLNF INSTTVQEQS IVRMQEITEY VDKLNFEQIL    420
VYENHFSDNG VVGAPLTVSG FLLGLTEKIK IGSLNHIITT HHPVRIAEEA CLLDQLSEGR    480
FILGFSDCEK KDEMHFFNRP VEYQQQLFEE CYEIINDALT TGYCNPDNDF YSFPKISVNP    540
HAYTPGGPRK YVTATSHHIV EWAAKKGIPL IFKWDDSNDV RYEYAERYKA VADKYDVDLS    600
EIDHQLMILV NYNEDSNKAK QETRAFISDY VLEMHPNENF ENKLEEIIAE NAVGNYTECI    660
TAAKLAIEKC GAKSVLLSFE PMNDLMSQKN VINIVDDNIK KYHTEYT                 707

SEQ ID NO: 49          moltype = AA  length = 263
FEATURE                Location/Qualifiers
REGION                 1..263
                       note = Synthetic Polypeptide
source                 1..263
                       mol_type = protein
                       organism = synthetic construct
SEQUENCE: 49
MREAVIAEVS TQLSEVVGVI ERHLEPTLLA VHLYGSAVDG GLKPHSDIDL LVTVTVRLDE     60
TTRRALINDL LETSASPGES EILRAVEVTI VVHDDIIPWR YPAKRELQFG EWQRNDILAG    120
IFEPATIDID LAILLTKARE HSVALVGPAA EELFDPVPEQ DLFEALNETL TLWNSPPDWA    180
GDERNVVLTL SRIWYSAVTG KIAPKDVAAD WAMERLPAQY QPVILEARQA YLGQEEDRLA    240
SRADQLEEFV HYVKGEITKV VGK                                           263

SEQ ID NO: 50          moltype = AA  length = 785
FEATURE                Location/Qualifiers
REGION                 1..785
                       note = Synthetic Polypeptide
source                 1..785
                       mol_type = protein
                       organism = synthetic construct
SEQUENCE: 50
MVKREFPPGF WKDDLIDSLT SSHKVAASDE KRIETLISEI KNMFRCMGYG ETNPSAYDTA     60
WVARIPAVDG SDNPHFPETV EWILQNQLKD GSWGEGFYFL AYDRILATLA CIITLTLWRT    120
GETQVQKGIE FFRTQAGKME DEADSHRPSG FEIVFPAMLK EAKILGLDLP YDLPFLKQII    180
EKREAKLKRI PTDVLYALPT TLLYSLEGLQ EIVDWQKIMK LQSKDGSFLS SPASTAAVFM    240
RTGNKKCLDF LNFVLKKFGN HVPCHYPLDL FERLWAVDTV ERLGIDRHFK EEIKEALDYV    300
YSHWDERGIG WARENPVPDI DDTAMGLRIL RLHGYNVSSD VLKTFRDENG EFFCFLGQTQ    360
RGVTDMLNVN RCSHVSFPGE TIMEEAKLCT ERYLRNALEN VDAFDKWAFK KNIRGEVEYA    420
LKYPWHKSMP RLEARSYIEN YGPDDVWLGK TVYMMPYISN EKYLELAKLD FNKVQSIHQT    480
ELQDLRRWWK SSGFTDLNFT RERVTEIYFS PASFIFEPEF SKCREVYTKT SNFTVILDDL    540
YDAHGSLDDL KLFTESVKRW DLSLVDQMPQ QMKICFVGFY NTFNDIAKEG RERQGRDVLG    600
YIQNVWKVQL EAYTKEAEWS EAKYVPSFNE YIENASVSIA LGTVVLISAL FTGEVLTDEV    660
LSKIDRESRF LQLMGLTGRL VNDTKTYQAE RGQGEVASAI QCMYKDHPKI SEEEALQHVY    720
SVMENALEEL NREFVNNKIP DIYKRLVFET ARIMQLFYMQ GDGLTLSHDM EIKEHVKNCL    780
FQPVA                                                               785

SEQ ID NO: 51          moltype = AA  length = 296
FEATURE                Location/Qualifiers
REGION                 1..296
                       note = Synthetic Polypeptide
source                 1..296
                       mol_type = protein
                       organism = synthetic construct
SEQUENCE: 51
MFDFNEYMKS KAVAVDAALD KAIPLEYPEK IHESMRYSLL AGGKRVRPAL CIAACELVGG     60
SQDLAMPTAC AMEMIHTMSL IHDDLPCMDN DDFRRGKPTN HKVFGEDTAV LAGDALLSFA    120
FEHIAVATSK TVPSDRTLRV ISELGKTIGS QGLVGGQVVD ITSEGDANVD LKTLEWIHIH    180
KTAVLLECSV VSGGILGGAT EDEIARIRRY ARCVGLLFQV VDDILDVTKS SEELGKTAGK    240
DLLTDKATYP KLMGLEKAKE FAAELATRAK EELSSFDQIK AAPLLGLADY IAFRQN        296

SEQ ID NO: 52          moltype = AA  length = 1049
FEATURE                Location/Qualifiers
REGION                 1..1049
                       note = Synthetic Polypeptide
source                 1..1049
                       mol_type = protein
                       organism = synthetic construct
SEQUENCE: 52
MTIKEMPQPK TFGELKNLPL LNTDKPVQAL MKIADELGEI FKFEAPGRVT RYLSSQRLIK     60
EACDESRFDK NLSQALKFVR DFAGDGLFTS WTHEKNWKKA HNILLPSFSQ QAMKGYHAMM    120
VDIAVQLVQK WERLNADEHI EVPEDMTRLT LDTIGLCGFN YRFNSFYRDQ PHPFITSMVR    180
ALDEAMNKLQ RANPDDPAYD ENKRQFQEDI KVMNDLVDKI IADRKASGEQ SDDLLTHMLN    240
GKDPETGEPL DDENIRYQII TFLIAGHETT SGLLSFALYF LVKNPHVLQK AAEEAARVLV    300
DPVPSYKQVK QLKYVGMVLN EALRLWPTAP AFSLYAKEDT VLGGEYPLEK GDELMVLIPQ    360
LHRDKTIWGD DVEEFRPERF ENPSAIPQHA FKPFGNGQRA CIGQQFALHE ATLVLGMMLK    420
HFDFEDHTNY ELDIKETLTL KPEGFVVKAK SKKIPLGGIP SPSTEQSAKK VRKKAENAHN    480
TPLLVLYGSN MGTAEGTARD LADIAMSKGF APQVATLDSH AGNLPREGAV LIVTASYNGH    540
PPDNAKQFVD WLDQASADEV KGVRYSVFGC GDKNWATTYQ KVPAFIDETL AAKGAENIAD    600
```

```
RGEADASDDF EGTYEEWREH MWSDVAAYFN LDIENSEDNK STLSLQFVDS AADMPLAKMH    660
GAFSTNVVAS KELQQPGSAR STRHLEIELP KEASYQEGDH LGVIPRNYEG IVNRVTARFG    720
LDASQQIRLE AEEEKLAHLP LAKTVSVEEL LQYVELQDPV TRTQLRAMAA KTVCPPHKVE    780
LEALLEKQAY KEQVLAKRLT MLELLEKYPA CEMKFSEFIA LLPSIRPRYY SISSSPRVDE    840
KQASITVSVV SGEAWSGYGE YKGIASNYLA ELQEGDTITC FISTPQSEFT LPKDPETPLI    900
MVGPGTGVAP FRGFVQARKQ LKEQGQSLGE AHLYFGCRSP HEDYLYQEEL ENAQSEGIIT    960
LHTAFSRMPN QPKTYVQHVM EQDGKKLIEL LDQGAHFYIC GDGSQMAPAV EATLMKSYAD   1020
VHQVSEADAR LWLQQLEEKG RYAKDVWAG                                    1049

SEQ ID NO: 53            moltype = AA   length = 142
FEATURE                  Location/Qualifiers
REGION                   1..142
                         note = Synthetic Polypeptide
source                   1..142
                         mol_type = protein
                         organism = synthetic construct
SEQUENCE: 53
AATLERIEKN FVITDPRLPD NPIIFASDSF LQLTEYSREE ILGRNCRFLQ GPETDRATVR     60
KIRDAIDNQT EVTVQLINYT KSGKKFWNLF HLQPMRDQKG DVQYFIGVQL DGTEHVRDAA    120
EREGVMLIKK TAENIDEAAK EL                                            142

SEQ ID NO: 54            moltype = AA   length = 748
FEATURE                  Location/Qualifiers
REGION                   1..748
                         note = Synthetic Polypeptide
source                   1..748
                         mol_type = protein
                         organism = synthetic construct
SEQUENCE: 54
MASVAGHASG SPAFGTADLS NCEREEIHLA GSIQPHGALL VVSEPDHRII QASANAAEFL     60
NLGSVLGVPL AEIDGDLLIK ILPHLDPTAE GMPVAVRCRI GNPSTEYDGL MHRPPEGGLI    120
IELERAGPPI DLSGTLAPAL ERIRTAGSLR ALCDDTALLF QQCTGYDRVM VYRFDEQGHG    180
EVFSERHVPG LESYFGNRYP SSDIPQMARR LYERQRVRVL VDVSYQPVPL EPRLSPLTGR    240
DLDMSGCFLR SMSPIHLQYL KNMGVRATLV VSLVVGGKLW GLVACHHYLP RFMHFELRAI    300
CELLAEAIAT RITALESFAQ SQSELFVQRL EQRMIEAITR EGDWRAAIFD TSQSILQPLH    360
AAGCALVYED QIRTIGDVPS TQDVREIAGW LDRQPRAAVT STASLGLDVP ELAHLTRMAS    420
GVVAAPISDH RGEFLMWFRP ERVHTVTWGG DPKKPFTMGD TPADLSPRRS FAKWHQVVEG    480
TSDPWTAADL AAARTIGQTV ADIVLQFRAV RTLIAREQYE QFSSQVHASM QPVLITDAEG    540
RILLMNDSFR DMLPAGSPSA VHLDDLAGFF VESNDFLRNV AELIDHGRGW RGEVLLRGAG    600
NRPLPLAVRA DPVTRTEDQS LGFVLIFSDA TDRRTADAAR TRFQEGILAS ARPGVRLDSK    660
SDLLHEKLLS ALVENAQLAA LEITYGVETG RIAELLEGVR QSMLRTAEVL GHLVQHAART    720
AGSDSSSNGS QNKKEFDSAG SAGSAGTS                                      748

SEQ ID NO: 55            moltype = AA   length = 295
FEATURE                  Location/Qualifiers
REGION                   1..295
                         note = Synthetic Polypeptide
source                   1..295
                         mol_type = protein
                         organism = synthetic construct
SEQUENCE: 55
MGMPTTIERE FEELDTQRRW QPLYLEIRNE SHDYPHRVAK FPENRNRNRY RDVSPYDHSR     60
VKLQNAENDY INASLVDIEE AQRSYILTQG PLPNTCCHFW LMVWQQKTKA VVMLNRIVEK    120
ESVKCAQYWP TDDQEMLFKE TGFSVKLLSE DVKSYYTVHL LQLENINSGE TRTISHFHYT    180
TWPDFGVPES PASFLNFLFK VRESGSLNPD HGPAVIHCSA GIGRSGTFSL VDTCLVLMEK    240
GDDINIKQVL LNMRKYRMGL IQTPDQLRFS YMAIIEGAKC IKGDSSIQKR WKELS         295

SEQ ID NO: 56            moltype = AA   length = 435
FEATURE                  Location/Qualifiers
REGION                   1..435
                         note = Synthetic Polypeptide
source                   1..435
                         mol_type = protein
                         organism = synthetic construct
SEQUENCE: 56
MEMEKEFEQI DKSGSWAAIY QDIRHEASDF PCRVAKLPKN KNRNRYRDVS PFDHSRIKLH     60
QEDNDYINAS LIKMEEAQRS YILTQGPLPN TCGHFWEMVW EQKSRGVVML NRVMEKGSLK    120
CAQYWPQKEE KEMIFEDTNL KLTLISEDIK SYYTVRQLEL ENLTTQETRE ILHFHYTTWP    180
DFGVPESPAS FLNFLFKVRE SGSLSPEHGP VVVHCSAGIG RSGTFCLADT CLLLMDKRKD    240
PSSVDIKKVL LEMRKFRMGL IQTADQLRFS YLAVIEGAKF IMGDSSVQDQ WKELSHEDLE    300
PPPEHIPPPP RPPKRILEPH NGKCREFFPN HQWVKEETQE DKDCPIKEEK GSPLNAAPYG    360
IESMSQDTEV RSRVVGGSLR GAQAASPAKG EPSLPEKDED HALSYWKPFL VNMCVATVLT    420
AGAYLCYRFL FNSNT                                                    435

SEQ ID NO: 57            moltype = AA   length = 473
FEATURE                  Location/Qualifiers
REGION                   1..473
                         note = Synthetic Polypeptide
source                   1..473
```

```
                          mol_type = protein
                          organism = synthetic construct
SEQUENCE: 57
MNIKKFAKQA  TVLTFTTALL  AGGATQAFAK  ETNQKPYKET  YGISHITRHD  MLQIPEQQKN   60
EKYQVPEFDS  STIKNISSAK  GLDVWDSWPL  QNADGTVANY  HGYHIVFALA  GDPKNADDTS  120
IYMFYQKVGE  TSIDSWKNAG  RVFKDSDKFD  ANDSILKDQT  QEWSGSATFT  SDGKIRLFYT  180
DFSGKHYGKQ  TLTTAQVNVS  ASDSSLNING  VEDYKSIFDG  DGKTYQNVQQ  FIDEGNYSSG  240
DNHTLRDPHY  VEDKGHKYLV  FEANTGTEDG  YQGEESLFNK  AYYGKSTSFF  RQESQKLLQS  300
DKKRTAELAN  GALGMIELND  DYTLKKVMKP  LIASNTVTDE  IERANVFKMN  GKWYLFTDSR  360
GSKMTIDGIT  SNDIYMLGYV  SNSLTGPYKP  LNKTGLVLKM  DLDPNDVTFT  YSHFAVPQAK  420
GNNVVITSYM  TNRGFYADKQ  STFAPSFLLN  IKGKKTSVVK  DSILEQGQLT  VNK         473

SEQ ID NO: 58             moltype = AA  length = 382
FEATURE                   Location/Qualifiers
REGION                    1..382
                          note = Synthetic Polypeptide
source                    1..382
                          mol_type = protein
                          organism = synthetic construct
SEQUENCE: 58
MSLKEKTQSL  FANAFGYPAT  HTIQAPGRVN  LIGEHTDYND  GFVLPCAIDY  QTVISCAPRD   60
DRKVRVMAAD  YENQLDEFSL  DAPIVAHENY  QWANYVRGVV  KHLQLRNNSF  GGVDMVISGN  120
VPQGAGLSSS  ASLEVAVGTV  LQQLYHLPLD  GAQIALNGQE  AENQFVGCNC  GIMDQLISAL  180
GKKDHALLID  CRSLGTKAVS  MPKGVAVVII  NSNFKRTLVG  SEYNTRREQC  ETGARFFQQP  240
ALRDVTIEEF  NAVAHELDPI  VAKRVRHILT  ENARTVEAAS  ALEQGDLKRM  GELMAESHAS  300
MRDDFEITVP  QIDTLVEIVK  AVIGDKGGVR  MTGGGFGGCI  VALIPEELVP  AVQQAVAEQY  360
EAKTGIKETF  YVCKPSQGAG  QC                                              382

SEQ ID NO: 59             moltype = AA  length = 593
FEATURE                   Location/Qualifiers
REGION                    1..593
                          note = Synthetic Polypeptide
source                    1..593
                          mol_type = protein
                          organism = synthetic construct
SEQUENCE: 59
MAQISESVSP  STDLKSTESS  ITSNRHGNMW  EDDRIQSLNS  PYGAPAYQER  SEKLIEEIKL   60
LFLSDMDDSC  NDSDRDLIKR  LEIVDTVECL  GIDRHFQPEI  KLALDYVYRC  WNERGIGEGS  120
RDSLKKDLNA  TALGFRALRL  HRYNVSSGVL  ENFRDDNGQF  FCGSTVEEEG  AEAYNKHVRC  180
MLSLSRASNI  LFPGEKVMEE  AKAFTTNYLK  KVLAGREATH  VDESLLGEVK  YALEFPWHCS  240
VQRWEARSFI  EIFGQIDSEL  KSNLSKKMLE  LAKLDFNILQ  CTHQKELQII  SRWFADSSIA  300
SLNFYRKCYV  EFYFWMAAAI  SEPEPFSGSRV  AFTKIAILMT  MLDDLYDTHG  TLDQLKFTE  360
GVRRWDVSLV  EGLPDFMKIA  FEFWLKTSNE  LIAEAVKAQG  QDMAAYIRKN  AWERYLEAYL  420
QDAEWIATGH  VPTFDEYLNN  GTPNTGMCVL  NLIPLLLMGE  HLPIDILEQI  FLPSRFHHLI  480
ELASRLVDDA  RDFQAEKDHG  DLSCIECYLK  DHPESTVEDA  LNHVNGLLGN  CLLEMNWKFL  540
KKQDSVPLSC  KKYSFHVLAR  SIQFMYNQGD  GFSISNKVIK  DQVQKVLIVP  VPI         593

SEQ ID NO: 60             moltype = AA  length = 546
FEATURE                   Location/Qualifiers
REGION                    1..546
                          note = Synthetic Polypeptide
source                    1..546
                          mol_type = protein
                          organism = synthetic construct
SEQUENCE: 60
MALTEEKPIR  PIANFPPSIW  GDQFLIYEKQ  VEQGVEQIVN  DLKKEVRQLL  KEALDIPMKH   60
ANLLKLIDEI  QRLGIPYHFE  REIDHALQCI  YETYGDNWNG  DRSSLWFRLM  RKQGYYVTCD  120
VFNNYKDKNG  AFKQSLANDV  EGLLELYEAT  SMRVPGEIIL  EDALGFTRSR  LSIMTKDAFS  180
TNPALFTEIQ  RALKQPLWKR  LPRIEAAQYI  PFYQQQDSHN  KTLLKLAKLE  FNLLQSLHKE  240
ELSHVCKWWK  AFDIKKNAPC  LRDRIVECYF  WGLGSSGYEPQ  YSRARVFFTK  AVAVITLIDD  300
TYDAYGTYEE  LKIFTEAVER  WSITCLDTLP  EYMKPIYKLF  MDTYTEMEEF  LAKEGRTDLF  360
NCGKEFVKEF  VRNLMVEAKW  ANEGHIPTTE  EHDPVVIITG  GANLLTTTCY  LGMSDIFTKE  420
SVEWAVSAPP  LFRYSGILGR  RLNDLMTHKA  EQERKHSSSS  LESYMKEYNV  NEEYAQTLIY  480
KEVEDVWKDI  NREYLTTKNI  PRPLLMAVIY  LCQFLEVQYA  GKDNFTRMGD  EYKHLIKSLL  540
VYPMSI                                                                  546

SEQ ID NO: 61             moltype = AA  length = 802
FEATURE                   Location/Qualifiers
REGION                    1..802
                          note = Synthetic Polypeptide
source                    1..802
                          mol_type = protein
                          organism = synthetic construct
SEQUENCE: 61
MSSSTGTSKV  VSETSSTIVD  DIPRLSANYH  GDLWHHNVIQ  TLETPFRESS  TYQERADELV   60
VKIKDMFNAL  GDGDISPSAY  DTAWVARLAT  ISSDGSEKPR  FPQALNWVFN  NQLQDGSWGI  120
ESHFSLCDRL  LNTTNSVIAL  SVWKTGHSQV  QQGAEFIAEN  LRLLNEEDEL  SPDFQIIFPA  180
LLQKAKALGI  NLPYDLPFIK  YLSTTREARL  TDVSAAADNI  PANMLNALEG  LEEVIDWNKI  240
MRFQSKDGSF  LSSPASTACV  LMNTGDEKCF  TFLNNLLDKF  GGCVPCMYSI  DLLERLSLVD  300
```

```
NIEHLGIGRH FKQEIKGALD YVYRHWSERG IGWGRDSLVP DLNTTALGLR TLRMHGYNVS    360
SDVLNNFKDE NGRFFSSAGQ THVELRSVVN LFRASDLAFP DERAMDDARK FAEPYLREAL    420
ATKISTNTKL FKEIEYVVEY PWHMSIPRLE ARSYIDSYDD NYVWQRKTLY RMPSLSNSKC    480
LELAKLDFNI VQSLHQEELK LLTRWWKESG MADINFTRHR VAEVYFSSAT FEPEYSATRI    540
AFTKIGCLQV LFDDMADIFA TLDELKSFTE GVKRWDTSLL HEIPECMQTC FKVWFKLMEE    600
VNNDVVKVQG RDMLAHIRKP WELYFNCYVQ EREWLEAGYI PTFEEYLKTY AISVGLGPCT    660
LQPILLMGEL VKDDVVEKVH YPSNMFELVS LSWRLTNDTK TYQAEKARGQ QASGIACYMK    720
DNPGATEEDA IKHICRVVDR ALKEASFEYF KPSNDIPMGC KSFIFNLRLC VQIFYKFIDG    780
YGIANEEIKD YIRKVYIDPI QV                                            802

SEQ ID NO: 62            moltype = AA  length = 317
FEATURE                  Location/Qualifiers
REGION                   1..317
                         note = Synthetic Polypeptide
source                   1..317
                         mol_type = protein
                         organism = synthetic construct
SEQUENCE: 62
MPTTIEREFE ELDTQRRWQP LYLEIRNESH DYPHRVAKFP ENRNRNRYRD VSPYDHSRVK     60
LQNAENDYIN ASLVDIEEAQ RSYILTQGPL PNTCCHFWLM VWQQKTKAVV MLNRIVEKES    120
VKCAQYWPTD DQEMLFKETG FSVKLLSEDV KSYYTVHLLQ LENINSGETR TISHFHYTTW    180
PDFGVPESPA SFLNFLFKVR ESGSLNPDHG PAVIHCSAGI GRSGTFSLVD TCLVLMEKGD    240
DINIKQVLLN MRKYRMGLIQ TPDQLRFSYM AIIEGAKCIK GDSSIQKRWK ELSKEDLSPA    300
FDHSPNKIMT EKYNGNR                                                  317

SEQ ID NO: 63            moltype = AA  length = 299
FEATURE                  Location/Qualifiers
REGION                   1..299
                         note = Synthetic Polypeptide
source                   1..299
                         mol_type = protein
                         organism = synthetic construct
SEQUENCE: 63
MSSGVDLGTE NLYFQSMSRV LQAEELHEKA LDPFLLQAEF FEIPMNFVDP KEYDIPGLVR     60
KNRYKTILPN PHSRVCLTSP DPDDDPLSSYI NANYIRGYGG EEKVYIATQG PIVSTVADFW   120
RMVWQEHTPI IVMITNIEEM NEKCTEYWPE EQVAYDGVEI TVQKVIHTED YRLRLISLKS    180
GTEERGLKHY WFTSWPDQKT PDRAPPLLHL VREVEEAAQQ EGPHCAPIIV HCSAGIGRTG    240
CFIATSICCQ QLRQEGVVDI LKTTCQLRQD RGGMIQTCEQ YQFVHHVMSL YEKQLSHQS     299

SEQ ID NO: 64            moltype = AA  length = 595
FEATURE                  Location/Qualifiers
REGION                   1..595
                         note = Synthetic Polypeptide
source                   1..595
                         mol_type = protein
                         organism = synthetic construct
SEQUENCE: 64
MVRWFHRDLS GLDAETLLKG RGVHGSFLAR PSRKNQGDFS LSVRVGDQVT HIRIQNSGDF     60
YDLYGGEKFA TLTELVEYYT QQQGVVQDRD GTIIHLKYPL NCSDPTSERW YHGHMSGGQA    120
ETLLQAKGEP WTFLVRESLS QPGDFVLSVL SDQPKAGPGS PLRVTHIKVM CEGGRYTVGG    180
LETFDSLTDL VEHFKKTGIE EASGAFVYLR QPYYATRVNA ADIENRVLEL NKKQESEDTA    240
KAGFWEEFES LQKQEVKNLH QRLEGQRPEN KGKNRYKNIL PFDHSRVILQ GRDSNIPGSD    300
YINANYIKNQ LLGPDENAKT YIASQGCLEA TVNDFWQMAW QENSRVIVMT TREVEKGRNK    360
CVPYWPEVGM QRAYGPYSVT NCGEHDTTEY KLRTLQVSPL DNGDLIREIW HYQYLSWPDH    420
GVPSEPGGVL SFLDQINQRQ ESLPHAGPII VHCSAGIGRT GTIIVIDMLM ENISTKGLDC    480
DIDIQKTIQM VRAQRSGMVQ TEAQYKFIYV AIAQFIETTK KKLEVLQSQK GQESEYGNIT    540
YPPAMKNAHA KASRTSSKHK EDVYENLHTK NKREEKVKKQ RSADKEKSKG SLKRK         595

SEQ ID NO: 65            moltype = AA  length = 593
FEATURE                  Location/Qualifiers
REGION                   1..593
                         note = Synthetic Polypeptide
source                   1..593
                         mol_type = protein
                         organism = synthetic construct
SEQUENCE: 65
MTSRRWFHPN ITGVEAENLL LTRGVDGSFL ARPSKSNPGD FTLSVRRNGA VTHIKIQNTG     60
DYYDLYGGEK FATLAELVQY YMEHHGQLKE KNGDVIELKY PLNCADPTSE RWFHGHLSGK    120
EAEKLLTEKG KHGSFLVRES QSHPGDFVLS VRTGDDKGES NDGKSKVTHV MIRCQELKYD    180
VGGGERFDSL TDLVEHYKKN PMVETLGTVL QLKQPLNTTR INAAEIESRV RELSKLAETT    240
DKVKQGFWEE FETLQQQECK LLYSRKEGQR QENKNKNRYK NILPFDHTRV VLHDGDPNEP    300
VSDYINANII MPEFETKCNN SKPKKSYIAT QGCLQNTVND FWRMVFQENS RVIVMTTKEV    360
ERGKSKCVKY WPDEYALKEY GVMRVRNVKE SAAHDYTLRE LKLSKVGQGN TERTVWQYHF    420
RTWPDHGVPS DPGGVLDFLE EVHHKQESIM DAGPVVVHCS AGIGRTGTFI VIDILIDIIR    480
EKGVDCDIDV PKTIQMVRSQ RSGMVQTEAQ YRFIYMAVQH YIETLQRRIE EEQKSKRKGH    540
EYTNIKYSLA DQTSGDQSPL PPCTPTPPCA EMREDSARVY ENVGLMQQQK SFR           593

SEQ ID NO: 66            moltype = AA  length = 425
FEATURE                  Location/Qualifiers
```

```
REGION                    1..425
                          note = Synthetic Polypeptide
source                    1..425
                          mol_type = protein
                          organism = synthetic construct
SEQUENCE: 66
MEQVEILRKF IQRVQAMKSP DHNGEDNFAR DFMRLRRLST KYRTEKIYPT ATGEKEENVK    60
KNRYKDILPF DHSRVKLTLK TPSQDSDYIN ANFIKGVYGP KAYVATQGPL ANTVIDFWRM   120
VWEYNVVIIV MACREFEMGR KKCERYWPLY GEDPITFAPF KISCEDEQAR TDYFIRTLLL   180
EFQNESRRLY QFHYVNWPDH DVPSSFDSIL DMISLMRKYQ EHEDVPICIH CSAGCGRTGA   240
ICAIDYTWNL LKAGKIPEEF NVFNLIQEMR TQRHSAVQTK EQYELVHRAI AQLFEKQLQL   300
YEIHGAQKIA DGVNEINTEN MVSSIEPEKQ DSPPPKPPRT RSCLVEGDAK EEILQPPEPH   360
PVPPILTPSP PSAFPTVTTV WQDNDRYHPK PVLQWFHQNN IQQTSTETIV NQQNFQGKMN   420
QQLNR                                                                425

SEQ ID NO: 67             moltype = AA   length = 299
FEATURE                   Location/Qualifiers
REGION                    1..299
                          note = Synthetic Polypeptide
source                    1..299
                          mol_type = protein
                          organism = synthetic construct
SEQUENCE: 67
MDQREILQKF LDEAQSKKIT KEEFANEFLK LKRQSTKYKA DKTYPTTVAE KPKNIKKNRY    60
KDILPYDYSR VELSLITSDE DSSYINANFI KGVYGPKAYI ATQGPLSTTL LDFWRMIWEY   120
SVLIIVMACM EYEMGKKKCE RYWAEPGEMQ LEFGPFSVSC EAEKRKSDYI IRTLKVKFNS   180
ETRTIYQFHY KNWPDHDVPS SIDPILELIW DVRCYQEDDS VPICIHCSAG CGRTGVICAI   240
DYTWMLLKDG IIPENFSVFS LIREMRTQRP SLVQTQEQYE LVYNAVLELF KRQMDVIRD    299

SEQ ID NO: 68             moltype = AA   length = 238
FEATURE                   Location/Qualifiers
REGION                    1..238
                          note = Synthetic Polypeptide
source                    1..238
                          mol_type = protein
                          organism = synthetic construct
SEQUENCE: 68
MRKGEELFTG VVPILVELDG DVNGHKFSVR GEGEGDATNG KLTLKFICTT GKLPVPWPTL    60
VTTLTYGVQC FARYPDHMKQ HDFFKSAMPE GYVQERTISF KDDGTYKTRA EVKFEGDTLV   120
NRIELKGIDF KEDGNILGHK LEYNFNSHNV YITADKQKNG IKANFKIRHN VEDGSVQLAD   180
HYQQNTPIGD GPVLLPDNHY LSTQSVLSKD PNEKRDHMVL LEFVTAAGIT HGMDELYK     238

SEQ ID NO: 69             moltype = AA   length = 245
FEATURE                   Location/Qualifiers
REGION                    1..245
                          note = Synthetic Polypeptide
source                    1..245
                          mol_type = protein
                          organism = synthetic construct
SEQUENCE: 69
MHHHHHHVSK GEELFTGVVP ILVELDGDVN GHKFSVRGEG EGDATNGKLT LKFICTTGKL    60
PVPWPTLVTT FGYGVACFSR YPDHMKQHDF FKSAMPEGYV QERTISFKDD GTYKTRAEVK   120
FEGDTLVNRI ELKGIDFKED GNILGHKLEY NFNSHNVYIT ADKQKNGIKA NFKIRHNVED   180
GSVQLADHYQ QNTPIGDGPV LLPDNHYLSH QSALSKDPNE KRDHMVLLEF VTAAGITHGM   240
DELYK                                                                245

SEQ ID NO: 70             moltype = DNA   length = 129
FEATURE                   Location/Qualifiers
misc_feature              1..129
                          note = Synthetic Polynucleotide
source                    1..129
                          mol_type = other DNA
                          organism = synthetic construct
SEQUENCE: 70
atccggatat agttcctcct ttcagcaaaa aaccccctcaa gacccgttta gaggccccaa    60
ggggttatgc tagttattgc tcagcggtgg cagcagccaa ctcagcttcc tttcgggctt   120
tgttagcag                                                            129

SEQ ID NO: 71             moltype = DNA   length = 426
FEATURE                   Location/Qualifiers
misc_feature              1..426
                          note = Synthetic Polynucleotide
source                    1..426
                          mol_type = other DNA
                          organism = synthetic construct
SEQUENCE: 71
ggctgttttg gcggatgaga gaagattttc agcctgatac agattaaatc agaacgcaga    60
agcggtctga taaaacagaa tttgcctggc ggcagtagcg cggtggtccc acctgacccc   120
atgccgaact cagaagtgaa acgccgtagc gccgatggta gtgtgggatc acccccatgcg   180
```

```
agagtaggga actgccaggc atcaaataaa acgaaaggct cagtcgaaag actgggcctt    240
tcgttttatc tgttgtttgt cggtgaacgc tctcctgagt aggacaaatc cgccgggagc    300
ggatttgaac gttgcgaagc aacgcccgg  agggtggcgg gcaggacgcc cgccataaac    360
tgccaggcat caaattaagc agaaggccat cctgacggat ggccttttg  cgtttctaca    420
aactct                                                               426

SEQ ID NO: 72           moltype = DNA  length = 158
FEATURE                 Location/Qualifiers
misc_feature            1..158
                        note = Synthetic Polynucleotide
source                  1..158
                        mol_type = other DNA
                        organism = synthetic construct
SEQUENCE: 72
tgcctggcgg cagtagcgcg gtggtcccac ctgaccccat gccgaactca gaagtgaaac     60
gccgtagcgc cgatggtagt gtggggtctc cccatgcgag agtagggaac tgccaggcat    120
caaataaaac gaaaggctca gtcgaaagac tgggccttt                           158

SEQ ID NO: 73           moltype = DNA  length = 867
FEATURE                 Location/Qualifiers
misc_feature            1..867
                        note = Synthetic Polynucleotide
source                  1..867
                        mol_type = other DNA
                        organism = synthetic construct
SEQUENCE: 73
atgggctcca agccgcagac tcagggcctg gccaaggatg cctgggagat ccctcgggag     60
tcgctgcggc tggaggtcaa gctgggccag ggctgctttg cgaggtgtg  gatggggacc    120
tggaacggta ccaccagggt ggccatcaaa accctgaagc ctggcacgat gtctccagag    180
gccttcctgc aggaggccca gtcatgaag  aagctgagag atgagaagct ggtgcagttg    240
tatgctgtgg tttcagagga gcccatttac atcgtcacgg agtacatgag caagggagt     300
ttgctggact ttctcaaggg ggagacaggc aagtaccgc  ggctgcctca gctggtggac    360
atggctgctc agatcgcctc aggcatggcg tacgtggagc ggatgaacta cgtccaccgg    420
gaccttcgtg cagccaacat cctggtggga gagaacctgg tgtgcaaagt ggccgacttt    480
gggctgctc  ggctcattga agacaatgag tacacgcgtc ggcaaggtgc caaattcccc    540
atcaagtgga cggctccaga agctgccctc tatggccgct tcaccatcaa gtcggacgtg    600
tggtccttcg ggatcctgct gactgagctc accacaaagg gacgggtgcc ctaccctggg    660
atggtgaacc gcgaggtgct ggaccaggtg gagcggggcc accggatgcc ctgcccgccg    720
gagtgtcccg agtccctgca cgacctcatg tgccagtgct ggcgaaagga gcctgaggag    780
cggcccacct tcgagtacct gcaggccttc ctggaggact acttcacgtc caccgagccc    840
cagtaccagc ccggggagaa cctctaa                                        867

SEQ ID NO: 74           moltype = DNA  length = 1137
FEATURE                 Location/Qualifiers
misc_feature            1..1137
                        note = Synthetic Polynucleotide
source                  1..1137
                        mol_type = other DNA
                        organism = synthetic construct
SEQUENCE: 74
atggtggact acagcgtgtg ggaccacatt gaggtgtctg atgatgaaga cgagacgcac     60
cccaacatcg acacgccag  tctcttccgc tggcggcatc aggcccgggt ggaacgcatg    120
gagcagttcc agaaggagaa ggaggaactg gacaggggct gccgcgagtg caagcgcaag    180
gtggccgagt gccagaggaa actgaaggag ctggaggtgg ccgagggcgg caaggcagag    240
ctggagcgcc tgcaggccga ggcacagcag ctgcgcaagg aggagcggga ctgggagcag    300
aagctggagg agatgcgcaa gaaggagaag agcatgccct ggaacgtgga cacgctcagc    360
aaagacggct tcagcaagag catggtaaat accaagcccg agaagacgga ggaggactca    420
gaggaggtga gggagcagaa acacaagacc ttcgtggaaa aatacgagaa acagatcaag    480
cactttggca tgcttcgccg ctgggatgac agccaaaagt acctgtcaga caacgtccac    540
ctggtgtgcg aggagagc   aattacctg gtcatttgt  gcattgacct agaggtggag    600
gagaaatgtg cactcatgga gcaggtggcc caccagacaa tcgtcatgca atttatcctg    660
gagctggcca agagcctaaa ggtggacccc cgggcctgct ccggcagtt  cttcactaag    720
attaagacag ccgatcgcca gtacatggag ggcttcaacg acgagctgga agccttcaag    780
gagcgtgtgc ggggcgtgc  caagctgcgc atcgagaagg ccatgaagga gtacgaggag    840
gaggagcgca gaagcgggct cggccccggc gcctggacc  ccgtcgaggt ctacgagtcc    900
ctccctgagg aactccagaa gtgcttcgat gtgaaggacg tgcagatgct gcaggacgcc    960
atcagcaaga tggaccccac cgacgcaaag taccacatgc agcgctgcat tgactctgc   1020
ctctgggtcc ccaactctaa ggccagcgag gccaaggagg agaggaggc  aggtcctggg   1080
gacccattac tggaagctgt tcccaagacg ggcgatgaga aggatgtcag tgtgtaa      1137

SEQ ID NO: 75           moltype = DNA  length = 1308
FEATURE                 Location/Qualifiers
misc_feature            1..1308
                        note = Synthetic Polynucleotide
source                  1..1308
                        mol_type = other DNA
                        organism = synthetic construct
SEQUENCE: 75
atggagatgg aaaaggagtt cgagcagatc gacaagtccg ggagctgggc ggccatttac     60
```

| | | | |
|---|---|---|---|
| caggatatcc | gacatgaagc | cagtgacttc | ccatgtagag tggccaagct tcctaagaac | 120 |
| aaaaaccgaa | ataggtacag | agacgtcagt | cccctttgacc atagtcggat taaactacat | 180 |
| caagaagata | atgactatat | caacgctagt | ttgataaaaa tggaagaagc ccaaaggagt | 240 |
| tacattctta | cccagggccc | tttgcctaac | acatgcggtc actttggga gatggtgtgg | 300 |
| gagcagaaaa | gcaggggtgt | cgtcatgctc | aacagagtga agaaaagg ttcgttaaaa | 360 |
| tgcgcacaat | actggccaca | aaaagaagaa | aaagagatga tctttgaaga cacaaatttg | 420 |
| aaattaacat | tgatctctga | agatatcaag | tcatattata cagtgcgaca gctagaattg | 480 |
| gaaaaccttg | caacccaaga | aactcgagag | atcttacatt tccactatac cacatggcct | 540 |
| gactttggag | tccctgaatc | accagcctca | ttcttgaact ttcttttcaa agtccgagag | 600 |
| tcagggtcac | tcagcccgga | gcacgggccc | gttgtggtgc actgcagtgc aggcatcggc | 660 |
| aggtctggaa | ccttctgtct | ggctgatacc | tgcctcttgc tgatggacaa gaggaaagac | 720 |
| ccttcttccg | ttgatatcaa | gaaagtgctg | ttagaaatga ggaagtttcg gatggggctg | 780 |
| atccagacag | ccgaccagct | gcgcttctcc | tacctggctg tgatcgaagg tgccaaattc | 840 |
| atcatgggg | actcttccgt | gcaggatcag | tggaaggagc tttcccacga ggacctggag | 900 |
| cccccacccg | agcatatccc | cccacctccc | cggccaccca aacgaatcct ggagccacac | 960 |
| aatgggaaat | gcagggagtt | cttcccaaat | caccagtggg tgaaggaaga cccccaggag | 1020 |
| gataaagact | gccccatcaa | ggaagaaaaa | ggaagcccct taaatgccgc accctacggc | 1080 |
| atcgaaagca | tgagtcaaga | cactgaagtt | agaagtcggg tcgtggggg aagtcttcga | 1140 |
| ggtgcccagg | ctgcctcccc | agccaaaggg | gagccgtcac tgcccgagaa ggacgaggac | 1200 |
| catgcactga | gttactggaa | gcccttcctg | gtcaacatgt gcgtggctac ggtcctcacg | 1260 |
| gccgcgctt | acctctgcta | caggttcctg | ttcaacagca cacatag | 1308 |

```
SEQ ID NO: 76          moltype = DNA   length = 1086
FEATURE                Location/Qualifiers
misc_feature           1..1086
                       note = Synthetic Polynucleotide
source                 1..1086
                       mol_type = other DNA
                       organism = synthetic construct
SEQUENCE: 76
```

| | | | |
|---|---|---|---|
| atgaaatttg | gaactttttt | gcttacatac | caacctcccc aattttccca aacagaggta | 60 |
| atgaaacgtt | tggttaaatt | aggtcgcatc | tctgaggagt gtggttttga taccgtatgg | 120 |
| ttactggagc | atcatttcac | ggagtttggt | ttgcttggta acctttatgt cgctgctgca | 180 |
| tatttacttg | gcgcgactaa | aaaattgaat | gtaggaacatg ccgctattgt tcttcccaca | 240 |
| gcccatccag | tacgccaact | tgaagatgtg | aatttattgg atcaaatgtc aaaaggacga | 300 |
| tttcggtttg | gtatttgccg | agggctttac | aacaaggact ttcgcgtatt cggcacagat | 360 |
| atgaataaca | gtcgcgcctt | agcggaatgc | tggtacgggc tgataaagaa tggcatgaca | 420 |
| gagggatata | tggaagctga | taatgaacat | atcaagttcc ataaggtaaa agtaaacccc | 480 |
| gcggcgtata | gcagaggtgg | cgcaccggtt | tatgtggtgg ctgaatcagc ttcgacgact | 540 |
| gagtgggctg | ctcaatttgg | cctaccgatg | atattaagtt ggattataaa tactaacgaa | 600 |
| aagaaagcac | aacttgagct | ttataatgaa | gtggctcaag aatatgggca cgatattcat | 660 |
| aatatcgacc | attgcttatc | atatataaca | tctgtagatc atgactcaat taaagcgaaa | 720 |
| gagatttgcc | ggaaatttct | ggggcattgg | tatgattctt atgtgaatgc tacgactttt | 780 |
| tttgatgatt | cagaccaaac | aagaggttat | gatttcaata aagggcagtg gcgtgacttt | 840 |
| gtattaaaag | gacataaaga | tactaatcgc | cgtattgatt cagttacga aatcaatccc | 900 |
| gtgggaacgc | cgcaggaatg | tattgacata | attcaaaaag acattgatgc tacaggaata | 960 |
| tcaaatattt | gttgtggatt | tgaagctaat | ggaacagtag acgaaattat tgcttccatg | 1020 |
| aagctcttcc | agtctgatgt | catgccattt | cttaaagaaa acaacgttc gctattatat | 1080 |
| tattaa | | | | 1086 |

```
SEQ ID NO: 77          moltype = DNA   length = 987
FEATURE                Location/Qualifiers
misc_feature           1..987
                       note = Synthetic Polynucleotide
source                 1..987
                       mol_type = other DNA
                       organism = synthetic construct
SEQUENCE: 77
```

| | | | |
|---|---|---|---|
| atgagcaaat | ttggattgtt | cttccttaac | ttcatcaatt caacaactgt tcaagaacag | 60 |
| agtatagttc | gcatgcagga | aataacggag | tatgttgata agttgaattt tgaacagatt | 120 |
| ttagtgtatg | aaaatcattt | ttcagataat | ggtgttgtcg gcgctcctct gactgtttct | 180 |
| ggttttctgc | tcggtttaac | agagaaaatt | aaaattggtt cattaaatca catcattaca | 240 |
| actcatcatc | ctgtccgcat | agcggaggaa | gcttgcttat tggatcagtt aagtgaaggg | 300 |
| agatttattt | tagggtttag | tgattgcgaa | aaaaagatg aaatgcattt ttttaatcgc | 360 |
| ccggttgaat | atcaacagca | actatttgaa | gagtgttatg aaatcattaa cgatgcttta | 420 |
| acaacaggct | attgtaatcc | agataacgat | ttttatagct tccctaaaat atctgtaaat | 480 |
| ccccatgctt | atacgccagg | cggacctcgg | aaatatgtaa cagcaaccag tcatcatatt | 540 |
| gttgagtggg | cggccaaaaa | aggtattcct | ctcatcttta gtgggatga ttctaatgga | 600 |
| gttagatatg | aaatatgctga | aagatataaa | gccgttcgg ataaatatga cgttgaccta | 660 |
| tcagagatag | accatcagtt | aatgatatta | gttaactata cgaagatag taataaagct | 720 |
| aaacaagaaa | cgcgtgcatt | tattagtgat | tatgttcttg aaatgcaccc taatgaaaat | 780 |
| ttcgaaaata | aacttgaaga | aataattgca | gaaacgctg tcgaaatta tacggagtgt | 840 |
| ataactgcgg | ctaagttggc | aattgaaaag | tgtggtgcga aagtgtatt gctgtccttt | 900 |
| gaaccaatga | atgatttgat | gagccaaaaa | aatgtaatca atattgttga tgataatatt | 960 |
| aagaagtacc | acacggaata | tacctaa | | 987 |

```
SEQ ID NO: 78          moltype = DNA   length = 276
FEATURE                Location/Qualifiers
misc_feature           1..276
```

```
                        note = Synthetic Polynucleotide
source                  1..276
                        mol_type = other DNA
                        organism = synthetic construct
SEQUENCE: 78
atggcacgcg taactgttca ggacgctgta gagaaaattg gtaaccgttt tgacctggta    60
ctggtcgccg cgcgtcgcgc tcgtcagatg caggtaggcg gaaaggatcc gctggtaccg   120
gaagaaaacg ataaaaccac tgtaatcgcg ctgcgcgaaa tcgaagaagg tctgatcaac   180
aaccagatcc tcgacgttcg cgaacgccag gaacagcaag agcaggaagc cgctgaatta   240
caagccgtta ccgctattgc tgaaggtcgt cgttaa                             276

SEQ ID NO: 79           moltype = DNA  length = 636
FEATURE                 Location/Qualifiers
misc_feature            1..636
                        note = Synthetic Polynucleotide
source                  1..636
                        mol_type = other DNA
                        organism = synthetic construct
SEQUENCE: 79
atgagtatca gcagcagggt aaaaagcaaa agaattcagc ttggacttaa ccaggctgaa    60
cttgctcaaa aggtggggac tacccagcag tctatagagc agctcgaaaa cggtaaaact   120
aagcgaccac gcttttacc agaacttgcg tcagctcttg gcgtaagtgt tgactggctg   180
ctcaatggca cctctgattc gaatgttaga tttgttgggc acgttgagcc caaagggaaa   240
tatccattga ttagcatggt tagagctcgt tcgtggtgtg aagcttgtga accctacgat   300
atcaaggaca ttgatgaatg gtatgacagt gacgttaact tattaggcaa tggattctgg   360
ctgaaggttg aaggtgattc catgacctca cctgtaggtc aaagcatccc tgaaggtcat   420
atggtgttag tagatactgg acgggagcca gtgaatggaa gccttgttgt agccaaactg   480
actgacgcga acgaagcaac attcaagaaa ctggtcatag atggcggtca gaagtacctg   540
aaaggcctga atccttcatg gcctatgact cctatcaacg gaaactgcaa gattatcggt   600
gttgtcgtgg aagcgagggt aaaattcgta gactaa                             636

SEQ ID NO: 80           moltype = DNA  length = 300
FEATURE                 Location/Qualifiers
misc_feature            1..300
                        note = Synthetic Polynucleotide
source                  1..300
                        mol_type = other DNA
                        organism = synthetic construct
SEQUENCE: 80
atgtggtatt ttgggaagat cactcgtcgg gagtccgagc ggctgctgct caaccccgaa    60
aaccccgggg gaaccttctt ggtccgggag agcgagacgg taaaaggtgc ctatgccctc   120
tccgtttctg actttgacaa cgccaagggg ctcaatgtga acactacct gatccgcaag   180
ctggacagcg gcggcttcta catcacctca cgcacacagt tcagcagcct gcagcagctg   240
gtggcctact actccaaaca tgctgatggc ttgtgccacc gcctgaccaa cgtctgctaa   300

SEQ ID NO: 81           moltype = DNA  length = 1116
FEATURE                 Location/Qualifiers
misc_feature            1..1116
                        note = Synthetic Polynucleotide
source                  1..1116
                        mol_type = other DNA
                        organism = synthetic construct
SEQUENCE: 81
atgaaaatcg aagaaggtaa actggtaatc tggattaacg gcgataaagg ctataacggt    60
ctcgctgaag tcggtaagaa attcgagaaa gataccggaa ttaaagtcac cgttgagcat   120
ccggataaac tggaagagaa attcccacag gttgcggcaa ctggcgatgg ccctgacatt   180
atcttctggg cacacgaccg cttggtggc tacgctcaat ctggcctgtt ggctgaaatc   240
accccgacaa aagcgttcca ggacaagctg tatccgttta cctgggatgc cgtacgttac   300
aacggcaagc tgattgctta cccgatcgct gttgaagcgt tatcgctgat ttataacaaa   360
gatctgctgc cgaaccccgcc aaaaacctgg gaagagatcc cggcgctgga taaagaactg   420
aaagcgaaag gtaagagcgc gctgatgttc aacctgcaag aaccgtactt cacctggccg   480
ctgattgctg ctgacggggg ttatgcgttc aagtatgaaa acggcaagta cgacattaaa   540
gacgtggcg tggataacgc tggcgcgaaa gcgggtctga ccttcctggt tgacctgatt   600
aaaaacaaac acatgaatgc agacaccgat tactccatcg cagaagctgc ctttaataaa   660
ggcgaaacag cgatgaccat caacggcccg tgggcatggt ccaacatcga caccagcaaa   720
gtgaattatg gtgtaacggt actgccgacc ttcaagggtc aaccatccaa accgttcgtt   780
ggcgtgctga gcgcaggtat taacgccgcc agtccgaaca aagagctggc gaaagagttc   840
ctcgaaaact atctgctgac tgatgaaggt ctggaagcgg ttaataaaga caaaccgctg   900
ggtgccgtag cgctgaagtc ttacgaggaa gagttggcga aagatccacg tattgccgcc   960
accatggaaa acgcccagaa aggtgaaatc atgccgaaca tcccgcagat gtccgctttc  1020
tggtatgccg tgcgtactgc ggtgatcaac gccgccagcg tcgtcagac tgtcgatgaa  1080
gccctgaaag acgcgcagac tcgtatcacc aagtaa                            1116

SEQ ID NO: 82           moltype = DNA  length = 36
FEATURE                 Location/Qualifiers
misc_feature            1..36
                        note = Synthetic Polynucleotide
source                  1..36
                        mol_type = other DNA
```

```
                          organism = synthetic construct
SEQUENCE: 82
tggatggagg actatgacta cgtccaccta cagggg                                36

SEQ ID NO: 83           moltype = DNA  length = 33
FEATURE                 Location/Qualifiers
misc_feature            1..33
                        note = Synthetic Polynucleotide
source                  1..33
                        mol_type = other DNA
                        organism = synthetic construct
SEQUENCE: 83
gaaccgcagt atgaagaaat tccgatttat ctg                                   33

SEQ ID NO: 84           moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 84
ccgcagcgct atctggtgat tcagggcgat                                       30

SEQ ID NO: 85           moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 85
gatcatcagt attataacga ttttccgggc                                       30

SEQ ID NO: 86           moltype = DNA  length = 5432
FEATURE                 Location/Qualifiers
misc_feature            1..5432
                        note = Synthetic Polynucleotide
misc_feature            1317
                        note = n is a, c, g, or t
source                  1..5432
                        mol_type = other DNA
                        organism = synthetic construct
SEQUENCE: 86
atgtcattac cgttcttaac ttctgcaccg ggaaaggtta ttattttttgg tgaacactct     60
gctgtgtaca acaagcctgc cgtcgctgct agtgtgtctg cgttgagaac ctacctgcta    120
ataagcgagt catctgcacc agatactatt gaattggact tcccggacat tagctttaat    180
cataagtggt ccatcaatga tttcaatgcc atcaccgagg atcaagtaaa ctcccaaaaa    240
ttggccaagg ctcaacaagc caccgatggc ttgtctcagg aactcgttag tcttttggat    300
ccgttgttag ctcaactatc cgaatccttc cactaccatg cagcgttttg tttcctgtat    360
atgtttgttt gcctatgccc ccatgccaag aatattaagt tttctttaaa gtctacttta    420
cccatcggtg ctgggttggg ctcaagcgcc tctatttctg tatcactggc cttagctatg    480
gcctacttgg gggggttaat aggatctaat gacttggaaa agctgtcaga aaacgataag    540
catatagtga atcaatgggc cttcataggt gaaaagtgta ttcacggtac cccttcagga    600
atagataacg ctgtgccac ttatggtaat gccctgctat ttgaaaaaga ctcacataat    660
ggaacaataa acacaaacaa ttttaagttc ttagatgatt tcccagccat tccaatgatc    720
ctaacctata ctagaattcc aaggtctaca aaagatcttg ttgctcgcgt tcgtgtgttg    780
gtcaccgaga aatttcctga agttatgaag ccaattctag atgccatggg tgaatgtgcc    840
ctacaaggct tagagatcat gactaagtta agtaaatgta aaggcaccga tgcgaggcct    900
gtagaaacta ataatgaact gtatgaacaa ctattggaat tgataagaat aaatcatgaa    960
ctgcttgtct caatcggtgt ttctcatcct ggattagaac ttattaaaaa tctgagcgat   1020
gatttgagaa ttggctccac aaaacttacc ggtgctggtg gcggcggttg ctctttgact   1080
ttgttacgaa gagacattac tcaagagcaa attgacagct tcaaaaagaa attgcaagat   1140
gattttagtt acgagacatt tgaaacagac ttgggtggga ctggctgctg tttgttaagc   1200
gcaaaaaatt tgaataaaga tcttaaaatc aaatccctag tattccaatt atttgaaaat   1260
aaaactacca caaagcaaca aattgacgat ctattattgc caggaaacac gaatttncca   1320
tggacttcat aggaggcaga tcaaatgtca gagttgagag ccttcagtgc cccagggaaa   1380
gcgttactag ctggtggata tttagtttta gatacaaaat atgaagcatt tgtagtcgga   1440
ttatcggcaa gaatgcatgc gtagcccat ccttacggtt cattgcaagg gtctgataag   1500
tttgaagtgc gtgtgaaaag taaacaattt aaagatgggg agtggctgta ccatataagt   1560
cctaaaagtg gctcattcc tgtttcgata ggcggatcta agaacccttt cattgaaaaa   1620
gttatcgcta acgtatttag ctactttaaa cctaacatgg acgactactg caatagaaac   1680
ttgttcgtta ttgatatttt ctctgatgat gcctaccatt tcaggagga tagcgttacc   1740
gaacatcgtg gcaacagaag attgagtttt cattcgcaca gaattgaaga agttcccaaa   1800
acagggctgg gctcctcggc aggtttagtc acagttttaa ctacagcttt ggcctccttt   1860
tttgtatcgg acctgaaaa taatgtgac aaatatagaa aagttattca taatttagca   1920
caagttgctc attgtcaagc tcagggtaaa attggaagcg gtttgatgt agcggcggca   1980
gcatatggat ctatcagata tagaagattc ccacccgcat taatctctaa tttgccagat   2040
attggaagtg ctacttacgg cagtaaactg gcgcatttgg ttgatgaaga agactggaat   2100
```

```
attacgatta aaagtaacca tttaccttcg ggattaactt tatggatggg cgatattaag  2160
aatggttcag aaacagtaaa actggtccag aaggtaaaaa attggtatga ttcgcatatg  2220
ccagaaagct tgaaaatata tacagaactc gatcatgcaa attctagatt tatgatgga   2280
ctatctaaac tagatcgctt acacgagact catgacgatt acagcgatca gatatttgag  2340
tctcttgaga ggaatgactg tacctgtcaa aagtatccgt aaatcacaga agttagagat  2400
gcagttgcca caattagacg ttcctttaga aaaataacta aagaatctgg tgccgatatc  2460
gaacctcccg tacaaactag cttattggat gattgccaga ccttaaaagg agttcttact  2520
tgcttaatac ctggtgctgg tggttatgac gccattgcag tgattactaa gcaagatgtt  2580
gatcttaggg ctcaaaccgc taatgacaaa agattttcta aggttcaatg gctggatgta  2640
actcaggctg actggggtgt taggaaagaa aaagatccgg aaacttatct tgataaatag  2700
gaggtaatac tcatgaccgt ttacacagca tccgttaccg cacccgtcaa catcgcaacc  2760
cttaagtatt gggggaaaag ggacacgaag ttgaatctgc ccaccaattc gtccatatca  2820
gtgactttat cgcaagatga cctcagaacg ttgacctctg cggctactgc acctgagttt  2880
gaacgcgaca ctttgtggtt aaatggagaa ccacacagca tcgacaatga aagaactcaa  2940
aattgtctgc gcgacctacg ccaattaaga aaggaaatgg aatcgaagga cgcctcattg  3000
cccacattat ctcaatggaa actccacatt gtctccgaaa ataactttcc tacagcagct  3060
ggtttagctt cctccgctgc tggctttgct gcattggtct ctgcaattgc taagttatac  3120
caattaccac agtcaacttc agaaatatct agaatagcaa gaaaggggtc tggttcagct  3180
tgtagatcgt tgtttggcgg atacgtggcc tgggaaatgg gaaaagctga agatggtcat  3240
gattccatgg cagtacaaat cgcagacagc tctgactggc ctcagatgaa agcttgtgtc  3300
ctagttgtca gcgatattaa aaaggatgtg agttccactc agggtatgca attgaccgtg  3360
gcaacctccg aactatttaa agaaagaatt gaacatgtcg taccaaagag atttgaagtc  3420
atgcgtaaag ccattgttga aaaagatttc gccacctttg caaaggaaac aatgatggat  3480
tccaactctt tccatgccac atgtttggac tctttccctc caatattcta catgaatgac  3540
acttccaagc gtatcatcag ttggtgccac accattaatc agtttacgg agaaacaatc   3600
gttgcataca cgtttgatgc aggtccaaat gctgtgttgt actacttagc tgaaaatgag  3660
tcgaaactct ttgcatttat ctataaattg tttggctctg ttcctggatg ggacaagaaa  3720
tttactactg agcagcttga ggctttcaac catcaatttg aatcatctaa ctttactgca  3780
cgtgaattgg atcttgagtt gcaaaaggat gttgccagag tgattttaac tcaagtcggt  3840
tcaggcccac aagaaacaaa cgaatctttg attgacgcaa agactggtct accaaaggaa  3900
taactgcagc ccgggaggag gattactata tgcaaacgga acacgtcatt ttattgaatg  3960
cacagggagt tccacgggt acgctggaaa agtatgccgc acacacggca gacacccgct   4020
tacatctcgc gttctccagt tggctgttta atgccaaagg acaattatta gttacccgcc  4080
gcgcactgag caaaaagca tggcctggcg tgtggactaa ctcggtttgt gggcacccac    4140
aactgggaga aagcaacgaa gacgcagtga tccgccgttg ccgttatgag cttggcgtgg  4200
aaattacgcc tcctgaatct atctatcctg actttcgcta ccgcgccacc gatccgagtg  4260
gcattgtgga aaatgaagtg tgtccggtat ttgccgcacg caccactagt gcgttacaga  4320
tcaatgatga tgaagtgatg gattatcaat ggtgtgattt agcagatgta ttacacggta  4380
ttgatgccac gccgtgggcg ttcagtccgt ggatggtgat gcaggcgaca aatcgcgaag  4440
ccagaaaacg attatctgca tttacccagc ttaaataacc cggggatcc actagttcta   4500
gagcggccgc caccgcggag gaggaatgag taatggactt tccgcagcaa ctcgaagcct  4560
gcgttaagca ggccaaccag gcgctgagcc gttttatcgc cccactgccc tttcagaaca  4620
ctcccgtggt cgaaaccatg cagtatgcg cattattagg tggtaagcgc ctgcgaccctt   4680
tcctggttta tgccaccggt catatgttcg gcgttagcac aaaacacgctg gacgcacccg  4740
ctgccgcgt tgagtgtatc cacgcttact cattaattca tgatgattta ccggcaatgg   4800
atgatgacga tctgcgtcgc ggtttgccaa cctgccatgt gaagtttggc gaagcaaacg  4860
cgattctcgc tggcgacgct ttacaaacgc tggcgttctc gatttttaagc gatgccgata  4920
tgccggaagt gtcggaccgc gacagaattt cgatgatttc tgaactggcg agcgccagtg  4980
gtattgccgg aatgtgcggt ggtcaggcat tagatttaga gcgcggaaggc aaacacgtac  5040
ctctggacgc gcttgagcgt attcatcgtc ataaaaccgg cgcattgatt cgcgccgccg  5100
ttcgccttgg tgcattaagc gccggagata aaggacgtcg tgctctgccg gtactcgaca  5160
agtatgcaga gagcatcggc cttgccttcc aggttcagga tgacatcctg gatgtggtgg  5220
gagatactgc aacgttggga aaacgccagg tgccgacca gcaacttggt aaaagtacct   5280
acccctgcact tctgggtctt gagcaagccc ggaagaaagc ccgggatctg atcgacgatg  5340
cccgtcagtc gctgaaacaa ctggctgaac agtcactcga tacctcggca ctggaagcgc  5400
tagcggacta catcatccag cgtaataaat aa                                 5432
```

SEQ ID NO: 87       moltype = DNA    length = 1638
FEATURE             Location/Qualifiers
misc_feature        1..1638
                    note = Synthetic Polynucleotide
source              1..1638
                    mol_type = other DNA
                    organism = synthetic construct
SEQUENCE: 87

```
gccctgaccg aagagaaacc gatccgcccg atcgctaact tccgccgtc tatctgggt    60
gaccagttcc tgatctacga aaagcaggtt gagcagggtg ttgaacagat cgtaaacgac  120
ctgaagaaag aagttcgtca gctgctgaaa gaagctctgg acatcccgat gaaacacgct  180
aacctgttga agctgatcga cgagatccag cgtctgtacca cttcgaaccgc           240
gaaatcgacc acgcactgca gtgcatctac gaaacctacg cgacaactg gaacggcgac  300
cgttcttctc tgtggttttcg tctgatgcgt aaacaggggct actacgttac ctgtgacgtt  360
tttaacaact acaaggacaa gaacggtgct ttcaaacagt ctctggctaa cgacgttgaa  420
ggcctgctgg aactgtacga agcgacctcc atgcgtgtac cgggtgaaat catcctggag  480
gacgcgctgg gtttcaccccg ttctcgtctg tccattatga ctaaagacgc tttctctact  540
aacccggctc tgttcaccga aatccagcgt gctctgaaac agcgcgctgtg gaaacgtctg   600
ccgcgtatcg aagcagcaca gtacattccg tttaccagc agcaggactc tcacaacaag  660
acctgctgaa aactggctaa gctggaattc aacctgctgc agtctctgca caagaagaa   720
ctgtctcacg tttgtaagtg gtggaaggca tttgacatca agaaaaacgc gccgtgcctg  780
cgtgaccgta tcgttgaatg ttacttctgg ggtctgggtt ctggttatga accacagtac  840
```

```
tcccgtgcac gtgtgttctt cactaaagct gtagctgtta tcaccctgat cgatgacact   900
tacgatgctt acggcaccta cgaagaactg aagatcttta ctgaagctgt agaacgctgg   960
tctatcactt gcctggacac tctgccggag tacatgaaac cgatctacaa actgttcatg  1020
gataccctaca ccgaaatgga ggaattcctg caaaagaag gccgtaccga cctgttcaac  1080
tgcggtaaag agtttgttaa agaattcgta cgtaacctga tggttgaagc taaatgggct  1140
aacgaaggcc atatcccgac taccgaagaa catgacccgg ttgttatcat caccggcggt  1200
gcaaacctgc tgaccaccac ttgctatctg ggtatgtccg acatctttac caaggaatct  1260
gttgaatggg ctgtttctgc accgccgctg ttccgttact ccggtattct gggtcgtcgt  1320
ctgaacgacc tgatgaccca caaagcagag caggaacgta aacactcttc ctcctctctg  1380
gaatcctaca tgaaggaata taacgttaac gaggagtacg cacagactct gatctataaa  1440
gaagttgaag acgtatggaa agacatcaac cgtgaatacc tgactactaa aaacatcccg  1500
cgcccgctgc tgatggcagt aatctacctg tgccagttcc tggaagtaca gtacgctggt  1560
aaagataact tcactcgcat gggcgacgaa tacaaacacc tgatcaaatc cctgctggtt  1620
tacccgatgt ccatctga                                                1638
```

SEQ ID NO: 88           moltype = DNA    length = 1782
FEATURE                 Location/Qualifiers
misc_feature            1..1782
                        note = Synthetic Polynucleotide
source                  1..1782
                        mol_type = other DNA
                        organism = synthetic construct
SEQUENCE: 88

```
atggctcaaa tcagcgaatc agtgtctcca agcaccgacc ttaaaagcac ggaatcttct    60
attaccagca accgccacgg taacatgtgg gaagatgacc gcattcagag cttaaacagc   120
ccatatggcg cacccgctta tcaggaacgt agcgaaaaat tgattgaaga aattaagctc   180
ctgtttctgt ccgatatgga cgatagttgc aatgattcgg atcgcgactt gatcaaacgc   240
ctggagatcg tagataccggt tgagtgtctg ggcattgatc gtcatttcca acctgaaatt   300
aagctggcgc tggattacgt gtaccgttgc tggaatgagc gtggcatcgg agaaggtagc   360
cgtgatagct taaaaaagga cctgaatgcg accgccttgg gctttcgggc tttacgctta   420
caccgtttata atgtaagctc aggagtgctg gagaacttcc gtgatgacaa tggtcaattc   480
ttttgcggtt ctactgtgga ggaggaaggc gcggaggcct acaataaaca tgtacgttgc   540
atgctgtccc tgtcccgcgc ttccaatatt ttattcccgg cgagaaagt gatggaagaa   600
gcgaaggcgt ttacgaccaa ctatcttaag aaagtcctgg cgggtcgtga agcaactcat   660
gtcgacgaga gtctccttgg agaggtcaag tatgcactag aatttccgtg gcattgttcc   720
gtgcagcgct gggaggcacg ttcttttatc gaaattttcg gtcagattga tagtgaactg   780
aaaagcaacc tctctaaaaa aatgctcgaa ctcgcaaaac ttgattttaa catactccaa   840
tgtacgcatc aaaaagagct ccagatcatt agtcgatggt tcgccgattc aagtatcgca   900
agtctgaact tttaccgtaa atgctatgtg gaatttact tctggatgc cgcggcaatt   960
tcagaaccag aatttagtgg ctctcgcgtg gcattcacta aaattgcgat cttgatgaca  1020
atgttagatg acttataga cacgcatggg acgctggatc aattgaaaat atttaccgaa  1080
ggtgtgcgca ggtgggacgt gtcgctggtg gagggcctgc cggatttcat gaaaattgcc  1140
tttgagttct ggttaaagac ctccaacgaa ctgattgcgg aggcggttaa ggcccaaggc  1200
caggatatgg cggcctatat ccgcaaaaac gcttgggaac gctatctgga agcgtatttg  1260
caggatgccg aatggatcgc caccggtcac gttccgacat cgatgaata tctgaacaat  1320
ggcacccccca acaccggtat gtgtgtactt aatctgatcc cgttgctgct tatgggcgaa  1380
cacttgccga tcgatattct tgaacagatc tttctgccga gccggttcca ccatctgatt  1440
gaactggcta gccgactggt cgatgatgcg agagattttc aagccgaaaa agatcatggt  1500
gatttatcct gcatcgaatg ctacctgaaa gaccatccgg aatcaacagt gaagacgcc  1560
ctgaatcacg tcaacggcct gctgggaat tgtttgctgg aaatgaattg gaaattctg  1620
aaaaaacagg actcggtacc tctgtcgtgt aaaaaatact cattccacgt cctggcgcgg  1680
tcgattcagt ttatgtataa ccagggggac gggttttcga tttcgaacaa agttattaaa  1740
gaccaggtcc agaaagttct aatcgttccg gttcctatat aa                     1782
```

SEQ ID NO: 89           moltype = DNA    length = 2351
FEATURE                 Location/Qualifiers
misc_feature            1..2351
                        note = Synthetic Polynucleotide
source                  1..2351
                        mol_type = other DNA
                        organism = synthetic construct
SEQUENCE: 89

```
tgaaacgaga atttcctcca ggattttgga aggatgatct tatcgattct ctaacgtcat    60
ctcacaaggt tgcagcatca gacgagaagc gtatcgagac attaatatcc gagattaaga   120
atatgtttag atgtatgggc tatggcgaaa cgaatccctc tgcatatgac actgcttggg   180
tagcaaggat tccagcagtt gatggctctg acaaccctca ctttcctgag acggttgaat   240
ggattcttca aaatcagttg aaagatgggt cttggggtga aggattctac ttcttggcat   300
atgacagaat actggctaca cttgcatgta ttattaccct tacccctctgg cgtactgggg   360
agacacaagt acagaaaggt attgaattct tcaggacaca agctggaaag atggaagatg   420
aagctgatag tcataggcca agtggatttg aaatagtatt tcctgcaatg ctaaaggaag   480
ctaaaatctt aggcttggat ctgccttacg atttgccatt cctgaaacaa atcatcgaaa   540
agcgggaggc taagcttaaa aggattccca ctgatgttct ctatgccctt ccaacaacgt   600
tattgtattc tttggaaggt ttacaagaaa tagtagactg cagaaaata atgaaacttc   660
aatccaagga tggatcattt ctcagctctc cggcatcatc agcggcgta ttcatgcgta   720
cagggaacaa aaagtgcttg gatttcttga actttgtctt gaagaaattc ggaaccatg   780
tgccttgtca ctatccgctt gatctatttg aacgtttgtg ggcggttgat acagttgagc   840
ggctaggtat cgatcgtcat ttcaagagag agatcaagga agcattggat tatgtttaca   900
gccattggga cgaaagaggc attggatggg cgagagagaa tcctgttcct gatattgatg   960
atacagccat gggccttcga atcttgagat acatggata caatgtatcc tcagatgttt  1020
```

```
taaaaacatt tagagatgag aatggggagt tcttttgctt cttgggtcaa acacagagag  1080
gagttacaga catgttaaac gtcaatcgtt gttcacatgt ttcatttccg ggagaaacga  1140
tcatggaaga agcaaaactc tgtaccgaaa ggtatctgag gaatgctctg gaaaatgtgg  1200
atgcctttga caaatgggct tttaaaaaga atattcgggg agaggtagag tatgcactca  1260
aatatccctg gcataagagt atgccaaggt tggaggctga aagctatatt gaaaactatg  1320
ggccagatga tgtgtggctt ggaaaaaactg tatatatgat gccatacatt tcgaatgaaa  1380
agtatttaga actagcgaaa ctggacttca ataaggtgca gtctatacac caaacagagc  1440
ttcaagatct tcgaaggtgg tggaaatcat ccggtttcac ggatctgaat ttcactcgtg  1500
agcgtgtgac ggaaatatat ttctcaccgg catcctttat ctttgagccc gagttttcta  1560
agtgcagaga ggtttataca aaaacttcca atttcactgt tattttagat gatcttatg  1620
acgcccatgg atctttagac gatcttaagt tgttcacaga atcagtcaaa agatgggatc  1680
tatcactagt ggaccaaatg ccacaacaaa tgaaaatatg ttttgtgggt ttctacaata  1740
cttttaatga tatagcaaaa gaaggacgtg agaggcaagg gcgcgatgtg ctaggctaca  1800
ttcaaaatgt ttggaaagtc caacttgaag cttcacacga agaagcagaa tggtctgaag  1860
ctaaatatgt gccatccttc aatgaataca tagagaatgc gagtgtgtca atagcattgg  1920
gaacagtcgt tctcattagt gctctttca ctggggaggt tcttacagat gaagtactct  1980
ccaaaattga tcgcgaatct agatttcttc aactcatggg cttaacaggg cgtttggtga  2040
atgacaccaa aacttatcag gcagagagag gtcaaggtga ggtggcttct gccatacaat  2100
gttatatgaa ggaccatcct aaaaatctctg aagaagaagc tctacaacat gtctatagtg  2160
tcatggaaaa tgccctcgaa gagttgaata gggagtttgt gaataacaaa ataccggata  2220
tttacaaaag actggttttt gaaactgcaa gaataatgca actctttat atgcaagggg  2280
atggtttgac actatcacat gatatggaaa ttaaagcagca tgtcaaaaat tgcctcttcc  2340
aaccagttgc c                                                        2351

SEQ ID NO: 90            moltype = DNA  length = 2409
FEATURE                  Location/Qualifiers
misc_feature             1..2409
                         note = Synthetic Polynucleotide
source                   1..2409
                         mol_type = other DNA
                         organism = synthetic construct
SEQUENCE: 90
atgagcagca gcactggcac tagcaaggtg gtttccgaga cttccagtac cattgtggat    60
gatatccctc gactctccgc caattatcat ggcgatctgt ggcaccacaa tgttatacaa   120
actctggaga caccgtttcg tgagagttct acttaccaag aacgggcaga tgagctggtt   180
gtgaaaatta aagatatgtt caatgcgctc ggagacggag atatcagtcc gtctgcatac   240
gacactgcgt gggtggcgag gctggcgacc atttcctctg atggatctga aagccacgg   300
tttcctcagg ccctcaactg ggttttcaac aaccagctcc aggatggatc gtggggtatc   360
gaatcgcact ttagtttatg cgatcgattg cttaacacga ccaattctgt tatcgccctc   420
tcggttttgga aaacagggca cagccaagta caacaaggtg ctgagtttat tgcagagaat   480
ctaagattac tcaatgagga agatgagttg tcccggatt tccaaataat ctttcctgct   540
ctgctgcaaa aggcaaaagc gttggggatc aatcttcctt cgatcttcc atttatcaaa   600
tatttgtcga caacgggga agccaggctt acagatgttt ctgcggcagc agacaatatt   660
ccagccaaca tgttaatgc gttggaagga ctcgaggaag ttattgactg gaacaagatt   720
atgaggtttc aaagtaaaga tggatctttc ctgagctccc ctgcctccac tgcctgtgta   780
ctgatgaata cagggggacga aaaatgtttc acttttctca caatctgct cgacaaattc   840
ggcggctgcg tgcctgtat gtattccatc gatctgctgg aacgcctttc gctggttgat   900
aacattgagc atctcggaat cggtcgccat ttcaaacaag aaatcaaagg agctcttgat   960
tatgtctaca gacattggag tgaaaggggc atcggttggg gcagagacag ccttgttcca  1020
gatctcaaca ccacagccct cggcctgcga actcttcgca tgcacggata caatgtttct  1080
tcagacgttt tgaataattt caaagatgaa aacgggcagt tcttctcctc tgcgggccaa  1140
acccatgtcg aattgagaag cgtggtgaat cttttcagag cttccgacct tgcatttcct  1200
gacgaaagag ctatgacga tgctagaaaa ttttcagaac catatcttag agaggcactt  1260
gcaacgaaaa tctcaaccaa tacaaaacta ttcaaagaga ttgagtacgt ggtggagtac  1320
cctggacaca tgagtatccc acgcttagaa gccagaagtt atattgattc atatgacgac  1380
aattatgtat ggcagaggaa gactctatat agaatgccat ctttgagtaa ttcaaaatgt  1440
ttagaattgg caaaattgga cttcaatatc gtacaatctt tgcatcaaga gggagttgaag  1500
cttctaacaa gatggtggaa ggaatccggc atggcagata taaatttcac tcgacaccga  1560
gtggcggagg tttattttttc atcagctaca tttgaacccg aatattctgc cactagaatt  1620
gccttcacaa aaattggttg ttacaagtc cttttttgatg atatggctga catctttgca  1680
acactagatg aattgaaaag tttcactgag ggagtaaaga gatgggatac atctttgcta  1740
catgagattc cagagtgtat gcaaacttgc ttaagtttt ggttcaaatt aatgaagaa   1800
gtaaataatg atgtggttaa ggtacaagga cgtgacatgc tcgctcacat aagaaaaccc  1860
tgggagttgt acttcaattg ttatgtacaa gaaagggagt ggcttgaagc cgggtatata  1920
ccaactttg aagagtactt aaagacttat gctatatcag taggccttgg accgtgtacc  1980
ctacaaccaa tactactaat gggtgagctt gtgaaagatg atgttgttga aaagtgcac   2040
tatccctcaa atatgtttga gcttgtatcc ttgagctggc gactaacaaa cgacaccaaa  2100
acatatcagg ctgaaaagc tcgaggacaa caagcctcag gcatagcatg ctatatgaag  2160
gataatccag gagcaactga ggaagatgcc attaagcaca tatgtcgtgt tgttgatcgg  2220
gccttgaaag aagcaagctt tgaatatttc aaaccatcca atgatatccc aatgggttgc  2280
aagtccttta ttttttaacct tagattgtgt gtccaaatct tttacaagtt tatagatggg  2340
tacggaatcg ccaatgagga gattaaggac tatataagaa aagtttatat tgatccaatt  2400
caagtatga                                                           2409

SEQ ID NO: 91            moltype = DNA  length = 891
FEATURE                  Location/Qualifiers
misc_feature             1..891
                         note = Synthetic Polynucleotide
source                   1..891
```

```
                        mol_type = other DNA
                        organism = synthetic construct
SEQUENCE: 91
atgtttgatt tcaatgaata tatgaaaagt aaggctgttg cggtagacgc ggctctggat    60
aaagcgattc cgctggaata tcccgagaag attcacgaat cgatcgcgcta ctccctgtta   120
gcaggaggga aacgcgttcg tccggcatta tgcatcgcgg cctgtgaact cgtcggcggt   180
tcacaggact tagcaatgcc aactgcttgc gcaatgaaaa tgattcacac aatgagcctg   240
attcatgatg atttgccttg catggacaac gatgactttc ggcgcggtaa acctactaat   300
cataaggttt ttggcgaaga tactgcagtg ctggcgggcg atgcgctgct gtcgtttgcc   360
ttcgaacata tcgccgtcgc gacctcgaaa accgtcccgt cggaccgtac gcttcgcgtg   420
atttccgagc tgggaaagac catcggctct caaggactcg tgggtggtca ggtagttgat   480
atcacgtctg agggtgacgc gaacgtggac ctgaaaaccc tggagtggat ccatattcac   540
aaaacggccg tgctgctgga atgtagcgtg tgtcagggg ggatcttggg gggcgccacg    600
gaggatgaaa tcgcgcgtat tcgtcgttat gcccgctgtg ttggactgtt atttcaggtg   660
gtggatgaca tcctggatgt cacaaaatcc agcgaagagc ttggcaagac cgcgggcaaa   720
gaccttctga cggataaggc tacatacccg aaattgatgg gcttggagaa agccaaggag   780
ttcgcagctg aacttgccac gcgggcgaag gaagaactct cttctttcga tcaaatcaaa   840
gccgcgccac tgctgggcct cgccgattac attgcgtttc gtcagaactg a            891

SEQ ID NO: 92          moltype = DNA   length = 3150
FEATURE                Location/Qualifiers
misc_feature           1..3150
                       note = Synthetic Polynucleotide
source                 1..3150
                       mol_type = other DNA
                       organism = synthetic construct
SEQUENCE: 92
atgacaatta aagaaatgcc tcagccaaaa acgtttggag agcttaaaaa tttaccgtta    60
ttaaacacag ataaaccggt tcaagctttg atgaaaattg cggatgaatt aggagaaatc   120
tttaaattcg aggcgcctgg tcgtgtaacg cgctactttat caagtcagcg tctaattaaa   180
gaagcatgcg atgaatcacg ctttgataaa aacttaagtc aagcgcttaa atttgtacgt   240
gattttgcag agacgggtt atttacaagc tggacgcatg aaaaaaattg gaaaaaagcg   300
cataatatct tacttccaag cttcagtcag caggcaatga aaggctatca tgcgatgatg   360
gtcgatatcg ccgtgcagct tgttcaaaag tgggagcgtc taaatgcaga tgagcatatt   420
gaagtaccgg aagcagtgac acgtttaacg cttgatcaaa ttggtctcttg cggctttaac   480
tatcgctttta acagctttta ccgagatcag cctcatccat ttattacaag tatggtccgt   540
gcactggatg aagcaatgaa caagctgcag cgagcaaatc cagacgaccc agcttatgat   600
gaaaacaagc gccagtttca agaagatatc aaggtgatga acgaccctagt agataaaatt   660
attgcagatc gcaaagcaag cggtgaacaa agcgatgatt tattaacgca tatgctaaac   720
ggaaaagatc cagaaacggg tgagccgctt gatgacgaga acattcgcta tcaaattatt   780
acattcttaa ttgcgggaca cgaaacaaca agtggtctttt tatcatttgc gctgtatttc   840
ttagtgaaaa atccacatgt attacaaaaa gcagcagaag aagcagcacg agttctagta   900
gatcctgttc caagctacaa acaagtcaaa cagcttaaat atgtcggcat ggtcttaaac   960
gaagcgctgc gcttatggcc aactgctcct gcgttttccc tatatgcaaa agaagatacg  1020
gtgcttggag gagaatatcc tttagaaaaa ggcgacgaaa taatggttct gattcctcag  1080
cttcaccgtg ataaaacaat tggggagac gatgtgaaag agttccgtcc agagcgtttt  1140
gaaaatccaa gtgcgattcc gcagcatgcg tttaaaccgt ttggaaacgg tcagcgtgcg  1200
tgtatcggtc agcagttcgc tcttcatgaa gcaacgctgg tacttggtat gatgctaaaa  1260
cactttgact tgaagatca tacaaactac gagctggata ttaaagaaac tttaacgtta  1320
aaacctgaag gctttgtggt aaaagcaaaa tcgaaaaaa ttccgcttgg cggtattcct  1380
tcacctagca ctgaacagtc tgctaaaaaa gtacgcaaaa aggcagaaa cgctcataat  1440
acgccgctgc ttgtgctata cggttcaaat atgggaacag ctgaaggaac ggcgcgtgat  1500
ttagcagata ttgcaatgag caaaggattt gcaccgcagg tcgcaacgct tgattcacac  1560
gccggaaatc ttccgcgcga aggagctgta ttaattgtaa cggcgtctta taacggtcat  1620
ccgcctgata acgcaaagca atttgtcgac tggttagacc aagcgtctgc tgatgaagta  1680
aaggcgttc gctactccgt atttggatgc ggcgataaaa actgggctac tacgtatcaa  1740
aaagtgcctg ctttatcga tgaaacgctt gccgctaaag gggcagaaaa catcgctgac  1800
cgcggtgaag cagatgcaag cgacgacttt gaaggcacat atgaagaatg gcgtgaacat  1860
atgtgagtg acgtagcagc ctactttaac ctcgacattg aaaacagtga agataataaa  1920
tctactcttt cacttcaatt tgtcgacagc gccgcggata tgccgcttgc gaaaatgcac  1980
ggtgcgtttt caacgaacgt cgtagcaagc aaagaacttc aacagccagg cagtgcacga  2040
agcacgcgac atcttgaaat tgaacttcca aagaagctt cttatcaaga aggagatcat  2100
ttaggtgtta ttcctcgcaa ctatgaagga atagtaaacc gtgtaacagc aaggttcggc  2160
ctagatgcat cacagcaaat ccgtctgaaa gcagaagaag aaaaattagc tcatttgcca  2220
ctcgctaaaa cagtatccgt agaagagctt ctgcaatacg tggagcttca agatcctgtt  2280
acgcgcacgc agcttcgcgc aatgctgct aaacgggtct gccgccgca taagtagag   2340
cttgaagcct tgcttgaaaa gcaagcctac aaagaacaag tgctggcaaa cgtttaaca  2400
atgcttgaac tgcttgaaaa ataccccggcg tgtgaaatga aatcagcga ttttatcgcc  2460
cttctgccaa gcatacgccc gcgctattac tcgatttctt catccacctcg tgtcgatgaa  2520
aaacaagcaa gcatcacggt cagcgttgtc tcaggagaa cgtggagcgg atatgagaa   2580
tataaaggaa ttgcgtcgaa ctatcttgcc gagctgcaag aaggagatac gattacgtgc  2640
tttatttcca caccgcagtc agaatttacg ctgccaaaag accctgaaac gccgcttatc  2700
atggtcgaac cgggaacagg cgtcgcgccg tttagaggct ttgtgcaggc gcgcaaacag  2760
ctaaaagaac aaggacagtc acttggagaa gcacatttat acttcggctg ccgttcacct  2820
catgaagact atctgtatca agaagagctt gaaacgcccc aaagcgaagg catcattacg  2880
cttcataccg ctttttctcg catgccaaat cagccgaaaa catcgtttca gcacgtaatg  2940
gaacaagacg gcaagaaatt gattgaactt cttgatcaag gagcgcactt ctatatttgc  3000
ggagacggaa gccaaatggc acctgccgtt gaagcaacgc ttatgaaaag ctatgctgac  3060
gttcaccaag tgagtgaagc agacgctcgc ttatggctgc agcagctaga agaaaaaggc  3120
```

```
cgatacgcaa aagacgtgtg ggctgggtaa                                      3150

SEQ ID NO: 93           moltype = DNA   length = 789
FEATURE                 Location/Qualifiers
misc_feature            1..789
                        note = Synthetic Polynucleotide
source                  1..789
                        mol_type = other DNA
                        organism = synthetic construct
SEQUENCE: 93
atgagggaag cggtgatcgc cgaagtatcg actcaactat cagaggtagt tggcgtcatc       60
gagcgccatc tcgaaccgac gttgctggcc gtacatttgt acggctccgc agtggatggc      120
ggcctgaagc cacacagtga tatttgatttg ctggttacgg tgaccgtaag gcttgatgaa     180
acaacgcggc gagctttgat caacgacctt ttggaaactt cggcttcccc tggagagagc      240
gagattctcc gcgctgtaga agtcaccatt gttgtgcacg acgacatcat tccgtggcgt      300
tatccagcta agcgcgaact gcaatttgga gaatggcagc gcaatgacat tcttgcaggt      360
atcttcgagc cagccacgat cgacattgat ctggctatct gctgacaaa agcaagagaa       420
catagcgttg ccttggtagg tccagcggcg gaggaactct ttgatccggt tcctgaacag      480
gatctatttg aggcgctaaa tgaaaccta acgctatgga actcgccgcc cgactgggct       540
ggcgatgagc gaaatgtagt gcttacgttg tcccgcattt ggtacagcgc agtaaccggc      600
aaaatcgcgc cgaaggatgt cgctgccgac tgggcaatgg agcgcctgcc ggcccagtat      660
cagcccgtca tacttgaagc tagacaggct tatcttggac aagaagaaga tcgcttggcc      720
tcgcgcgcag atcagttgga agaatttgtc cactacgtga aaggcgagat caccaaggta      780
gtcggcaaa                                                              789

SEQ ID NO: 94           moltype = DNA   length = 432
FEATURE                 Location/Qualifiers
misc_feature            1..432
                        note = Synthetic Polynucleotide
source                  1..432
                        mol_type = other DNA
                        organism = synthetic construct
SEQUENCE: 94
ttggctacta cacttgaacg tattgagaag aactttgtca ttactgaccc aaggttgcca       60
gataatccca tttatattcg cgtccgatagt ttcttgcagt tgacagaata tagccgtgaa     120
gaaattttgg gaagaaactg caggtttcta caaggtcctg aaactgatcg cgcgacagtg      180
agaaaaatta gagatgccat agataaccaa acagaggtca ctgttcagct gattaattat      240
acaaagagtg gtaaaaagtt ctggaacctc tttcacttgc agcctatgcg agatcagaag      300
ggagatgtcc agtactttat tggggttcag ttggatggaa ctgagcatgt ccgagatgct      360
gccgagagag agggagtcat gctgattaag aaaactgcag aaaatattga tgaggcggca      420
aaagaacttc ca                                                          432

SEQ ID NO: 95           moltype = DNA   length = 2244
FEATURE                 Location/Qualifiers
misc_feature            1..2244
                        note = Synthetic Polynucleotide
source                  1..2244
                        mol_type = other DNA
                        organism = synthetic construct
SEQUENCE: 95
atggctagcg tggcaggtca tgcctctggc agcccgcat tcgggaccgc cgatctttcg        60
aattgcgaac gtgaagagat ccacctcgcc ggctcgatcc agccgcatgg cgcgcttctg      120
gtcgtcagcg agccggatca tcgcatcatc caggccagcg ccaacgccgc ggaatttctg      180
aatctcggaa gcgtgctcgg cgttccgctc gccgagatcg acggcgatct gttgatcaag      240
atcctgccgc atctcgatcc caccgccgaa ggcatgccgg tcggtgcg ctgccggatc        300
ggcaatccct ccacggagta cgacggtctg atgcatcggc ctccggaagg cgggctgatc      360
atcgagctcg aacgtgccgg cccgccgatc gatcgtccg gcacgctggc gcggcgctg        420
gagcggatcc gcacggcggg ctcgctgcgc gcgctgtgcg atgacaccgc gctgctgttt      480
cagcagtgca ccggctacga ccgggtgatg gtgtatcgct tcgacgagca gggccacggc      540
gaagtgttct ccgagcgcca cgtgcccggg ctcgaatcct atttcggcaa ccgctatccg      600
tcgtcggaca ttccgcagat ggcgcggcgg ctgtacgagc ggcagcgcgt ccgcgtgctg      660
gtcgacgtca gctatcagcc ggtgccgctg agccgcggc tgtcgccgct gaccgggcgc       720
gatctcgaca tgtcgggctg cttcctgcgc tcgatgtcgc cgatccatct gcagtacctg      780
aagaacatgg gcgtgcgcgc cacccctggtg gtgtcgctgg tggtcggcgg caagctgtg     840
ggcctggttg cctgtcatca ttatctgccg cgcttcatgc atttcgagct gcggggcgatc     900
tgcgaactgc tcgccgaagc gatcgcgacg cggatcaccg cgcttgagag cttcgcgcag      960
agccagtcgg agctgttcgt gcagcggctc gaacagcgca tgatcgaagc gattacccgt     1020
gaaggcgatt ggcgcgcagc gattttcgac accagcaat cgatcctgca gccgctgcac      1080
gccgcggtt gcgcgctggt gtacgaagac agatcgaga ccatcgacga cgtgcttcg        1140
acgcaggatg tgcgcgagat cgccgggtgg ctcgatcgcc agccgcgcgc ggcggtgacc     1200
tcgaccgcgt cgctcggtct cgacgtgccg gagctcgcgc atctgacgcg gatggcgagc     1260
ggcgtggtcg cggcgccgat ttcggatcat cgcggcgagt ttctgatgtg gttccgcccc    1320
gagcgcgtcc acaccgttac ctgggcggc gatccgaaga agccgttcac gatgggcgat       1380
acaccggcag atcgtgccg gcggcgtcc ttcgccaaat ggcatcaggt tgtcgaaggc       1440
acgtccgatc cgtggacggc cgccgatctc gccgcggctc gcaccatcgg tcagaccgtc     1500
gccgacatcg tgctgcaatt ccgcgcgtg cggacactga tcgcccgcga acagtacgaa      1560
cagttttcgt cccaggtgca cgcttcgatg cagccggtgc tgatcaccga cgccgaaggc     1620
cgcatcctgc tgatgaacga ctcgttccgc gacatgttcg cggcgggttc gccatccgcc     1680
gtccatctcg acgatctcgc cgggttcttc gtcgaatcga acgatttcct gcgcaacgtc    1740
```

```
gccgaactga tcgatcacgg ccgcgggtgg cgcggcgaag ttctgctgcg cggcgcaggc   1800
aaccgcccgt tgccgctggc agtgcgcgcc gatccggtga cgcgcacgga ggaccagtcg   1860
ctcggcttcg tgctgatctt cagcgacgct accgatcgtc gcaccgcaga tgccgcacgc   1920
acgcgtttcc aggaaggcat tcttgccagc gcacgtcccg gcgtgcggct cgactccaag   1980
tccgacctgt tgcacgagaa gctgctgtcc gcgctggtcg agaacgcgca gcttgccgca   2040
ttggaaatca cttacggcgt cgagaccgga cgcatcgccg agctgctcga aggcgtccgc   2100
cagtcgatgc tgcgcaccgc cgaagtgctc ggccatctgg tgcagcacgc ggcgcgcacg   2160
gccggcagcg acagctcgag caatggctcg cagaacaaga aggaattcga tagtgctggt   2220
agtgctggta gtgctggtac tagt                                         2244

SEQ ID NO: 96           moltype = DNA  length = 1308
FEATURE                 Location/Qualifiers
misc_feature            1..1308
                        note = Synthetic Polynucleotide
source                  1..1308
                        mol_type = other DNA
                        organism = synthetic construct
SEQUENCE: 96
atggagatgg aaaaggagtt cgagcagatc gacaagtccg ggagctgggc ggccatttac    60
caggatatcc gacatgaagc cagtgacttc ccatgtagag tggccaagct tcctaagaac   120
aaaaaccgaa ataggtacag agacgtcagt cccctttgacc atagtcggat taaactcat   180
caagaagata atgactatat caacgctagt ttgataaaaa tggaagaagc ccaaaggagt   240
tacattctta cccagggccc tttgcctaac acatgcggtc acttttggga gatggtgtgg   300
gagcagaaaa gcaggggtgt cgtcatgctc aacagagtga tggagaaagg ttcgttaaaa   360
tgcgcacaat actggccaca aaagaagaa aagagatga tctttgaaga cacaaatttg   420
aaattaacat tgatctctga agatatcaag tcatattata cagtcgaca gctagaattg   480
gaaaacctta caacccaaga aactcgagag atcttacatt ccactatac cacatggcct   540
gactttggag tccctgaatc accagcctca ttcttgaact ttctttcaa agtccgagag   600
tcagggtcac tcagcccgga gcacgggccc gttgtggtgc actgcagtgc aggcatcggc   660
aggtctggaa ccttctgtct ggctgatacc tgcctcttgc tgatgaacaa gaggaaagac   720
ccttcttccg ttgatatcaa gaaagtgctg ttagaaatga ggaagtttcg gatggggctg   780
atccagacag ccgaccagct gcgcttctcc tacctggctg tgatcgaagg tgccaaattc   840
atcatggggg actcttccgt gcaggatcag tggaaggagc tttcccacga ggacctggag   900
ccccaccgg agcatatccc cccacctccc cggccacca acgaatcct ggagccacac   960
aatgggaaat gcagggagtt cttcccaaat caccagtggg tgaaggaaga gacccaggag   1020
gataaagact gccccatcaa ggaagaaaaa ggagcccct aaatgccgc accctacggc   1080
atcgaaagca tgagtcaaga cactgaagtt agaagtcggg tcgtgggggg aagtcttcga   1140
ggtgcccagg ctgcctcccc agccaaaggg gagccgtcac tgcccgagaa ggacgaggac   1200
catgcactga gttactggaa gcccttcctg gtcaacatgt gcgtggctac ggtcctcacg   1260
gccggcgctt acctctgcta caggttcctg ttcaacagca acatag               1308

SEQ ID NO: 97           moltype = DNA  length = 951
FEATURE                 Location/Qualifiers
misc_feature            1..951
                        note = Synthetic Polynucleotide
source                  1..951
                        mol_type = other DNA
                        organism = synthetic construct
SEQUENCE: 97
atgcccacca ccatcgagcg ggagttcgaa gagttggata tcagcgtcg ctggcagccg    60
ctgtacttgg aaattcgaaa tgagtcccat gactatcctc atagagtggc caagtttcca   120
gaaaacagaa atcgaaacag atacagagat gtaagcccat atgatcacag tcgtgttaaa   180
ctgcaaaatg ctgagaatga ttatattaat gccagtttag ttgacataga agaggcacaa   240
aggagttaca tcttaacaca gggtccactt cctaacacat gctgccattt ctggcttatg   300
gtttggcagc agaagaccaa agcagttgtc atgctgaacc gcattgtgga gaaagaatcg   360
gttaaatgtg cacagtactg gccaacagat gaccaagaga tgctgttta agaaacagga   420
ttcagtgtga agctcttgtc agaagatgtg agtcgtatt atacagtaca tctactacaa   480
ttagaaaata tcaatagtgg tgaaaccaga acaaatatct actttcatta tactacctgg   540
ccagattttg gagtccctga tcaccagct tcatttctca atttcttgtt taaagtgaga   600
gaatctggct ccttgaaccc tgaccatggg cctgcggtga tccactgtag tgcaggcatt   660
gggcgctctg gcaccttctc tctggtagac acttgtcttg ttttgatgga aaaggagat   720
gatattaaca taaaacaagt gttactgaac atgagaaat accgaatggg tcttattcag   780
accccagatc aactgagatt ctcatacatg gctataatga aggagcaaa atgtataag   840
ggagattcta gtatacagaa acgatggaaa gaactttcta aggaagactt atctcctgcc   900
tttgatcatt caccaaacaa aataatgact gaaaaataca atgggaacag a            951

SEQ ID NO: 98           moltype = DNA  length = 900
FEATURE                 Location/Qualifiers
misc_feature            1..900
                        note = Synthetic Polynucleotide
source                  1..900
                        mol_type = other DNA
                        organism = synthetic construct
SEQUENCE: 98
atgtcttctg gtgtagatct gggtaccgag aacctgtact ccaatccat gtcccgtgtc    60
ctccaagcag aagagcttca tgaaaaggcc ctggaccctt cctgctgca ggcggaattc   120
tttgaaatcc ccatgaactt tgtggatccg aagagtacg acatccctgg ctggtgcgg   180
aagaaccggt acaaaaccat acttcccaac cctcacagca gagtgtgtct gacctcacca   240
gaccctgacg accctctgag ttcctacatc aatgccaact acatccgggg ctatggtggg   300
```

```
gaggagaagg tgtacatcgc cactcaggga cccatcgtca gcacggtcgc cgacttctgg    360
cgcatggtgt ggcaggagca cacgcccatc attgtcatga tcaccaacat cgaggagatg    420
aacgagaaat gcaccgagta ttggccggag gagcaggtgg cgtacgacgg tgttgagatc    480
actgtgcaga aagtcattca cacggaggat taccggctgc gactcatctc cctcaagagt    540
gggactgagg agcgaggcct gaagcattac tggttccaga cctggcccga ccagaagacc    600
ccagaccggg ccccccccact cctgcacctg gtgcgggagg tggaggaggc agcccagcag    660
gaggggcccc actgtgcccc catcatcgtc cactgcagtg cagggattgg gaggaccggc    720
tgcttcattg ccaccagcat ctgctgccag cagctgcggc aggagggtgt agtggacatc    780
ctgaagacca cgtgccagct ccgtcaggac aggggcggca tgatccagac atgcgagcag    840
taccagtttg tgcaccacgt catgagcctc tacgaaaagc agctgtccca ccagtcctga    900
```

SEQ ID NO: 99          moltype = DNA    length = 1788
FEATURE                Location/Qualifiers
misc_feature           1..1788
                       note = Synthetic Polynucleotide
source                 1..1788
                       mol_type = other DNA
                       organism = synthetic construct
SEQUENCE: 99
```
atggtgaggt ggtttcaccg agacctcagt gggctggatg cagagaccct gctcaagggc     60
cgaggtgtcc acgtagcttc cctggctcgg cccagtcgca agaaccaggg tgactcttcg    120
ctctccgtca gggtgggga tcaggtgacc catattcgag tccagaactc aggggatttc    180
tatgacctgt atggagggga gaagtttgcg actctgacag agctggtgga gtactacact    240
cagcagcagg gtgtggtgca ggaccgcgac ggcaccatca tccacctcaa gtacccgctg    300
aactgctccg atcccactag tgagaggtgg taccatggcc acatgtctgg cgggcaggca    360
gagacgctgc tgcaggccaa gggcgagccc tggacgtttc ttgtgcgtga gagcctcagc    420
cagcctggag acttcgtgct ttctgtgctc agtgaccagc ccaaggctgg cccaggctcc    480
ccgctcaggg tcacccacat caaggtcatg tgcgagggtg acgctacac agtgggtggt    540
ttggagacct cgacagcct cacggacctg gtggagcatt tcaagaagac ggggattgag    600
gaggcctcag gcgcctttgt ctacctgcgg cagccgtact atgccacgag ggtgaatgcg    660
gctgacattg agaaccgagt gttggaactg aacaagaagc aggagtccga ggatacagcc    720
aaggctggct tctgggagga gttgagagt ttgcagaagc aggaggtgaa gaacttgcac    780
cagcgtctgc aagggcaacg gccagagaac aagggcaaga accgctacaa gaacattctc    840
ccctttgacc acagccgagt gatcctgcag ggacgggaca gtaacatccc cggtgccac    900
tacatcaatg ccaactacat caagaaccag ctgctaggcc ctgatgagaa cgctaagacc    960
tacatcgcca gccagggctg tctggaggcc acgtcaatga cttctggca gatggcgtgg   1020
caggagaaca gccgtgtcat cgtcatgacc acccgagagg tggagaaagg ccggaacaaa   1080
tgcgtcccat actggcccga ggtgggcatg cagccgtgct tatgggccta ctctgtgacc   1140
aactgcaggg agcatgacac aaccgaatac aaactccgta ccttacaggt ctccccgctg   1200
gacaatggag acctgattcg ggagatctgg cattaccagt acctgagctg gcccgaccat   1260
ggggtcccca gtgagcctgg gggtgtcctc agcttcctgg accagatcaa ccagcggcag   1320
gaaagtctgc tcacgcaggg gcccatcatc gtgcactgca gcgccggcat cggccgcaca   1380
ggcaccatca ttgtcatcga catgctcatg gagaacatct ccaccaaggg cctggactgt   1440
gacattgaca tccagaagac catccagatg gtgcgggcgc agcgctcggg catggtgcag   1500
acggaggcgc agtacaagtt catctacgtg gccatcgccc agttcattga aaccactaag   1560
aagaagctgg aggtcctgca gtcgcagaag ggccaggagt cggagtacgg gaacatcacc   1620
tatcccccag ccatgaagaa tgcccatgcc aaggcctccc gcacctcgtc caaacacaag   1680
gaggatgtgt atgagaacct gcacactaag aacaagaggg aggagaaagt gaagaagcag   1740
cggtcagcag acaaggagaa gagcaagggt tccctcaaga ggaagtga              1788
```

SEQ ID NO: 100         moltype = DNA    length = 1782
FEATURE                Location/Qualifiers
misc_feature           1..1782
                       note = Synthetic Polynucleotide
source                 1..1782
                       mol_type = other DNA
                       organism = synthetic construct
SEQUENCE: 100
```
atgacatcgc ggagatggtt tcacccaaat atcactggtg tggaggcaga aaacctactg     60
ttgacaagag gagttgatgg cagttttttg gcaaggccta gtaaaagtaa ccctggagac    120
ttcacacttt ccgttagaag aaatggagct gtcacccaca tcaagattca gaacactggt    180
gattactatg acctgtatgg aggggagaaa tttgccactt ggctgagtt ggtccagtat    240
tacatggaac atcacgggca attaaaagag aagaatggag atgtcattga gcttaaatat    300
cctctgaact gtgcagatcc tacctctgaa aggtggttc atggacatct ctctgggaaa    360
gaagcagaga aattattaac tgaaaaagga aaacatggta gttttcttgt acgagggagc    420
cagagccacc ctgagatttt tgttctttct gtgcgcactg gtgatgacaa aggggagagc    480
aatgacggca agtctaaagt gacccatgtt atgattcgct gtcaggaact gaaatacgac    540
gttggtggag gagaacggtt tgattctttg acagatcttg tggaacatta taagaagaat    600
cctatggtgg aaacattggg tacagtacta caactcaagc agccccttaa cacgactcgt    660
ataaatgctg ctgaaataga aagcagagtt cgagaactaa gcaaattagc tgagaccaca    720
gataaagtca acaaggcttt tgggaagaa tttgagacac tacaacaaca ggagtgcaaa    780
cttctctaca gccgaaaaga gggtcaaagg caagaaaaca aaacaaaaa tagatataaa    840
aacatcctgc cctttgatca taccaggttt gtcctacacg atggtgatcc caatgagcct    900
gtttcagatt acatcaatgc aaatatcatc gtgcctgaat ttgaaaccaa gtgcaacaat    960
tcaaagccca aaagagttta cattgccaca caaggctgcc tgcaaaacac ggtgaatgac    1020
ttttggcgga tggtgttcca agaaaactcc cgagtgattg tcatgacaac gaaagaagtg    1080
gagagaggaa agagtaaatg tgtcaaatac tggcctgatg agtatgctct aaaagaatat    1140
ggcgtcatgc gtgttaggaa cgtcaaagaa agcgccgctc atgactatac gctaagagaa    1200
cttaaactt caaaggttgg acaagggaat acggagagaa cggtctggca ataccacttt    1260
```

```
cggacctggc cggaccacgg cgtgcccagc gaccctgggg gcgtgctgga cttcctggag   1320
gaggtgcacc ataagcagga gagcatcatg gatgcagggc cggtcgtggt gcactgcagt   1380
gctggaattg gccggacagg gacgttcatt gtgattgata ttcttattga catcatcaga   1440
gagaaaggtg ttgactgcga tattgacgtt cccaaaacca tccagatggt gcggtctcag   1500
aggtcaggga tggtccagac agaagcacag taccgattta tctatatggc ggtccagcat   1560
tatattgaaa cactacagcg caggattgaa gaagagcaga aaagcaagag gaaagggcac   1620
gaatatacaa atattaagta ttctctagcg gaccagacga gtggagatca gagccctctc   1680
ccgccttgta ctccaacgcc accctgtgca gaaatgagag aagacagtgc tagagtctat   1740
gaaaacgtgg gcctgatgca acagcagaaa agtttcagat ga                     1782

SEQ ID NO: 101          moltype = DNA   length = 1275
FEATURE                 Location/Qualifiers
misc_feature            1..1275
                        note = Synthetic Polynucleotide
source                  1..1275
                        mol_type = other DNA
                        organism = synthetic construct
SEQUENCE: 101
atggagcaag tggagatcct gaggaaattc atccagaggg tccaggccat gaagagtcct     60
gaccacaatg gggaggacaa cttcgcccgg gacttcatgc ggttaagaag attgtctacc    120
aaatatagaa cagaaaagat atatcccaca gccactggag aaaaagaaga aaatgttaaa    180
aagaacagat acaaggacat actgccattt gatcacgacc gagttaaatt gacattaaag    240
actccttcac aagattcaga ctatatcaat gcaattttta taaagggcgt ctatgggcca    300
aaaagcatatg tagcaactca aggaccttta gcaaatacag taatagattt ttggaggatg    360
gtatgggagt ataatgttgt gatcattgta atggcctgcc gagaatttga gatgggaagg    420
aaaaaatgtg agcgctattg gccttttgat ggagaagacc ccataacgct tgcaccattt    480
aaaatttctt gtgaggatga acaagcaaga acagactact tcatcaggac actcttactt    540
gaatttcaaa atgaatctcg taggctgtat cagtttcatt atgtgaactg ccagaccat    600
gatgttcctt catcatttga ttctattctg gacatgataa gcttaatgag gaaatatcaa    660
gaacatgaag atgttcctat ttgtattcat tgcagtgcag gctgtggaag aacaggtgcc    720
atttgtgcca tagattatac gtggaattta ctaaagctg gaaaatacc agaggaattt    780
aatgtattta atttaataca agaaatgaga acacaaggc attctgcagt acaaacaaag    840
gagcaatatg aacttgttca tagagctatt gcccaactgt ttgaaaaaca gctacaacta    900
tatgaaattc atggagctca gaaaattgct gatggagtga atgaaattaa cactgaaaac    960
atggtcagct ccatagagcc tgaaaaacaa gattctcctc ctccaaaacc accaaggacc   1020
cgcagttgcc ttgttgaagg ggatgctaaa aagaaatac tgcagccacc ggaacctcat   1080
ccagtgccac ccatcttgac accttctccc ccttcagctt ttccaacagt cactactgtg   1140
tggcaggaca atgatagata ccatccaaag ccagtgttgc aatggtttca tcagaacaac   1200
attcagcaga cctcaacaga aactatagta aatcaacaga cttccaggg aaaaatgaat   1260
caacaattga acaga                                                    1275

SEQ ID NO: 102          moltype = DNA   length = 899
FEATURE                 Location/Qualifiers
misc_feature            1..899
                        note = Synthetic Polynucleotide
source                  1..899
                        mol_type = other DNA
                        organism = synthetic construct
SEQUENCE: 102
atggaccaaa gagaaattct gcagaagttc ctgatgagg cccaaagcaa gaaaattact     60
aaagaggagt ttgccaatga atttctgaag ctgaaaaggc aatctaccaa gtacaaggca    120
gacaaaacct atcctacaac tgtggctgag aagcccaaga atatcaagaa aaacagatat    180
aaggatattt tgcccatga ttatagccgg gtagaactat ccctgataac ctctgatgag    240
gattccagct acatcaatgc caacttcatt aagggagttt atggacccaa ggcttatatt    300
gccacccgag gtcctttatc tacaacccctc ctggacttca gtgaggatga ttgggaatat    360
agtgtcctta tcattgttat ggcatgcatg gagtatgaaa tgggaaagaa aaagtgtgag    420
cgctactggg ctgagccagg agagatgcag ctggaatttg ccctttctc tgtatcctgt    480
gaagctgaaa aaggaaatc tgattatata atcaggactc taaagtaa gttcaatagt    540
gaaactcgaa ctatctacca gtttcattac aagaattggc cagaccatga tgtaccttca    600
tctatagacc ctattcttga gctcatctgg gatgtacgtt gttaccaaga ggatgacagt    660
gttcccatat gcattcactg cagtgctggc tgtggaagga ctggtgttat ttgtgctatt    720
gattatacat ggatgttgct aaaagatggg ataattcctg agaacttcag tgttttcagt    780
ttgatccggg aaatgcggac acagaggcct tcattagttc aaacgcagga caatatgaa    840
ctggtctaca atgctgtatt agaactattt aagagacaga tggatgttat cagagataa    899

SEQ ID NO: 103          moltype = DNA   length = 1149
FEATURE                 Location/Qualifiers
misc_feature            1..1149
                        note = Synthetic Polynucleotide
source                  1..1149
                        mol_type = other DNA
                        organism = synthetic construct
SEQUENCE: 103
atgagtctga agaaaaaaac acaatctctg tttgccaacg catttggcta ccctgccact     60
cacaccattc aggcgcctgg ccgcgtgaat ttgattggtg aacacaccga ctacaacgac    120
ggtttcgttc tgccctgcgc gattgattat caaaccgtga tcagttgtgc accacgcgat    180
gaccgtaaag ttcgcgtgat ggcagccgat tatgaaaatc agctcgacga gttttccctc    240
gatgcgccca ttgtcgcaca tgaaaactat caatgggcta actacgttcg tggcgtggta    300
aacatctgc aactgcgtaa caacagcttc ggcggcgtgg acatggtgat cagcggcaat    360
```

```
gtgccgcagg gtgccgggtt aagttcttcc gcttcactgg aagtcgcggt cggaaccgta    420
ttgcagcagc tttatcatct gccgctggac ggcgcacaaa tcgcgcttaa cggtcaggaa    480
gcagaaaacc agtttgtagg ctgtaactgc gggatcatgg atcagctaat ttccgcgctc    540
ggcaagaaag atcatgcctt gctgatcgat tgccgctcac tggggaccaa agcagtttcc    600
atgcccaaag gtgtggctgt cgtcatcatc aacagtaact tcaaacgtac cctggttggc    660
agcgaataca acacccgtcg tgaacagtgc gaaaccggtg cgcgtttctt ccagcagcca    720
gccctgcgtg atgtcaccat tgaagagttc aacgctgttg cgcatgaact ggacccgatc    780
gtggcaaaac gcgtgcgtca tatactgact gaaaacgccc gcaccgttga agctgccagc    840
gcgctggagc aaggcgacct gaaacgtatg ggcgagttga tggcggagtc tcatgcctct    900
atgcgcgatg atttcgaaat caccgtgccg caaattgaca ctctggtaga aatcgtcaaa    960
gctgtgattg gcgacaaagg tggcgtacgc atgaccggcg gcggatttgg cggctgtatc   1020
gtcgcgctga tcccggaaga gctggtgcct gccgtacagc aagctgtcgc tgaacaatat   1080
gaagcaaaaa caggtattaa agagactttt tacgtttgta aaccatcaca aggagcagga   1140
cagtgctga                                                           1149

SEQ ID NO: 104         moltype = DNA   length = 1422
FEATURE                Location/Qualifiers
misc_feature           1..1422
                       note = Synthetic Polynucleotide
source                 1..1422
                       mol_type = other DNA
                       organism = synthetic construct
SEQUENCE: 104
atgaacatca aaaagtttgc aaaacaagca acagtattaa cctttactac cgcactgctg     60
gcaggaggcg caactcaagc gtttgcgaaa gaaacgaacc aaaagccata taaggaaaca    120
tacggcattt cccatattac acgccatgat atgctgcaaa tccctgaaca gcaaaaaaat    180
gaaaaatatc aagttcctga attcgattcg tccacaatta aaaatatctc ttctgcaaaa    240
ggcctggacg tttgggacag ctggccatta caaaacgctg acggcactgt cgcaaactat    300
cacggctacc acatcgtctt tgcattagcc ggagatccta aaaatgcgga tgacacatcg    360
atttacatgt tctatcaaaa agtcggcgaa acttctattg acagctggaa aaacgctggc    420
cgcgtcttta aagacagcga caattcgat gcaaatgatt ctatcctaaa agaccaaaca    480
caagaatggt caggttcagc cacatttaca tctgacggaa aaatccgttt attctacact    540
gatttctccg gtaaacatta cggcaaacaa acactgacaa ctgcacaagt taacgtatca    600
gcatcagaca gctctttgaa catcaacggt gtagaggatt ataaatcaat ctttgacggt    660
gacggaaaaa cgtatcaaaa tgtacagcag ttcatcgatg aaggcaacta cagctcaggc    720
gacaaccata cgctgagaga tcctcactac gtagaagata aaggccacaa atacttagta    780
tttgaagcaa acactggaac tgaagatggc taccaaggcg aagaatcttt atttaacaaa    840
gcatactatg gcaaaagcac atcattcttc cgtcaagaaa gtcaaaaact tctgcaaagc    900
gataaaaaac gcacggctga gttagcaaac ggcgctctcg gtatgattga gctaaacgat    960
gattacacac tgaaaaagt gatgaaaccg ctgattgcat ctaacacagt aacagatgaa   1020
attgaacgcg cgaacgtctt taaaatgaac ggcaaatggt acctgttcac tgactccgc   1080
ggatcaaaaa tgacgattga cggcattacg tctaacgata tttacatgct tggttatgtt   1140
tctaattctt taactggccc atacaagccg ctgaaacaaa ctggccttgt gttaaaaatg   1200
gatcttgatc ctaacgatgt aacctttact tactcacact tcgctgtacc tcaagcgaaa   1260
ggaaacaatg tcgtgattac aagctatatg acaaacagag gattctacgc agacaaacaa   1320
tcaacgtttg cgccaagctt cctgctgaac atcaaaggca agaaaacatc tgttgtcaaa   1380
gacagcatcc ttgaacaagg acaattaaca gttaacaaat aa                     1422
```

GENETICALLY ENCODED SYSTEM FOR CONSTRUCTING AND DETECTING BIOLOGICALLY ACTIVE AGENTS

CROSS-REFERENCE

This application is a Divisional of U.S. application Ser. No. 17/141,321, filed Jan. 5, 2021, which is a Continuation of International Application No. PCT/US2019/040896, filed Jul. 8, 2019, which claims benefit of U.S. Provisional Application No. 62/694,838, filed Jul. 6, 2018, which are incorporated herein by reference in their entirety.

STATEMENT OF GOVERNMENT SUPPORT

This invention was made with government support under Award 1750244 and 1804897 awarded by the National Science Foundation. The government has certain rights in the invention.

SEQUENCE LISTING

The instant application contains a Sequence Listing which has been submitted electronically in XML, file format and is hereby incorporated by reference in its entirety. Said XML copy, created on Dec. 9, 2022, is named 57123-701_401_SL.xml and is 196,880 bytes in size.

FIELD OF THE INVENTION

This invention relates to the field of genetic engineering. Specifically, the invention relates to the construction of operons to produce biologically active agents. For example, operons may be constructed to produce agents that control the function of biochemical pathway proteins (e.g, protein phosphatases, kinases and/or proteases). Such agents may include inhibitors and modulators that may be used in studying or controlling phosphatase function associated with abnormalities in a phosphatase pathway or expression level. Fusion proteins, such as light activated protein phosphatases, may be genetically encoded and expressed as photoswitchable phosphatases. Systems are provided for use in controlling phosphatase function within living cells or in identifying small molecule inhibitors/activator/modulator molecules of protein phosphatases associated with cell signaling.

BACKGROUND

Protein phosphorylation is involved with cell signaling as in part it controls the location and timing of cellular differentiation, movement, proliferation, and death[1-4]; its misregulation is implicated in cancer, diabetes, obesity, and Alzheimer's disease, among other disorders[5-9]. Optical tools to exert spatiotemporal control over the activity of phosphorylation-regulating enzymes in living cells could elucidate the mechanisms by which cells transmit, filter, and integrate chemical signals[10,11], reveal links between seemingly disparate physiological processes (e.g., memory[12] and metabolism[13]), and facilitate the identification of new targets for phosphorylation-modulating therapeutics (a class of pharmaceuticals[14]). Therefore, there is a need for developing tools to control, reduce, or enhance the activity of phosphorylation-regulating enzymes in living cells.

SUMMARY OF THE INVENTION

This invention relates to the field of genetic engineering. Specifically, the invention relates to the construction of operons to produce biologically active agents. For example, operons may be constructed to produce agents that control the function of biochemical pathway proteins (e.g, protein phosphatases, kinases and/or proteases). Such agents may include inhibitors and modulators that may be used in studying or controlling phosphatase function associated with abnormalities in a phosphatase pathway or expression level. Fusion proteins, such as light activated protein phosphatases, may be genetically encoded and expressed as photoswitchable phosphatases. Systems are provided for use in controlling phosphatase function within living cells or in identifying small molecule inhibitors/activator/modulator molecules of protein phosphatases associated with cell signaling.

In one embodiment, the present invention contemplates a genetic operon comprising: a) providing; i) a first gene encoding a first fusion protein, the first fusion protein comprising a substrate recognition domain and either a DNA-binding domain or an anchoring unit for RNA polymerase; ii) a second gene encoding a second fusion protein, the second fusion protein comprising an enzyme substrate domain and either an anchoring unit for RNA polymerase or a DNA binding domain; iii) a first DNA sequence comprising a binding site for said DNA-binding domain; iv) a second DNA sequence comprising a binding site, proximal to the first, for said anchoring unit and for said RNA polymerase; v) a third gene encoding a first enzyme, wherein said first enzyme is capable of modifying said substrate domain, thereby changing the affinity of said substrate recognition domain; vi) a fourth gene encoding a second enzyme, wherein said second enzyme is capable of unmodifying said substrate domain; vii) a reporter gene encoding at least one capable of having a detectable output when said RNA polymerase and said anchoring unit binds to said second DNA sequence binding site after association of the two fusion proteins. In one embodiment, said substrate domain is a peptide substrate of a protein kinase. In one embodiment, said substrate domain is a peptide substrate of a protein tyrosine kinase. In one embodiment, said substrate domain is a peptide substrate of Src kinase (a protein tyrosine kinase). In one embodiment, said substrate recognition domain is capable of binding to said substrate domain in its phosphorylated state. In one embodiment, said substrate recognition domain is capable of binding to said substrate domain in its unphosphorylated state. In one embodiment, said DNA-binding domain is the 434 cI repressor and said DNA binding site is the binding sequence for that repressor. In one embodiment, said anchoring unit is the omega subunit of RNA polymerase and said second DNA binding site is the binding site for RNA polymerase. In one embodiment, said substrate domain is a peptide substrate of a protein kinase. In one embodiment, said operon further comprises a system of proteins. In one embodiment, said first enzyme is a protein phosphatase. In one embodiment, said first enzyme is a protein tyrosine phosphatase. In one embodiment, said first enzyme is protein tyrosine phosphatase 1B. In one embodiment, said second enzyme is a protein kinase. In one embodiment, said second enzyme is a protein tyrosine kinase. In one embodiment, said second enzyme is Src kinase. In one embodiment, said reporter protein yields a detectable output. In one embodiment, said reporter protein that yields a detectable output is a LuxAB bioreporters (e.g., output is a luminescence). In one embodiment, said reporter protein that yields a detectable output is a fluorescent protein. In one embodiment, said reporter protein that yields a detectable output is mClover. In one embodiment, said reporter protein that yields a detectable output confers antibiotic resistance. In one embodiment, said antibiotic resistance is to spectinomycin. In one embodiment, said operon further comprises a gene encoding a decoy protein fusion comprising: (i) a second enzyme substrate domain that is different from the first enzyme substrate domain and (ii) a protein that that does not bind specifically to DNA and/or to RNA polymerase, and a fifth gene encoding a third enzyme, wherein said third enzyme is capable of being active on the decoy substrate domain. In one embodiment, both said first enzyme substrate domain (of the base system) and said second enzyme substrate domain (of the decoy) are substrates of a protein kinases. In one embodiment, both said first enzyme substrate domain (of the base system) and said second enzyme substrate domain (of the decoy) are substrates of a protein tyrosine kinase. In one embodiment, both said first enzyme substrate domain (of the base system) and said second enzyme substrate domain (of the decoy) are substrates of Src kinase. In one embodiment, both said first enzyme substrate domain (of the base system) and said second substrate domain (of the decoy) are substrates of a protein phosphatase. In one embodiment, both said first enzyme substrate domain (of the base system) and said second substrate domain (of the decoy) are substrates of a protein tyrosine phosphatase. In one embodiment, both said first enzyme substrate domain (of the base system) and said second substrate domain (of the decoy) are substrates of protein tyrosine phosphatase 1B. In one embodiment, said first enzyme is a light modulated enzyme. In one embodiment, said first enzyme is a protein-LOV2 chimera. In one embodiment, said first enzyme is a PTP1B-LOV2 chimera. In one embodiment, said proteins that yield a detectable output include a protein that generates a toxic product in the presence of a non-essential substrate. In one embodiment, said additional protein is SacB, which converts sucrose to a nonstructural polysaccharide that is toxic in *E. coli*. In one embodiment, said operon further comprises an expression vector and a bacterial cell.

In one embodiment, the present invention contemplates a system for detecting inhibitors of an enzyme, comprising: a) providing; i) an operon comprising a gene encoding an enzyme; ii) a bacterium cell; iii) a small molecule test compound; and b) contacting said bacterium with said operon such that said contacted bacterium is capable of producing a detectable output; c) growing said contacted bacterium in the presence of said test compound under conditions allowing said detectable output; and d) assessing the influence of the test compound on said detectable output. In one embodiment, said enzyme is a protein phosphatase. In one embodiment, said enzyme is a protein tyrosine phosphatase. In one embodiment, said enzyme, is protein tyrosine phosphatase 1B.

In one embodiment, the present invention contemplates a method for evolving inhibitors of an enzyme, comprising: a) providing: i) an operon comprising a gene encoding an enzyme; a library of bacteria cells, wherein each said bacteria cells has at least one mutated metabolic pathway; b) growing said library of bacteria cells; and c) screening said library of bacterial cells for a detectable output. In one embodiment, said operon further comprises an expression vector.

In one embodiment, the present invention contemplates a method for detecting selective inhibitors of a first enzyme over a second enzyme, comprising: a) providing; i) a system as described above comprising a library of bacterial cells; and ii) a small molecule test compound; b) growing said library of bacterial cells in the presence of the test compound; and c) assessing an influence of the test compound on a detectable output. In one embodiment, the system further provides an operon comprising a gene encoding a decoy fusion protein, said decoy fusion protein comprising; (i) a second enzyme substrate domain that is different from the first enzyme substrate domain and (ii) a protein that that does not bind specifically to DNA and/or RNA polymerase. In one embodiment, said operon further comprises an expression vector.

In one embodiment, the present invention contemplates a method for evolving selective inhibitors of a first enzyme over a second enzyme, comprising; a) providing; a system as described herein comprising a library of bacterial cells having mutated metabolic pathways; b) growing said bacterial cell library; and b) screening the bacterial cell library for a detectable output. In one embodiment, the method further provides an operon comprising a gene encoding a decoy fusion protein, the decoy fusion protein comprising; (i) a second enzyme substrate domain that is different from the first enzyme substrate domain and (ii) a protein that that does not bind specifically to DNA and/or RNA polymerase. In one embodiment, said operon further comprises an expression vector.

In one embodiment, the present invention contemplates a method for evolving photoswitchable enzymes, comprising; a) providing; i) a system as described herein comprising a bacterial cell library having mutated photoswitchable enzymes; b) growing the bacterial cell library under at least two different light conditions; and c) comparing differences in detectable output for each cell between each of said two different light conditions. In one embodiment, said operon further comprises an expression vector.

In one embodiment, the present invention contemplates a method for evolving photoswitchable enzymes, comprising: a) providing; i) a system as described herein comprising a library of bacterial cells have mutated photoswitchable enzymes; b) growing the library of bacterial cells under a first light source in which activity is desired; c) subsequently growing the library of bacterial cells from step b) in the presence of: (i) a non-essential substrate; and (ii) a second light source in which activity is not desired; d) subsequently screening survivors of step c) for a mutant bacterial cell; and e) examining the mutant bacterial cell for activity under the first light source and the second light source. In one embodiment, the method further comprises an operon comprising a gene encoding a decoy fusion protein, the decoy fusion protein comprising; (i) a second enzyme substrate domain that is different from the first enzyme substrate domain; and (ii) a protein that that does not bind specifically to DNA and/or RNA polymerase. In one embodiment, said operon further comprises an expression vector.

In one embodiment, the present invention contemplates a method for evolving selective mutants of an enzyme, comprising: a) providing; a system as described above comprising a library of bacterial cells having a mutant enzyme; b) growing the library of bacterial cells; and c) comparing a detectable output between the cells to identify the mutant enzyme. In one embodiment, the method further comprises an operon comprising a gene encoding a decoy fusion protein, the decoy fusion protein comprising; (i) a second enzyme substrate domain that is different from the first enzyme substrate domain; and (ii) a protein that that does not bind specifically to DNA and/or RNA polymerase. In one embodiment, said operon further comprises an expression vector.

In one embodiment, the present invention contemplates a method for evolving substrate domains selective for an enzyme, comprising: a) providing; a method as described above comprising a library of bacterial cells comprising substrate domains fused to DNA binding domains; b) growing the library of bacterial cells in the presence of an inducer for a first enzyme and a non-essential substrate; c) subsequently growing the library of bacterial cells from step b) in the presence of an inducer for a second enzyme; and d) subsequently screening for survivor bacterial cells, thereby identifying substrates that bind to the first enzyme but not to the second enzyme. In one embodiment, said system comprises a reporter protein that yields a detectable output. In one embodiment, the reporter protein generates a toxic product in the presence of a non-essential substrate. In one embodiment, the system further comprises an operon comprising a gene selected from the group consisting of a first inducible promoter for a first enzyme and a second inducible promoter for a second enzyme, wherein the second enzyme has a similar activity to the first enzyme.

In one embodiment, the present invention contemplates a method of using a microbial biosensor comprising an operon, wherein said operon comprises; a) providing a reporter gene and a sensor fusion protein gene; and b) expressing said sensor fusion protein with a post-translational modification and the reporter gene. In one embodiment, said expressed sensor fusion protein has a protein tyrosine phosphatase substrate domain and is capable of binding to said DNA binding sequences in the presence of at least one expressible sensor fusion protein as a recognition domain (SH2) for said protein tyrosine phosphatase substrate domain attached to a phosphate molecule. In one embodiment, said operon further comprises gene segments encoding: i) a first expressible sensor fusion protein as a protein tyrosine phosphatase substrate domain capable of attaching to said phosphate molecule, said first expressible sensor fusion protein is in an operable combination with a DNA-binding protein; and ii) a second expressible sensor fusion protein as a recognition domain (SH2) for said protein tyrosine phosphatase substrate domain when attached to a phosphate molecule, said second expressible sensor fusion protein is in operable combination with a subunit of an RNA polymerase; and iii) individual expressible fragments including, but not limited to, a Src kinase protein; a protein tyrosine phosphatase 1B (PTP1B) and conjugated to said transcriptionally active binding sequences capable of binding to said DNA-binding protein of sensor fusion protein and said subunit of an RNA polymerase in operable combination with said reporter gene.

In one embodiment, the present invention contemplates a method of using a microbial biosensor comprising; a) providing; i) an operon, wherein said operon comprises a reporter gene and a sensor fusion protein gene; ii) a living bacterium; and iii) a test small molecule inhibitor of said protein tyrosine phosphatase enzyme; b) expressing said sensor fusion protein with a post-translational modification and a reporter gene; c) contacting said bacterium with said test small molecule; and d) determining whether said test small molecule is an inhibitor for said protein phosphatase enzyme by expression of said reporter gene. In one embodiment, said expressed sensor fusion protein has a protein tyrosine phosphatase substrate domain that is capable of binding to a DNA binding sequence in the presence of at least one expressible sensor fusion protein as a recognition domain (SH2) for said protein tyrosine phosphatase substrate domain attached to a phosphate molecule. In one embodiment, said expressed sensor fusion protein has a protein tyrosine phosphatase 1B substrate domain that is capable of binding to said DNA binding sequences in the presence of at least one expressible sensor fusion protein as a recognition domain (SH2) for said protein tyrosine phosphatase substrate domain attached to a phosphate molecule. In one embodiment, said operon further comprises gene segments encoding: i) said first expressible sensor fusion protein as said protein tyrosine phosphatase substrate domain capable of attaching to said phosphate molecule that is in operable combination with a DNA-binding; and ii) said second expressible sensor fusion protein as a recognition domain (SH2) for said protein tyrosine phosphatase substrate domain when attached to a phosphate molecule that is in operable combination with a subunit of an RNA polymerase; and iii) individual expressible fragments including but not limited to, a Src kinase protein; a protein tyrosine phosphatase 1B (PTP1B) and conjugated to said transcriptionally active binding sequences capable of binding to said DNA-binding protein of sensor fusion protein and said subunit of an RNA polymerase in operable combination with said reporter gene. In one embodiment, said biosensor further comprises an operon component for expressing a second gene. In one embodiment, said biosensor further comprises an operon component for expressing a second PTP that is different from the first PTP for identifying a said inhibitor selective for one of the TPT enzymes. In one embodiment, said test small molecule inhibitor includes, but is not limited to, abietane-type diterpenes, abietic acid (AA), dihydroabietic acid and structural variants thereof.

In one embodiment, the present invention contemplates a method of using a microbial biosensor, comprising: a) providing; i) an operon, wherein said operon comprises a reporter gene and a sensor fusion protein gene; ii) a living bacterium; and iii) a test small molecule inhibitor of said protein tyrosine phosphatase enzyme; b) expressing said sensor fusion protein with a post-translational modification and the reporter gene; c) expressing said expressible sensor fusion proteins in said bacterium; d) contacting said bacterium with said test small molecule; and e) determining whether said test small molecule is an inhibitor for said protein phosphatase enzyme by expression of said reporter gene. In one embodiment, said expressed sensor fusion protein has a protein tyrosine phosphatase substrate domain and is capable of binding to said DNA binding sequences in the presence of at least one expressible sensor fusion protein as a recognition domain (SH2) for said protein tyrosine phosphatase substrate domain attached to a phosphate molecule. In one embodiment, the expressed sensor fusion protein has a protein tyrosine phosphatase 1B substrate domain and capable of binding to said DNA binding sequences in the presence of at least one expressible sensor fusion protein as a recognition domain (SH2) for said protein ty rosin phosphatase substrate domain attached to a phosphate molecule, and an individual expressible fragment for a photoswitchable protein tyrosine phosphatase 1B. In one embodiment, said operon comprises gene segments encoding: i) said first expressible sensor fusion protein as said protein tyrosine phosphatase substrate domain that is capable of attaching to said phosphate molecule in operable combination with a DNA-binding protein; ii) said second said expressible sensor fusion protein as a recognition domain (SH2) for said protein tyrosine phosphatase substrate domain when attached to a phosphate molecule that is in operable combination with a subunit of an RNA polymerase; and iii) individual expressible fragments including, but not limited to, a Src kinase protein; a protein tyrosine phosphatase 1B (PTP1B) and conjugated to said transcriptionally active binding sequences capable of binding to said DNA-binding protein of sensor fusion protein and said subunit of an RNA polymerase in operable combination with said reporter gene.

In one embodiment, the present invention contemplates a method for providing variants of chemical structures for use as a potential therapeutic, comprising: a) providing; i) an *E. coli* bacterium comprising a metabolic terpenoid chemical structure-producing pathway providing an altered chemical structure, wherein said metabolic pathway comprises a synthetic enzyme, wherein said *E. coli* further comprises a microbial biosensor operon for detecting PTP inhibition; and ii) a mutated synthetic enzyme of system of enzymes; a) introducing said mutated synthetic enzyme of system of enzymes; c) expressing said mutated synthetic enzyme under conditions wherein said mutated synthetic enzyme or system of enzymes alters/alter the chemical structure of said terpenoid chemical structure; and d) determining whether said altered chemical structure is an inhibitor for said PTP as a test inhibitor for use as a potential therapeutic. In one embodiment, said metabolic pathway comprises synthetic enzymes including, but not limited to, terpene synthases, cytochrome P450s, halogenases, methyl transferases, or terpenoid-functionalizing enzymes. In one embodiment, said terpenoid includes, but is not limited to, labdane-related diterpenoids. In one embodiment, said terpenoid includes but is not limited to, abietane-type diterpenoids. In one embodiment, said terpenoid is abietic acid.

In one embodiment, the present invention contemplates a fusion protein DNA construct, comprising a protein phosphatase gene and a protein light switch gene conjugated within said phosphatase gene, wherein said protein phosphatase gene encodes a protein with a C-terminal domain and said protein light switch gene encodes a protein with an N-terminal alpha helical region such that said C-terminal domain is conjugated to said N-terminal alpha helical region. In one embodiment, said construct further comprises an expression vector and a living cell. In one embodiment, said protein phosphatase is a protein tyrosine phosphatase. In one embodiment, said protein phosphatase is protein tyrosine phosphatase 1B (PTP1B). In one embodiment, said C-terminal domain encodes an $\alpha 7$ helix of PTP1B. In one embodiment, said construct encodes PTP1B$_{PS}$-A. In one embodiment, said construct encodes PTP1B$_{PS}$-B. In one embodiment, said protein phosphatase is T-Cell protein tyrosine phosphatases (TC-PTP). In one embodiment, said protein light switch is a light-oxygen-voltage (LOV) domain. In one embodiment, said protein light switch is the LOV2 domain of phototropin 1 form *Avena sativa*. In one embodiment, said LOV2 domain comprises an A' a helix of LOV2. In one embodiment, said LOV2 has at least one mutation resulting in an amino acid mutation. It is not meant to limit such mutations. In fact, a mutation may include but is not limited to a nucleotide substitution, the addition of a nucleotide, and the deletion of a nucleotide from said gene. In one embodiment, said mutation is a substitution of a nucleotide. In one embodiment, said A' a helix of LOV2 has a T406A mutation. In one embodiment, said protein light switch is a phytochrome protein. In one embodiment, said phytochrome protein is a bacterial phytochrome protein. In one embodiment, said bacterial phytochrome protein is a bacterial phytochrome protein 1 (BphP1) from *Rhodopseudomonas palustris*. In one embodiment, said protein light switch is a light-oxygen-voltage (LOV) domain with an artificial chromophore. In one embodiment, said protein light switch is a phytochrome protein with an artificial chromophore.

In one embodiment, the present invention contemplates a fusion protein, comprising a protein phosphatase and a protein light switch conjugated within said phosphatase, wherein said protein phosphatase has a C-terminal domain and said protein light switch has a N-terminal alpha helical region such that said C-terminal domain is conjugated to said N-terminal alpha helical region. In one embodiment, said fusion protein further comprises an expression vector and a living cell. In one embodiment, said protein phosphatase is a protein tyrosine phosphatase. In one embodiment, said protein phosphatase is protein tyrosine phosphatase 1B (PTP1B). In one embodiment, said C-terminal domain encodes an $\alpha 7$ helix. In one embodiment, said fusion protein is PTP1B$_{PS}$-A. In one embodiment, said fusion protein is PTP1B$_{PS}$-B. In one embodiment, said protein phosphatase is T-Cell protein tyrosine phosphatases (TC-PTP). In one embodiment, said protein light switch is a light-oxygen-voltage (LOV) domain. In one embodiment, said protein light switch is the LOV2 domain of phototropin 1 form *Avena sativa*. In one embodiment, said LOV2 domain comprises an A' a helix of LOV2. In one embodiment, said A' a helix of LOV2 has a T406A mutation. In one embodiment, said protein light switch is a light-oxygen-voltage (LOV) domain with an artificial chromophore. In one embodiment, said protein light switch is a phytochrome protein with an artificial chromophore. In one embodiment, said protein light switch is a phytochrome protein. In one embodiment, said phytochrome protein is a bacterial phytochrome protein. In one embodiment, said bacterial phytochrome protein is a bacterial phytochrome protein 1 (BphP1) from *Rhodopseudomonas palustris*. In one embodiment, said protein light switch is a light-oxygen-voltage (LOV) domain with an artificial chromophore. In one embodiment, said protein light switch is a phytochrome protein with an artificial chromophore.

In one embodiment, the present invention contemplates a method of using a fusion protein, comprising; a) providing; i) a fusion protein; ii) a protein phosphatase, and iii) a living cell; and b) introducing said fusion protein in said a living cell such that illumination of said light switch alters a feature in said living cell. In one embodiment, said feature includes but is not limited to controlling cell movement, morphology, controlling cell signaling and having a modulatory effect. In one embodiment, said modulatory effect includes but is not limited to inactivation, activation, reversible inactivation and reversible activation. In one embodiment, said modulatory effect is dose dependent. In one embodiment, said illumination is light within the range of 450-500 nm. In one embodiment, said illumination is light within the range of 600-800 nm. In one embodiment, said protein light switch undergoes light-induced conformational change and said protein phosphatase has allosterically modulated catalytic activity that is altered by said conformational change. In one embodiment, said altering is enhanced or reduced. In one embodiment, said protein light switch is a light-oxygen-voltage (LOV) domain with an artificial chromophore. In one embodiment, said protein light switch is a phytochrome protein with an artificial chromophore. In one embodiment, said living cell has an activity. In one embodiment, said living cell is in vivo. In one embodiment, said method further comprises a step of controlling said cellular activity in vivo.

In one embodiment, the present invention contemplates a method for detecting a small molecule modulator of a protein phosphatase, comprising: a) providing; i) a fusion protein comprising a protein phosphatase and protein light switch; ii) a visual readout for phosphatase activity; iii) an optical source, wherein said source is capable of emitting light radiation; iv) a living cell; and v) a small molecule test compound; b) expressing said fusion protein in said living cell; c) contacting said living cell with said small molecule test compound; d) illuminating said fusion protein within said cell with said optical source; e) measuring a visual readout for a change in phosphatase activity for identifying said small molecule test compound as a modulator of said activity of said phosphatase; and f) using said modulatory small molecule test compound for treating a patient exhibiting at least one symptom of a disease associated with said phosphatase. In one embodiment, said method further comprises identifying said small molecule test compound as an inhibitor of the activity of said phosphatase. In one embodiment, said method further comprises identifying said small molecule test compound as an activator of the activity of said phosphatase. In one embodiment, said disease includes but is not limited to diabetes, obesity, cancer, anxiety, autoimmunity, or neurodegenerative diseases. In one embodiment, said protein light switch is a light-oxygen-voltage (LOV) domain with an artificial chromophore. In one embodiment, said protein light switch is a phytochrome protein with an artificial chromophore. In one embodiment, said method further provides a fluorescence-based biosensor, and comprises a step of introducing said fluorescence-based biosensor into said cell. In one embodiment, said method further comprises a step of controlling said cellular activity in vivo. In one embodiment, said visual readout for phosphatase activity is selected from the group consisting of a fluorescence-based biosensor; changes in cell morphology; and changes in cell motility.

In one embodiment, the present invention contemplates a photoswitchable protein tyrosine phosphatase enzyme construct comprising an N-terminal alpha helix of a protein light switch conjugated to a C-terminal allosteric domain region. In one embodiment, said protein tyrosine phosphatase enzyme is protein tyrosine phosphatase 1B (PTP1B). In one embodiment, said protein light switch is a LOV2 domain of phototropin 1 derived from *Avena sativa* (wild oats). In one embodiment, said enzyme construct further comprises an expression vector. In one embodiment, the present invention contemplates a biosensor for enzyme activity, comprising; a) a substrate domain as described above; b) a substrate recognition domain; c) a first fluorescent protein; and d) a second fluorescent protein.

In one embodiment, the invention provides a genetically encoded system for detecting small molecules that modulate enzyme activity, comprising, a. a first region in operable combination comprising: i. a first promoter; ii. a first gene encoding a first fusion protein comprising a substrate recognition domain linked to a DNA-binding protein; iii. a second gene encoding a second fusion protein comprising a substrate domain linked to a protein capable of recruiting RNA polymerase to DNA; iv. a second promoter; v. a third gene for a protein kinase; vi. a fourth gene for a molecular chaperone; vii. a fifth gene for a protein phosphatase; b. a second region in operable combination comprising: i. a first DNA sequence encoding an operator for said DNA-binding protein; ii. a second DNA sequence encoding a binding site for RNA polymerase; and iii. one or more genes of interest (GOI). In one embodiment, said first promoter is ProI. In one embodiment, said substrate recognition domain is a substrate homology 2 (SH2) domain from *H. sapiens*. In one embodiment, said DNA-binding protein is the 434 phage cI repressor. In one embodiment, said substrate domain is a peptide substrate of both said kinase and said phosphatase. In one embodiment, said second promoter is ProD. In one embodiment, said protein capable of recruiting RNA polymerase to DNA is the omega subunit of RNA polymerase (i.e., RpoZ or RP$_\omega$). In one embodiment, said protein kinase is Src kinase from *H. sapiens*. In one embodiment, said molecular chaperone is CDC37 (i.e., the Hsp90 co-chaperone) from *H. sapiens*. In one embodiment, said protein phosphatase is protein tyrosine phosphatase 1B (PTP1B) from *H. sapiens*. In one embodiment, said operator is the operator for 434 phage cI repressor. In one embodiment, said binding site for RNA polymerase is the −35 to −10 region of the lacZ promoter. In one embodiment, said gene of interest is SpecR, a gene that confers resistance to spectinomycin. In one embodiment, said genes of interest are LuxA and LuxB, two genes that yield a luminescent output. In one embodiment, said gene of interest is a gene that confers resistance to an antibiotic. In one embodiment, said protein phosphatase is PTPN6 from *H. sapiens*. In one embodiment, said protein phosphatase is a protein tyrosine phosphatase (PTP). In one embodiment, said protein phosphatase is the catalytic domain of a PTP. In one embodiment, an alignment of the X-ray crystal structures of (i) the catalytic domain of said protein phosphatase and (ii) the catalytic domain of PTP1B yields a root-mean-square deviation (RMSD) of less than or equal to 0.95 Å (as defined by a function similar to the PyMol function align). In one embodiment, said catalytic domain of said protein phosphatase has at least 34.1% sequence identity with the catalytic domain of PTP1B. In one embodiment, said catalytic domain of said phosphatase has at least 53.5% sequence similarity with the catalytic domain of PTP1B. In one embodiment, said protein kinase is a protein tyrosine kinase (PTK). In one embodiment, said protein kinase is the catalytic domain of a PTK. In one embodiment, said first promoter is a constitutive promoter. In one embodiment, said second promoter is a constitutive promoter. In one embodiment, said first promoter is an inducible promoter. In one embodiment, said second promoter is an inducible promoter. In one embodiment, said binding site for RNA polymerase comprises part of a third promoter. In one embodiment, said first region lacks a gene for a molecular chaperone. In one embodiment, said first fusion protein consists of a substrate recognition domain linked a protein capable of recruiting RNA polymerase to DNA, and said second fusion protein consists of a substrate domain linked to a DNA-binding protein. In one embodiment, said first region further contains a third fusion protein (i.e., a "decoy") comprising a second substrate domain, which is distinct from the first substrate domain, linked to a protein that is incapable of recruiting RNA polymerase to DNA. In one embodiment, said substrate domain of said third fusion protein is a peptide substrate of both said kinase and said phosphatase. In one embodiment, said substrate domain of said third fusion protein is a peptide substrate of said kinase but is a poor substrate of said phosphatase. In one embodiment, said first region further contains a sixth gene for a second protein phosphatase, which is distinct from the first protein phosphatase and which acts on said substrate domain of said third fusion protein.

In one embodiment, the invention provides a method for using both (i) a genetically encoded system for detecting small molecules that modulate enzyme activity and (ii) a genetically encoded pathway for terpenoid biosynthesis to identify and/or build terpenoids that modulate enzyme activity, comprising, a. providing, i. a genetically encoded system for detecting small molecules that modulate enzyme activity, comprising, 1. a first region in operable combination comprising: a. a first promoter; b. a first gene encoding a first fusion protein comprising a substrate recognition domain linked to a DNA-binding protein; c. a second gene encoding a second fusion protein comprising a substrate domain linked to a protein capable of recruiting RNA polymerase to DNA; d. a second promoter; e. a third gene for a protein kinase; f. a fourth gene for a molecular chaperone; g. a fifth gene for a protein phosphatase; 2. a second region in operable combination comprising: a. a first DNA sequence encoding an operator for said DNA-binding protein; b. a second DNA sequence encoding a binding site for RNA polymerase; c. one or more genes of interest (GOI); ii. a genetically encoded pathway for terpenoid biosynthesis comprising: 1. a pathway that generates linear isoprenoid precursors; 2. a gene for a terpene synthase (TS); 3. a plurality of E. coli bacteria; b. transforming said bacteria with both (i) said genetically encoded system for detecting small molecules and (ii) said genetically encoded pathway for terpenoid biosynthesis, and allowing said transformed bacteria to replicate; c. observing the expression of a gene of interest through a measurable output. In one embodiment, said pathway that generates linear isoprenoid precursors generates farnesyl pyrophosphate (FPP). In one embodiment, said pathway that generates linear isoprenoid precursors is all or part of the mevalonate-dependent isoprenoid pathway of S. cerevisiae. In one embodiment, said pathway that generates linear isoprenoid precursors is carried by the plasmid pMBIS. In one embodiment, said gene of interest is SpecR, a gene that confers resistance to spectinomycin. In one embodiment, said TS gene is carried on a separate plasmid (pTS) from the rest of the terpenoid pathway. In one embodiment, said TS gene encodes for amorphadiene synthase (ADS) from Artemisia annua. In one embodiment, said TS gene encodes for γ-humulene synthase (GHS) from Abies grandis. In one embodiment, said TS gene encodes for abietadiene synthase (ABS) from Abies grandis, and this gene is carried in operable combination with a gene for geranylgeranyl diphosphate synthase (GPPS). In one embodiment, said TS gene encodes for taxadiene synthase (TXS) from Taxus brevifolia, and this gene is carried in operable combination with a gene for GGPPS. In one embodiment, the method further comprises, d. extracting terpenoids that enable the highest measurable output (e.g., growth at the highest concentration of spectinomycin); e. identifying said terpenoids; f. purifying said terpenoids. In one embodiment, the method further comprises, providing, g. a mammalian cell culture, h. treating said cell cultures with purified terpenoids, i. measuring a biochemical effect that results from changes in the activity of a protein phosphatase or protein kinase. In one embodiment, the method further comprises, j. providing, a purified enzyme target, k. measuring the modulatory effect of purified terpenoids on the enzyme target, l. quantifying that modulatory effect (e.g., by calculating an $IC_{50}$). In one embodiment, said TS gene has at least one mutation. In one embodiment, said TS gene is in operable combination with a gene for an enzyme that functionalizes terpenoids. In one embodiment, said TS gene is in operable combination with a gene for a cytochrome P450. In one embodiment, said TS gene is in operable combination with a gene for cytochrome P450 BM3 from Bacillus megaterium. In one embodiment, said TS gene is in operable combination with a gene for a halogenase. In one embodiment, said TS gene is in operable combination with a gene for 6-halogenase (SttH) from Streptomyces toxytricini. In one embodiment, said TS gene is in operable combination with a gene for vanadium haloperoxidase (VHPO) from Acaryochloris marina. In one embodiment, said mammalian cell is a HepG2, Hela, Hek393t, MCF-7, and/or Cho-hIR cell. In one embodiment, said cells are BT474, SKBR3, or MCF-7 and MDA-MB-231 cells. In one embodiment, said biochemical effect is insulin receptor phosphorylation, which can be measured by a western blot or enzyme-linked immunosorbent assay (ELISA). In one embodiment, said cells are triple negative (TN) cell lines. In one embodiment, said cells are TN cells from the American Type Culture Collection (ATCC). In one embodiment, said cells are TN cells from ATCC TCP-1002. In one embodiment, said biochemical effect is cellular migration. In one embodiment, said biochemical effect is cellular viability. In one embodiment, said biochemical effect is cellular proliferation. In one embodiment, said protein phosphatase is PTP1B from H. sapiens. In one embodiment, said protein kinase is Src kinase from H. sapiens. In one embodiment, said gene of interest confers resistance to an antibiotic. In one embodiment, said gene of interest is SacB, a gene that confers sensitivity to sucrose. In one embodiment, said gene of interest confers conditional toxicity (i.e., toxicity in the presence of an exogenously added molecule). In one embodiment, said genes of interest are SpecR and SacB. In one embodiment, said protein phosphatase is the wild-type enzyme. In one embodiment, said protein phosphatase has at least one mutation. In one embodiment, said protein phosphatase has at least one mutation that reduces its sensitivity to a small molecule that modulates the activity of the wild-type protein phosphatase. In one embodiment, said protein kinase is the wild-type enzyme. In one embodiment, said protein kinase has at least one mutation. In one embodiment, said protein kinase has at least one mutation that reduces its sensitivity to a small molecule that modulates the activity of the wild-type protein kinase. In one embodiment, said at least one of said terpenoids inhibit a protein phosphatase. In one embodiment, said at least one of said terpenoids inhibit a PTP. In one embodiment, said least one of said terpenoids inhibit PTP1B. In one embodiment, said at least one of said terpenoids activate a protein phosphatase. In one embodiment, said least one of said terpenoids activates a PTP. In one embodiment, said at least one of aid terpenoids activate protein tyrosine phosphatase non-receptor type 12 (PTPN12). In one embodiment, said at least one of said terpenoids inhibit a protein kinase. In one embodiment, said at least one of said terpenoids inhibit a PTK. In one embodiment, said at least one of said terpenoid inhibit Src kinase. In one embodiment, said at least one of said terpenoids activate a protein kinase. In one embodiment, said at least one of said terpenoids activate a PTK. In one embodiment, said genetically encoded system for detecting small molecules further contains both (i) a third fusion protein comprising a second substrate domain, which is distinct from the first substrate domain, linked to a protein that is incapable of recruiting RNA polymerase to DNA and (ii) a sixth gene for a second protein phosphatase, which is distinct from the first protein phosphatase. In one embodiment, said genetically encoded system for detecting small molecules further contains both (i) a third fusion protein comprising a second substrate domain, which is distinct from the first substrate domain, linked to a protein that is incapable of recruiting RNA polymerase to DNA and (ii) a sixth gene for a second protein kinase, which is distinct from the first protein kinase. In one embodiment, said genetically encoded pathway for terpenoid biosynthesis comprises, instead, a library of pathways that differ in the identity of the TS gene such that upon transformation, the majority of cells contain a distinct TS gene (i.e., a gene that differs by at least one mutation). In one embodiment, said genetically encoded pathway for terpenoid biosynthesis comprises, instead, a library of pathways that differ in the identity of a gene that functionalizes terpenoids (e.g., a cytochrome P450 or halogenase), in operable combination with the SI gene, such that upon transformation, the majority of cells contain a distinct gene that functionalizes terpenoids (i.e., a gene that differs by at least one mutation). In one embodiment, said genetically encoded pathway for terpenoid biosynthesis comprises, instead, a library of pathways in which the TS gene has been replaced by a component of a eukaryotic complementary DNA (cDNA) library such that upon transformation, the majority of cells contain a distinct gene in place of the TS gene. In one embodiment, said genetically encoded pathway for terpenoid biosynthesis comprises, instead, a library of pathways in which the TS gene accompanied by a component of a eukaryotic complementary DNA (cDNA) library such that upon transformation, the majority of cells contain a distinct gene in operable combination with the TS gene (e.g., a gene that may encode for a terpenoid-functionalizing enzyme). In one embodiment, said genetically encoded system for detecting small molecules comprises, instead, a library of such systems that differ in the identity of the protein phosphatase gene such that upon transformation, the majority of cells contain a distinct protein phosphatase gene (i.e., a gene that differs by at least one mutation). In one embodiment, said genetically encoded pathway for terpenoid biosynthesis generates a terpenoid that modulates the activity of the wild-type form of said protein phosphatase, thereby enabling the growth study to isolate a mutant of said protein phosphatase that is less sensitive to the modulatory effect of the small molecule. In one embodiment, said genetically encoded system for detecting small molecules comprises, instead, a library of such systems that differ in the identity of the protein kinase gene, such that upon transformation, the majority of cells contain a separate protein kinase gene (i.e., a gene that differs by at least one mutation). In one embodiment, said genetically encoded pathway for terpenoid biosynthesis generates a terpenoid that modulates the activity of the wild-type form of said protein kinase, thereby enabling the growth study to isolate a mutant of said protein kinase that is less sensitive to the modulatory effect of the small molecule. In one embodiment, said at least one of said terpenoids modulates the activity of the wild-type form of said protein phosphatase, but not a mutated form of said protein phosphatase. In one embodiment, said at least one of said terpenoids modulates the activity of the said first protein phosphatase, but not the activity of said second protein phosphatase. In one embodiment, said at least one of said terpenoids modulates the activity of the wild-type form of said protein kinase, but not a mutated form of said protein kinase. In one embodiment, said at least one of said terpenoids modulates the activity of said first protein kinase, but not the activity of said second protein kinase.

In one embodiment, the invention provides an inhibitor detection operon comprising A: a first region in operable combination under control of a first promoter including: i. a first DNA sequence encoding a first fusion protein comprising a substrate recognition homology 2 domain (SH2) and a repressor; ii. a second DNA sequence encoding a second fusion protein comprising a phosphate molecule binding domain of a substrate recognition domain, said substrate recognition domain and an omega subunit of RNA polymerase (RpoZ or RP$_\omega$); iii. a third DNA sequence encoding a Cell Division Cycle 37 protein (CDC37); iv. a protein phosphatase; and B: a second region in operable combination under control of a second promoter comprising: i. an operator comprising a repressor binding domain said repressor, ii. a ribosome binding site (RB); and iii. a gene of interest (GOI). In one embodiment, said SH2 domain is a substrate recognition domain of said protein phosphatase. In one embodiment, said repressor is a 434 phage cI repressor. In one embodiment, said substrate recognition domain binds said protein phosphatase. In one embodiment, said decoy substrate domain is a Src kinase gene. In one embodiment, said operator is a 434cI operator. In one embodiment, said gene of interest encodes an antibiotic protein. In one embodiment, said protein phosphatase is a protein tyrosine phosphatase. In one embodiment, said first promoter is constitutive promoter. In one embodiment, said second promoter is an inducible promoter.

In one embodiment, the invention provides a method of using an inhibitor detection operon, comprising, a. providing, i. a detection operon, comprising A: a first region in operable combination under control of a first promoter including: 1. a first DNA sequence encoding a first fusion protein comprising a protein phosphatase enzyme's substrate recognition homology 2 domain (SH2) and a repressor binding domain; 2. a second DNA sequence encoding a second fusion protein comprising a phosphate molecule binding domain of a protein phosphatase enzyme's substrate recognition domain, said protein phosphatase enzyme's substrate recognition domain and an omega subunit of RNA polymerase (RpoZ or RP$_\omega$); 4. a third DNA sequence encoding a Cell Division Cycle 37 (CDC37) protein; 5. a protein phosphatase enzyme; and B: a second region in operable combination under control of a second promoter comprising: 6. an operator comprising a repressor binding domain biding said repressor, 7. a ribosome binding site (RB); and 8. a gene of interest (GOI); and ii. a mevalonate pathway operon having a missing gene, such that said pathway operon does not contain at least one gene in said pathway for producing said terpenoid compound, under control of a third promoter comprising a second gene of interest for producing a terpenoid compound, iii. a fourth DNA sequence under control of a fourth promoter comprising said missing gene from said mevalonate pathway operon and a third gene of interest; and iv. a plurality of E. coli bacteria, and b. transfecting said E. coli bacteria with said first operon for expressing said first gene of interest; c. transfecting said E. coli bacteria with said mevalonate pathway operon for expressing said first and said second gene of interest; d. transfecting said E. coli bacteria with said fourth DNA sequence for expressing said first and said second and said third gene of interest; e. growing said cells wherein said inhibitor terpenoid compounds for protein phosphatase enzymes are produced by said cells. In one embodiment, said method further comprising step e. isolating said protein phosphatase inhibitor molecules and providing a mammalian cell culture for step f. treating said cell cultures for reducing activity of said protein phosphatase enzyme. In one embodiment, said method further providing an inducer compound for inducing said inducible promoter and a step of contacting said bacteria with said compound. In one embodiment, said method wherein reducing activity of said protein phosphatase enzyme reduces growth of said mammalian cells. In one embodiment, said protein phosphatase enzyme is human PTP1B. In one embodiment, said protein phosphatase enzyme is wild-type. In one embodiment, said protein phosphatase enzyme has at least one mutation. In one embodiment, said missing enzyme is a terpene synthase enzyme. In one embodiment, said terpene synthase enzyme is selected from the group consisting of amorphadiene synthase (ADS) and γ-humulene synthase (GHS). In one embodiment, said fourth DNA sequence further comprises a geranylgeranyl diphosphate synthase (GPPS) and said missing enzyme is selected from the group consisting of abietadiene synthase (ABS) and taxadiene synthase (TXS). In one embodiment, said terpene synthase enzyme is wild-type. In one embodiment, said terpene synthase enzyme has at least one mutation. In one embodiment, said terpenoid compounds are structural variants of terpenoid compounds. In one embodiment, said genes of interest are antibiotic genes. In one embodiment, said genes of interest are each different antibiotic genes.

In one embodiment, said genetically encoded detection operon system, comprising; Part A: a first region of DNA in operable combination comprising: a region of DNA encoding a first promoter; a first gene encoding a first fusion protein comprising a substrate recognition domain linked to a DNA-binding protein; a second gene encoding a second fusion protein comprising a substrate domain linked to a protein capable of recruiting RNA polymerase to DNA; a region of DNA encoding a second promoter; a third gene for a protein kinase; a fourth gene for a molecular chaperone; a fifth gene fora protein phosphatase; Part B: a second region of DNA in operable combination under control of a second promoter comprising: a first DNA sequence encoding an operator for said DNA-binding protein; a second DNA sequence encoding a binding site for RNA polymerase; and at least one gene of interest (GOI). In one embodiment, said substrate recognition domain is a substrate homology 2 (SH2) domain. In one embodiment, said DNA-binding protein is the 434 phage cI repressor. In one embodiment, said substrate domain is a peptide substrate of both said kinase and said phosphatase. In one embodiment, said protein capable of recruiting RNA polymerase to DNA is the omega subunit of RNA polymerase ($RP_\omega$). In one embodiment, said gene for a kinase is a Src kinase gene. In one embodiment, said molecular chaperone is CDC37. In one embodiment, said molecular chaperone is the Hsp90 co-chaperone) from *H. sapiens*. In one embodiment, said operator is a 434 phage cI operator. In one embodiment, said gene of interest is a gene for antibiotic resistance. In one embodiment, said gene for antibiotic resistance produces an enzyme that allow the bacteria to degrade an antibiotic protein. In one embodiment, said protein phosphatase enzyme is protein tyrosine phosphatase 1B. In one embodiment, said first and second promoters of part A are constitutive promoters. In one embodiment, said second promoter of Part B is an inducible promoter.

In one embodiment, the invention provides a method of using a genetically encoded detection operon system, comprising, a. providing, i. an inhibitor detection operon, comprising Part A: a first region of DNA in operable combination comprising: 1. a region of DNA encoding a first promoter; 2. a first gene encoding a first fusion protein comprising a substrate recognition domain linked to a DNA-binding protein; 3. a second gene encoding a second fusion protein comprising a substrate domain linked to a protein capable of recruiting RNA polymerase to DNA; 4. a region of DNA encoding a second promoter; 5. a third gene fora protein kinase; 6. a fourth gene for a molecular chaperone; 7. a fifth gene for a protein phosphatase; Part B: a second region of DNA in operable combination under control of a second promoter comprising: 8. a first DNA sequence encoding an operator for said DNA-binding protein; 9. a second DNA sequence encoding a binding site for RNA polymerase; and 10. at least one gene of interest (GOI). ii. a mevalonate-terpene pathway operon not containing a terpene synthase gene, under control of a fourth promoter comprising a second gene of interest for producing a terpenoid compound, iii. a fourth DNA sequence under control of a fifth promoter comprising said terpene synthase gene and a third gene of interest; and iv. a plurality of bacteria, and b. transfecting said bacteria with said inhibitor detection operon for expressing said first gene of interest; c. transfecting said bacteria with said mevalonate pathway operon for expressing said said second gene of interest; d. transfecting said bacteria with said fourth DNA sequence for expressing said third gene of interest; e. growing said bacteria cells expressing said three genes of interest wherein said inhibitor terpenoid compounds are produced by said bacteria cells inhibiting said protein phosphatase enzyme. In one embodiment, said method further comprising step e. isolating said protein phosphatase inhibitor molecules and providing a mammalian cell culture for step f. treating said cell cultures for reducing activity of said protein phosphatase enzyme. In one embodiment, said method wherein reducing activity of said protein phosphatase enzyme reduces growth of said mammalian cells. In one embodiment, said protein phosphatase enzyme is human PTP1B. In one embodiment, said protein phosphatase enzyme is wild-type. In one embodiment, said protein phosphatase enzyme has at least one mutation. In one embodiment, said mevalonate pathway operon comprises genes for expressing mevalonate kinase (ERG12), phosphomevalonate kinase (ERGS), mevalonate pyrophosphate decarboxylatse (MVD1), Isopentenyl pyrophosphate isomerase (IDI gene), and Farnesyl pyrophosphate (FPP) synthase (ispA). In one embodiment, said missing enzyme is a terpene synthase enzyme. In one embodiment, said terpene synthase enzyme is selected from the group consisting of amorphadiene synthase (ADS) and γ-humulene synthase (GHS). In one embodiment, said fourth DNA sequence further comprises a geranylgeranyl diphosphate synthase (GPPS) and said terpene synthase is selected from the group consisting of abietadiene synthase (ABS) and taxadiene synthase (TXS). In one embodiment, said terpene synthase enzyme is wild-type. In one embodiment, said terpene synthase enzyme has at least one mutation. In one embodiment, said terpenoid compounds are structural variants of terpenoid compounds. In one embodiment, said genes of interest are antibiotic genes. In one embodiment, said genes of interest are each different antibiotic genes. In one embodiment, said method further provides an inducer compound for inducing said inducible promoter and a step of contacting said bacteria with said compound.

In one embodiment, the invention provides a method for using both (i) a genetically encoded system for detecting small molecules that modulate enzyme activity and (ii) a genetically encoded pathway for polyketide biosynthesis to identify and/or build polyketides that modulate enzyme activity, comprising, providing, A genetically encoded system for detecting small molecules that modulate enzyme activity, comprising, a first region in operable combination comprising: a first promoter; a first gene encoding a first fusion protein comprising a substrate recognition domain linked to a DNA-binding protein; a second gene encoding a second fusion protein comprising a substrate domain linked to a protein capable of recruiting RNA polymerase to DNA; a second promoter; a third gene for a protein kinase; a fourth gene for a molecular chaperone; a fifth gene for a protein phosphatase; a second region in operable combination comprising: a first DNA sequence encoding an operator for said DNA-binding protein; a second DNA sequence encoding a binding site for RNA polymerase; one or more genes of interest (GOI); a genetically encoded pathway for polyketide biosynthesis comprising; a gene fora polyketide synthase; a plurality of *E. coli* bacteria. In one embodiment, said polyketide synthase is 6-deoxyerythronolide B synthase (DEBS). In one embodiment, said polyketide synthase (PKS) is a modular combination of different PKS components.

In one embodiment, the invention provides a method for using both (i) a genetically encoded system for detecting small molecules that modulate enzyme activity and (ii) a genetically encoded pathway for polyketide biosynthesis to identify and/or build alkaloids that modulate enzyme activity, comprising, a. providing, a genetically encoded system for detecting small molecules that modulate enzyme activity, comprising, a first region in operable combination comprising: a first promoter; a first gene encoding a first fusion protein comprising a substrate recognition domain linked to a DNA-binding protein; a second gene encoding a second fusion protein comprising a substrate domain linked to a protein capable of recruiting RNA polymerase to DNA; a second promoter; a third gene for a protein kinase; a fourth gene for a molecular chaperone; a fifth gene for a protein phosphatase; a second region in operable combination comprising: a first DNA sequence encoding an operator for said DNA-binding protein; a second DNA sequence encoding a binding site for RNA polymerase; one or more genes of interest (GOI); a genetically encoded pathway for polyketide biosynthesis comprising, a pathway for alkaloid biosynthesis. a plurality of E. coli bacteria. In one embodiment, said pathway for alkaloid biosynthesis described herein.

In one embodiment, the invention provides an engineered bacteria cell line comprising expression plasmid 1, plasmid 2, plasmid 3 and plasmid 4.

In one embodiment, the invention provides a phosphatase inhibitor molecule produced by a bacterium expressing a plasmid 1 in contact with an inducer molecule for inducing a promoter expressing a terpenoid synthesis pathway operon in plasmid 2 and a terpene synthase enzyme in plasmid 3, wherein said plasmid 2 and plasmid 3 are coexpressed in said bacteria with plasmid 1. In one embodiment, said plasmid 2 and said plasmid 3 are under control of an inducible promoter. In one embodiment, said bacterium is contacted by an inducible molecule for inducing said promoter.

In one embodiment, the invention provides a bacteria strain producing a phosphatase inhibitor molecule. In one embodiment, said inhibitor is a terpenoid molecule.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A illustrates one embodiment of a design of PTP1B$_{PS}$: Light-induced unwinding of the A'α helix of LOV2 destabilizes the α7 helix of PTP1B and, thus, inhibits catalysis. FIG. 1B illustrates one embodiment of Elaboration: In the competitively inhibited structure of PTP1B (orange), the α7 helix is stable, and the WPD loop (black) adopts a closed, catalytically competent conformation. In the apo structure (yellow), the α7 helix is disordered, and the WPD loop (blue) adopts an open, inactive conformation. We attached the C-terminal α7 helix of PTP1B (SEQ ID NO: 1) to the N-terminal A'α (SEQ ID NO: 2) helix of LOV2 at homologous crossover points (1-7) to create a chimera for which the photoresponsive of LOV2 destabilizes the α7 helix. FIG. 1C shows exemplary results of optimization of one embodiment: Construct 7 exhibited the largest dynamic range of the crossover variants; 7.1 had an improved activity over 7, while 7.1(T406A) had an improved dynamic range over 7.1. FIG. 1D shows an exemplary analysis of the activity of PTP1B$_{PS}$ on pNPP indicates that light affects $k_{cat}$, but not $K_m$. FIG. 1E shows the dynamic range of PTP1B$_{PS}$ is similar for substrates of different sizes. FIG. 1F shows exemplary illustrations of two small molecules: p-nitrophenyl-phosphate (or pNPP), and 4-methylumbelliferyl phosphate (or 4MU) and a peptide domain from EGFR. FIG. 1G shows exemplary activity of PTP1B-LOV2 chimeras that differ in (A-D) crossover location and (E-E4) linker composition in the presence and absence of 455 nm light. Substrate: 4-methylumbelliferyl phosphate.

FIG. 2A shows exemplary mutations that (i) prevent the formation of the cysteine adduct in LOV2 (C450M), (ii) destabilize the A'α and Jα helices if LOV2 (I532E, I539E, and ΔJα), or (iii) disrupt the allosteric network of PTP1B (Y152A/Y153A) reduced the photosensitivity of 7.1 and, with the exception of I532E and C450M, lowered its specific activity. FIG. 2B shows exemplary exposure of PTP1B$_{PS}$ to 455 nm light reduces its α-helical content ($CD_{222\ nm}$). FIG. 2C shows exemplary optical modulation of α-helical content (i.e., $\delta_{222}=CD_{222\text{-}dark}-CD_{222\text{-}light}$) is necessary, but not sufficient for optical modulation of catalytic activity. The dashed line denotes $\delta_{222}$ for an equimolar solution of PTP1B$_{WT}$ and LOV2$_{WT}$. FIG. 2D shows exemplary fluorescence of six tryptophan residues in the catalytic domain of PTP1B which enables optical monitoring of its conformational state. FIG. 2E-F shows exemplary thermal recovery of (FIG. 2E) α-helical content and (FIG. 2F) tryptophan fluorescence of PTP1B$_{PS}$. FIG. 2G shows exemplary kinetic constants for thermal resetting are larger for α-helical content than for tryptophan fluorescence, suggesting that LOV2 resets more quickly than the PTP1B domain. This discrepancy is smallest for the most photosensitive variant: 7.1 (T406A). FIG. 2H shows exemplary alignments of the crystal structures of PTP1B$_{PS}$ (blue) and apo PTP1B$_{WT}$ (orange) indicate that LOV2 does not distort the structure of the catalytic domain. The LOV2 domain of PTP1B$_{PS}$ could not be resolved; a flexible loop at the beginning of the α7 helix likely causes LOV2 to adopt variable orientations in the crystal lattice. The α6 and α7 helices of an inhibited structure of PTP1B (yellow) are shown for reference. FIG. 2I shows an exemplary gap in the crystal structure of PTP1B$_{PS}$ that can accommodate LOV2. FIG. 2J shows where exemplary crystals of a PTP1B-LOV2 fusion are green and turn clear when illuminated with 455 nm light; LOV2 is, thus, unequivocally present Error bars for A, C, and G denote standard error (n>3). Note: PTP1B$_{PS}$ corresponds to construct 7.1(T406A) from FIG. 1.

FIG. 3A shows one embodiment of a sensor for PTP1B activity. This sensor consists of a kinase substrate domain, a short flexible linker, and a phosphorylation recognition domain, sandwiched between two fluorescent proteins (e.g., a cyan fluorescent protein and a yellow fluorescent protein). When the sensor is in its unphosphorylated state, Förster resonance energy transfer (FRET) between the two fluorophores causes a decrease in CFP fluorescence and an increase in YFP fluorescence; when the sensor is in its phosphorylated state, the absence of FRET causes the opposite effect. FIG. 3B shows an exemplary increase in the ratio of donor fluorescence (CFP) to acceptor fluorescence (YPet) evidences the presence of Src kinase (i.e., a tyrosine kinase). When either (i) EDTA, which chelates a metal cofactor of Src, or (ii) PTP1B, which dephosphorylates the substrate domain, are additionally added, this increase does not occur. FIG. 3C shows one embodiment as another variety of the FRET sensor for A; this one uses mClover3 and mRuby3. The excitation and emission wavelengths of these proteins make them compatible with LOV2-based imaging experiments. FIG. 3D shows an exemplary repeat of the experiment from B with the sensor from C.

FIG. 4A-C shows embodiments of three constructs are expressed in Cos-7 cells: (FIG. 4A) GFP-PTP1B$_{PS}$, (FIG. 4B) GFP-PTP1B$_{PS}$-A, and (FIG. 4C) GFP-PTP1B$_{PS}$-B. Here, GFP-PTP1B$_{PS}$ is a fusion of green fluorescent protein (GFP) and the N-terminus of 7.1(T406A) from FIG. 1B-C (without the histidine tag); GFP-PTP1B$_{PS}$-A is a fusion of GFP-PTP1B$_{PS}$ and the C-terminal domain of full-length PTP1B; and GFP-PTP1B$_{PS}$-B is fusion of GFP-PTP1B$_{PS}$ and the C-terminal endoplasmic reticulum (ER) anchor of full-length PTP1B (see below). GFP-PTP1B$_{PS}$ localizes to the cytosol and nucleus, while GFP-PTP1B$_{PS}$-A and GFP-PTP1B$_{PS}$-B localize to the ER. FIG. 4D-H shows exemplary results of cell-based studies of PTP1B$_{PS}$. We transformed Cos-7 cells with a plasmid containing (i) the FRET sensor from FIGS. 3C-3D and (ii) PTP1B$_{PS}$ or PTP1B$_{PS}$/C450M (a light-insensitive mutant). In this experiment, we illuminated individual cells with 447 nm light and immediately imaged them with 561 nm light. Light-modulated changes in FRET ratio (as defined in FIG. 3) allowed us to detect light-modulated changes in PTP1B activity. FIG. 4D-E shows an exemplary Cos-7 cell transformed with PTP1B$_{PS}$ at two time points: (FIG. 4D) immediately after excitation with 447 nm light and (FIG. 4E) after 1 min. A slight increase in FRET ratio (dark green to lighter green) evidences photoactivation of PTP1B. (F-G). A Cos-7 cell transformed with PTP1B$_{PS}$ (C450M) at two time points: (FIG. 4F) immediately after excitation with 447 nm light and (G) after 1 min. The absence of a detectable change in FRET-ratio indicates that the change observed in D-E results from light-induced changes in PTP1B activity. FIG. 4H shows an exemplary average fractional change in FRET ratio observed in the nucleus (nuc) and cytosol (cyt) after 1 min and 2.67 min. The change is higher for PTP1B$_{PS}$ than for PTP1B$_{PS}$(C450M), the light-insensitive mutant. Error bars indicate standard error.

FIG. 5A shows an exemplary use of a phosphatase, i.e. drug target (upper left depiction of PTP1B) for identifying a synthetic enzyme (lower right depiction) where the enzyme is then used for providing an inhibitor or modulatory molecule for the phosphatase, thus showing a general framework for using enzymes to build inhibitors of chosen protein targets. FIG. 5B shows an exemplary analysis of structural relationships between binding pockets. A matrix compares individual properties (e.g., volume) between binding pocket 1 and all other binding pockets (2 to n) capable of functionalizing (e.g., P450) or binding to (e.g., PTP1B) ligands synthesized within pocket 1. FIG. 5C shows an exemplary comparison of the ability of binding pockets in a biosynthetic pathway to bind to intermediates.

FIG. 7A shows embodiments of two binding partners of PTP1B: LMO4 and Stat3. FIG. 7B shows an exemplary binding isotherm based on binding-induced changes in the tryptophan fluorescence of PTP1B (the ligand isTCS 401, a competitive inhibitor).

FIG. 8B illustrates an exemplary structure of PTK6. Both STEP and PTK6 possess a C-terminal alpha-helix that is compatible with actuation by the N-terminal helix of LOV2 (i.e., an photomodulatory architecture similar to that depicted in FIG. 1).

FIG. 10A shows an exemplary illustration where in its active state (here the far-red state), PTP1B dephosphorylates the substrate domain, prevents substrate-SH2 association, and, thus, prevents transcription. FIG. 10B shows an exemplary illustration where in its inactive state (here, the red state), the phosphorylated substrate domain binds SH2, permitting transcription of a gene for antibiotic resistance.

FIG. 11A illustrates where we will compare the growth of colonies on replicate plates exposed to red and infrared light and select colonies that exhibit differential growth. FIG. 11B illustrates where we will further characterize the photosensitivity of top hits in liquid culture.

FIG. 14A illustrates Abietic acid. FIG. 14B demonstrates inhibition of PTP1B by abietic acid at concentrations (dark to light) of 0-400 uM. Analysis of different fits suggests noncompetitive or mixed-type inhibition. FIG. 14C illustrates Abietic acid (green) docked in the allosteric site of PTP1B. We have since shown that abietic acid binds to the active site of PTP1B. Inset highlights active site in black. FIG. 14D shows an exemplary X-ray crystal structure of a known allosteric inhibitor (blue).

FIG. 15B shows exemplary Abietadiene titers generated by E. Coli DH5a transformed with the plasmids from A (with no P450). FIG. 15C-D shows exemplary GC-MS analysis of products of FIG. 15C) abietadiene-producing strain and FIG. 15D abietic-acid-producing strain: (1) abietadiene, (2) levopimaradiene, and (3) abietic acid (ion counts in 10,000 for C and 1,000 for FIG. 15D). Note: E. coli DH5a avoids protein overexpression is commonly used in metabolic engineering*[4].

FIG. 16A illustrates clockwise from abietic acid (1), neoabietic acid (2), levopimaric acid (3), dihydroabietic acid (4). FIG. 16B shows exemplary initial rates in PTP1B on 10 mM of p-NP phosphate in the presence of 200 uM inhibitor. No inhibitor. Error bars=standard error (n>5).

FIG. 17A N-HSQC spectra of PTP1B (red) and PTP1B bound to abietic acid (blue). Inset: Crystal structure of PTP1B. FIG. 17B-C shows exemplary Tryptophan (W) fluorescence of PTP1B in the presence of FIG. 17B culture extract of control ($ABS_X$), abietadiene-producing (ABS), and abietic-acid producing (ABS/BM3) strains and (FIG. 17C) various concentrations of abietic acid and 25 uM of known allosteric inhibitor (BBR). Error bars represent standard error (n>5).

FIG. 19D-E shows exemplary residues targeted for mutagenesis in FIG. 19D P450 BM3 and FIG. 19E SttH.

FIG. 21A-E illustrates an exemplary high-throughput screens for PTP1B inhibitors.

FIG. 21A Growth-coupled (i.e., selection; strategy 1). FIG. 21B) FRET sensor for PTP1B activity (strategy 2). FIG. 21C) FRET sensor and FIG. 21D) tryptophan fluorescence for changes in PTP1B conformation (strategies 3 and 4). FIG. 21E. Results for an operon similar to that shown in FIG. 21A, where Amp is replaced with Lux. Error bars=SD (n≥3).

FIG. 22A-D illustrates exemplary inhibition of PTP1B. Error bars in FIG. 22C denote SE (n≥3 independent reactions).

FIG. 22A shows exemplary alignments of the backbone of PTP1B in competitively inhibited (yellow and orange, PDB entry 2F71) and allosterically inhibited (gray and black, PDB entry 1T4J) poses. The binding of substrates and competitive inhibitors to the active site causes the WPD loop to adopt a closed (orange) conformation that stabilizes the C-terminal alpha7 helix through an allosteric network; this helix is unresolvable in allosterically inhibited, noncompetitively inhibited, and uninhibited structures, which exhibit WPD-open conformations (black). FIG. 22B shows an exemplary illustration of a chemical structure of abietic acid (AA). FIG. 22C shows exemplary initial rates of PTP1B-catalyzed hydrolysis of pNPP in the presence of increasing concentrations of AA. Lines show a fit to a model for mixed inhibition. FIG. 22D an exemplary illustration of this model, where the inhibitor (I) binds to the enzyme (E) and enzyme-substrate complex (ES) with different affinities.

FIG. 23A shows exemplary weighted differences in chemical shifts ($\Delta\delta$) between 1H-15 N-HSQC spectra collected in the absence and presence of AA (PTP1B:AA of 10:1). The dashed red line delineates the threshold for values of $\Delta\delta$ larger than two standard deviations ($\sigma$) above the mean; gray bars mark residues for which chemical shifts broadened beyond recognition. FIG. 23B illustrates an exemplary crystal structure of PTP1B (PDB entry 3A5J, gray) highlights the locations of assigned residues (blue); inhibitors in the allosteric site (PDB entry 1T4J, green) and active site (PDB entry 3EB1, yellow) are overlaid for reference. Residues with significant CSPs (i.e., $\Delta\delta > \Delta\delta$ mean+$2\sigma$) are distributed across the protein (red) and, with the exception of two residues in the WPD loop, outside of known binding sites. FIG. 23C illustrates an exemplary detail of the active site (upper panel) and known allosteric site (lower panel) with inhibitors from (FIG. 23B) overlaid.

FIG. 24A-C illustrates an exemplary mutational analysis of the AA binding site.

FIG. 24A illustrates an exemplary crystal structure of PTP1B (gray, PDB entry 3A5J) shows the location of mutations introduced at five sites: the active site (red), the allosteric site (green), site 1 (orange), site 2 (yellow), and the L11 loop (blue). The bound configurations of BBR (allosteric site, PDB entry 1 T4J) and TCS401 (active site, PDB entry 1C83) are overlaid for reference. FIG. 24B illustrates exemplary disruptive mutations introduced at each site. Mutations were designed to alter the size and/or polarity of targeted residues. The mutation denoted "YAYA" (Y152A/Y153A), which was identified in a previous study, attenuates allosteric communication between the C-terminus and the WPD loop. FIG. 24C illustrates exemplary fractional change in inhibition (F in Eq. 1) caused by the mutations from (B). Five mutations distributed across the protein reduced inhibition by AA and TCS401, but had negligible effect on inhibition by BBR. The similar effects of most mutations on AA and TCS401 suggest that both inhibitors bind to the active site. Error bars denote SE (propagated from n≥9 independent measurements of each V in Eq. 1).

FIG. 25A-B illustrates exemplary results of molecular dynamics simulations: backbone traces of PTP1B in (A) AA-free and FIG. 25B illustrates exemplary amino acid (AA)-bound states. The thickness of traces indicates the amplitude and direction of local motions (Methods). The binding of AA increases the flexibility of the WPD, E, and L10 loops. The WPD and L10 loops contain residues with significant CSPs (red), suggesting consistency between the results of MD and NMR analyses. FIG. 25C illustrates an exemplary representative bound conformation if AA (green). Upon binding to the active site, AA (i) forms a hydrogen bond with R221 that weakens a bond between R221 and E115 and (ii) prevents the formation of a hydrogen bond (red) between W179 and R221 that forms when the WPD loop closes. Both effects enhance the conformational dynamics of the WPD loop. FIG. 25D shows exemplary results of docking calculations are consistent with mixed-type inhibition: the binding of AA prevents the WPD loop from closing and disrupts, but does not preclude, the binding of pNPP (blue spheres).

FIG. 26A-C illustrates exemplary terpenoids showing differences in stereochemistry, shape, size, and chemical functionality. FIG. 26A) Structural analogues of abietic acid (AA): continentalic acid (CA), isopimaric acid (IA), dehydroabietic acid (DeAA), and dihydroabietic acid (DiAA). FIG. 26B) Differences in degree of saturation yield pronounced differences in potency (i.e., IC 50), but not selectivity. Error bars represent 95% confidence intervals. FIG. 26C shows binding of three of the analogues depicted in FIG. 26A.

FIG. 27A-C Analysis of pathologically relevant mutations.

FIG. 27A illustrates an exemplary Histogram of kinetically characterized mutations. All mutations proximal (<4 A) to five or more network residues were "influential" (i.e., they altered $k_{cat}$ or KM by >50% or had a detectable influence on inhibition); non-consequential mutations, by contrast, had fewer neighboring network residues. FIG. 27B illustrates an exemplary crystal structure of PTP IB (gray, PDB entry 3A5J) highlights the locations of influential mutations on network residues; colors indicate whether they were introduced in biophysical studies or found in diseases. FIG. 27C illustrates an exemplary two cumulative distribution functions describe numbers of network residues proximal to (i) mutations identified in diseases and (ii) a random selection of sites. The two distributions are indistinguishable from one another (P<0.05), suggesting that disease-associated mutations do not occur preferentially near the allosteric network.

FIG. 28A shows embodiments of Operon A. An example of the operon. S, tyrosine substrate; P, phosphate group; cI, the 434 phage cI repressor; RpoZ and $RP_\omega$, the omega subunit of RNA polymerase; cI OP, the binding sequence for the 434 phage cI repressor; and RB, the binding site for RNA polymerase (RNAP). Phosphorylation of the tyrosine substrate (by c-Src kinase) causes binding of the substrate-$RP_\omega$ fusion to the SH2-cI fusion; this binding event, in turn, localizes the RNA polymerase to RB, triggering transcription of the GOI. PTP1B dephosphorylates the substrate domain, preventing the association of substrate-$RP_\omega$ fusion and the SH2-cI, thereby, halting transcription of the GOI. Inactivation of PTP1B, in turn, re-enables transcription of the GOI. FIG. 28B illustrates one embodiment of a proposed medium-throughput screen for membrane-permeable inhibitors: A strain of the E. coli is transformed with the operon and grown in the presence of small molecules; small-molecule inhibitors of PTP1B modulate transcription of the GOI (e.g., a gene for luminescence, fluorescence, or antibiotic resistance) in a dose-dependent manner. The bar graph shows a predicted trend in data. FIG. 28C shows embodiments of Operon B. An operon that enables screens for selective inhibitors. This operon comprises operon A with (i) a second substrate-protein fusion (red), a "decoy", that can bind to the SH2-cI fusion but not specifically to DNA or RNA polymerase, and (ii) a second PTP (e.g., TC-PTP) that is active on the substrate domain of the decoy. Because complexes between the decoy and SH2-cI do not trigger transcription, the decoy inhibits transcription by competing with cI-substrate for binding sites. Accordingly, molecules that inhibit PTP1B, but not TC-PTP (which dephosphorylates the decoy)—that is, selective inhibitors—cause the greatest transcriptional activation. Molecules that inhibit both enzymes, by contrast, cause less activation. FIG. 28D shows embodiments of Operon C. This operon enables screens for photoswitchable enzymes. This operon comprises a version of operon A in which PTP1B has been replaced with a photoswitchable version of PTP1B. In this case, transcription of the GOI is different (e.g., higher or lower) under different sources of light. In the example shown, light inhibits the activity of a PTP1B-LOV2 chimera and, thus, enhances transcription of the GOI.

FIG. 29A shows one embodiment of Operon A in which the GOI is a bacterial luciferase (LuxAB). PTP1B inhibits luminescence (i.e., reduces transcription of the GOI), while a catalytically inactive version of PTP1B (a mimic for an inhibited version of PTP1B) enhances luminescence. FIG. 29B shows one embodiment of Operon A in which the GOI is a gene for spectinomycin resistance (SpecR). PTP1B inhibits growth on spectinomycin, while a catalytically inactive version of PTP1B (a mimic for an inhibited version of PTP1B) enhances growth. The MidT substrate is used herein.

FIG. 30A shows one embodiment of operon from A in which the GOI is a bacterial luciferase (LuxAB), the PTP1B is missing, and the substrate is a peptide from Kras, midT, ShcA, or EGFR. Although all substrates can be phosphorylated by Src kinase, only two substrates bind to the SH2 domain tightly enough to enable significant luminescence over background (0% arabinose). FIG. 30B shows one embodiment of operon from A (here, contained on a single plasmid) in which the GOI is a bacterial luciferase (LuxAB) and PTP1B is missing. The Y/F mutation on the substrate domain (blue) prevents it from being phosphorylated. The RBS sites toggle expression of the Src kinase.

FIG. 31A illustrates an exemplary conceptualization of a screen for microbially synthesizable inhibitors of PTP1B. When transformed with one embodiment of Operon A (or operon B), a cell capable of synthesizing PTP1B-inhibiting metabolites will produce a different GOI output than a cell that does not produce such metabolites. Because abietane-type diterpenoids can both (i) inhibit PTP1B and (ii) be synthesized in E. coli, we believe that a strain of E. coli that contains both Operon A and a pathway for building abietane-type diterpenoids could be "evolved" to build inhibitors of PTP1B. Here, the GOI could be a gene for luminescence or fluorescence (low throughput) or antibiotic resistance (high throughput). FIG. 31B illustrates an exemplary conceptualization of a screen for photoswitchable enzymes. Consider a fusion of PTP1B to LOV2 or BphP1 (here, the highlighted helices show N-terminal connection points on these two proteins). For this example, illumination of the PTP1B-LOV2 with 455 nm light reduces its activity; illumination of the PTP1B-BphP1 fusion with 650 nm light reduces its activity, while illumination of the PTP1B-BphP1 fusion with 750 nm light enhances its activity. When transformed with operon C (which would contain one of these fusions), a cell will produce a different GOI output under different illumination conditions. FIG. 31C illustrates an exemplary conceptualization of a screen for selective mutants of enzymes. When transformed with a version of operon B where (i) PTP1B is also active on the decoy and (ii) the second PTP (TC-PTP in our example) is missing a cell containing a mutant of PTP1B will most effectively transcribe the GOI when PTP1B is only active on the decoy substrate. FIG. 31D illustrates an exemplary conceptualization of a screen for selective substrates. When transformed with a version of operon B where (i) the decoy is missing, (ii) the first enzyme (PTP1B in our example) is under an inducible promoter, (iii) a second PTP (TC-PTP in our example) is under a second inducible promoter, and (iv) the GOI includes a gene for antibiotic resistance and a gene that produces a toxic product in the presence of a non-essential substrate, a cell containing a mutated substrate domain will grow under both condition 1 (inducer of PTP1B and non-essential substrate) and condition 2 (inducer of TC-PTP), when it binds to PTP1B, but not to TC-PTP.

FIG. 32A refers to an exemplary results of a statistical coupling analysis. The orange and blue clusters represent two groups of interconnected residues, termed "sectors", that exhibit strong intra-group correlations in nonrandom distributions of amino acids. The allosteric site (green inhibitor, PDB entry 1T4J), WPD loop (purple spheres), and active site (red inhibitor, 3EB1) are highlighted for reference. FIG. 32B refers to an exemplary analysis of crosstalk between pockets of PTP1B modeled with MD simulations. Pockets are represented as spheres, colored according to their persistency along the MD trajectory; the size of each sphere indicates its average volume in MD simulations. Links have thicknesses proportional to the frequency of inter-pocket merging and splitting events (i.e., communication). Two independent sets of inter-connected pockets map closely to the sectors identified in SCA and, thus, suggest that these two sectors represent distinct domains of an evolutionarily conserved allosteric network. In the PTP1B-LOV2 fusions of FIG. 1, LOV2 modulates the activity of PTP1B by tapping into the allosteric network defined by sector A. Identification of sector A with a statistical coupling analysis of the PTP family thus indicates that the architecture for photocontrol described in FIG. 1 is broadly applicable to all protein tyrosine phosphatases.

FIG. 33A illustrates an embodiment of a bacterial two-hybrid system that detects phosphorylation-dependent protein-protein interactions. Components include (i) a substrate domain fused to the omega subunit of RNA polymerase (yellow), (ii) an SH2 domain fused to the 434 phage cI repressor (light blue), (iii) an operator for 434cI (dark green), (iv) a binding site for RNA polymerase (purple), (v) Src kinase, and (vi) PTP1B. Src-catalyzed phosphorylation of the substrate domain enables a substrate-SH2 interaction that activates transcription of a gene of interest (GOI, black). PTP1B-catalyzed dephosphorylation of the substrate domain prevents that interaction; inhibition of PTP1B re-enables it. FIG. 33B refers to an embodiment of the two-hybrid system from FIG. 33A that (i) lacks PTP1B and (ii) contains luxAB as the GOI. We used an inducible plasmid to increase expression of specific components; overexpression of Src enhanced luminescence. FIG. 33C refers to an embodiment of the two-hybrid system from FIG. 33A that (i) lacks both PTP1B and Src and (ii) includes a "superbinder" SH2 domain (SH2*, i.e., an SH2 domain with mutations that enhance its affinity for phosphopeptides), a variable substrate domain, and LuxAB as the GOI. We used an inducible plasmid to increase expression of Src; luminescence increased most prominently for p130cas and MidT, suggesting that Src acts on both substrate domains. FIG. 33D refers to an embodiment of a two-hybrid system from FIG. 33C with one of two substrates: p130cas or MidT. We used a second plasmid to overexpress either (i) Src and PTP1B or (ii) Src and an inactive variant of PTP1B (C215S). The difference in luminescence between systems containing PTP1B or PTP1B (C215S) was greatest for MidT, suggesting that PTP1B acts on this substrate. Right: An optimized version of the two-hybrid system (with bb030 as the RBS for PTP1B) appears for reference. FIG. 33E displays the results of an exemplary growth-coupled assay performed using an optimized B2H including SH2*, a midT substrate, optimized promoters and ribosome binding sites (bb034 for PTP1B), and SpecR as the GOI. This system is illustrated at the top of the figure. Exemplary growth results demonstrate that inactivation of PTP1B enables strain of E. coli harboring this system to survive at high concentrations of spectinomycin (>250 µg/ml).

FIG. 36A depicts a plasmid-borne pathway for terpenoid biosynthesis: (i) pMBIS, which harbors the mevalonate-dependent isoprenoid pathway of S. cerevisiae, converts mevalonate to isopentyl pyrophosphate (IPP) and farnesyl pyrophosphate (FPP). (ii) pTS, which encodes a terpene synthase (TS) and, when necessary, a geranylgeranyl diphosphate synthase (GPPS), converts IPP and FPP to sesquiterpenes and/or diterpenes.

FIG. 36B depicts exemplary terpene synthases: amorphadiene synthase (ADS) from *Artemisia annua*, γ-humulene synthase (GHS) from *Abies grandis*, abietadiene synthase (ABS) from *Abies grandis*, and taxadiene synthase (TXS) from *Taxus brevifolia*.

FIG. 36C shows the results of an exemplary growth-coupled assay of strain of E. coli that contains both (i) an embodiment of the optimized bacterial two-hybrid (B2H) system (i.e., the B2H system from FIG. 33E) and (ii) an embodiment of a pathway for terpenoid biosynthesis (i.e., the pathway from FIG. 35A).

FIG. 37A depicts the results of our analysis of the inhibitory effect of DMSO containing (i) no inhibitor and (ii) extracted compounds from the culture broth of the ADS-containing strain. FIG. 37B depicts the results of our analysis of the inhibitory effect of DMSO containing (i) extracted compounds from the culture broth of the GHS-containing strain (gHUM) or (ii) extracted compounds from the culture broth of the strain including the L450Y mutant of GHS. FIG. 37C depicts the results of our analysis of the inhibitory effect of DMSO containing (i) no inhibitor, (ii) extracted compounds from the culture broth of the ABS-containing strain, (iii) extracted compounds from the culture broth of the TXS-containing strain, and (iv) extracted compounds from the culture broth of the train strain containing a catalytically inactive variant of ABS.

FIG. 40A-E depicts exemplary embodiments of genetically encoded systems that link the activity of an enzyme to the expression of a gene of interest, and the application of those embodiments to (i) the prediction of resistance mutations, (ii) the construction of inhibitors that combat resistance mutations, and (ii) the evolution of inhibitors of kinases.

FIG. 40A depicts an exemplary first step in examining potential resistance mutations. By evolving a metabolic pathway to produce molecules that inhibit a known drug target (e.g., PTP1B); these molecules will permit expression of a gene of interest (GOI) that confers survival in the presence of a selection pressure (e.g., the presence of spectinomycin, an antibiotic). FIG. 40B depicts an exemplary second step in examining potential resistance mutations. In a second strain of E. coli, we will replace the original gene of interest with a second (GOI2) that confers conditional toxicity (e.g., SacB, which converts sucrose to levan, a toxic product); we will evolve the drug target to become resistant to the endogenous inhibitors, while still retaining its activity. This mutant will prevent expression of the toxic gene. FIG. 40C depicts an exemplary third step in combating resistance mutations. In a third strain of E. coli, we will evolve a metabolic pathway that produces molecules that inhibit the mutated drug target. In this way, we will both predict—and, through our second evolved pathway, address—mutations that might cause resistance to terpenoid-based drugs. FIG. 40D depicts an exemplary genetically encoded system that detects inhibitors of an Src kinase. In brief, Src activity enables expression of a toxic gene (GOI2); inhibition of Src, in turn, would confer survival. FIG. 40E demonstrates one embodiment of a roof of principle for the B2H system describe in FIG. 40B. The system shown here includes two GOIs: SpecR and SacB. Expression of the GOIs confers survival in the presence of spectinomycin; expression of the GOIs causes toxicity in the presence of sucrose. The images depict the results of a growth-coupled assay performed on a strain of E. coli in the presence of various concentrations of sucrose. The strain harboring an active form of PTP1B (WT) grows better at high sucrose concentrations that the strain harboring an inactive form of PTP1B (C215 S).

FIG. 41A depicts an exemplary strategy for the evolution of inhibitors of PTP1B.

FIG. 41A depicts an exemplary structural analysis used to identify targets for mutagenesis in the active sites of terpene synthases. It shows an alignment of the class I active site of ABS (gray, PDB entry 3s9v) and TXS (blue, PDB entry 3p5r) with the locations of sites targeted for site-saturation mutagenesis (SSM) highlighted on ABS (red). A substrate analogue (yellow) of TXS appears for reference. FIG. 41B depicts an exemplary strategy for introducing diversity into libraries of metabolic pathways: An iterative combination of SSM of key sites on a terpene synthase (as in a), error-prone PCR (ePCR) of the entire terpene synthase gene, SSM of sites on a terpene-functionalizing enzyme (e.g., P450), and ePCR of the entire terpene-functionalizing enzyme. FIG. 41C depicts an exemplary quantification the total terpenoids present in DMSO samples with extracts of various TS-containing strains. In brief, we performed site-saturation mutagenesis of six sites on ADS (analogous to the sites shown in FIG. 41A); we plated the SSM library on agar plates containing different concentrations of spectinomycin; we picked colonies that grew on a plate containing a high concentration (800 µg/ml) of spectinomycin and used each colony to inoculate a separate culture; we used a hexane overlay to extract the terpenoids secreted into each culture broth; we dried the hexane extract in a rotary evaporator and re-suspended the solid in DMSO; and we used a GC-MS to quantify the total amount of terpenoids present in the DMSO. FIG. 41D depicts an exemplary analysis of the inhibitory effect of various extracts on PTP1B. In brief, the figure shows initial rates of PTP1B-catalyzed hydrolysis of p-nitrophenyl phosphate (pNPP) in the presence of terpenoids quantified in FIG. 41C. Two mutants of ADS (G439A and G400L) generate particularly potent inhibitors of PTP1B.

FIG. 44A-D provides exemplary structural and sequence-based evidence that supports the extension the B2H system to other protein tyrosine phosphatases (PTPs).

FIG. 44A provides an exemplary structural alignment PTP1B and PTPN6, two PTPs that are compatible with the B2H system (see FIGS. 1e and 7 of Update A for evidence of compatibility). We used the align function of PyMol to align each structure of PTPN6 with either (i) the ligand-free (3A5J) or (ii) ligand-bound (2F71) structure of the catalytic domain of PTP1B. The align function carries out a sequence alignment followed by a structural superposition and, thus, effectively aligns the catalytic domains of both proteins. FIG. 44B provides an exemplary structural comparison of PTP1B and PTPN6; the root-mean-square deviations (RMSD) of aligned structures of PTP1B and PTPN6 range from 0.75 to 0.94 Å. FIG. 44C proves an exemplary sequence alignment of the catalytic domains of PTP1B (SEQ ID NO: 3) and PTPN6 (SEQ ID NO: 4) (EMBOSS Needle[1]). FIG. 44D provides an exemplary sequence comparison of the catalytic domains of PTP1B and TPPN6. The sequences share 34.1% sequence identity and 53.5% sequence similarity. In summary, the results of this figure indicate that our B2H system can be readily extended to PTPs that possess catalytic domains that are (i) structurally similar to the catalytic domain of PTP1B (here, we define structural similarity as two structures that when aligned, have with an RMSD of ≤0.94 Å RMSD with the framework similar to the one used by the align function of PyMol) and/or (ii) sequence similar to the catalytic domain of PTP1B (here, we define sequence similarity as ≥34% sequence identity or ≥53.5% sequence similarity as defined by the EMBOSS Needle algorithm).

DEFINITIONS

Figure 1A:
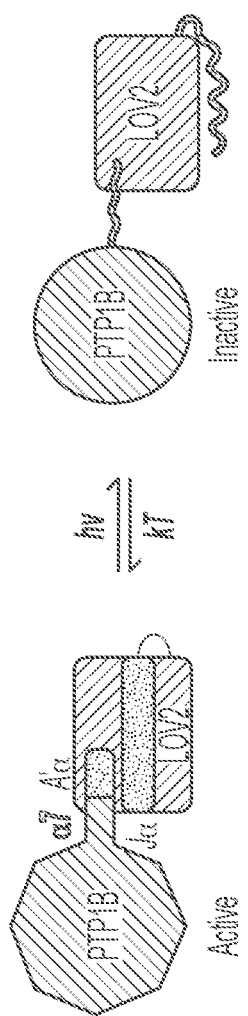
FIG. 1A-G illustrates embodiments and shows exemplary results of developing a photoswitchable phosphatase, e.g. PTP1B$_{PS}$.

As used herein, the use of the term "operon" may refer to a cluster of genes under the control of a single promoter (as in a classical definition of an operon) and may also refer to a genetically encoded system comprising multiple operons (e.g., the bacterial two-hybrid system).

As used herein, "phosphorylation-regulating enzymes" refer to proteins that regulate phosphorylation.

As used herein, "phosphorylation" refers to a biochemical process that involves the addition of phosphate to an organic compound.

As used herein, "optogenetic actuator" refers to a genetically encodable protein that undergoes light-induced changes in conformation.

As used herein, "dynamic range" refers to the ratio of activity in dark and light state (i.e., the initial rate in the dark/the initial rate in the presence of 455 nm light).

As used herein, "operon" refers to a unit made up of multiple genes that regulate other genes responsible for protein synthesis, As used herein, "operably linked" refers to one or more genes (i.e. DNA sequences) suitably positioned and oriented in a DNA molecule for transcription to be initiated from the same promoter. DNA sequences that are operably linked to a promoter means that expression of the DNA sequence(s) is under transcriptional initiation regulation of the promoter.

As used herein, "construct" refers to an engineered molecule, e.g. ligated pieces of DNA as a DNA construct; a RNA construct as one contiguous sequence resulting from the expression of a DNA construct.

As used herein, "fusion" refers to an expressed product of an engineered construct i.e. a combination of several ligated sequences as one molecule or a single gene that encodes for a protein-protein fusion originally encoded by two genes.

As used herein, "expression vector" or "expression construct" refers to an operon, plasmid or virus designed for DNA expression of a construct in host cells, typically containing a promoter sequence operable within the host cell.

As used herein, "promoter" refers to a region of DNA that initiates transcription of a particular DNA sequence. Promoters are located near the transcription start sites of, towards the 5' region of the sense strand. Promoters may be constitutive promoters, such as cytomegalovirus (CMV) promoters in mammalian cells, or inducible promoters, such as tetracycline-inducible promoters in mammalian cells.

As used herein, "transformation" refers to a foreign nucleic acid sequence or plasmid delivery into a prokaryotic host cell, for example, an expression plasmid (e.g. a plasmid expression construct) inserted into or taken up by a host cell.

As used herein, "transfection" refers to the insertion of a nucleic acid sequence into a eukaryotic cell.

Transformation and transfection may be transient, such that the nucleic acid sequence or plasmid introduced into the host cell is not permanently incorporated into the cellular genome. A stable transformation and transfection refers to a host cell retaining the foreign nucleic acid sequence or plasmid for multip generations regardless of whether the nucleic acid or plasmid was integrated into the genome of the host cell.

As used herein, "host" in reference to a cell refers to a cell intended for receiving a nucleic acid sequence or plasmid or already harboring a a nucleic acid sequence or plasmid, eg. a bacterium.

As used herein, "conjugate" refers to a covalently attachment of at least two compounds, for example, a photosensing element attached to a phosphatase protein.

As used herein, "decoy" in reference to a protein construct that cannot bind to DNA and/or RNA polymerase.

DETAILED DESCRIPTION OF INVENTION

This invention relates to the field of genetic engineering. Specifically, the invention relates to the construction of operons to produce biologically active agents. For example, operons may be constructed to produce agents that control the function of biochemical pathway proteins (e.g, protein phosphatases, kinases and/or proteases). Such agents may include inhibitors and modulators that may be used in studying or controlling phosphatase function associated with abnormalities in a phosphatase pathway or expression level. Fusion proteins, such as light activated protein phosphatases, may be genetically encoded and expressed as photoswitchable phosphatases. Systems are provided for use in controlling phosphatase function within living cells or in identifying small molecule inhibitors/activator/modulator molecules of protein phosphatases associated with cell signaling.

The invention also relates to the assembly of genetically encoded systems (e.g., one or more operons) for detecting and/or constructing biologically active agents. For example, systems may be assembled in order to accomplish one or more goals, e.g. (i) to detect and/or synthesize small molecules that affect the activity of regulatory enzymes (e.g., protein phosphatases, kinases, and/or proteases); (ii) to detect and/or evolve regulatory enzymes modulated by light (e.g., light-responsive protein phosphatases, kinases, or proteases), etc. Small molecule modulators may include inhibitors of phosphatases known to be associated with human diseases or implicated with causing or perpetuating human diseases; activators of phosphatases implicated or known to be associated in human diseases (e.g., diabetes, obesity, and cancer); such small molecules may serve as chemical probes in studies of cell signaling; as structural starting points (i.e., leads); etc., for the development of pharmaceutical compounds for use in treating a human disease. Light-sensitive enzymes may include protein tyrosine phosphatases fused to optogenetic actuators (e.g., a LOV domain if phototropin 1). Such fusions could serve as tools for exerting spatiotemporal control over protein tyrosine phosphorylation in living cells Further, microbial operons are provided that are designed for use in identifying either small molecule inhibitors, activators, or modulator molecules, photoswitchable enzymes, or biological components, including intracellularly expressed molecules, including, for examples, operons having components for use in whole cell microbial screening assay systems. Inhibitors/modulator molecules discovered using compositions, systems and methods described herein are contemplated for use in treating diseases such as diabetes, type II diabetes, obesity, cancer, and Alzheimer's disease, among other disorders associated with protein phosphatase enzymes.

In one embodiment, the present invention relates to a Protein tyrosine phosphatase 1B (PTP1B). PTP1B represents a valuable starting point for this study for four reasons: (i) It is implicated in diabetes[5], obesity[6], cancer[30], anxiety[31], inflammation[32], the immune response[7], and neural specification in embryonic stem cells[33], (ii) The mechanisms underlying its subcellular localization are well understood (a short C-terminal anchor connects it to the ER; proteolysis of this anchor releases it to the cytosol)[29,34]. (iii) It can be expressed, purified, and assayed with ease[35], (iv) It is a member of a class of structurally similar enzymes (PTPs) that could facilitate the rapid extension of architectures for making it photoswitchable. PTP1B represents both an experimentally tractable model system for testing strategies for optical control, and an enzyme for which optical modulation is contemplated to permit detailed analyses of a wide range of diseases and physiological processes.

Figure 10A:
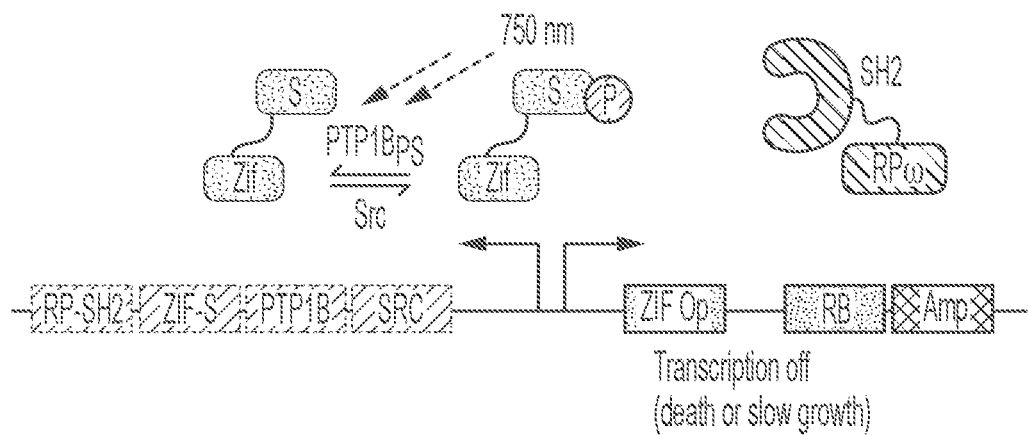
FIG. 10A-B illustrates an exemplary operon for screening photoswitchable variants of PTP1B.
Figure 10B:
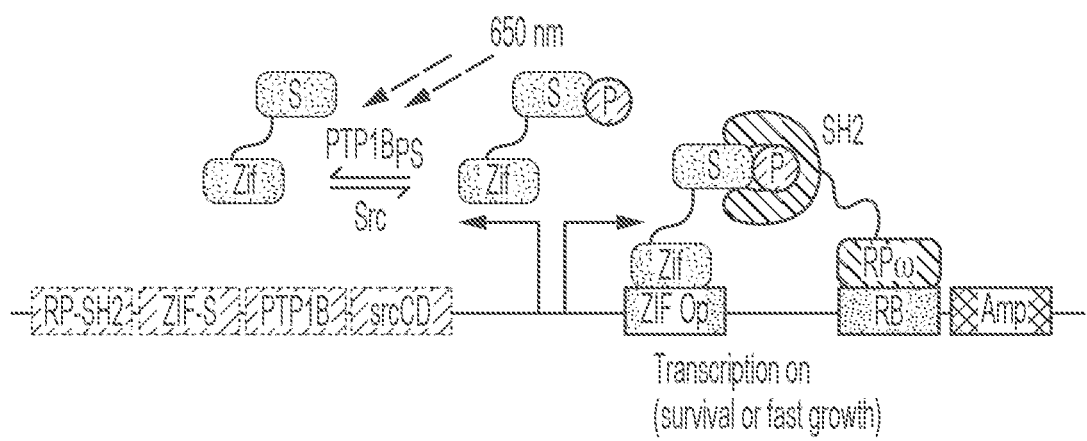
Figure 11A:
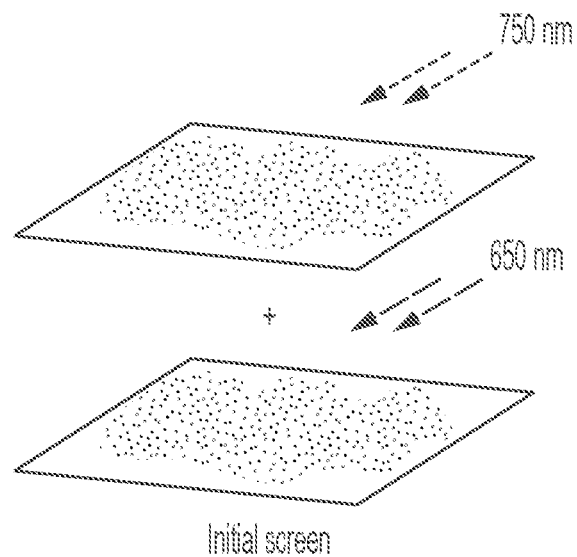
FIG. 11A-B illustrates an exemplary strategy for evolution of photoswitchable proteins.

Specifically related to exemplary Figures: FIGS. 1, 2, 3, 4, 8, 9, 12, and 13 describe optogenetic and imaging technologies (i.e., light-sensitive enzymes and genetically encodable biosensors) that could be evolved, improved, or optimized with the operon; FIGS. 10 and 11 describe strategies for using the operon to evolve, improve, or optimize light-sensitive enzymes; FIGS. 5, 6, 14, 15, 16, 17, 18, 19, 20, 28, 29, 30, and 31 support both (i) the development of an operon for detecting and/or evolving small molecules that inhibit known drug targets and (ii) the subsequent characterization of those molecules; FIGS. 22, 23, 24, 25, 26, 27, and 32 provide examples of kinetic and biophysical characterizations of a microbially synthesizable molecule that inhibits PTP1B.

I. Protein Tyrosine Phosphatases (PTPs) and Protein Tyrosine Kinases (PTKs) in Relation to Disease.

Protein tyrosine phosphatases (PTPs) and protein tyrosine kinases (PTKs) are two classes of enzymes contributing to anomalous signaling events in a wide range of diseases (e.g., diabetes, cancer, atherosclerosis, and Alzheimer's disease, among others) and understanding disease progression[14,36]. Further, they are involved with regulating memory, fear, appetite, energy expenditure, and metabolism, thus use of such phosphorylation regulating enzymes may reveal links between seemingly disparate physiological processes[14,22,13].

Embodiments for using light as photoswitchable constructs for controlling PTPs and PTKs is described herein. Accordingly, examples of photoswitchable constructs of PTPs and PTKs developed as described herein, should be broadly useful to biomedical researchers interested in understanding how healthy and diseased cells process chemical signals in addition to use for identifying specific alleles of PTPs and/or PTKs (i.e. gene sequences or proteins)—or other enzymes that they regulate—linked to specific diseases, such as diabetes, etc., including subtypes of diseases, i.e. early onset, late onset, etc., and specific types of cancer, and for screening and testing molecules, including small molecules, for treating diseases associated with these alleles.

Although other references describe photocontrol of proteins, including using LOV2 conjugates, these references do not mention using phosphatases. Fan, et al., "Optical Control Of Biological Processes By Light-Switchable Proteins." Wiley Interdiscip Rev Dev Biol. 4(5): 545-554. 2015. This reference describes blue light-oxygen-voltage-sensing (LOV) domains including the LOV2 C-terminal α-helix, termed Jα, from *Avena sativa* phototropin. Linkage to the LOV domain can cage a protein of interest (POI), while light-induced conformational change in the LOV domain results in its uncaging. As one example, peptide kinase inhibitors can be caged by fusion to the C-terminus of LOV2. Exposure to light results in uncaging of the inhibitors for light modulating protein kinase activities in cells. WO2011133493. "Allosteric regulation of kinase activity." Published Oct. 27, 2011. This reference describes fusion proteins comprising a kinase, including as examples, a tyrosine kinase (Src), a serine/threonine kinase (p38), and a ligand binding domain, e.g. a light-regulated LOV domain (where illumination is considered "ligand binding"), inserted in the N-terminal and/or C-terminal end or near the catalytic domain to produce allosteric regulation using a light-dependent kinase. Further, a LOV domain includes a LOV2 domain and/or Jα domain from *A. sativa* phototropin I. WO2012111772 (A1) In Japanese with an English abstract. This reference abstract describes a polypeptide for the optical control of calcium signaling comprising an amino acid sequence including: a LOV2 domain composed of SEQ ID NO: 1 or an amino acid sequence having at least 80% sequence identity with SEQ ID NO: 1. The construct has a LOV2 domain followed by a LOV2-Jalpha optical switch at the N terminus of the construct. U.S. Pat. No. 8,859,232. "Genetically encoded photomanipulation of protein and peptide activity." Issued Oct. 14, 2014. This reference describes fusion proteins comprising protein light switches and methods of photomanipulating the activity of the fusion proteins to study protein function and analyze subcellular activity, as well as diagnostic and therapeutic methods. More specifically, a fusion protein comprising a protein of interest fused to a protein light switch comprising a light, oxygen or voltage (LOV2) domain of *Avena sativa* (oat) phototropin 1, wherein illumination of the fusion protein activates or inactivates the protein of interest. The protein of interest is a functional domain of a human protein. As an example, a LOV2-Jα sequence of phototropin1 (404-547) was fused to the N-terminus of RacI so that the LOV domain in its closed conformation would reversibly block the binding of effectors to RacI.

A. Protein Tyrosine Phosphatases (PTPs).

Protein tyrosine phosphatases (PTPs) are a class of regulatory enzymes that exhibit aberrant activities in a wide range of diseases. A detailed mapping of allosteric communication in these enzymes could, thus, reveal the structural basis of physiologically relevant—and, perhaps, therapeutically informative—perturbations (i.e., mutations, post-translational modifications, or binding events) that influence their catalytic states. This study combines detailed biophysical studies of protein tyrosine phosphatase IB (PTP IB) with large-scale bioinformatic analyses to examine allosteric communication in PTPs. Results of X-ray crystallography, molecular dynamics simulations, and sequence-based statistical analyses indicate that PTP D3 possesses a broadly distributed allosteric network that is evolutionarily conserved across the PTP family, and findings from kinetic studies show that this network is functionally intact in sequence-diverse PTPs. The allosteric network resolved in this study reveals new sites for targeting allosteric inhibitors of PTPs and helps explain the functional influence of a diverse set of disease-associated mutations.

In one embodiment, a tyrosine phosphatase and photosensitive protein as described herein may be attached to a drug for use in medical treatments. In contrast to EP2116263, "Reversibly light-switchable drug-conjugates." Published Nov. 11, 2009 which does not mention tyrosine phosphatase, and which describes photoswitchable conjugates of protein phosphatase calcineurin attached to a photoisomerizable group B and also attached to a drug for use in medical treatments (neither of these groups are genetically encodable). As one example in EP2116263, tumor growth is suppressed by inhibition of the protein phosphatase calcineurin. A photoisomerizable group B, for near UV (e.g. 370 nm) or near IR (e.g. 740 nm) induced activity, does not include a light responsive plant protein phototropin 1 LOV2 N-terminal alpha helix.

Receptor PTPs are contemplated for conjugation to light sensing proteins, as described herein. In contrast, Karunarathne, et al., "Subcellular optogenetics—controlling signaling and single-cell behavior." J Cell Sci. 128(1):15-25, 2015, describes photosensitive domains, such as bacteria light-oxygen-voltage-sensing (LOV and LOV2) domains including a C-terminal helical Jα region, tagged to receptor tyrosine kinases (RTKs), there were no specific examples, there was no mention of a tyrosine phosphatase nor a plant phototropin 1 LOV2 N-terminal alpha helix. Optical activation of an inositol 5-phosphatase was shown, but inositol 5-phosphatase is not a protein phosphatase.

B. Enzymatic Phosphorylation of Tyrosine Residues.

Enzymatic phosphorylation of tyrosine residues has a role in cellular function and is anomalously regulated in an enormous range of diseases (e.g., diabetes, cancer, autoimmune disorders, and Noonan syndrome. It is controlled by the concerted action of two classes of structurally flexible—and dynamically regulatable—enzymes: protein tyrosine kinases (PTKs), which catalyze the ATP-dependent phosphorylation of tyrosine residues, and protein tyrosine phosphatases (PTPs), which catalyze the hydrolytic dephosphorylation of phosphotyrosines (5, 6). A detailed understanding of the mechanisms by which these enzymes respond to activity-modulating structural perturbations (i.e., mutations, post-translational modifications, or binding events) can, thus, illuminate their contributions to various diseases and facilitate the design of new PTK- or PTP-targeted therapeutics.

Over the last several decades, many biophysical studies have dissected the catalytic mechanisms and regulatory functions of PTKs (7, 8), which are common targets of pharmaceuticals. (9) Detailed analyses of PTPs, by contrast, have lagged behind. (10) These enzymes represent an underdeveloped source of biomedical insight and therapeutic potential (no inhibitors of PTPs have cleared clinical trials); they are, thus, the focus of this study.

PTPs uses two loops to dephosphorylate tyrosine residues. The eight-residue P-loop binds phosphate moieties through a positively charged arginine, which enables nucleophilic attack by a nearby cysteine, and the ten-residue WPD loop contains a general acid catalyst—an aspartate—that protonates the tyrosine leaving group and hydrolyzes the phosphoenzyme intermediate^11-13) During catalysis, the P-loop remains fixed, while the WPD loop moves ~10A between open and closed states; nuclear magnetic resonance (NMR) analyses suggest this movement controls the rate of catalysis. (14)

Recent analyses of protein tyrosine phosphatase IB (PTP IB) a drug target for the treatment of diabetes, obesity, and breast cancer, indicate that motions of its WPD loop are regulated by an allosteric network that extends to its C-terminus (FIG. 1B) (15, 16). This network is susceptible to modulation by both (i) inhibitors that displace its C-terminal α7 helix (17, 18) and (ii) mutations that disrupt communication between the a(alpha)7 helix and the WPD loop (15); the specific collection of residues that enable allosteric communication in PTP1B and other PTPs has yet to be fully resolved.

Protein tyrosine phosphatase 1B (PTP1B). PTP1B represents a valuable tool for use in identifying potential therapeutics for at least four reasons: (i) It is implicated in diabetes[5], obesity[6], cancer[30], anxiety[31], inflammation[32], the immune response[7], and neural specification in embryonic stem cells[33], (ii) The mechanisms underlying its subcellular localization are well understood (a short C-terminal anchor connects it to the ER; proteolysis of this anchor releases it to the cytosol)[29,34]. (iii) It can be expressed, purified, and assayed with ease[35], (iv) It is a member of a class of structurally similar enzymes (PTPs) that could facilitate the rapid extension of architectures for making it photoswitchable. PTP1B, thus, represents both an experimentally tractable model system for testing strategies for optical control, and an enzyme for which optical modulation will permit detailed analyses of a wide range of diseases and physiological processes.

Spatial regulation and intracellular signaling. PTP1B demonstrates, by example, the value of photoswitchable enzymes for studying spatial regulation in intracellular signaling. It is hypothesized to inactivate receptor tyrosine kinases through (i) contacts between endosomes and the ER[37,38], (ii) contacts between the plasma membrane and extended regions of the ER[39], and (iii) direct protein-protein interactions enabled by its partial proteolysis and release into the cytosol[34]. The role of different mechanisms (or locations) of PTP2B-substrate interaction in determining the outcomes of those interactions is poorly understood. Evidence suggesting a relationship between the location of PTP1B and its role in signaling has arisen in studies of tumorigenesis. Inhibition of PTP1B can suppress tumor growth and metastasis in breast[30,40], lung[3,41], colorectal[9], and prostate cancers,[42,43] while its upregulation has similar effects in lymphoma[3,44]. Recent evidence suggest that the former effect may result from inhibition of cytosolic PTP1B[45]; the cause of the latter is unclear. At present, there are no tools to investigate the differential influence of spatially distinct subpopulations of PTP1B on tumor-associated signaling events within the same cell. Photoswitchable variants of PTP1B represent such a tool.

Network biology. Signaling networks are often represented as nodes (proteins) connected by lines (interactions)[46]. Such maps capture the connectivity of biochemical relay systems, but obscure spatial context—the ability of a single interaction to occur in multiple locations and, perhaps, to stimulate multiple signaling outcomes. This study develops a set of tools that will enable detailed studies of the role of spatial context in guiding the propagation of signals through biochemical networks; such an examination contributes to understanding the role of PTP1B in cell signaling (and processes associated with tumorigenesis), and generally relevant to the study of any enzyme that exists in spatially distinct subpopulations within the cell.

II. Optogenetic Actuators.

Optogenetic actuators (genetically encodable proteins that undergo light-induced changes in conformation) provide a convenient means of placing biochemical events under optical control. Alone, or when fused to other proteins, they have enabled optical manipulation of biomolecular transport, binding, and catalysis with millisecond and submicron resolution in living cells. Our approach addresses two major deficiencies in existing technologies: Observational interference and illuminating half the story. Existing strategies to control the activity of enzymes with light interfere with native patterns of protein production, localization, and interaction (often by design) and, thus, make direct interrogation and/or control of those patterns—which determine how biochemical signals are processed—difficult. There are several methods to control protein kinases with light, but no analogous methods for controlling protein phosphatases. As signaling networks are regulated by the concerted action of both classes of enzyme, comprehensive control and/or detailed dissections of those networks require methods for controlling both.

Embodiments described herein comprise (i) an approach for controlling the activity of proteins with light without disrupting their wild-type activities and (ii) a demonstration of this approach on a protein of particular importance: protein tyrosine phosphatase 1B (PTP1B), a regulator of cell signaling and a validated drug target for the treatment of diabetes, obesity, and cancer. There are no known photoswitchable protein tyrosine phosphatases. The PTP1B-LOV2 construct reported in this filing is the first. (ii) The N-terminal alpha helix of LOV2 is ignored in most studies (even reviews of optical switches) and has not been used as an exclusive connection point for optical modulation of enzymes.

We have developed a photoswitchable version of PTP1B by fusing the C-terminal allosteric domain of this enzyme to the N-terminal alpha helix of a protein light switch (i.e., the LOV2 domain of phototropin 1 from *Avena sativa*). We present evidence that this general architecture—which is unique in the placement of LOV2 away from the active site of PTP1B (minimally disruptive)—can be extended to other PTPs and, perhaps, PTKs. For example, we used a statistical coupling analysis to show that the allosteric network exploited in our PTP1B design is preserved across the PTP family.

Alone, or when fused to other proteins, optogenetic actuators have enabled optical manipulation of biomolecular transport, binding, and catalysis with millisecond and submicron resolution[15,16]. At least three deficiencies limit their use in detailed studies of signaling networks: Observational interference. Existing strategies to control the activity of enzymes with light interfere with native patterns of protein production, localization, and interaction[16,17] (often by design) and, thus, make direct interrogation of those patterns—which determine how biochemical signals are processed[10] difficult. Illuminating half the story. There are several methods to control protein kinases with light[18,19], but no analogous methods for controlling protein phosphatases. As signaling networks are regulated by the concerted action of both classes of enzyme, detailed dissections of those networks require methods for controlling both. A limited palette of actuators. Optogenetic actuators that enable subcellular control of enzyme activity require the use of blue or green light's. These wavelengths exhibit significant phototoxicity[20], suffer from short biological penetration depths[21], and, as a result of their spectral similarity, limit actuation to individual signaling events, rather than multiple events simultaneously.

A. Photoswitchable Constructs: Advantages Over Other Exemplary Technologies.

As described herein, a photoswitch describes a protein-protein architecture (e.g., a PTP1B-LOV2 fusion) that is optically active in its monomeric form. A reference, WO2013016693. "Near-infrared light-activated proteins." Publication Date Jan. 31, 2013, relies on homodimerization. In contrast, optical control as described herein is over a larger range of proteins, including both those that require homodimerization and those that do not, unlike in WO2013016693. Further, this reference describes types of photosensory modules including blue light-sensitive flavoproteins found in plants; photoreceptors of blue-light using flavin adenine dinucleotide (BLUF); Light, Oxygen, or Voltage sensing (LOV) types, which includes plant and bacterial photoreceptors; and plant/microbe phytochromes, sensitive to light, i.e. light-induced helix rotation in the red-to-NIR region. More specifically described with examples are bacteriophytochrome (Bph)-based photoactivated fusion proteins, using light-responsive alpha helixes from *Rhodobacter sphaeroides* (BphG) fused to proteins such as protein phosphatases, protein kinases, membrane receptors, etc. *E. coli*, are modified so as to exhibit the level of photoactivity of these expressed fusion proteins, i.e. in the presence or absence of red-to-NIR light. Although blue color changes in *E. coli* expressing fusion proteins are described in response to light, these blue bacteria are the result of using far-red/NIR-light for photoactivating a fusion protein that in turn activates lacZ expression in the presence of Xgal, not a photoresponse to exposure to blue light. However, there is no specific mention of a tyrosine phosphatase or a plant phototropin 1 LOV2 N-terminal alpha helix. In fact, reviews on optogenetics tend to depict LOV2 as having one terminal helix: The C-terminal Jalpha helix. While there are studies/patents indicating that simple insertion of the LOV2 domain enables photocontrol they rely on the underlying assumption that the Jalpha helix is unwinding to produce the controlling effect, not the A alpha helix as described herein.

B. A "Cage-Free" Approach to Control Protein Tyrosine Phosphatases and Protein Tyrosine Kinases with Light.

Current strategies for using light to control the activity of enzymes (as opposed to their concentration or location) rely on cage-based systems: a light-responsive protein, when fused to an enzyme of interest, controls access to its active site[16,47]. Unfortunately, such architectures can alter the affinity of enzymes for binding partners and change their susceptibility to activity modulating modifications (e.g., phosphorylation)[16,18]. These effects complicate the use of optogenetics to study signaling. This study will develop a "cage-free", allostery-based approach for optical control that minimizes interference between enzymes and their substrates (and other binding partners). This approach will help preserve native patterns of protein localization, interaction, and post-translational modification and, thus, facilitate studies of the influence of those patterns on intracellular signaling.

2. A genetically encoded photoswitchable phosphatase. There are no genetically encodable photoswitchable phosphatases; the chimeras developed in this proposal will be the first. Photoswitchable variants of PTP1B will enable detailed studies of a wide range of interesting PTP1B-regulated processes (e.g., insulin, endocannabinoid, and epidermal growth factor signaling[49,51], and cell adhesion and migration[52]). Photoswitchable phosphatases, in general, will provide a useful class of tools for studying cell biology (particularly in concert with photoswitchable kinases, which could enable complementation experiments).

Hypothesis: The catalytic domains of PTPs and PTKs possess C-terminal a-helices that are distal to their active sites, yet capable of modulating their catalytic activities (for at least a subset of enzymes—the generality of this function is not known)[23,24]. We hypothesize that the fusion of this helix to the N-terminal a-helix of the light-oxygen voltage 2 (LOV2) domain of phototropin 1 from *Avena sativa*—a photosensory domain with terminal helices that unwind in response to blue light[25,26]—will yield enzyme-LOV2 chimeras that exhibit light-dependent catalytic activities, yet retain their native substrate specificities and binding affinities.

Experimental approach: We will attach the C-terminal a-helix of PTP1B to the N-terminal a-helix of LOV2 at homologous crossover points, and we will assess the influence of photoactivation on the catalytic activity of the resulting chimeras. This effort will involve the use of (i) kinetic assays and binding studies to characterize the substrate specificities and binding affinities of photoswitchable constructs and (ii) crystallographic and spectroscopic analyses to examine the structural basis of photocontrol. Informed by these studies, we will extend our approach to striatal-enriched protein tyrosine phosphatase (STEP) and protein tyrosine kinase 6 (PTK6), enzymes implicated in Alzheimer's disease and triple-negative breast cancer, respectively.

We will combine sophisticated biophysical studies, synthetic biology, and fluorescence microscopy to (i) develop protein architectures that enable optical control of protein tyrosine phosphatases (PTPs) and protein tyrosine kinases (PTKs) without interfering with their wild-type activities or binding specificities, (ii) evolve PTPs and PTKs modulated by red light, and (iii) develop an imaging methodology to study spatially localized signaling events in living cells.

We will begin our study with PTP1B, a validated drug target for the treatment of diabetes, obesity, and breast cancer, and an enzyme for which optogenetic tools will be particularly useful to address current gaps in knowledge (e.g., the role of spatially distinct subpopulations of PTP1B in promoting or suppressing the growth of tumors[22]). Using it as a model, we will establish the generality of our methods by extending them to other PTPs and PTKs.

C. A Photo Switchable Variant of PTP1B.

Figure 1B:
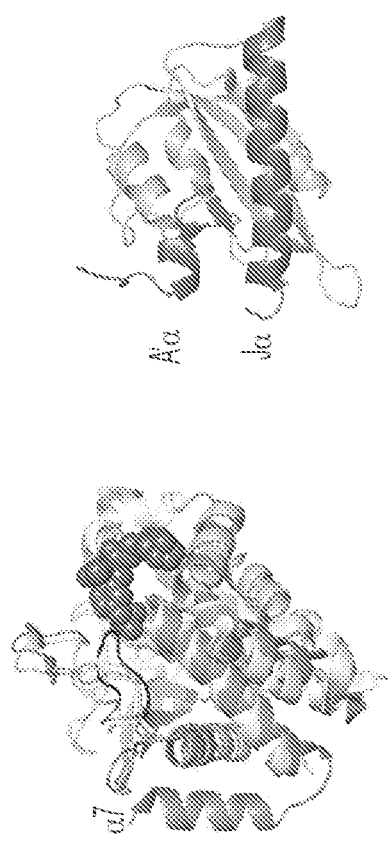
Figure 1B:
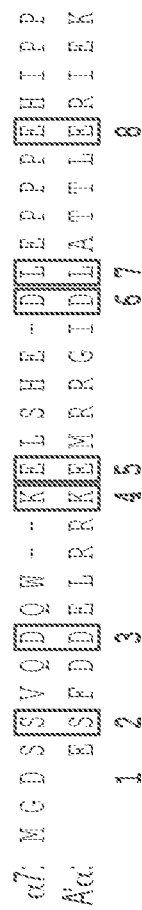
Figure 6:
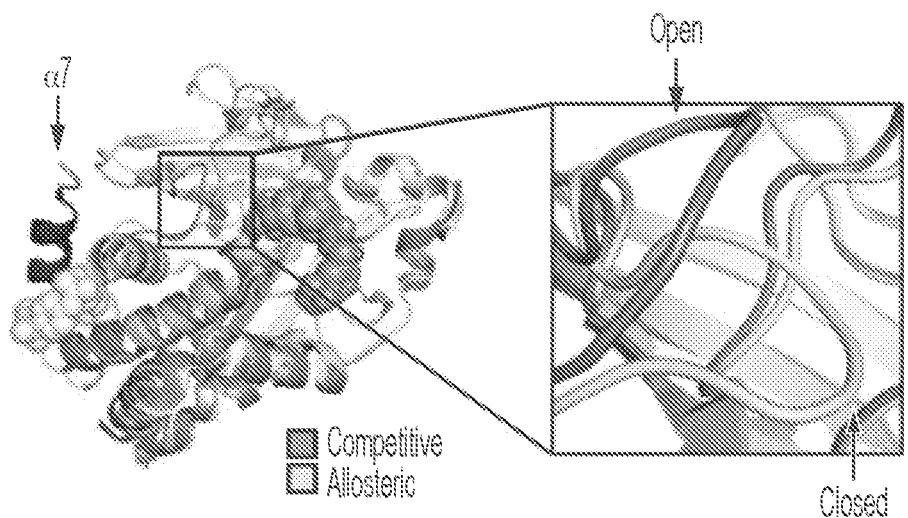
FIG. 6 illustrates PTP1B showing an overlay of allosterically inhibited (green) and competitively inhibited (orange) structures of PTP1B (PDB entries 1t4j and 2f71, respectively) show activity-modulating conformational changes: Unwinding of the α7 helix of LOV2 (blue) causes its catalytically essential WPD loop (right) to adopt an open, catalytically compromised conformation. Competitive (red) and allosteric (yellow) inhibitors highlight the active site and allosteric site, respectively.

Our first objective seeks to use LOV2, a protein with terminal helices that unwind in response to blue light, to control the activity of PTP1B, an enzyme for which unwinding of the C-terminal a-helix disrupts activity by distorting its catalytically essential WPD loop (FIG. 1AB, FIG. 6). To assess the feasibility of this goal, we constructed five PTP1B-LOV2 chimeras (joined at homologous crossover points): three chimeras showed light-dependent catalytic activity on 4-methylumbelliferyl phosphate (4M) (FIG. 1G). A subsequent mutational analysis of one chimera indicated that mutations in the $\alpha$-helix that links PTP1B to LOV2 can improve catalytic activity and dynamic range (DR, the ratio of dark/light activities; FIG. 1G). Our ability to build—and begin optimizing—a photoswitchable PTP1B-LOV2 chimera by screening a small number of constructs suggests that rational design will allow us to build a chimera sufficient for intracellular signaling studies. We note: Our most photoswitchable chimera has a DR of 2.2; previous imaging studies suggest that a DR of 3-10 is sufficient to control intracellular signaling[18,19].

Figure 1C:
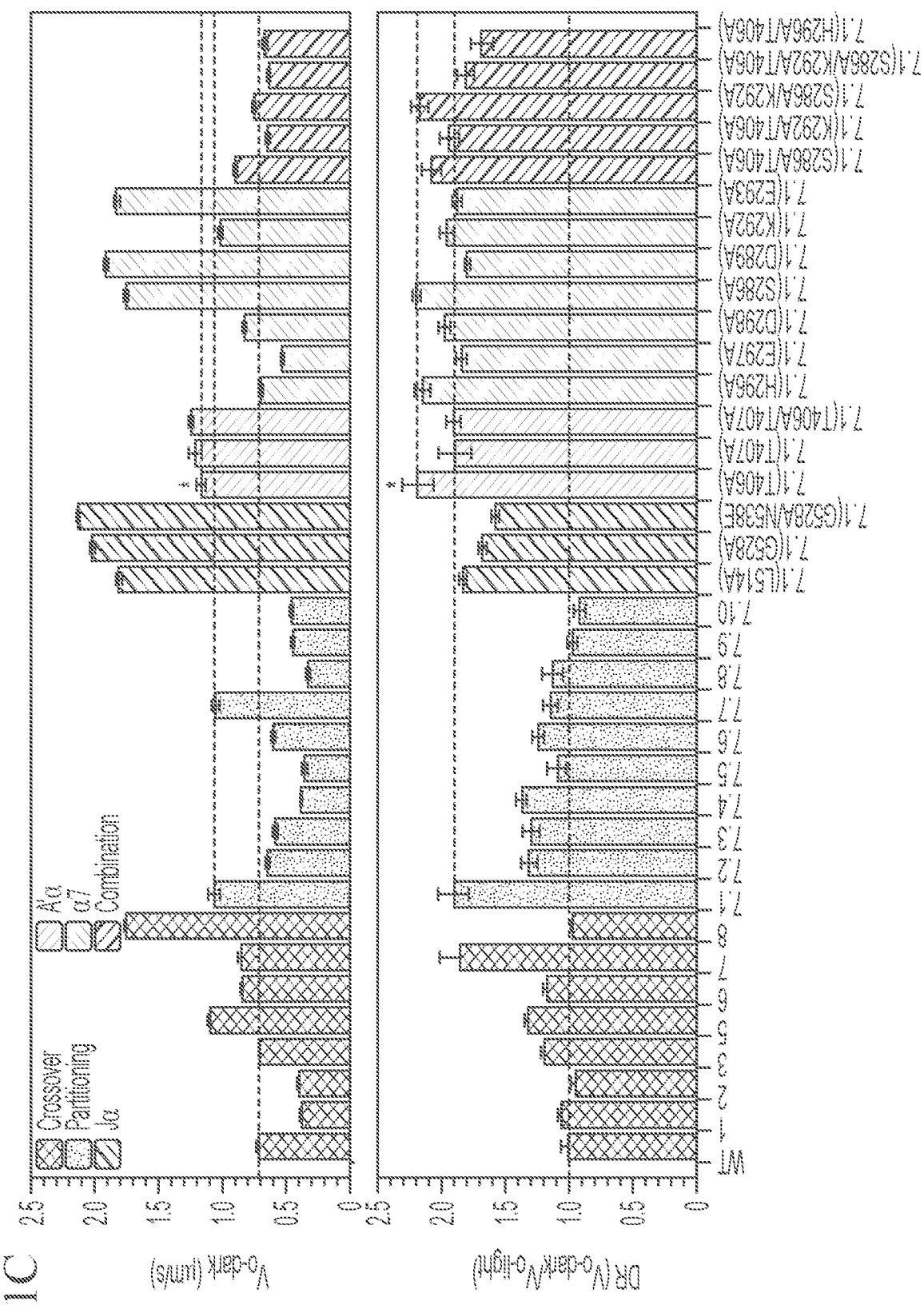
Figure 1F:
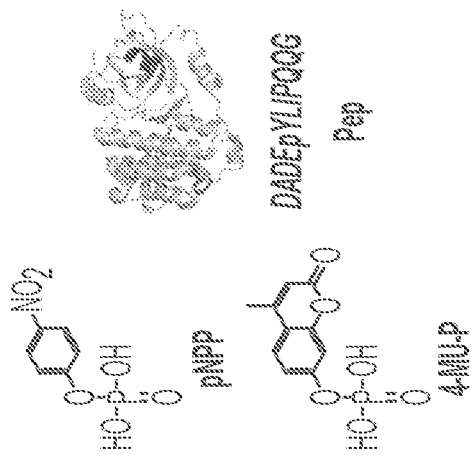

More specifically, FIG. 1C demonstrates some of differences over other types of optical control. The y-axis of the top plot indicates the activity of each construct in the dark (i.e., the initial rate of PTP1B-catalyzed hydrolysis of p-nitrophenyl phosphate); the y-axis of the bottom plot indicates the ratio of activity in dark and light state (i.e., the initial rate in the dark/the initial rate in the presence of 455 nm light), i.e. dynamic range.

Black bars show the activity and dynamic range for a set of eight initial constructs that differ in the crossover point (see the bottom of FIG. 1B). Some of these constructs are photoswitchable, and some are not. Version 7 shows the greatest photoswitchability—the dynamic range is approximately 1.8.

More specifically, colors are associated with different types of constructs. Black: different crossover point (see FIG. 1B for crossover points); Gray: different partitioning of the linker (see, Linker section below); Light blue: the Jalpha helix—this is at the C-terminus of the LOV2 domain; Dark blue: the A'alpha helix—this is at the N-terminus of the LOV2 domain and, thus, on the region that links it to PTP1B; Yellow: the alpha7 helix of PTP1B—this is at the C-terminus of PTP1B and, thus, on the region that links PTP1B to LOV2; Orange: combination: a combination of sites from the previous colors, see below for additional information.

These results were surprising, in part, because a recent review on optogenetics shows that that photocontrol of activity requires the J$\alpha$ helix of LOV2, where J$\alpha$ is a C-terminal helix which resides in a folded state against the LOV domain core, to be attached to a protein of interest, see Repina, N. A., Rosenbloom, A., Mukherjee, A., Schaffer, D. V. & Kane, R. S. At Light Speed: Advances in Optogenetic Systems for Regulating Cell Signaling and Behavior. *Annu. Rev. Chem. Biomol. Eng.* 8, 13-39 (2017). Photoactivation with blue light converts the noncovalent interaction between the LOV core and its bound flavin chromophore, FMN, into a covalent one through a conserved cysteine residue. The accompanying light-induced conformational change displaces the J$\alpha$ helix away from the protein core, leading to uncaging of a fused effector domain (e.g., the kinase domain of phot1). J$\alpha$ helix reverts to its dark-state caged conformation within minutes owing to spontaneous decay of the protein-cofactor bond.

Several limitations of the native AsLOV2 domain have motivated efforts to engineer improved variants. First, when fused to foreign protein domains, spontaneous undocking of the J$\alpha$ helix can lead to a relatively high dark-state activity, resulting in a low dynamic range upon AsLOV2 uncaging (26). For example, the light-inducible DNA-binding system LovTAP has only a fivefold change in DNA affinity between the dark and illuminated states (27). To address this issue, Strickland et al. (26) used rational design to introduce four mutations into AsLOV2 that stabilized the docking of J$\alpha$ to the LOV core. This increased the dynamic range of LovTAP from 5-fold to 70-fold, an approach that can be applied to other LOV domain optogenetic systems to reduce dark-state activity. AsLOV2 fusions are also particularly sensitive to linker lengths and the size and structure of attached domains (28, 29), and as a result, each new fusion protein switch requires optimization to achieve low dark-state and high light-state activity in mammalian cells.

In contrast to the J$\alpha$ helix-protein chimers, as shown herein, the A'$\alpha$ helix not the J$\alpha$ helix is attached to the protein of interest to form photoswitchable constructs, e.g. PTPB1.

Exemplary Linkers.

Gray bars of FIG. 1C show the activity and dynamic range of mutants of version 7 in which the linker has been re-partitioned. In other words, version 7 has the following linker region: LSHEDLATTL (SEQ ID NO: 5), where the underlined region "LSHED" (SEQ ID NO: 6) corresponds to the C-terminus of PTP1B, and the region "LATTL" (SEQ ID NO: 7) corresponds to the N-terminus of LOV2. Version 7.1 has sequence LSHEDATTL (SEQ ID NO: 8); version 7.2 has sequence LSHEDTTL (SEQ ID NO: 9), and so on. Here, we find that version 7.1 has the same dynamic range as version 7, but a higher activity. We, thus, used version 7.1 for further optimization.

Exemplary Mutations.

Light blue bars show the activity and dynamic range of mutants of version 7.1 in which the J$\alpha$ helix contains helix-stabilizing mutations. Curiously, these improve the activity of 7.1, but do not improve its dynamic range.

Dark blue bars show the activity and dynamic range for mutants of version 7.1 in which the A'$\alpha$ helix contains helix-stabilizing mutations. One of these mutations (T406A) improves dynamic range; we used this version for further studies.

Yellow bars show the activity and dynamic range of mutants of version 7.1 in which the $\alpha$7 of PTP1B has helix-stabilizing mutations; the orange bars show the activity and dynamic range for mutants of version 7.1 in which the multiple mutations are combined. Neither of the constructs associated with yellow and orange bars show improved characteristics of 7.1 (T406A).

Figure 2D:
FIG. 2A-J shows exemplary biophysical characterizations of PTP1B$_{PS}$.

A minimally disruptive approach. Two kinetic studies indicate that our architecture for photocontrol does not interfere with the native substrate specificity or binding behavior of PTP1B: (i) An analysis of the activity of chimera E3 (from FIG. 1D) on p-nitrophenyl phosphate (pN) indicates that light affects $k_{cat}$, but not $K_m$ (FIGS. 2K and L). (ii) An analysis of activities on three substrates of different sizes (4M, pN, and a peptide) shows that DR is the same for all three (FIG. 2L-K). The results of both studies are consistent with our hypothesized mechanism of photocontrol: LOV2-induced unwinding of the C-terminal a-helix of PTP1B disrupts the movement of its catalytically essential WPD loop, which controls the rate of catalysis, but has little influence on substrate binding affinity.

Figure 2E:
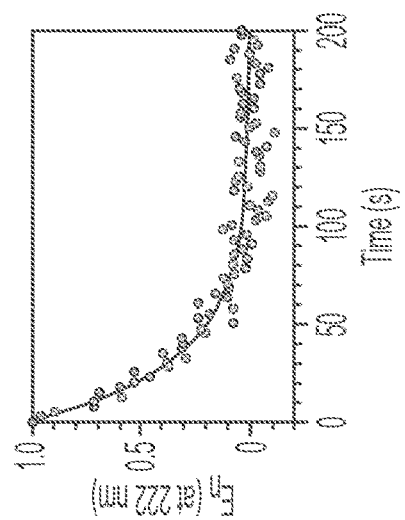
Figure 2B:
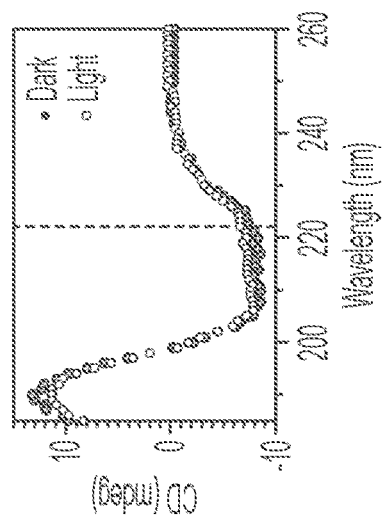
Figure 2C:
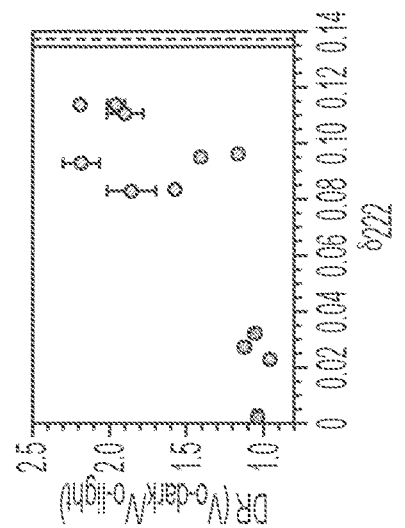
Figure 2A:
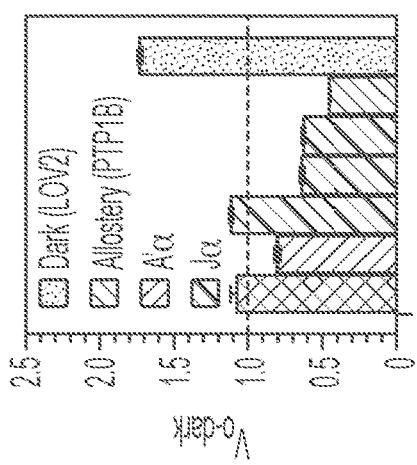
Figure 2A:
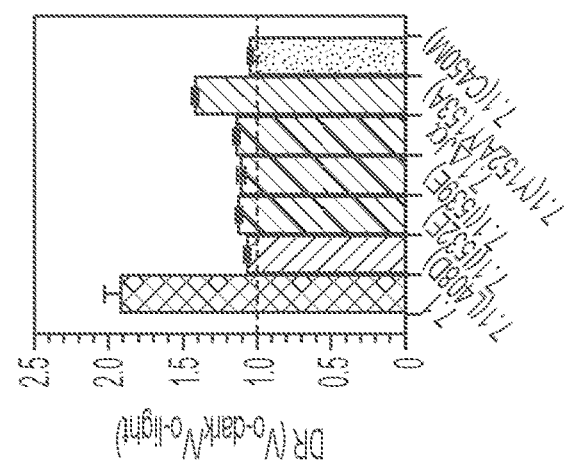
Figure 2H:
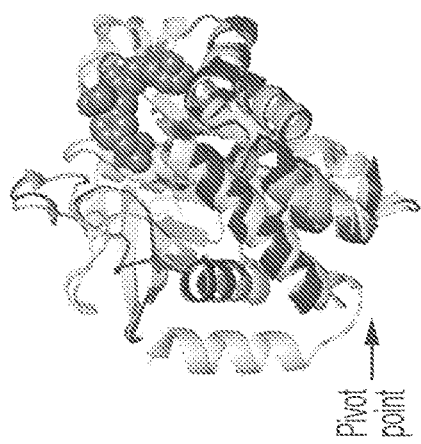
Figure 2J:
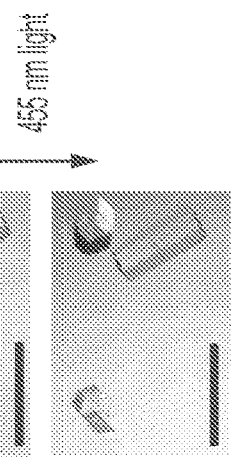
Figure 2G:
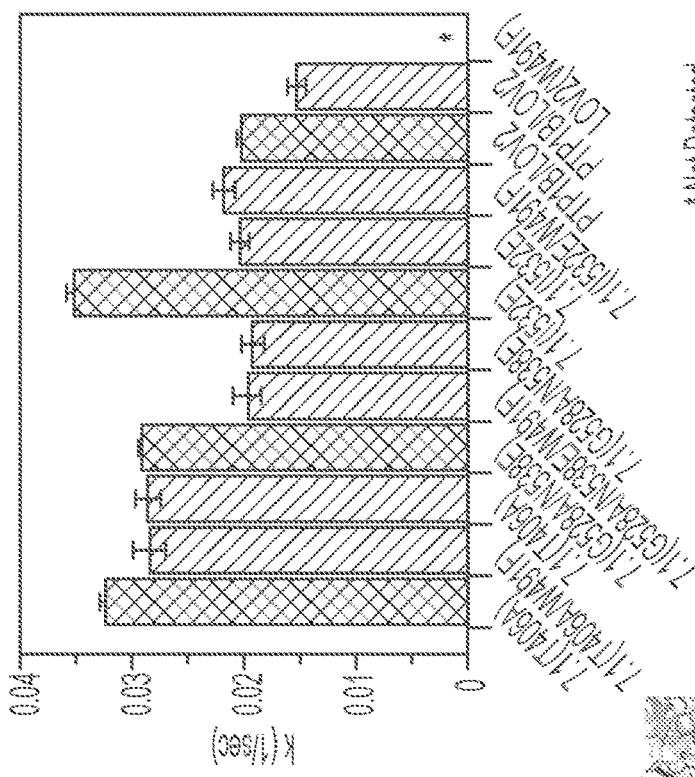
Figure 2I:
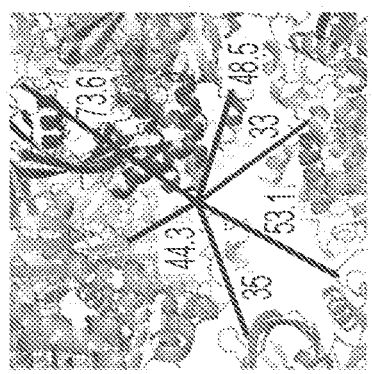
Figure 2F:
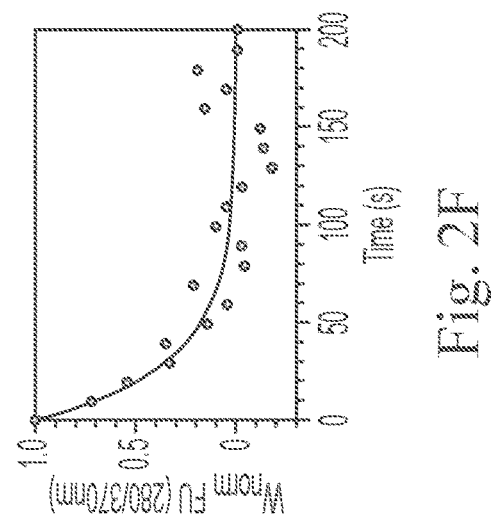

Biophysical studies. Photoswitchable chimeras express at titers (~100 mg/L) sufficient to carry out detailed biophysical analyses. We performed a preliminary set of these analyses on chimera E3. (i) We use circular dichroism (CD) to examine the influence of photoactivation on its secondary structure; spectral measurements indicate that photoactivation reduces a-helical content (222 nm; FIG. 2B). (ii) We used the amplitude at 222 nm to measure a post-activation recovery time for a-helical content: $T_r$~30 s (FIG. 2E). This value is similar to the recovery times of previously developed LOV2-based photoswitchable constructs, (iii) We used tryptophan fluorescence to measure a post-activation recovery time of tryptophan residues: $T_r$~50 s (FIG. 2F). Tryptophan fluorescence is a rough metric for the conformation of PTP1B (which has seven tryptophan residues, compared to one in LOV2); this slower recovery time, thus, suggests that PTP1B takes longer than LOV2 to refold, (iv) We identified a set of crystallization conditions (those previously used to crystallize $PTP1B_{WT}$) to grow crystals of E3 (FIG. 2F). (V) We collected a two-dimensional $^1$-$^{15}$N HSQC spectrum of $PTP1B_{WT}$, and assigned-65% of non-proline peaks. These NMR experiments, which are recent, have yet to include PTP1B-LOV2 chimeras; but the ease with which we carried them out (a single try) suggests that similar analyses of chimeras will be straightforward. The experimental tractability of PTP1B-LOV2 chimeras will enable a comprehensive biophysical analysis of variants with different photophysical properties.

Example 1. To develop a "cage-free" approach to control protein tyrosine phosphatases and kinases with light. This section develops an approach for placing enzymes under optical control without disrupting their native interactions. We will demonstrate this approach with PTP1B and, then, extend it to STEP and PTK6. We will know that we are successful when we have a PTP1B-LOV2 chimera that exhibits a three- to ten-fold change in activity between light and dark states, and when we have identified structure-based design rules that facilitate fine-tuning of the photophysical properties of photoswitchable variants of PTP1B, STEP, and PTK6.

D. Development of a Photoswitchable Variant of PTP1B.

The efforts in this section assume—and with crystallographic, kinetic, and binding studies, attempt to confirm—that optogenetic actuation systems located far from active sites are less likely to disrupt wild-type behaviors that actuation systems located nearby. Kinetic studies of preliminary PTP1B-LOV2 chimeras (i.e., chimeras in which the C-terminal helix of PTP1B is connected to the N-terminal helix of the LOV2 domain of phototropin 1 from *Avena sativa*) support this hypothesis: light inhibits their activity by affecting $k_{cat}$, not $K_m$, and they show wild-type kinetics on 4-methylumbelliferyl phosphate (4M), a model substrate (FIG. 1G and FIG. 2K). Photomodulation of $k_{cat}$, but not $K_m$ suggests that LOV2 exploits an allosteric network to distort the WPD loop (FIG. 6).

Our initial constructs, which represent the first reported examples photoswitchable protein phosphatases, will facilitate a systematic study of the functional advantages of different chimera architectures. We are particularly interested in understanding how (i) the length of the linker that connects PTP1B and LOV2 and (ii) the stability of the terminal helices of LOV2 affect catalytic activity and dynamic range. We will study these relationships by combing spectroscopic analyses with kinetic studies. Spectroscopic analyses will show how different PTP1B-LOV2 chimeras rearrange under illumination (e.g., we will use CD and fluorescence spectroscopy to measure photomodulation of a-helical content and tryptophan fluorescence), and kinetic studies will reveal the influence of those rearrangements on catalytic activity and dynamic range.

The results of our biophysical analyses will facilitate the optimization of our chimera for in vitro cell studies. We will target a chimera—hereafter, referred to as $PTP1B_{PS}$—with the following properties: a dynamic range (DR) of 3-10, a recovery time of $T_r$~15-60 s, and wild-type activity (in its activated state). Previous optogenetic studies suggest that these attributes enable optical control of cell signaling[2,18,19]. We note: Biophysical studies of PTP1B indicate that the removal of its C-terminal a-helix can reduce its activity by a factor of four[57]; accordingly, we believe that LOV2 can modulate the activity of PTP1B by at least fourfold (of course, LOV2 may trigger structural distortions more pronounced than those of a simple truncation).

E. Characterization of PTP1B-Substrate and PTP1B-Protein Interactions.

We will assess the influence of LOV2 on the substrate specificity of PTP1B by using kinetic analyses. Specifically, we will compare the activities of $PTP1B_{WT}$ and $PTP1B_{PS}$ on three substrates: (i) p-nitrophenyl phosphate, a general substrate for tyrosine phosphatases, (ii) ETGTEEpYMKMDLG (SEQ ID NO: 10), a substrate of PTPs closely related to PTP1B, and (iii) RRLIEDAEpYAARG (SEQ ID NO: 11), a substrate specific to PTP1B. A comparison of values of $k_{cat}$ and $K_m$ on these substrates (FIG. 2K shows an example kinetic study) will reveal differences in the catalytic activities and specificities of $PTP1B_{WT}$ and $PTP1B_{PS}$. These studies will also allow us to assess the substrate-dependence of photoswitchability (i.e., DR). Photomodulation is often assumed to be independent of substrate; there is, however, no biochemical basis for this assumption (particularly in cage-based systems, where substrates may bind with different affinities and, thus, have different abilities to compete with the caging protein). We will test it.

Figure 7A:
FIG. 7A-B shows and exemplary analysis of binding affinity.
Figure 7B:
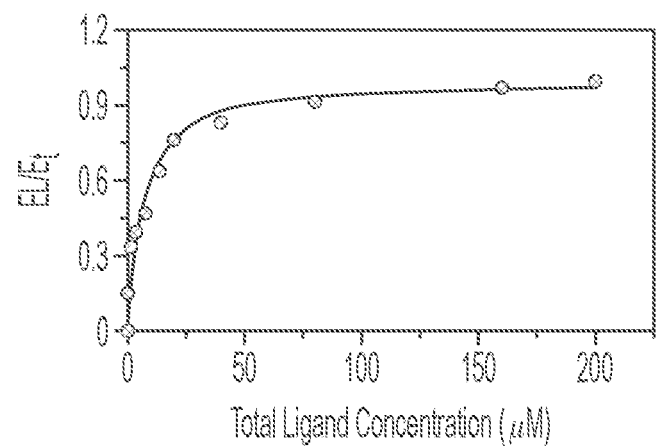

We will assess the ability of $PTP1B_{PS}$ to engage in the same protein-protein interactions as $PTP1B_{WT}$ by measuring the affinity of both enzymes for two native binding partners of $PTP1B_{WT}$: LM04 and Stat3. Binding isotherms based on changes in tryptophan fluorescence of PTP1B will facilitate this study (FIG. 7).

Our biochemical comparison of $PTP1B_{WT}$ and $PTP1B_{PS}$ may seem tedious, but we believe that this analysis is necessary to establish the relevance of future optogenetic observations to wild-type processes.

Biostructural characterization. We will investigate the structural basis of photocontrol in $PTP1B_{PS}$ by using X-ray crystallography and NMR spectroscopy. X-ray crystal structures will show how LOV2 affects the structure of PTP1B (and vice versa); NMR spectroscopy will show how LOV2 modulates catalytic activity. For crystallographic studies, we will crystallize $PTP1B_{PS}$ in its dark state (we will use the C450S mutation, which prevents formation of the cysteine adduct[2,26]) by screening crystallization conditions previously used for LOV2, PTP1B, and LOV2-protein chimeras (all of which have crystal structures[2,35,58]); preliminary results suggest that those used to grow crystals of PTP1B$_W$T also yield crystals of PTP1B-LOV2 chimeras (FIG. 2J). For NMR studies, we will use heteronuclear single quantum coherence (HSQC) spectroscopy and transverse relaxation-optimized spectroscopy (TROSY) to monitor changes in the conformation and backboned dynamics of PTP1B$_{PS}$ before and after illumination. (We note: Backbone $^1$H, $^{13}$C, and $^{15}$N chemical shifts have been assigned for PTP1B and L-OV2[59,60]).

G. Exemplary Imaging Methodology to Study Subcellular Signaling Events in Living Cells.

This section uses PTP1B$_{PS}$ (a PTP1B-LOV2 chimera) to develop an approach for using confocal microscopy to probe—and study—subcellular signaling events. We will know that this objective is successful when we can inactivate a within subcellular regions, monitor the effect of that inactivation with an FRET-based sensor, and isolate the contributions of different subpopulations of PTP1B (e.g., ER-bound and cytosolic) to sensor phosphorylation.

Hypothesis. The sub cellular localization of PTPs and PTKs is controlled by domains proximal to their catalytic cores[23,24]. We hypothesize that the attachment of these domains to photoswitchable chimeras will give them wild-type localization patterns, and enable the use of confocal microscopy to study the contribution of spatially distinct subpopulations of PTPs and PTKs to cell signaling. Experimental approach: Within the cell, PTP1B exists in two spatially distinct subpopulations: attached to the cytosolic face of the endoplasmic reticulum, and free in the cytosol—a result of proteolysis of its short (~80 residue) C-terminal ER anchor[29]. We will (i) attach the ER anchor of wild-type PTP1B (PTP1B$_W$T) to our PTP1B-LOV2 chimera, (ii) compare the subcellular localization of the resulting chimera with that of PTP1B$_W$T, (iii) use confocal microscopy—in conjunction with a FRET-based sensor for phosphatase activity—to control and monitor PTP1B activity within the cell, and (iv) develop a reaction-diffusion model to assess the contributions of spatially distinct subpopulations of PTP1B to changes in sensor pho sphorylation over time and space. This work will yield a general approach for studying spatially localized signaling events in living cells.

Localization of PTP1B$_{PS}$.

To examine the localization of PTP1B$_{PS}$ in living cells, we will express three variants in COS-7 cells: (i) PTP1B$_{PS\_C}$45os, (ii) PTP1B$_{PS}$ c45os attached to a short segment (~20 amino acids[29]) of the C-terminal ER anchor of PTP1B$_W$T that contains only the transmembrane domain (but not the proteolysis site), and (iii) PTP1B$_{PS}$-c45os attached to the full C-terminal ER anchor of PTP1B$_W$T (~80 amino acids[29]). We hypothesize that these constructs will have (i) cytosolic, ER-bound, and (iii) both cytosolic and ER-bound (i.e., wild-type) localization patterns, respectively. Using confocal microscopy, we will test this hypothesis by using the fluorescence of LOV2 to locate each chimera[70]. (In these studies, we will locate the ER with fluorescently-labeled SEC61B, an ER-associated transport complex[71]. The C450S mutation, which locks LOV2 in its fluorescent state, will prevent photoactivation during imaging).

COS-7 cells, fibroblast-like cells derived from the kidney tissue of the African green monkey, are particularly compatible with the aforementioned analysis for three reasons: (i) They are large and flat and, thus, facilitate imaging of spatially segregated subcellular regions[72], (ii) They are compatible with commercially available transfection reagents[73], (iii) Methods for inducing endocytosis[71] and calpain expression[74], two processes that influence the subcellular activity and localization of PTP1B, are well developed for these cells.

Figure 12A:
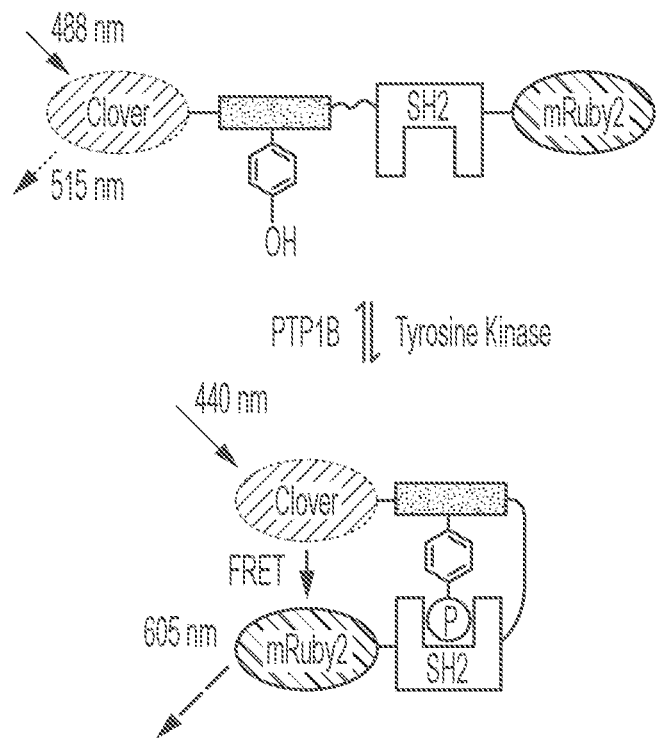
FIG. 12A-B illustrates an exemplary FRET-based sensor developed for measuring intracellular phosphatase or kinase activity. Binding of the substrate and SH2 domain either (FIG. 12A) enhance or (FIG. 12B) reduce FRET, depending on architecture.
Figure 12B:
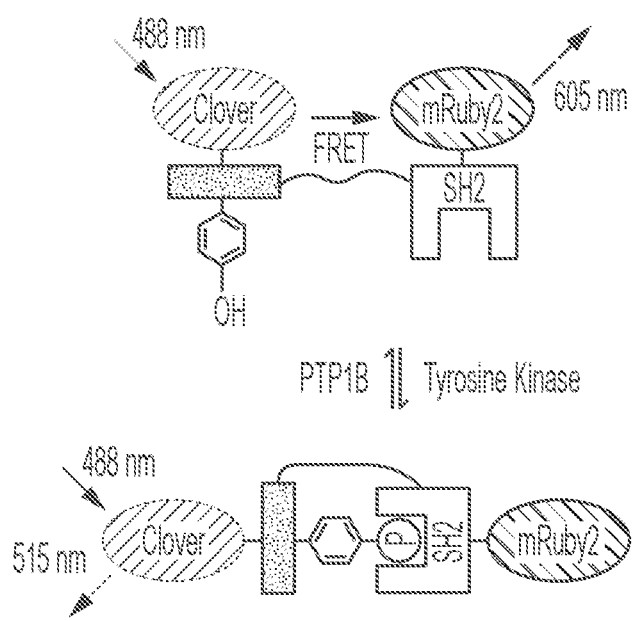

Control of PTP1B$_{PS}$ in living cells. We will examine the activity of PTP1B within subcellular regions by pairing confocal microscopy with a FRET-based sensor for protein phosphorylation (developed by the Umezawa group[54]; FIG. 12). This sensor will consist of a kinase substrate domain, a short flexible linker, and a phosphorylation recognition domain—all sandwiched between two fluorescent proteins (Clover, a green fluorescent protein, and mRuby2, a red fluorescent protein). Phosphorylation of the substrate domain will cause it to bind to the recognition domain, modulating (i.e., enhancing or reducing) FRET between the two fluorescent proteins. Our preliminary sensor, which uses substrate and SH2 domains compatible with PTP1B and src[23,55], exhibits a 20% change in FRET in response to phosphorylation. We will attempt to optimize our sensor further by screening different substrate domains, SH2 domains, and linker lengths. Ouyang et al. built a FRET sensor for Src kinase activity that exhibits a −120% change in FRET when phosphorylated[55]; we will use the architecture of this sensor—or, perhaps the sensor itself—to inform our designs.

Figure 13:
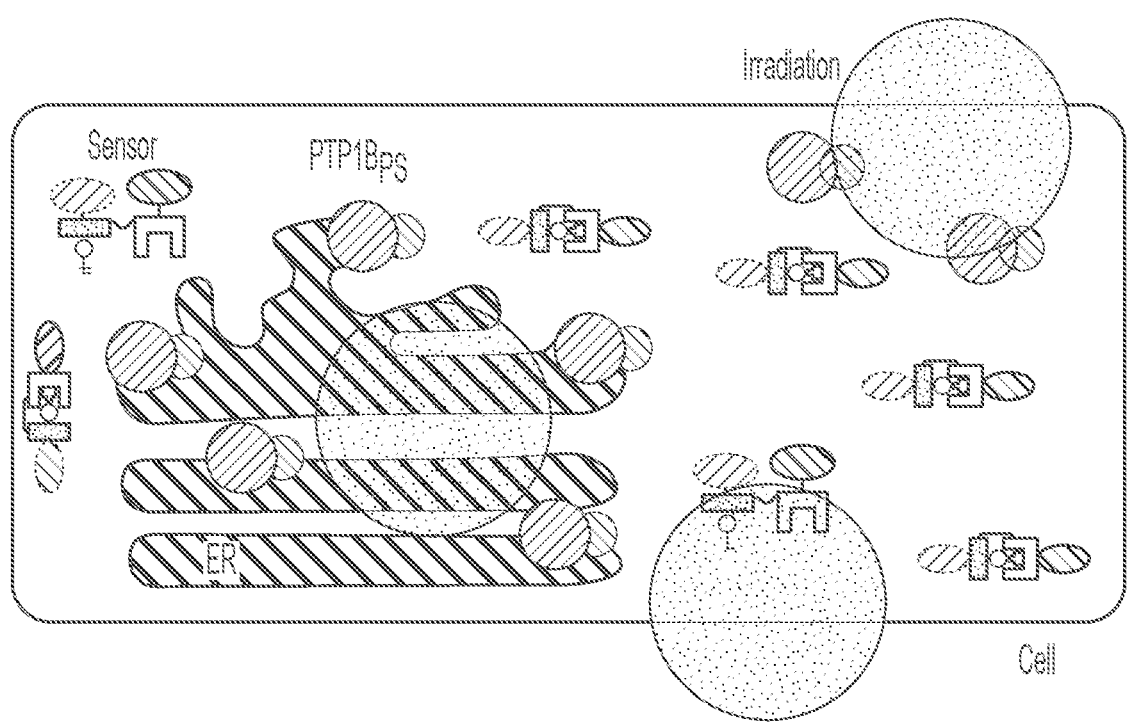
FIG. 13 shows a cartoon of imaging experiments. We will inactivate PTP1B PS within sub cellular regions (1-10 μm) containing different amounts of plasma membrane, ER, and cytosol, and we will use fluorescence lifetime imaging to examine the phosphorylation state of our FRET-based sensor (from FIG. 12) throughout the cell.
Figure 14A:
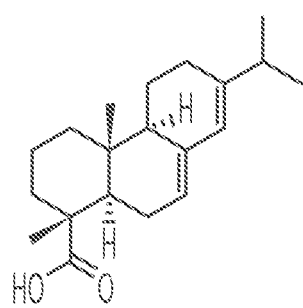
FIG. 14A-D illustrates an exemplary starting point for lead drug design and discovery.
Figure 14B:
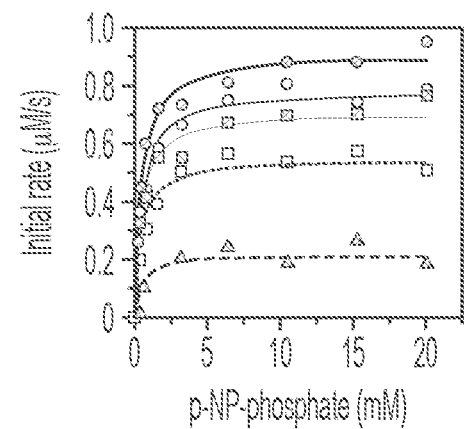
Figure 14C:
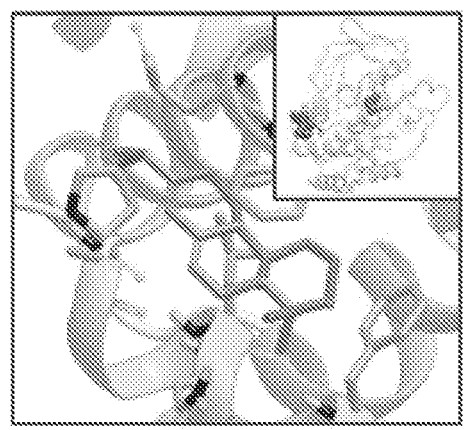
Figure 14D:
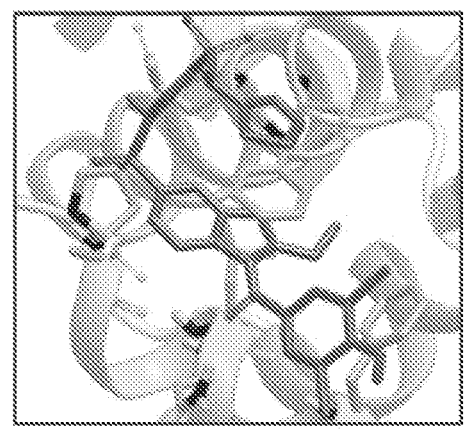
Figure 15A:
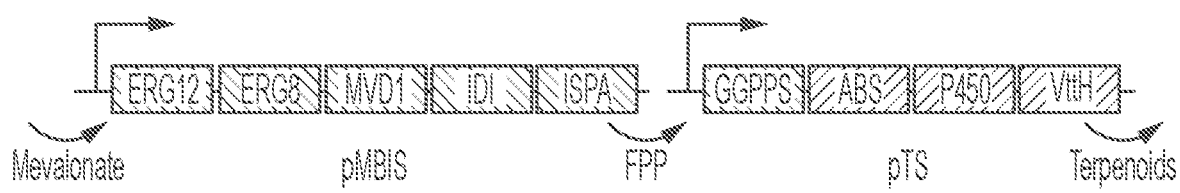
FIG. 15A-D illustrates an exemplary FIG. 15A Pathway for the synthesis of terpenoids (mevalonate can be synthesized through pMevT or added to the media).
Figure 15B:
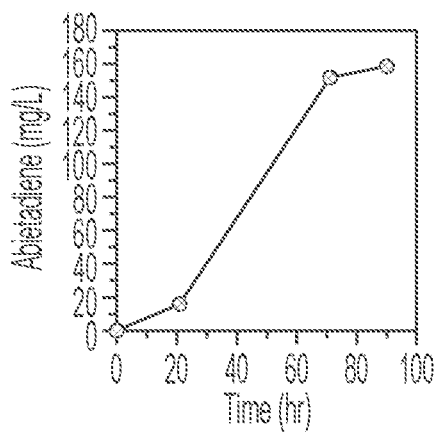
Figure 15C:
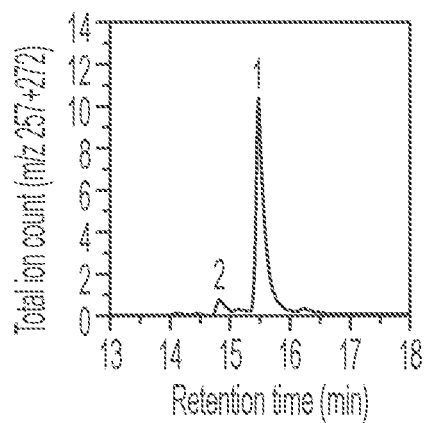
Figure 15D:
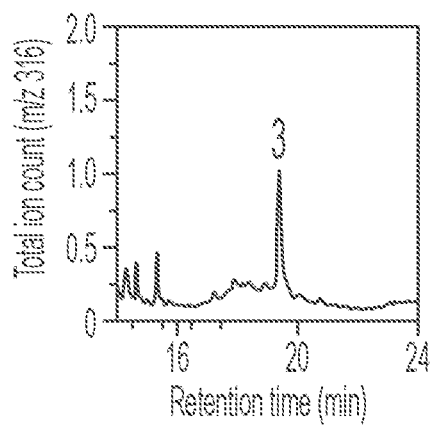
Figure 16A:
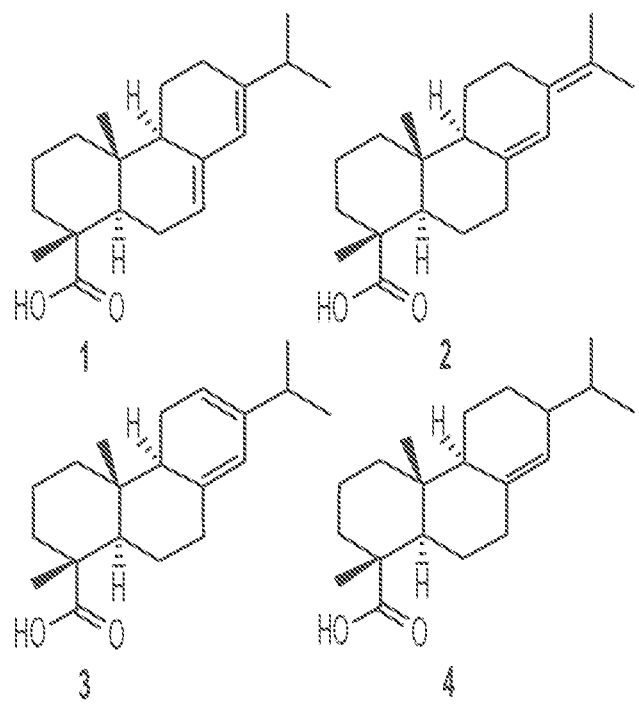
FIG. 16A-B illustrates exemplary terpenoids showing differences in stereochemistry, shape, size, and chemical functionality.
Figure 16B:
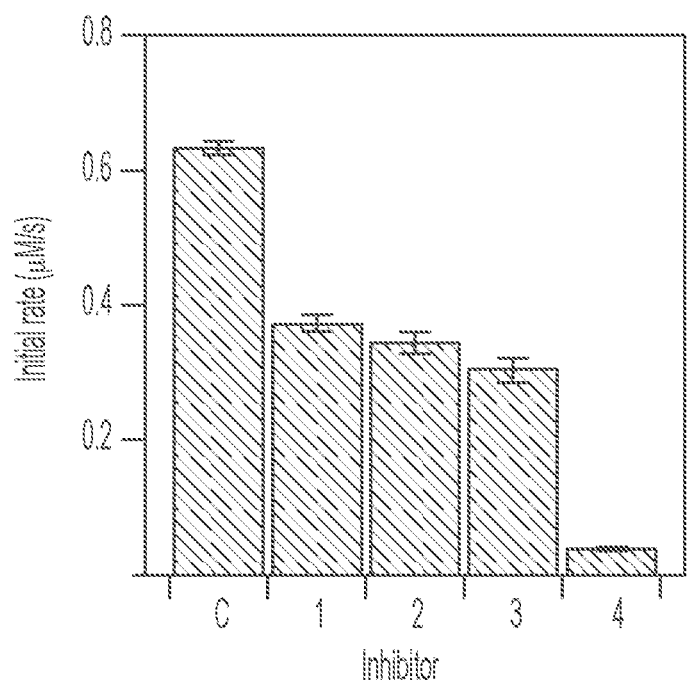

In our imaging experiments, we will use a 455-nm laser to inactivate PTP1B within sub cellular regions (1-10 urn circles) and fluorescence lifetime imaging microscopy (FLIM) to monitor changes in sensor phosphorylation that result from that inactivation (FIG. 13). For these experiments, we will use siRNA to deplete PTP1B$_W$T and SEC61B to label the ER. The output will be a series of images in which the intensity of a pixel is proportional to the fluorescence lifetime of Clover (and, thus, the extent of sensor phosphorylation).

With this study, we are particularly interested in examining relationships between (i) the location of PTPIB$_{PS}$ activation/inactivation, (ii) the size of the region of activation/inactivation, and (iii) the location and timing of changes in the phosphorylation state of the sensor. We will investigate these relationships by using a reaction-diffusion model. Equation 1 provides a simple example of a governing equation:

$$\frac{\partial S_p(r,t)}{\partial t} = D_S \nabla^2 S_p + k_{cat}^K [KS] - k_{cat}^P [PS_p] - k_{on}^K [P][S_p] \quad \text{(Eq. 1)}$$

for the phosphorylated sensor ($S_P$). Here, $D_s$ is the diffusion coefficient for the sensor; KS is the concentration of tyrosine kinase bound to unphosphorylated sensor; $PS_p$ is the concentration of PTP1B bound to phosphorylated sensor; P and $S_p$ are the concentrations of free PTP1B and free phosphorylated sensor, respectively; $k^{at}$ and $k^{\hat{}}_{at}$ are the catalytic constants for the tyrosine kinase and PTP1B, respectively; and k %$_n$ is the kinetic constant for sensor-PTP1B association. The kinase and phosphatase are assumed to bind only weakly with their products (an assumption that can be easily re-examined later). We may also supplement this model with tools such as BioNetGen, a web-based platform for generating biochemical reaction networks from user-specified rules for the mechanisms and locations of biomolecular interactions[75]; such a tool, which can accommodate cellular heterogeneity (e.g., organelles and other compartments), will help to support and expand our kinetic model.

We hypothesize that a version of our kinetic model in which the phosphatase diffuses freely will more accurately capture the phosphorylation state of the sensor (at a specified time and position from the irradiation region) in the presence of cytosolic $PTP1B_{PS}$. By contrast, a version of the model in which phosphatase does not diffuse freely will more accurately capture the behavior of sensors in the presence of ER-bound $PTP1B_{PS}$. Regression of either model against imaging data will enable estimation of the extent to which cytosolic and ER-bound PTP1B contribute to changes in sensor phosphorylation over time and space.

Image analysis. The ER exists as a vesicular network that is spread throughout the cell; inactivation of sub cellular regions that are entirely ER or entirely cytosol is difficult. To enable analysis of spatially distinct subpopulations of PTP1B, we must, thus, estimate the amount of ER in different regions of irradiation. The discrepancy in length scales of ER heterogeneity (~20-100 pm) and irradiation (~1-10 pm) will permit such an estimation. We will work with two metrics: (i) the total fluorescence of labeled ER, and (ii) the anisotropy of labeled ER. Both metrics, by facilitating estimates of the populations of cytosolic and ER-bound PTP1B in an illuminated region, will help us to assess the contributions of those populations to changes in sensor phosphorylation.

Spatial Regulation and Intracellular Signaling.

PTP1B demonstrates, by example, the value of photoswitchable enzymes for studying spatial regulation in intracellular signaling. It is hypothesized to inactivate receptor tyrosine kinases through (i) contacts between endosomes and the ER[37,38], (ii) contacts between the plasma membrane and extended regions of the ER[39], and (iii) direct protein-protein interactions enabled by its partial proteolysis and release into the cytosol[34]. The role of different mechanisms (or locations) of PTP1B-substrate interaction in determining the outcomes of those interactions is poorly understood. Evidence suggesting a relationship between the location of PTP1B and its role in signaling has arisen in studies of tumorigenesis. Inhibition of PTP1B can suppress tumor growth and metastasis in breast[30,40], lung[3,41], colorectal[9], and prostate cancers[42,43], while its upregulation has similar effects in lymphoma[3,44]. Recent evidence suggests that the former effect may result from inhibition of cytosolic PTP1B[45]; the cause of the latter is unclear. At present, there are no tools to investigate the differential influence of spatially distinct subpopulations of PTP1B on tumor-associated signaling events within the same cell. Photo switchable variants of PTP1B represent such a tool.

Network biology. Signaling networks are often represented as nodes (proteins) connected by lines (interactions)[46]. Such maps capture the connectivity of biochemical relay systems, but obscure spatial context—the ability of a single interaction to occur in multiple locations and, perhaps, to stimulate multiple signaling outcomes. This study develops a set of tools that will enable detailed studies of the role of spatial context in guiding the propagation of signals through biochemical networks; e.g. understanding the role of PTP1B in cell signaling (and processes associated with tumorigenesis), and generally relevant to the study of any enzyme that exists in spatially distinct subpopulations within the cells.

Generalization of Approach to Protein Tyrosine Phosphatases and Kinases.

Two observations suggest that our architecture for photocontrol (i.e., attachment of the N-terminus of LOV2 to the C-terminal a-helix of an enzyme) is broadly applicable to PTPs and PTKs. (i) Structural alignments show that all PTPs possess, or, with a few mutations, can possess—the same allosteric communication network as PTP1B (FIG. 8A)[23]. (ii) PTKs contain a C-terminal a-helix that is distal to their active sites, yet capable of modulating their catalytic activities (FIG. 8B)[61].

Figure 8A:
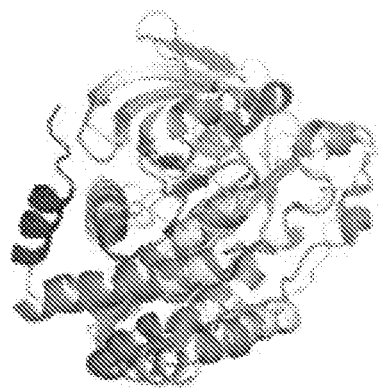
FIG. 8A-B illustrates exemplary structural alignment of PTP1B (light blue) and STEP (orange), FIG. 8A, which have only 31% sequence identity, shows remarkable structural similarity.

We will assess the generalizability of our approach by building photoswitchable variants of striatal-enriched protein tyrosine phosphatase (STEP) and protein tyrosine kinase 6 (PTK6;

FIG. 8A). STEP is a neuron-specific phosphatase that is overactive in several neurological disorders, prominently Alzheimer's disease, schizophrenia, and drug addiction[62,63]. PTK6, which may function orthogonally to PTP1B in some signaling pathways, is expressed in approximately 70% of triple-negative breast cancers and promotes metastasis[50,64]. Photoswitchable variants of STEP and PTK6, both of which exist in multiple spatially distinct subpopulations within cells[50,62], will enable detailed studies of their intracellular signaling roles, which remain poorly characterized.

For STEP and PTK6, we will develop—and measure the substrate specificities of—photoswitchable chimeras by using several kinetic assays. For STEP, we will use assays analogous to those employed with PTP1B. For PTK6, we will use the ADP-Glo kit developed by Promega, Inc.[65]. This assay, which is compatible with any peptide substrate, converts ADP produced by PTK-catalyzed peptide phosphorylation to a luminescent signal. For both enzymes, we will collect crystal structures of optimal chimeras.

Exemplary photoswitch construct sequences for use in expressing in mammalian cells or within an operon for microbial cells. In some embodiments, the sequences may be optimized for microbial expression.

```
PPTP1B-LOV2, version 7.1 (T406A): DNA sequence SEQ ID NO: 12:
ATGGAGATGGAAAAGGAGTTCGAGCAGATCGACAAGTCCGGGAGCTGGGCGGCC

ATTTACCAGGATATCCGACATGAAGCCAGTGACTTCCCATGTAGAGTGGCCAAGCT

TCCTAAGAACAAAAACCGAAATAGGTACAGAGACGTCAGTCCCTTTGACCATAGTC

GGATTAAACTACATCAAGAAGATAATGACTATATCAACGCTAGTTTGATAAAAATGG

AAGAAGCCCAAAGGAGTTACATTCTTACCCAGGGCCCTTTGCCTAACACATGCGGT

CACTTTTGGGAGATGGTGTGGGAGCAGAAAAGCAGGGGTGTCGTCATGCTAACA

GAGTGATGGAGAAAGGTTCGTTAAAATGCGCACAATACTGGCCACAAAAAGAAGAA

AAAGAGATGATCTTTGAAGACACAAATTTGAAATTAACATTGATCTCTGAAGATATC

AAGTCATATTATACAGTGCGACAGCTAGAATTGGAAAACCTTACAACCCAAGAAAC
```

-continued

```
TCGAGAGATCTTACATTTCCACTATACCACATGGCCTGACTTTGGAGTCCCTGAAT

CACCAGCCTCATTCTTGAACTTTCTTTTCAAAGTCCGAGAGTCAGGGTCACTCAGC

CCGGAGCACGGGCCCGTTGTGGTGCACTGCAGTGCAGGCATCGGCAGGTCTGGA

ACCTTCTGTCTGGCTGATACCTGCCTCTTGCTGATGGACAAGAGGAAAGACCCTTC

TTCCGTTGATATCAAGAAAGTGCTGTTAGAAATGAGGAAGTTTCGGATGGGGCTGA

TCCAGACAGCCGACCAGCTGCGCTTCTCCTACCTGGCTGTGATCGAAGGTGCCAA

ATTCATCATGGGGGACTCTTCCGTGCAGGATCAGTGGAAGGAGCTTTCCCACGAG

GACGCTGCTACACTTGAACGTATTGAGAAGAACTTTGTCATTACTGACCCAAGGTT

GCCAGATAATCCCATTATATTCGCGTCCGATAGTTTCTTGCAGTTGACAGAATATAG

CCGTGAAGAAATTTTGGGAAGAAACTGCAGGTTTCTACAAGGTCCTGAAACTGATC

GCGCGACAGTGAGAAAAATTAGAGATGCCATAGATAACCAAACAGAGGTCACTGTT

CAGCTGATTAATTATACAAAGAGTGGTAAAAAGTTCTGGAACCTCTTTCACTTGCAG

CCTATGCGAGATCAGAAGGGAGATGTCCAGTACTTTATTGGGGTTCAGTTGGATG

GAACTGAGCATGTCCGAGATGCTGCCGAGAGAGAGGGAGTCATGCTGATTAAGAA

AACTGCAGAAAATATTGATGAGGCGGCAAAAGAACTTCTCGAGCACCACCACCAC

CACCACTGA
```

Protein sequence: SEQ ID NO: 13:

```
MEMEKEFEQIDKSGSWAAIYQDIRHEASDFPCRVAKLPKNKNRNRYRDVSPFDHSRIKL

HQEDNDYINASLIKMEEAQRSYILTQGPLPNTCGHFWEMVWEQKSRGVVMLNRVMEK

GSLKCAQYWPQKEEKEMIFEDTNLKLTLISEDIKSYYTVRQLELENLTTQETREILHFHY

TTWPDFGVPESPASFLNFLFKVRESGSLSPEHGPVVVHCSAGIGRSGTFCLADTCLLLMD

KRKDPSSVDIKKVLLEMRKFRMGLIQTADQLRFSYLAVIEGAKFIMGDSSVQDQWKELS

HEDAATLERIEKNFVITDPRLPDNPIIFASDSFLQLTEYSREEILGRNCRFLQGPETDRATV

RKIRDAIDNQTEVTVQLINYTKSGKKFWNLFHLQPMRDQKGDVQYFIGVQLDGTEHVR

DAAEREGVMLIKKTAENIDEAAKELLEHHHHHH
```

PTP1B-LOV2, version 7.1(S286A): DNA sequence: SEQ ID NO: 14:

```
ATGGAGATGGAAAAGGAGTTCGAGCAGATCGACAAGTCCGGGAGCTGGGCGGCCAT

TTACCAGGATATCCGACATGAAGCCAGTGACTTCCCATGTAGAGTGGCCAAGCTTCC

TAAGAACAAAAACCGAAATAGGTACAGAGACGTCAGTCCCTTTGACCATAGTCGGA

TTAAACTACATCAAGAAGATAATGACTATATCAACGCTAGTTTGATAAAAATGGAA

GAAGCCCAAAGGAGTTACATTCTTACCCAGGGCCCTTTGCCTAACACATGCGGTCAC

TTTTGGGAGATGGTGTGGGAGCAGAAAAGCAGGGGTGTCGTCATGCTCAACAGAGT

GATGGAGAAAGGTTCGTTAAAATGCGCACAATACTGGCCACAAAAAGAAGAAAAA

GAGATGATCTTTGAAGACACAAATTTGAAATTAACATTGATCTCTGAAGATATCAAG

TCATATTATACAGTGCGACAGCTAGAATTGGAAAACCTTACAACCCAAGAAACTCG

AGAGATCTTACATTTCCACTATACCACATGGCCTGACTTTGGAGTCCCTGAATCACC

AGCCTCATTCTTGAACTTTCTTTTCAAAGTCCGAGAGTCAGGGTCACTCAGCCCGGA

GCACGGGCCCGTTGTGGTGCACTGCAGTGCAGGCATCGGCAGGTCTGGAACCTTCTG

TCTGGCTGATACCTGCCTCTTGCTGATGGACAAGAGGAAAGACCCTTCTTCCGTTGA

TATCAAGAAAGTGCTGTTAGAAATGAGGAAGTTTCGGATGGGGCTGATCCAGACAG

CCGACCAGCTGCGCTTCTCCTACCTGGCTGTGATCGAAGGTGCCAAATTCATCATGG

GGGACTCTGCCGTGCAGGATCAGTGGAAGGAGCTTTCCCACGAGGACGCTACTACA
```

-continued

CTTGAACGTATTGAGAAGAACTTTGTCATTACTGACCCAAGGTTGCCAGATAATCCC

ATTATATTCGCGTCCGATAGTTTCTTGCAGTTGACAGAATATAGCCGTGAAGAAATT

TTGGGAAGAAACTGCAGGTTTCTACAAGGTCCTGAAACTGATCGCGCGACAGTGAG

AAAAATTAGAGATGCCATAGATAACCAAACAGAGGTCACTGTTCAGCTGATTAATT

ATACAAAGAGTGGTAAAAAGTTCTGGAACCTCTTTCACTTGCAGCCTATGCGAGATC

AGAAGGGAGATGTCCAGTACTTTATTGGGGTTCAGTTGGATGGAACTGAGCATGTCC

GAGATGCTGCCGAGAGAGAGGGAGTCATGCTGATTAAGAAAACTGCAGAAAATATT

GATGAGGCGGCAAAAGAACTTCTCGAGCACCACCACCACCACCACTGA

Protein sequence: SEQ ID NO: 15:
MEMEKEFEQIDKSGSWAAIYQDIRHEASDFPCRVAKLPKNKNRNRYRDVSPFDHSRIKL

HQEDNDYINASLIKMEEAQRSYILTQGPLPNTCGHFWEMVWEQKSRGVVMLNRVMEK

GSLKCAQYWPQKEEKEMIFEDTNLKLTLISEDIKSYYTVRQLELENLTTQETREILHFHY

TTWPDFGVPESPASFLNFLFKVRESGSLSPEHGPVVVHCSAGIGRSGTFCLADTCLLLMD

KRKDPSSVDIKKVLLEMRKFRMGLIQTADQLRFSYLAVIEGAKFIMGDSAVQDQWKELS

HEDATTLERIEKNFVITDPRLPDNPIIFASDSFLQLTEYSREEILGRNCRFLQGPETDRATV

RKIRDAIDNQTEVTVQLINYTKSGKKFWNLFHLQPMRDQKGDVQYFIGVQLDGTEHVR

DAAEREGVMLIKKTAENIDEAAKELLEHHHHHH

TCPTP-LOV2, best version:
DNA sequence: SEQ ID NO: 16:
ATGCCCACCACCATCGAGCGGGAGTTCGAAGAGTTGGATACTCAGCGTCGCTGGCA

GCCGCTGTACTTGGAAATTCGAAATGAGTCCCATGACTATCCTCATAGAGTGGCCAA

GTTTCCAGAAAACAGAAATCGAAACAGATACAGAGATGTAAGCCCATATGATCACA

GTCGTGTTAAACTGCAAAATGCTGAGAATGATTATATTAATGCCAGTTTAGTTGACA

TAGAAGAGGCACAAAGGAGTTACATCTTAACACAGGGTCCACTTCCTAACACATGC

TGCCATTTCTGGCTTATGGTTTGGCAGCAGAAGACCAAAGCAGTTGTCATGCTGAAC

CGCGTGATGGAGAAAGGTTCGTTAAAATGTGCACAGTACTGGCCAACAGATGACCA

AGAGATGCTGTTTAAAGAAACAGGATTCAGTGTGAAGCTCTTGTCAGAAGATGTGA

AGTCGTATTATACAGTACATCTACTACAATTAGAAAATATCAATAGTGGTGAAACCA

GAACAATATCTCACTTTCATTATACTACCTGGCCAGATTTTGGAGTCCCTGAATCACC

AGCTTCATTTCTCAATTTCTTGTTTAAAGTGAGAGAATCTGGCTCCTTGAACCCTGAC

CATGGGCCTGCGGTGATCCACTGTAGTGCAGGCATTGGGCGCTCTGGCACCTTCTCT

CTGGTAGACACTTGTCTTTTGCTGATGGACAAGAGGAAAGACCCTTCTTCCGTTG

ATATCAAGAAAGTGCTGTTAGAAATGAGGAAGTTTCGGATGGGGCTGATCCAG

ACAGCCGACCAGCTGCGCTTCTCCTACCTGGCTGTGATCGAAGGTGCCAAATT

CATCATGGGGACTCTTCCGTGCAGGATCAGTGGAAGGAGCTTTCCCACGAGG

ACGCTGCTACACTTGAACGTATTGAGAAGAACTTTGTCATTACTGACCCAAGGTTGC

CAGATAATCCCATTATATTCGCGTCCGATAGTTTCTTGCAGTTGACAGAATATAGCC

GTGAAGAAATTTTGGGAAGAAACTGCAGGTTTCTACAAGGTCCTGAAACTGATCGC

GCGACAGTGAGAAAAATTAGAGATGCCATAGATAACCAAACAGAGGTCACTGTTCA

GCTGATTAATTATACAAAGAGTGGTAAAAAGTTCTGGAACCTCTTTCACTTGCAGCC

TATGCGAGATCAGAAGGGAGATGTCCAGTACTTTATTGGGGTTCAGTTGGATGGAAC

TGAGCATGTCCGAGATGCTGCCGAGAGAGAGGGAGTCATGCTGATTAAGAAAACTG

```
CAGAAAATATTGATGAGGCGGCAAAAGAACTTCTCGAGCACCACCACCACCACCA

CTGA
```

The underlined letters indicate sequence fromPTPIB. Protein sequence: SEQ ID NO: 17:
MPTTIEREFEELDTQRRWQPLYLEIRNESHDYPHRVAKFPENRNRNRYRDVSPYDHSRV KLQNAENDYINASLVDIEEAQRSYILTQGPLPNTCCHFWLMVWQQKTKAVVMLNR<u>VM</u>

<u>EKGSLK</u>CAQYWPTDDQEMLFKETGFSVKLLSEDVKSYYTVHLLQLENINSGETRTISHF

HYTTWPDFGVPESPASFLNFLFKVRESGSLNPDHGPAVIHCSAGIGRSGTFSLVDTCLLL

MDKRKDPSSVDIKKVLLEMRKFRMGLIQTADQLRFSYL<u>AVIEGAKFIMGDSSVQDQWK</u>

<u>ELSHED</u>AATLERIEKNFVITDPRLPDNPIIFASDSFLQLTEYSREEILGRNCRFLQGPETDR

ATVRKIRDAIDNQTEVTVQLINYTKSGKKFWNLFHLQPMRDQKGDVQYFIGVQLDGTE

HVRDAAEREGVMLIKKTAENIDEAAKELLEHHHHHH

TCPTP-LOV2 V2: DNA sequence: SEQ ID NO: 18:
```
ATGCCCACCACCATCGAGCGGGAGTTCGAAGAGTTGGATACTCAGCGTCGCTGGCA

GCCGCTGTACTTGGAAATTCGAAATGAGTCCCATGACTATCCTCATAGAGTGGCCAA

GTTTCCAGAAAACAGAAATCGAAACAGATACAGAGATGTAAGCCCATATGATCACA

GTCGTGTTAAACTGCAAAATGCTGAGAATGATTATATTAATGCCAGTTTAGTTGACA

TAGAAGAGGCACAAAGGAGTTACATCTTAACACAGGGTCCACTTCCTAACACATGC

TGCCATTTCTGGCTTATGGTTTGGCAGCAGAAGACCAAAGCAGTTGTCATGCTGAAC

CGCATTGTGGAGAAGAATCGGTTAAATGTGCACAGTACTGGCCAACAGATGACCA

AGAGATGCTGTTTAAAGAAACAGGATTCAGTGTGAAGCTCTTGTCAGAAGATGTGA

AGTCGTATTATACAGTACATCTACTACAATTAGAAAATATCAATAGTGGTGAAACCA

GAACAATATCTCACTTTCATTATACTACCTGGCCAGATTTTGGAGTCCCTGAATCACC

AGCTTCATTTCTCAATTTCTTGTTTAAAGTGAGAGAATCTGGCTCCTTGAACCCTGAC

CATGGGCCTGCGGTGATCCACTGTAGTGCAGGCATTGGGCGCTCTGGCACCTTCTCT

CTGGTAGACACTTGTCTTTT<u>GCTGATGGACAAGAGGAAAGACCCTTCTTCCGTTGAT</u>

<u>ATCAAGAAAGTGCTGTTAGAAATGAGGAAGTTTCGGATGGGGCTGATCCAGACAGC</u>

<u>CGACCAGCTGCGCTTCTCCTACCTGGCTGTGATCGAAGGTGCCAAATTCATCATGGG</u>

<u>GGACTCTTCCGTGCAGGATCAGTGGAAGGAGCTTTCCCACGAGGAC</u>GCTGCTACACT

TGAACGTATTGAGAAGAACTTTGTCATTACTGACCCAAGGTTGCCAGATAATCCCAT

TATATTCGCGTCCGATAGTTTCTTGCAGTTGACAGAATATAGCCGTGAAGAAATTTT

GGGAAGAAACTGCAGGTTTCTACAAGGTCCTGAAACTGATCGCGCGACAGTGAGAA

AAATTAGAGATGCCATAGATAACCAAACAGAGGTCACTGTTCAGCTGATTAATTATA

CAAAGAGTGGTAAAAAGTTCTGGAACCTCTTTCACTTGCAGCCTATGCGAGATCAGA

AGGGAGATGTCCAGTACTTTATTGGGGTTCAGTTGGATGGAACTGAGCATGTCCGAG

ATGCTGCCGAGAGAGAGGGAGTCATGCTGATTAAGAAAACTGCAGAAAATATTGAT

GAGGCGGCAAAAGAACTTCTCGAGCACCACCACCACCACCACTGA
```

Protein sequence: SEQ ID NO: 19:
MPTTIEREFEELDTQRRWQPLYLEIRNESHDYPHRVAKFPENRNRNRYRDVSPYDHSRV

KLQNAENDYINASLVDIEEAQRSYILTQGPLPNTCCHFWLMVWQQKTKAVVMLNRIVE

KESVKCAQYWPTDDQEMLFKETGFSVKLLSEDVKSYYTVHLLQLENINSGETRTISHFH

YTTWPDFGVPESPASFLNFLFKVRESGSLNPDHGPAVIHCSAGIGRSGTFSLVDTCLLLM

-continued

DKRKDPSSVDIKKVLLEMRKFRMGLIQTADQLRFSYL<u>AVIEGAKFIMGDSSVQDQWKEL</u>

<u>SHED</u>AATLERIEKNFVITDPRLPDNPIIFASDSFLQLTEYSREEILGRNCRFLQGPETDRAT

VRKIRDAIDNQTEVTVQLINYTKSGKKFWNLFHLQPMRDQKGDVQYFIGVQLDGTEHV

RDAAEREGVMLIKKTAENIDEAAKELLEHHHHHH

Figure 21A:
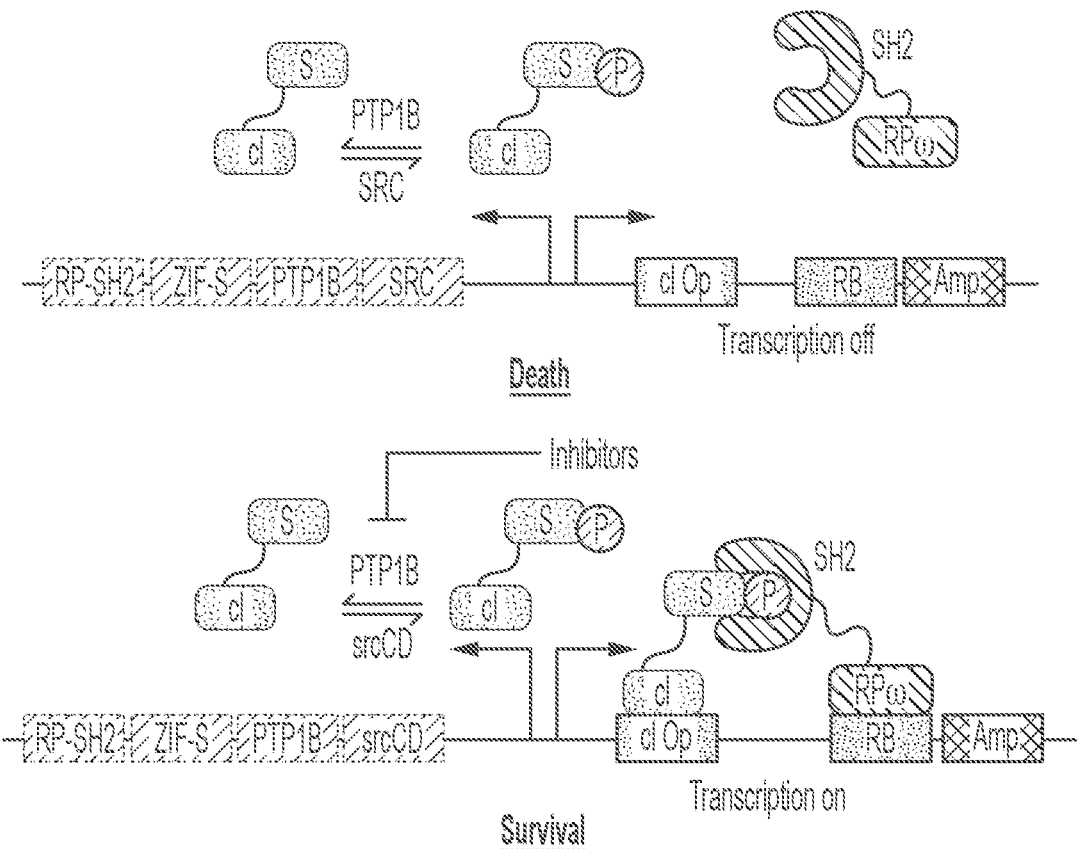
Figure 21B:
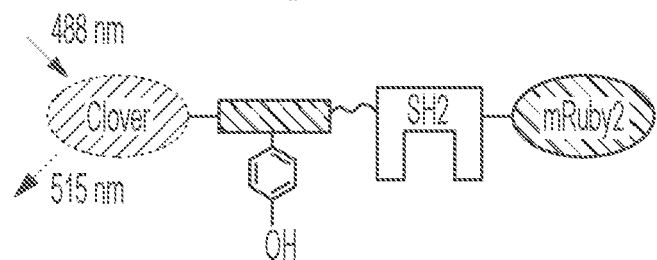
Figure 21B:
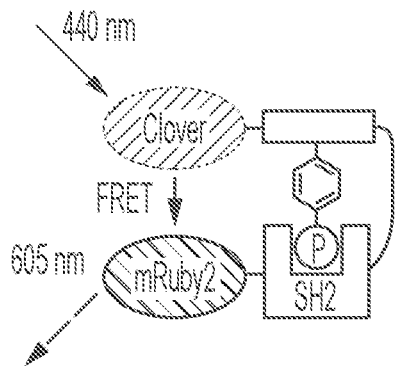

FRET sensors. Forster resonance energy transfer (FRET) is contemplated for use to monitor the activity of PTP1B in living cells. Sensor exhibits a 20% reduction in FRET signal when treated with Src kinase (FIG. 21B). Previous imaging studies indicate that a 20% change in FRET is sufficient to monitor intracellular kinase activity[54-56]. To enhance spatial resolution in imaging studies, we will attempt to optimize our sensor further (and use it to measure the activity of PTP1B in vitro).

Exemplary FRET sensors: underlined mClover3-SH2-Linker-Bold Substrate—underlined and Bold mRuby3.

mClover3-mRuby3: DNA sequence: SEQ ID NO: 20:
ATGCATCATCATCATCATCAT<u>GTGAGCAAGGGCGAGGAGCTGTTCACCGGGGTGG</u>

<u>TGCCCATCCTGGTCGAGCTGGACGGCGACGTAAACGGCCACAAGTTCAGCGTCCGC</u>

<u>GGCGAGGGCGAGGGCGATGCCACCAACGGCAAGCTGACCCTGAAGTTCATCTGCAC</u>

<u>CACCGGCAAGCTGCCCGTGCCCTGGCCCACCCTCGTGACCACCTTCGGCTACGGCGT</u>

<u>GGCCTGCTTCAGCCGCTACCCCGACCACATGAAGCAGCACGACTTCTTCAAGTCCGC</u>

<u>CATGCCCGAAGGCTACGTCCAGGAGCGCACCATCTCTTTCAAGGACGACGGTACCT</u>

<u>ACAAGACCCGCGCCGAGGTGAAGTTCGAGGGCGACACCCTGGTGAACCGCATCGAG</u>

<u>CTGAAGGGCATCGACTTCAAGGAGGACGGCAACATCCTGGGGCACAAGCTGGAGTA</u>

<u>CAACTTCAACAGCCACTACGTCTATATCACGGCCGACAAGCAGAAGAACTGCATCA</u>

<u>AGGCTAACTTCAAGATCCGCCACAACGTTGAGGACGGCAGCGTGCAGCTCGCCGAC</u>

<u>CACTACCAGCAGAACACCCCCATCGGCGACGGCCCCGTGCTGCTGCCCGACAACCA</u>

<u>CTACCTGAGCCATCAGTCCAAGCTGAGCAAAGACCCCAACGAGAAGCGCGATCACA</u>

<u>TGGTCCTGCTGGAGTTCGTGACCGCCGCCGGGATTACACATGGCATGGACGAGCTGT</u>

<u>ACAAGTGGTATTTTGGGAAGATCACTCGTCGGGAGTCCGAGCGGCTGCTGCTCAACC</u>

<u>CCGAAAACCCCCGGGGAACCTTCTTGGTCCGGGAGAGCGAGACGACAAAAGGTGCC</u>

<u>TATTGCCTCTCCGTTTCTGACTTTGACAACGCCAAGGGGCTCAATGTGAAGCACTAC</u>

<u>AAGATCCGCAAGCTGGACAGCGGCGGCTTCTACATCACCTCACGCACACAGTTCAG</u>

<u>CAGCCTGCAGCAGCTGGTGGCCTACTACTCCAAACATGCTGATGGCTTGTGCCACCG</u>

<u>CCTGACTAACGTCTGTGGGTCTACATCTGGATCTGGGAAGCCGGGTTCTGGTGAGGG</u>

<u>TTCT</u>TGGATGGAGGACTATGACTACGTCCACCTACAGGGGGAGCTCGTGTCTAA

GGGCGAAGAGCTGATCAAGGAAAATATGCGTATGAAGGTGGTCATGGAAGGTT

CGGTCAACGGCCACCAATTCAAATGCACAGGTGAAGGAGAAGGCAGACCGTAC

GAGGGAACTCAAACCATGAGGATCAAAGTCATCGAGGGAGGACCCCTGCCATT

TGCCTTTGACATTCTTGCCACGTCGTTCATGTATGGCAGCCGTACTTTTATCAA

GTACCCGGCCGACATCCCTGATTTCTTTAAACAGTCCTTTCCTGAGGGTTTTAC

TTGGGAAAGAGTTACGAGATACGAAGATGGTGGAGTCGTCACCGTCACGCAGG

ACACCAGCCTTGAGGATGGCGAGCTCGTCTACAACGTCAAGGTCAGAGGGGTA

AACTTTCCCTCCAATGGTCCCGTGATGCAGAAGAAGACCAAGGGTTGGGAGCC

TAATACAGAGATGATGTATCCAGCAGATGGTGGTCTGAGAGGATACACTGACA

TCGCACTGAAAGTTGATGGTGGTGGCCATCTGCACTGCAACTTCGTGACAACTT

ACAGGTCAAAAAAGACCGTCGGGAACATCAAGATGCCCGGTGTCCATGCCGTT

GATCACCGCCTGGAAAGGATCGAGGAGAGTGACAATGAAACCTACGTAGTGCA

ACGCGAAGTGGCAGTTGCCAAATACAGCAACCTTGGTGGTGGCATGGACGAGC

TGTACAAGTAA

Protein sequence: SEQ ID NO: 21:
MHHHHHHVSKGEELFTGVVPILVELDGDVNGHKFSVRGEGEGDATNGKLTLKFICTTG

KLPVPWPTLVTTFGYGVACFSRYPDHMKQHDFFKSAMPEGYVQERTISFKDDGTYKTR

AEVKFEGDTLVNRIELKGIDFKEDGNILGHKLEYNFNSHYVYITADKQKNCIKANFKIRH

NVEDGSVQLADHYQQNTPIGDGPVLLPDNHYLSHQSKLSKDPNEKRDHMVLLEFVTAA

GITHGMDELYKWYFGKITRRESERLLLNPENPRGTFLVRESETTKGAYCLSVSDFDNAK

GLNVKHYKIRKLDSGGFYITSRTQFSSLQQLVAYYSKHADGLCHRLTNVCGSTSGSGKP

GSGEGSWMEDYDYVHLQGELVSKGEELIKENMRMKVVMEGSVNGHQFKCTGEGE

GRPYEGTQTMRIKVIEGGPLPFAFDILATSFMYGSRTFIKYPADIPDFFKQSFPEGFT

WERVTRYEDGGVVTVTQDTSLEDGELVYNVKVRGVNFPSNGPVMQKKTKGWEP

NTEMMYPADGGLRGYTDIALKVDGGGHLHCNFVTTYRSKKTVGNIKMPGVHAVD

HRLERIEESDNETYVVQREVAVAKYSNLGGGMDELYK

Exemplary Mammalian expression vector(s) for expressing a photoswitch construct in a mammalian cell.

For insertion into a mammalian expression vector, e.g. lentiviral vector, pAcGFP1-C1 (Clontech); PTP1B-LOV2 (above), a promoter, e.g. CMV: SEQ ID NO: 22: GCAAATGGGCGGTAGGCGTGTACGGTGGGAGGTC-TATATAAGCAGAGCTGGTTTAG TGAACCGTCA-GATC; a RBS, e.g. Kozak consensus translation initiation site: GCCACCATG; an Intergenic spacer (e.g. P2A: DNA sequence: SEQ ID NO: 23: GGCAGCGGCGCCAC-CAACTTCTCCCTGCTGAAGCAGGCCGGCGACGTG-GAGGAGAA CCCCGGCCCC; a protein sequence: SEQ ID NO: 24: GSGATNFSLLKQAGDVEENPGP, etc.

An exemplary FRET Sensor included: a Promoter: Same as above; a RBS: Same as above, etc.

Exemplary FRET sensors are contemplated to avoid overlap between the excitation/emission wavelengths of LOV2 (455/495, we note that LOV2 is only weakly fluorescent[70]) and our FRET pair (505/515 for Clover and 560/605 for mRuby2), while we still expect to see some crosstalk during imaging, previous three-color imaging studies[71] suggest that it will not interfere with our ability to carry out the experiments described in this section.

Contemplative Embodiments Include but at not Limited to Invadopodia Formation and EGFR Regulation.

A photoswitchable variant of PTP1B is contemplated to determine if cytosolic PTP1B, released from the ER by proteolysis, is exclusively responsible for regulating the formation of invadopodia, or if ER-bound PTP1B can function similarly. Cancer cell invasion and metastasis is facilitated by the formation of invadopodia, actin-rich protrusions that enable matrix degradation[45].

Both PTP1B and PTK6 regulate epidermal growth factor receptor (EGFR), a regulator of cell proliferation and migration that exhibits aberrant activity in numerous cancers and inflammatory diseases[51,76]. We will use a variant of PTP1B stimulated by red light and a variant of PTK6 stimulated by blue light (or vice versa) to carry out a combinatorial analysis of the cooperative contribution of PTP1B and PTK6 to EGFR regulation within different regions of the cell.

REFERENCES FOR SECTIONS I, II, AND V ARE LISTED BELOW AND HEREIN INCORPORATED BY REFERENCE

1. Wray, J., Kalkan, T., Gomez-Lopez, S., Eckardt, D., Cook, A., Kemler, R. & Smith, A. Inhibition of glycogen synthase kinase-3 alleviates Tcf3 repression of the pluripotency network and increases embryonic stem cell resistance to differentiation. Nat. Cell Biol. 13, 838-45 (2011).
2. Wu, Y. I., Frey, D., Lungu, O. I., Jaehrig, A., Schlichting, I., Kuhlman, B. & Hahn, K. M. A genetically encoded photoactivatable Rac controls the motility of living cells. Nature 461, 104-108 (2009).
3. Liu, H., Wu, Y., Zhu, S., Liang, W., Wang, Z., Wang, Y., Lv, T., Yao, Y., Yuan, D. & Song Y. PTP1B promotes cell proliferation and metastasis through activating src and ERK1/2 in non-small cell lung cancer. Cancer Lett. 359, 218-225 (2015).
4. Danial, N. N. & Korsmeyer, S. J. Cell Death: Critical Control Points. Cell 116, 205-219 (2004).
5. Johnson, T. O., Ermolieff, J. & Jirousek, M. R. Protein tyrosine phosphatase 1B inhibitors for diabetes. Nat. Rev. Drug Discov. 1, 696-709 (2002).
6. Koren, S. & Fantus, I. G. Inhibition of the protein tyrosine phosphatase PTP1B: potential therapy for obesity, insulin resistance and type-2 diabetes mellitus. Best Pract. Res. Clin. Endocrinol. Metab. 21, 621-640 (2007).
7. Pike, K. a, Hutchins, A. P., Vinette, V., Theberge, J.-F., Sabbagh, L., Tremblay, M. L. & Miranda-Saavedra, D. Protein tyrosine phosphatase 1B is a regulator of the interleukin-10-induced transcriptional program in macrophages. Sci. Signal. 7, ra43 (2014).
8. Rhee, I. & Veillette, a. Protein tyrosine phosphatases in lymphocyte activation and autoimmunity. Nat. Immunol. 13, 439-447 (2012).
9. Zhu, S., Bjorge, J. D. & Fujita, D. J. PTP1B contributes to the oncogenic properties of colon cancer cells through Src activation. Cancer Res. 67, 10129-10137 (2007).
10. Volinsky, N. & Kholodenko, B. N. Complexity of receptor tyrosine kinase signal processing. Cold Spring Harb. Perspect. Biol. 5, (2013).

11. Kennedy, M. B. Signal-Processing Machines at the Postsynaptic Density. Science. 290, 750-754 (2000).
12. Lee, H. K., Takamiya, K., Han, J. S., Man, H., Kim, C. H., Rumbaugh, G., Yu, S., Ding, L., He, C, Petralia, R. S., Wenthold, R. J., Gallagher, M. & Huganir, R. L. Phosphorylation of the AMPA receptor GluR1 subunit is required for synaptic plasticity and retention of spatial memory. Cell 112, 631-643 (2003).
13. Bence, K. K., Delibegovic, M., Xue, B., Gorgun, C. Z., Hotamisligil, G. S., Neel, B. G. & Kahn, B. B. Neuronal PTP1B regulates body weight, adiposity and leptin action. Nat. Med. 12, 917-24 (2006).
14. Wu, P., Nielsen, T. E. & Clausen, M. H. FDA-approved small-molecule kinase inhibitors. Trends Pharmacol. Sci. 36, 422-439 (2015).
15. Repina, N. A., Rosenbloom, A., Mukherjee, A., Schaffer, D. V. & Kane, R. S. At Light Speed: Advances in Optogenetic Systems for Regulating Cell Signaling and Behavior. Annu. Rev. Chem. Biomol. Eng. 8, 13-39 (2017).
16. Gautier, A., Gauron, C, Volovitch, M., Bensimon, D., Jullien, L. & Vriz, S. How to control proteins with light in living systems. Nat. Chem. Biol. 10, 533-41 (2014).
17. Krauss, U., Lee, J., Benkovic, S. J. & Jaeger, K. E. LOVely enzymes—Towards engineering light-controllable biocatalysts. Microb. Biotechnol. 3, 15-23 (2010).
18. Dagliyan, O., Tarnawski, M., Chu, P.-H., Shirvanyants, D., Schlichting, I., Dokholyan, N. V. & Hahn, K. M. Engineering extrinsic disorder to control protein activity in living cells. Science. 354, 1441-1444 (2016).
19. Zhou, X. X., Fan, L. Z., Li, P., Shen, K. & Lin, M. Z. Optical control of cell signaling by single-chain photoswitchable kinases. Science. 355, 836-842 (2017).
20. Lukyanov, K. a, Chudakov, D. M., Lukyanov, S. & Verkhusha, V. V. Photoactivatable fluorescent proteins. Nat. Rev. Mol. Cell Biol. 6, 885-890 (2005).
21. Rodriguez, E. A., Campbell, R. E., Lin, J. Y., Lin, M. Z., Miyawaki, A., Palmer, A. E., Shu, X., Zhang, J. & Tsien, R. Y. The Growing and Glowing Toolbox of Fluorescent and Photoactive Proteins. Trends Biochem. Sci. 42, 111-129 (2017).
22. Lessard, L., Stuible, M. & Tremblay, M. L. The two faces of PTP1B in cancer. Biochim. Biophys. Acta—Proteins Proteomics 1804, 613-619 (2010).
23. Barr, A. J., Ugochukwu, E., Lee, W. H., King, O. N. F., Filippakopoulos, P., Alfano, I., Savitsky, P., Burgess-Brown, N. A., Mtiller, S. & Knapp, S. Large-Scale Structural Analysis of the Classical Human Protein Tyrosine Phosphatome. Cell 136, 352-363 (2009).
24. Hubbard, S. R. & Till, J. H. Protein tyrosine kinase structure and function. Annu. Rev. Biochem. 69, 373-398 (2000).
25. Zayner, J. P., Antoniou, C. & Sosnick, T. R. The amino-terminal helix modulates light-activated conformational changes in AsLOV2. J. Mol. Biol. 419, 61-74 (2012).
26. Peter, E., Dick, B. & Baeurle, S. A. Mechanism of signal transduction of the LOV2-Ja photosensor from *Avena sativa*. Nat. Commun. 1, 122 (2010).
27. Kaberniuk, A. A., Shemetov, A. A. & Verkhusha, V. V. A bacterial phytochrome based optogenetic system controllable with near-infrared light. Nat. Methods 13, 1-15 (2016).
28. Auldridge, M. E. & Forest, K. T. Bacterial phytochromes: more than meets the light. Crit. Rev. Biochem. Mol. Biol. 46, 67-88 (2011).
29. Anderie, I., Schulz, I. & Schmid, A. Characterization of the C-terminal ER membrane anchor of PTP1B. Exp. Cell Res. 313, 3189-3197 (2007).
30. Tonks, N. K. & Muthuswamy, S. K. A Brake Becomes an Accelerator: PTP1B-A New Therapeutic Target for Breast Cancer. Cancer Cell 11, 214-216 (2007).
31. Krishnan, N. & Tonks, N. K. Anxious moments for the protein tyrosine phosphatase PTP1B. Trends Neurosci. 38, 462-465 (2015).
32. T raves, P. G., Pardo, V., Pimentel-Santillana, M., Gonzalez-Rodrfguez, A., Mojena, M., Rico, D., Montenegro, Y., Cales, C, Martfn-Sanz, P., Valverde, a M. & Bosca, L. Pivotal role of protein tyrosine phosphatase 1B (PTP1B) in the macrophage response to pro inflammatory and anti-inflammatory challenge. Cell Death Dis. 6, e1125 (2014).
33. Matulka, K., Lin, H. H., Hrfbkova, H., Uwanogho, D., Dvorak, P. & Sun, Y. M. PTP1B is an effector of activin signaling and regulates neural specification of embryonic stem cells. Cell Stem Cell 13, 706-719 (2013).
34. Cortesio, C. L., Chan, K. T., Perrin, B. J., Burton, N. O., Zhang, S., Zhang, Z. Y. & Huttenlocher, A. Calpain 2 and PTP1B function in a novel pathway with Src to regulate invadopodia dynamics and breast cancer cell invasion. J. Cell Biol. 180, 957-971(2008).
35. Wiesmann, C, Barr, K. J., Kung, J., Zhu, J., Erlanson, D. A., Shen, W., Fahr, B. J., Zhong M, Taylor, L., Randal, M., McDowell, R. S. & Hansen, S. K. Allosteric inhibition of protein tyrosine phosphatase 1B. Nat. Struct. Mol. Biol. 11, 730-737 (2004).
36. Alonso, A., Sasin, J., Bottini, N., Friedberg, I., Friedberg, I., Osterman, A., Godzik, A., Hunter, T., Dixon, J. & Mustelin, T. Protein tyrosine phosphatases in the human genome. Ce//117, 699-711 (2004).
37. Haj, F. G., Verveer, P. J., Squire, A., Neel, B. G. & Bastiaens, P. I. H. Imaging sites of receptor dephosphorylation by PTP1B on the surface of the endoplasmic reticulum. Science 295, 1708-1711 (2002).
38. Romsicki, Y., Reece, M., Gauthier, J. Y., Asante-Appiah, E. & Kennedy, B. P. Protein Tyrosine Phosphatase-1B Dephosphorylation of the Insulin Receptor Occurs in a Perinuclear Endosome Compartment in Human Embryonic Kidney 293 Cells. J. Biol. Chem. 279, 12868-12875 (2004).
39. Haj, F. G., Sabet, O., Kinkhabwala, A., Wimmer-Kleikamp, S., Roukos, V., Han, H. M., Grabenbauer, M., Bierbaum, M., Antony, C, Neel, B. G. & Bastiaens, P. I. Regulation of signaling at regions of cell-cell contact by endoplasmic reticulum-bound protein-tyrosine phosphatase 1B. PLoS One 7, (2012).
40. Soysal, S., Obermann, E. C, Gao, F., Oertli, D., Gillanders, W. E., Viehl, C. T. & Muenst, S. PTP1B expression is an independent positive prognostic factor in human breast cancer. Breast Cancer Res. Treat. 137, 637-644 (2013).
41. Zhang, S. & Zhang, Z. Y. PTP1B as a drugtarget: recent developments in PTP1B inhibitor discovery. Drug Discov. Today 12, 373-381 (2007).
42. Wu, C, Zhang, L, Bourne, P. A., Reeder, J. E., Di Sant' Agnese, P. A., Yao, J. L, Na, Y. & Huang, J. Protein tyrosine phosphatase PTP1B is involved in neuroendocrine differentiation of prostate cancer. Prostate 66, 1124-1135 (2006).
43. Lessard, L, DP, L, Deblois, G., Begin, L, Hardy, S., Mes-Masson, A., Saad, F., Trotman, L, Giguere, V. & Tremblay, M. PTP1B is an androgen receptor-regulated 43. phosphatase that promotes the progression of prostate cancer. Cancer Res. 72, 1529-1537 (2012).
44. Dube, N., Bourdeau, A., Heinonen, K. M., Cheng, A., Loy, A. L. & Tremblay, M. L. Genetic ablation of protein tyrosine phosphatase 1B accelerates lymphomagenesis of p53-null mice through the regulation of B-cell development. Cancer Res. 65, 10088-10095 (2005).
45. Weaver, A. M. Invadopodia: Specialized cell structures for cancer invasion. Clin. Exp. Metastasis 23, 97-105 (2006).
46. Cui, Q., Ma, Y., Jaramillo, M., Bari, H., Awan, A., Yang, S., Zhang, S., Liu, L., Lu, M., O'Connor-McCourt, M., Purisima, E. O. & Wang, E. A map of human cancer signaling. Mol. Syst. Biol. 3, 152 (2007).
47. Repina, N. A., Rosenbloom, A., Mukherjee, A., Schaffer, D. V. & Kane, R. S. At Light Speed: Advances in Optogenetic Systems for Regulating Cell Signaling and Behavior. Annu. Rev. Chem. Biomol. Eng. 8, 13-39 (2017).
48. Lee, J., Natarajan, M., Nashine, V. C, Socolich, M., Vo, T., Russ, W. P., Benkovic, S. J. & Ranganathan, R. Surface sites for engineering allosteric control in proteins. Science 322, 438-442 (2008).
49. Qin, Z., Zhou, X., Pandey, N. R., Vecchiarelli, H. A., Stewart, C. A., Zhang, X., Lagace, D. C, Brunei, J. M., Beique, J. C, Stewart, A. F. R., Hill, M. N. & Chen, H. H. Chronic Stress Induces Anxiety via an Amygdalar Intracellular Cascade that Impairs Endocannabinoid Signaling Neuron 85, 1319-1331(2015).
50. Fan, G., Lin, G., Lucito, R. & Tonks, N. K. Protein-tyrosine phosphatase 1B antagonized signaling by insulin-like growth factor-1 receptor and kinase BRK/PTK6 in ovarian cancer cells. J. Biol. Chem. 288, 24923-34 (2013).
51. Eden, E. R., White, I. J., Tsapara, A. & Futter, C. E. Membrane contacts between endosomes and ER provide sites for PTP1B-epidermal growth factor receptor interaction. Nat. Cell Biol. 12, 267-72 (2010).
52. Arregui, C. O., Gonzalez, A., Burdisso, J. E. & Gonzalez Wusener, A. E. Protein tyrosine phosphatase PTP1B in cell adhesion and migration. Cell Adh. Migr. 7, 418-423 (2013).
53. Badran, A. H., Guzov, V. M., Huai, Q., Kemp, M. M., Vishwanath, P., Kain, W., Nance, A. M., Evdokimov, A., Moshiri, F., Turner, K. H., Wang, P., Malvar, T. & Liu, D. R. Continuous evolution of *Bacillus thuringiensis* toxins overcomes insect resistance. Nature 533, 58-63 (2016).
54. Sato, M. & Umezawa, Y. in Cell Biol. Four-Volume Set 2, 325-328 (2006).

55. Ouyang, M., Sun, J., Chien, S. & Wang, Y. Determination of hierarchical relationship of Src and Rac at subcellular locations with FRET biosensors. Proc Natl Acad Sci USA 105, 14353-14358 (2008).

56. Ting, a Y., Kain, K. H., Klemke, R. L. & Tsien, R. Y. Genetically encoded fluorescent reporters of protein tyrosine kinase activities in living cells. Proc. Natl. Acad. Sci. U.S.A 98, 15003-15008 (2001).

57. Wiesmann, C, Barr, K. J., Kung, J., Zhu, J., Erlanson, D. A., Shen, W., Fahr, B. J., Zhong M, Taylor, L, Randal, M., McDowell, R. S. & Hansen, S. K. Allosteric inhibition of protein tyrosine phosphatase 1B. Nat. Struct. Mol. Biol. 11, 730-737 (2004).

58. Halavaty, A. S. & Moffat, K. N- and C-terminal flanking region s modulate light-induced signal transduction in the LOV2 domain of the blue light sensor phototropin 1 from *Avena sativa*. Biochemistry 46, 14001-14009 (2007).

59. Yao, X., Rosen, M. K. & Gardner, K. H. Estimation of the available free energy in a LOV2-Ja photoswitch. Nat. Chem. Biol. 4, 491-497 (2008).

60. Choy, M. S., Li, Y., Machado, L. E. S. F., Kunze, M. B. A., Connors, C. R., Wei, X., Lindorff-Larson, K., Page, R. & Peti, W. Conformational Rigidity and Protein Dynamics at Distinct Timescales Regulate PTP1B Activity and Allostery. Mol. Cell 65, 644-658 (2017).

61. Hubbard, S. R. & Till, J. H. Protein tyrosine kinase structure and function. Annu. Rev. Biochem. 69, 373-398 (2000).

62. Zhang, Y., Kurup, P., Xu, J., Carty, N., Fernandez, S. M., Nygaard, H. B., Pittenger, C, Greengard, P., Strittmatter, S. M., Nairn, A. C. & Lombroso, P. J. Genetic reduction of striatal-enriched tyrosine phosphatase (STEP) reverses cognitive and cellular deficits in an Alzheimer's disease mouse model. Proc. Natl. Acad. Sci. 107, 19014-19019 (2010).

63. He, R., Yu, Z., Zhang, R. & Zhang, Z. Protein tyrosine phosphatases as potential therapeutic targets. Acta Pharmacol. Sin. 35, 1227-1246 (2014).

64. Ito, K., Park, S. H., Nayak, A., Byerly, J. H. & Irie, H. Y. PTK6 inhibition suppresses metastases of triple-negative breast cancer via SNAIL-dependent E-cadherin regulation. Cancer Res. 76, 4406-4417 (2016).

65. Zegzouti, H., Zdanovskaia, M., Hsiao, K. & Goueli, S. A. ADP-Glo: A Bioluminescent and Homogeneous ADP Monitoring Assay for Kinases. Assay Drug Dev. Technol. 7, 560-572 (2009).

66. Strickland, D., Yao, X., Gawlak, G., Rosen, M. K., Gardner, K. H. & Sosnick, T. R. Rationally improving LOV domain-based photoswitches. Nat. Methods 7, 623-6 (2010).

67. Cosentino, C, Alberto, L., Gazzarrini, S., Aquila, M., Romano, E., Cermenati, S., Zuccolini, P., Petersen, J., Beltrame, M., Van Etten, J. L., Christie, J. M., Thiel, G. & Moroni, A. Engineering of a light-gated potassium channel. Science. 348, 707-710(2015).

68. Krishnan, N., Koveal, D., Miller, D. H., Xue, B., Akshinthala, S. D., Kragelj, J., Jensen, M R., Gauss, C.-M., Page, R., Blackledge, M., Muthuswamy, S. K., Peti, W. & Tonks, N. K. Targeting the disordered C terminus of PTP1B with an allosteric inhibitor. Nat. Chem. Biol. 10, 558-566 (2014).

69. Piserchio, A., Cowburn, D. & Ghose, R. Expression and purification of Src-family kinases for solution NMR studies. Methods Mol. Biol. 831, 111-131 (2012).

70. Van Stokkum, I. H. M., Gauden, M., Crosson, S., Van Grondelle, R., Moffat, K. & Kennis, J. T. M. The primary photophysics of the *Avena sativa* phototropin 1 LOV2 domain observed with time-resolved emission spectroscopy. Photochem. Photobiol. 87, 534-541 (2011).

71. Rowland, A. A., Chitwood, P. J., Phillips, M. J. & Voeltz, G. K. ER contact sites define the position and timing of endosome fission. Ce//159, 1027-1041 (2014).

72. Fehr, M., Lalonde, S., Lager, I., Wolff, M. W. & Frommer, W. B. In vivo imaging of the dynamics of glucose uptake in the cytosol of COS-7 cells by fluorescent nanosensors. J. Biol. Chem. 278, 19127-19133 (2003).

73. Feigner, P. L., Gadek, T. R., Holm, M., Roman, R., Chan, H. W., Wenz, M., Northrop, J. P., Ringold, G. M. & Danielsen, M. Lipofection: a highly efficient, lipid-mediated DNA-transfection procedure. Proc. Natl. Acad. Sci. U.S.A 84, 7413-7 (1987).

74. Gil-Parrado, S., Fernandez-Montalvan, A., Assfalg-Machleidt, I., Popp, O., Bestvater, F., Holloschi, A., Knoch, T. A., Auerswald, E. A., Welsh, K., Reed, J. C, Fritz, H., Fuentes-Prior, P., Spiess, E., Salvesen, G. S. & Machleidt, W. Ionomycin-activated calpain triggers apoptosis. A probable role for Bcl-2 family members. J. Biol. Chem. 277, 27217-27226 (2002).
75. Faeder, J. R., Blinov, M. L. & Hlavacek, W. S. Rule-based modeling of biochemical systems with BioNetGen. Methods Mol. Biol. 500, 113-167 (2009).
76. Tiganis, T., Bennett, A. M., Ravichandran, K. S. & Tonks, N. K. Epidermal growth factor receptor and the adaptor protein p52Shc are specific substrates of T-cell protein tyrosine phosphatase. Mol. Cell. Biol. 18, 1622-34 (1998).

III. Genetically Encoded System for Constructing and Detecting Biologically Active Agents: Microbial Inhibitor Screening Systems.

Several types of operons were developed as described herein, each for a specific purpose, including but not limited to testing small molecules for their ability to inhibit, activate, or otherwise modulate a chosen PTP and/or PTK; operons for testing intracellularly provided small molecules for inhibiting, activating, or modulating effects on a chosen PTP and/or PTK; and evolving one or more proteins or small molecules of interest. More specifically, genetic operons were contemplated for insertion, using transfection and breeding techniques well known in the art, for providing microbial cells wherein the activity of an enzyme of interest (e.g., protein tyrosine phosphatase 1B, a drug target for the treatment of diabetes, obesity, and cancer) is linked to (i) cellular luminescence, (ii) cellular fluorescence, or (iii) cellular growth. In some embodiments, such operons are modified for use in detecting and/or evolving biologically active metabolites. When modified and/or induced to build various metabolites, the cell will be used for detection of metabolites that inhibit/activate a protein of interest (e.g., PTP1B).

These operons allow operon-containing microbial cells to be used to carry out the following tasks: Detecting biologically active molecules and non-native biologically active metabolites. When grown in the presence of biologically active molecules as a small molecule that is both (i) cell permeable and (ii) capable of inhibiting a protein of interest (e.g., PTP1B), the cell will enable detection of that molecule. That is, it will exhibit a concentration-dependent response in luminescence, fluorescence, or growth. Many non-native biologically active metabolites have useful pharmaceutical properties. Examples include paclitaxel and artemisinin, plant-derived terpenoids that are used to treat cancer and malaria, respectively. When the metabolic pathways responsible for making such natural metabolites are installed into microbial cells that also contain our operon, those cells will enable detection of interesting metabolite-based biological activities (e.g., the ability to inhibit PTP1B).

Genetic operons that, when installed into microbial cells, link the activity of an enzyme of interest (e.g., protein tyrosine phosphatase 1B, a drug target for the treatment of diabetes, obesity, and cancer) to (i) cellular luminescence, (ii) cellular fluorescence, or (iii) cellular growth.

Detect and/or evolve biologically active metabolites. When modified and/or induced to build various metabolites, the cell will enable detection of metabolites that inhibit/activate a protein of interest (e.g., PTP1B).

These operons allow operon-containing microbial cells to be used to carry out the following tasks: Detecting biologically active molecules and non-native biologically active metabolites. When grown in the presence of a biologically active molecules as a small molecule that is both (i) cell permeable and (ii) capable of inhibiting a protein of interest (e.g., PTP1B), the cell will enable detection of that molecule. That is, it will exhibit a concentration-dependent response in luminescence, fluorescence, or growth. Many non-native biologically active metabolites have useful pharmaceutical properties. Examples include paclitaxel and artemisinin, plant-derived terpenoids that are used to treat cancer and malaria, respectively. When the metabolic pathways responsible for making such natural metabolites are installed into microbial cells that also contain our operon, those cells will enable detection of metabolite-based biological activities (e.g., the ability to inhibit PTP1B).

In some embodiments, methods of evolving molecules may be modified from Moses, et al., "Bioengineering of plant (tri)terpenoids: from metabolic engineering of plants to synthetic biology in vivo and in vitro." New Phytologist, Volume 200, Issue 1, where this reference describes synthesis of artemisinic acid, the precursor of the antimalarial drug artemisinin, as diterpenoids expressed in *E. coli*. Further, enzyme engineering or directed evolution of terpenoid biosynthetic enzymes, e.g. engineer enzymes to accept unnatural substrates and to catalyze regions and stereospecific reactions with an efficiency comparable with that of the natural enzymes is described, along with discussions on enhancing the production of terpenoids in *Escherichia coli*. In some embodiments, methods of evolving molecules may be modified from Badran, et al., "Continuous evolution of *Bacillus thuringiensis* toxins overcomes insect resistance". Nature, Vol 533:58, 2016, where this reference describes a phage-assisted continuous evolution selection that rapidly evolves high-affinity protein-protein interactions, and applied this system to evolve variants of the Bt toxin Cry1Ac that bind a cadherin-like receptor from the insect pest *Trichoplusia ni* (TnCAD) that is not natively bound by wild-type Cry1Ac.

A. Protein Evolving Systems and Evolving Biologically Active Metabolites.

In some embodiments, methods of evolving molecules may be used to construct drug leads that can be readily synthesized in microbial hosts. It addresses a longstanding challenge—the development of low-cost pharmaceuticals—by using a sophisticated set of biophysical tools and analytical methodologies to narrow the molecular search space in lead discovery, and by explicitly considering the biosynthetic accessibility of therapeutic molecules. The approach, which departs from contemporary efforts to use microbial systems for the synthesis of clinically approved drugs and their precursors, is unique in its focus on using biology for the systematic construction of new molecules. It will accelerate the rate—and lower the cost—of pharmaceutical development.

The development of a drug requires optimization of many of its pharmacological properties—affinity, absorption, distribution, metabolism, excretion, toxicology, pharmacokinetics, and pharmacodynamics[1]. The first of these properties—protein-ligand binding affinity—generally determines whether the others are worth measuring or enhancing, and, thus, represents a property of drug leads[2]. Despite advances in computational chemistry and structural biology, the rational design of ligands that bind tightly to proteins—ligands, henceforth, referred to collectively as inhibitors—remains exceptionally difficult[3]; as a result, the development of drugs often begins with screens of large libraries of molecules[4]. An inhibitor, once discovered, must be synthesized in quantities sufficient for subsequent analysis, optimization, formulation, and clinical evaluation.

The difficulties associated with developing protein inhibitors are particularly problematic for natural products. These molecules, which account for over 50% of clinically approved drugs, tend to have favorable pharmacological properties (e.g., membrane permeability)[5]. Unfortunately, their low natural titers—which hamper the extraction of testable quantities from natural sources and their chemical complexity—which complicates chemical synthesis—make the preparation of quantities sufficient for post-screen analyses time-consuming and expensive[6].

In some embodiments, enzymes are contemplated for use to construct terpenoid inhibitors that can be synthesized in ESCHERICHIA COLI; such an approach takes advantage of the chemical diversity (and generally favorable pharmacological properties) of natural products without the constraints of their natural scarcity. In some embodiments, detailed biophysical study of the molecular-level origin and thermodynamic basis of affinity and activity in protein-terpenoid interactions are included for the rapid construction of high-affinity inhibitors. In some embodiments, development of selective inhibitors of protein tyrosine phosphatase 1B (PTP1B), a target for the treatment of diabetes, obesity, and cancer is contemplated in part for using enzymes to evolve readily synthesizable drug leads.

Structurally Varied Terpenoids with Different Affinities for the Allosteric Binding Pocket of Protein Tyrosine Phosphatase 1B (PTP1B).

Hypothesis. Results indicate that abietic acid, a monocarboxylated variant of abietadiene, is an allosteric inhibitor of PTP1B. Derivatives or structural analogs of abietadiene that differ in stereochemistry, shape, size, and/or chemical functionality (including carboxylation position) are likely to have different affinities for the allosteric binding pocket of PTP1B.

In some embodiments, (i) mutants of abietadiene synthase, cytochrome P450s, and halogenases are contemplated for use to make structural variants of abietadiene, (ii) GC/MS to identify those variants, (iii) preparative HPLC and flash chromatography to isolate them, and (iii) isothermal titration calorimetry to determine their free energies, enthalpies, and entropies of binding. In some embodiments, a set of structurally varied inhibitors with (i) affinities that differ by 100-fold and/or (ii) enthalpies and entropies of binding that suggest alternative binding geometries is contemplated.

To Examine the Molecular Basis and Thermodynamic Origin of Affinity and Activity in Enzyme-Terpenoid Interactions.

Hypothesis. Enzymes that bind, functionalize, and/or synthesize terpenoids possess large nonpolar binding pockets. We hypothesize that both (i) the affinity of an enzyme for terpenoids and (ii) the activity of an enzyme ON terpenoids is determined by the general shape and hydration structure of its binding pocket, not the position of specific protein-terpenoid contacts.

In some embodiments, a sophisticated set of biophysical tools (isothermal titration calorimetry, X-ray crystallography, molecular dynamics (MD) simulations, and NMR spectroscopy) are contemplated for use to (i) determine how protein-ligand contacts, rearrangements of water, and conformational constraints contribute to differences in affinity between terpenoid inhibitors and to (ii) develop a set of empirical relationships that predict how mutations in terpene synthases and terpene-functionalizing enzymes influence general attributes (e.g., shape) of their products.

To Evolve High-Affinity Terpenoid Inhibitors of PTP1B.

Hypothesis. Mutants from secondary metabolism (e.g., terpene synthases, cytochrome P450s, and halogenases) are highly promiscuous; a single mutation in or near their active sites can dramatically alter their product profiles. Mutagenesis of a small number (i.e., 2-4) of such enzymes, selected for their ability to synthesize and/or functionalize diterpenoids, will enable the development of inhibitors of PTP1B with sub-micromolar affinities.

In some embodiments, high-affinity inhibitors of PTP1B by pairing (i) high-throughput methods for detecting inhibitors with (ii) site-saturation and random mutagenesis is contemplated. For (i) we will develop four alternative fluorescence or growth-coupled assays to screen libraries of mutated pathways (and their respective products). For (ii) we use biostructural analyses and sequence alignments to identify residues likely to yield enzymes with favorable product profiles.

To Identify Structure-Activity Relationships that Enable the Evolution of Terpenoid Inhibitors of Arbitrary Protein Targets.

Hypothesis. Proteins that interact with similar classes of molecules (through binding or catalysis) have structurally similar binding pockets. Methods for evaluating these structural similarities—and their implications for enzyme activity—may enable the identification of enzymes capable of synthesizing inhibitors of ANY specified protein.

In some embodiments, a biophysical framework for using the crystal structure of a protein as a starting point to identify enzymes capable of synthesizing inhibitors of that protein is contemplated. We will examine (and formalize) structural relationships between (i) the active sites of enzymes used to synthesize allosteric inhibitors of PTP1B and (ii) the allosteric binding pocket of PTP1B, and we will validate these relationships by using them to identify—and, then, test new enzymes capable of synthesizing inhibitors of PTP1B and (separately) undecaprenyl diphosphate synthase, a target for the treatment of antibiotic-resistant bacterial infections.

Diabetes, Obesity, and Cancer.

Protein tyrosine phosphatase 1B (PTP1B) contributes to insulin resistance in type 2 diabetes[7], leptin resistance in obesity[8], and tumor growth in breast, colorectal, and lung cancers[9,11]. To date, the development of selective, tight-binding inhibitors of PTP1B (i.e., treatments for diabetes, obesity, and cancer) has been hindered by the structure of its active site, where polar residues limit tight binding to charged, membrane-impermeable molecules, and where structural similarities to the active sites of other protein tyrosine phosphatases (PTPs) lead to off-target interactions[12,14]. In this proposal, we will construct selective inhibitors of PTP1B that bind to its C-terminal allosteric site, a largely nonpolar region that is not conserved across phosphatases[15]. Previous screens of large molecular libraries have identified several ligands that bind to this site, but have yet to yield clinically approved drugs[16,13]. The identification of new molecular alternatives—a feat tackled in this proposal—remains a goal in efforts to develop selective PTP1B-inhibiting therapeutics.

Development of pharmaceuticals. The development of enzyme inhibitors—or leads represents an expensive part of drug development; for each successful drug, lead identification and optimization takes an average of 3 years and $250M to complete (~20-30% of the total time and cost to bring a drug to market)[17]. By narrowing the molecular search space in lead discovery, by enabling rapid construction of structurally-varied leads (often referred to as "backups"[18]), and by facilitating scale-up of molecular synthesis, the technology developed in this proposal could accelerate the rate—and lower the cost—of pharmaceutical development.

Molecular recognition. The hydrophobic effect—the free energetically favorable association of nonpolar species in aqueous solution—is, on average, responsible for ~75% of the free energy of protein-ligand association[19]. Unfortunately, hydrophobic interactions between ligands and proteins—which differ dramatically in rigidity, topography, chemical functionality, and hydration structure—remain difficult to predict[20]. This study uses detailed biophysical analyses and explicit-water calculations to examine the thermodynamic basis of hydrophobic interactions between terpenoids and protein binding pockets. It will develop a model system—and corresponding conceptual framework—for studying the hydrophobic effect in the context of structurally varied protein-ligand complexes, for accounting for that effect in the design of biosynthetic pathways, and for exploiting it in the construction of new drug leads.

Biosynthesis of New Natural Products.

Synthetic biology offers a promising route to the discovery and production of natural products. When the metabolic machinery of one organism is installed into a genetically tractable production host (e.g., S. CEREVISIAE or E. COLI), it enables the synthesis of complex compounds at high titers (relative to the native host). This approach has enabled the efficient production of pharmaceutically relevant metabolites from unculturable or low-yielding organisms[21,22], but, unfortunately, requires large investments of time and resources in pathway discovery and optimization; its use, as a result, is generally limited to the low-throughput characterization of newly discovered gene clusters or to the production of known, pharmaceutically relevant molecules (e.g., paclitaxel, artemisinin, or opioids)[22,24].

In some embodiments, a strategy for using synthetic biology to build new molecular function is contemplated. It begins with a pathologically relevant protein target and engineers pathway enzymes to produce molecules that selectively inhibit that target. This approach will yield molecules that can be produced in microbial hosts without extensive pathway optimization (it relies on enzymes that are expressible by default); it will, thus, expand the use of synthetic biology to the production of leads and backups. It is not a replacement for conventional approaches to the synthesis of complex natural products, but rather, a complementary strategy for constructing new compounds that will enhance the efficiency with which pharmaceuticals are developed.

In the presence of mutated metabolic pathways (e.g., version of a plant-based terpenoid-producing pathway in which the terpene synthase has been mutated), our operon will enable screens of large numbers of metabolites for their ability to inhibit our protein of interest (e.g., PTP1B). Such a platform could be used to evolve metabolites with specific biological activities.

Detect and/or evolve highly selective molecules. We have developed an idea for a version of our operon to detect molecules that inhibit one protein over a highly similar protein. Screens for molecular selectivity are, at present, remain very difficult.

Advantages of methods and systems described herein, over some other systems for detecting small molecule inhibitors includes but is not limited to enabling the detection of molecules that modulate or change the catalytic activity of an enzyme. Moreover, some embodiments of the systems described herein allow for the detection of test molecules that change the activity of an enzyme by binding anywhere on its surface. As one example, detection of an inhibitor is contemplated that inactivates PTP1B by binding to its C-terminal allosteric site; this binding event, which distorts catalytically essential motions of the WPD loop, would not necessarily prevent enzyme-substrate association. U.S. Pat. No. 6,428,951, herein incorporated by reference in its entirety, in contrast, enables the detection of molecules that prevent enzyme-substrate binding by competing for substrate binding sites (i.e., the active site). As another example, detection of molecules that activate an enzyme of interest is contemplated as an embodiment. U.S. Pat. No. 6,428,951, herein incorporated by reference in its entirety, in contrast, has methods that merely detect molecules that prevent enzymes from binding to their substrates, or that otherwise change the affinity of enzymes for their substrates. As another example, detection of molecules that do not require an enzyme and substrate to interact with any particular affinity, orientation, or half-life is contemplated as an embodiment. U.S. Pat. No. 6,428,951, herein incorporated by reference in its entirety, in contrast, requires an enzyme and substrate to bind one another with an affinity and orientation that enable assembly of a split reporter. As a result, it may require modifications to the enzyme; in contrast, the inventors use a "substrate trapping" mutant of PTP1B to improve its affinity for a substrate domain.

As another example, some embodiments enables the detection of inhibitors of wild-type enzymes. Tu S., U.S. Pat. No. 6,428,951, herein incorporated by reference in its entirety, in contrast, requires enzymes to be fused to one-half of a split reporter.

Further, the following two publications are examples of methods that for detecting molecules that merely disrupt the binding of an enzyme to a substrate. This characteristic, among others, is in contrast to U.S. Pat. No. 6,428,951. "Protein fragment complementation assays for the detection of biological or drug interactions." Pub. Date: Jan. 31, 2008, herein incorporated by reference in its entirety, which describes a high throughput bacteria based protein-fragment complementation assays (PCAs) wherein when two protein fragments derived from the enzyme dihydrofolate reductase (DHFR), coexpressed as fusion molecules in Escherichia coli, that interact in the absence of an inhibitor, then concentration dependent colony growth was observed. This reference states that PCA can be adapted to detecting interactions of proteins small molecules and provide examples, including complementary fragment fusions and a bait-fused fragment. In fact, protein tyrosine phosphatase PTP1B was provided in an example for detecting enzyme substrate interactions and an example of survival assay for detecting protein substrate interactions using aminoglycoside kinase (AK), an example of antibiotic resistance marker used for dominant selection of an E. coli,-based PCA. Further, a PCA is described as being applied to identify small molecule inhibitors of enzymes; natural products or small molecules from compound libraries of potential therapeutic value; may be used as survival assay for library screening; for detecting endogenous DHFR inhibitors, e.g. rapamycin; and for protein-drug interactions. Expression of PCA complementary fragments and fused cDNA libraries/target genes can be assembled on single plasmids as individual operons under the control of separate inducible or constitutive promoters with interceding region sequences, e.g. derived from a mel operon, or have polycistronic expression. The PCA can be adapted to detecting interactions of proteins with small molecules. In this conception, two proteins are fused to PCA complementary fragments, but the two proteins do not interact with each other. The interaction must be triggered by a third entity, which can be any molecule that will simultaneously bind to the two proteins or induce an interaction between the two proteins by causing a conformational change in one or both of the partners. Moreover, exemplary applications of the PCA Strategy in bacteria to protein engineering/evolution to generate peptides or proteins with novel binding properties that may have therapeutic value using phage display technology. One example of evolution produced novel zipper sequences; other examples of evolutions were described to produce endogenous toxins.

WO2004048549. Dep-1 Receptor Protein Tyrosine Phosphatase Interacting Proteins And Related Methods. Published Jun. 10, 2004, herein incorporated by reference in its entirety; describes screening assays for inhibitors that alter the interaction between a PTP and a tyrosine phosphorylated protein that is a substrate of the PTP, e.g. dephosphorylation by Density Enhanced Phosphatase-1 (DEP-1) of a DEP-1 substrate. DEP-1 polypeptides can be expressed in bacteria cells, including $E.$ $coli$, under the control of appropriate promoters, e.g. $E.$ $coli$ arabinose operon ($P_{BAD}$ or $P_{ARA}$). This reference is similarly limited in focus as U.S. Pat. No. 6,428,951, herein incorporated by reference in its entirety; it enables the detection of molecules that disrupt the binding of a substrate to an enzyme, rather than the detection of molecules that modulate (i.e., enhance or reduce) the activity of an enzyme.

Advantages of methods and systems described herein, over some other systems for detecting small molecule inhibitors includes but is not limited to enabling the evolution of metabolites that change the catalytic activity of an enzyme. The technology described in Badran, et al., "Continuous evolution of $Bacillus$ $thuringiensis$ toxins overcomes insect resistance". Nature, Vol 533:58, 2016, herein incorporated by reference in its entirety; and the platform of continuous evolution in general, has been used to evolve proteins with different affinities for other proteins/peptide substrates. It has not, however, been used to evolve enzymes that produce small molecules (i.e., metabolites) that alter the activities of enzymes or the strength of protein-protein interactions.

Another advantage of methods and systems described herein, over some other systems for detecting small molecule inhibitors includes the discovery of metabolites with targeted biological activities but unknown structures (e.g., the ability to inhibit protein tyrosine phosphatase 1B). There are many inventions relevant to the production of terpenoids in *E. coli* or *S. cerevisiae* (e.g., Moses, et al., "Bioengineering of plant (tri)terpenoids: from metabolic engineering of plants to synthetic biology in vivo and in vitro." New Phytologist, Volume 200, Issue 1, where this reference describes synthesis of artemisinic acid, the precursor of the antimalarial drug artemisinin, as diterpenoids expressed in *E. coli*. Further, enzyme engineering or directed evolution of terpenoid biosynthetic enzymes, e.g. engineer enzymes to accept unnatural substrates and to catalyze regions and stereospecific reactions with an efficiency comparable with that of the natural enzymes is described, along with discussions on enhancing the production of terpenoids in *Escherichia coli*.); in many cases, the metabolic pathways responsible for making these terpenoids are mutated to improve production levels. However, the use of biosensors (i.e., constructs that report on the concentrations of various metabolites) has focused on the detection of specific intermediates (e.g., farnesyl pyrophosphate, a precursor to terpenoids) not for combining (i) mutagenesis of a metabolic pathway and (ii) a biosensor for specific biological activity (e.g., the ability to inhibit PTP1B) for the discovery of new biologically active molecules (which may possess unknown structures).

High-Throughput Metabolic Engineering.

Microbial pathways are most efficiently optimized with high-throughput screens. Unfortunately, at present, such screens are sparse, and those available rely on signals (e.g., absorbance or fluorescence, association with a product-specific transcription factor, or growth permitted by an essential metabolite) that are difficult to extend to broad classes of molecules (e.g, those without distinct optical or metabolic properties)[27]. The proposed work develops high-throughput screens for terpenoids with a targeted activity—the ability to inhibit PTP1B—rather than a targeted structure; these activity-focused screens could be broadly useful for building (i.e., evolving) new biologically active small molecules.

Identification of new inhibitors: a starting point. We recently discovered that abietic acid, the primary component of resin acid, is an allosteric inhibitor of PTP1B (FIG. 22). We will use abietadiene, the immediate precursor of this molecule, as a starting point for the design of inhibitors. Abietadiene has several attributes that make it particularly compatible with our approach: (i) It can be synthesized in E. *COLI* at titers (200 mg/L) that permit purification, NMR analysis, and calorimetric studies[28], (ii) Mutants of its associated terpene synthase—abietadiene synthase—yield a range of hydrocarbon scaffolds that differ in stereochemistry, shape, and size (and that still enable analysis and purification)[29-31], (iii) It—and similar molecules—can be functionalized by cytochrome P450s and halogenases[32-34].

Metabolic engineering. We have engineered a strain of *E. COLI* to produce abietadiene at titers (>150 mg/L) sufficient to permit the analytical methods (i.e., GC/MS, ITC, and NMR). Our biosynthetic pathway has two requisite operons: MBIS, which converts (RJ-mevalonate to farnesyl pyrophosphate (FPP), and TS, which converts farnesyl pyrophosphate to abietadiene. One optional operon—MevT, which converts acetyl-CoA to (RJ-mevalonate—is necessary when mevalonate is not included in the media[35]. The plasmids pMevT and pMBIS were developed by the Keasling Laboratory[36]. The plasmid pTS, which contains abietadiene synthase (ABS) from *ABIES GRANDIS*, was developed as in Morrone[28] with a gene for geranylgeranyl diphosphate synthase from Ajikumar[37].

Improved inhibitors. We assessed the ability of minor structural perturbations of abietadiene derivatives to yield improved inhibitors by comparing four structurally related (and commercially available) molecules (FIG. 16): abietic, neoabietic, levopimaric, and dihydroabietic acid. Surprisingly, dihydroabietic acid was ten times more inhibitory than abietic acid (K, ~25 uM vs. 250 uM). Our ability to find an improved inhibitor in this small screen suggests that the kinds of structural variations explored in this study—and the sizes of molecular libraries generated—are likely yield improved inhibitors.

Functionalization of abietadiene. We assessed the ability of mutants of cytochrome $P450_{b}m3$ to functionalize abietadiene-like molecules by installing five readily available mutants (G3, KSA-4, 9-1 OA, 139-3, and J, which were engineered for activity on amorphadiene[38] and steroids[39]) into our heterologous pathway; three mutants yielded hydroxylated and/or carb oxylated products, generating up to 0.3 mg/L of abietic acid (FIG. 17). The abietadiene-functionalizing activity of mutants originally engineered for other targets suggests that we will be able to develop mutants of P450$_b$m3 with even higher activities on abietadiene-like molecules.

Figure 17A:
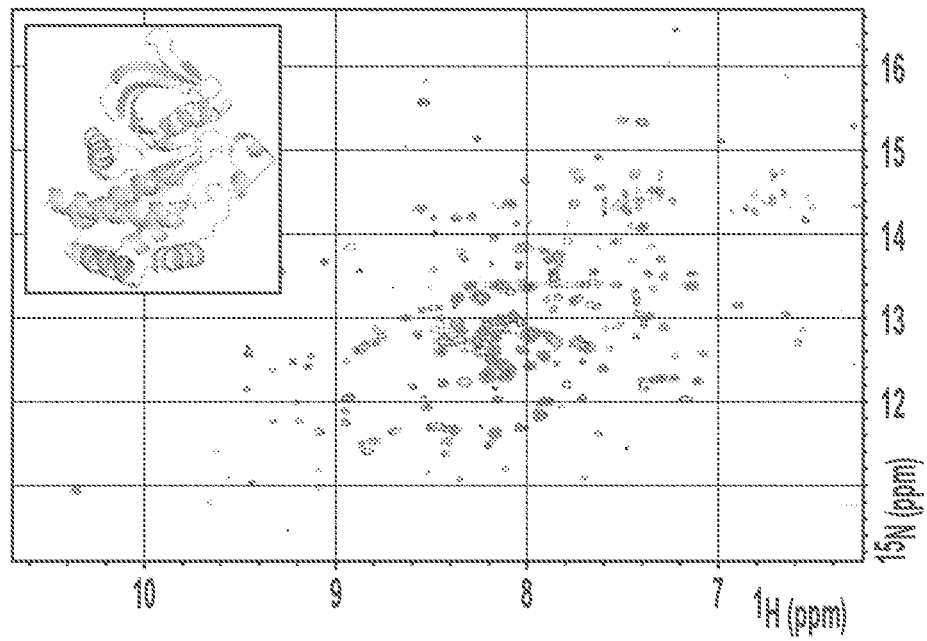
FIG. 17A-C shows results from exemplary studies.

Biostructural analyses. We have crystallized PTP1B in our lab, collected X-ray diffraction data in collaboration with Peter Zwart at Lawrence Berkeley National Lab (LBNL), and solved its crystal structure (FIG. 17A inset). We have also co-crystallized PTP1B with abietic acid; we will analyze these crystals in late July (first available beam time).

Recently, we expressed N[15]-labeled PTP1B and used it to collect two-dimensional $^1$H-$^{15}$N HSQC spectra in collaboration with Haribabu Arthanari at Harvard Medical School (FIG. 17A main). The spectra include PTP1B bound (separately) to abietic acid and known inhibitors; at present, we are processing the data. Preliminary results (X-ray and NMR) suggest that biostructural studies of PTP1B bound to different inhibitors will be straightforward.

Figure 17B:
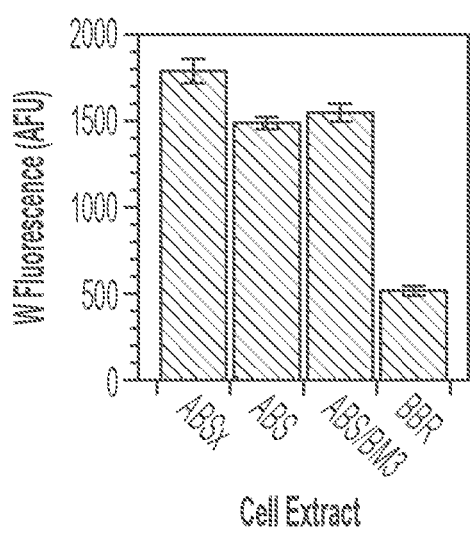
Figure 17C:
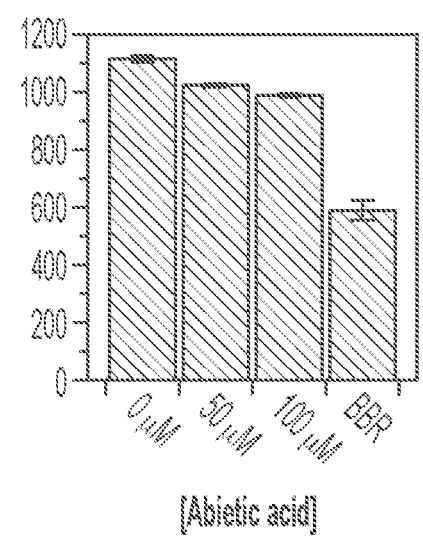
Figure 18A:
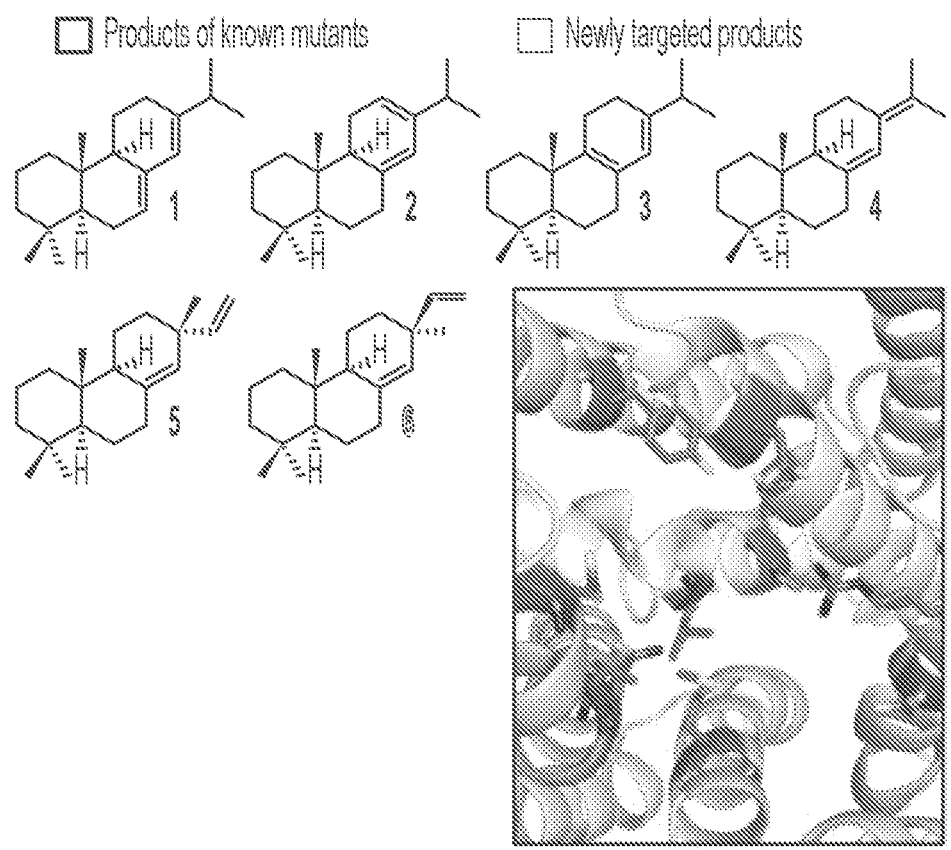
FIG. 18A-B illustrates exemplary terpenoids that differ in FIG. 18A stereochemistry and FIG. 18B shape. Inset: residues targeted for mutagenesis in class I site of ABS.
Figure 18B:
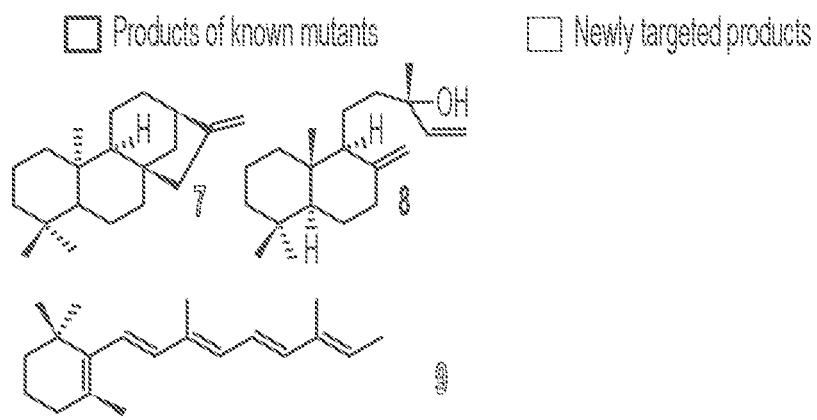

High-throughput screens. Upon binding to inhibitors (both competitive and allosteric), PTP1B exhibits changes in conformation that quench its tryptophan fluorescence (the basis of one of our four high-throughput screens). FIG. 17B indicates that such quenching can be used to distinguish between inhibitory extract (i.e., a hexane overlay) from an abietadiene-producing strain of *E. COLI* and non-inhibitory extract from a control strain (i.e., one with a catalytically inactive ABS). FIG. 17C indicates that such changes can also be used to detect 50 uM (15 mg/L) of abietic acid. Our ability to detect (i) abietadiene in culture extract and (ii) abietic acid at low concentrations (i.e., tenfold lower than our titers of abietadiene) suggests that we will be able to detect improved inhibitors of PTP1B, even if they are accompanied by reductions in titer.

Providing structurally varied terpenoids with different affinities for the allosteric binding pocket. This section describes developing a set of inhibitors with incremental differences in affinity that result from systematic differences in structure. The goal (metric for success): a minimum of –15 structurally varied inhibitors with (i) affinities for PTP1B that differ by 100-fold and/or (ii) enthalpies and entropies of binding that suggest alternative binding geometries.

Research plan. In the sections that follow, we use enzymes to build selective terpenoid inhibitors of PTP1B. This enzyme is the initial focus of our work because it is a therapeutic target for diabetes, obesity, and cancer, and it can be expressed, crystallized, and assayed with ease[15]. It, thus, serves as a pharmaceutically relevant model system with which to develop a general approach for the enzymatic construction of drug leads.

Hypothesis for structural changes. In this section, we use promiscuous enzymes to construct terpenoids that differ in stereochemistry, shape, size, and chemical functionality. We believe that these modifications will affect the affinity of ligands for PTP1B by altering (i) their ability to engage in van der Waals interactions with nonpolar residues (e.g., F280, L192, and F196) in the allosteric binding pocket, (ii) their ability to engage in direct or water-mediated hydrogen bonds with proximal polar residues (e.g., N193, E200, and E276), (iii) their ability to engage in halogen bonds with either set of residues, (iv) their influence on molecular conformational constraints, and, (v) their ability to reorganize water during binding. This hypothesis (which is supported, in part, by FIG. 16) motivates the synthetic strategy described herein.

Figure 8B:
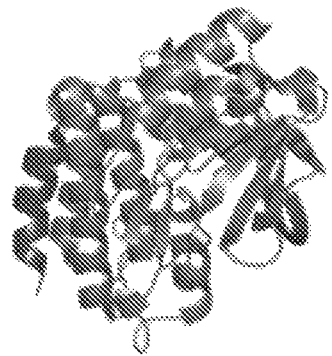
Figure 9A:
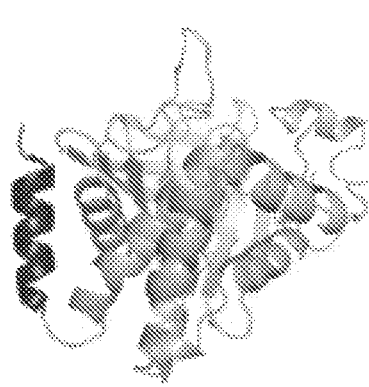
FIG. 9A-B illustrates an exemplary framework for building an enzyme modulated by red light We will attach the C-terminal α-helix of PTP1B to the N-terminal α-helix of BphP1.
Figure 9B:

Stereochemistry, shape, and size. We will begin by using mutants of ABS to generate diterpenoids that differ in stereochemistry and shape FIG. 18A). ABS uses two active sites to catalyze sequential class II (protonation-dependent) and class I (ionization-dependent) cyclization of geranylgeranyl pyrophosphate (GGPP, C$_{20}$) into abietadiene[29]. Previous studies indicate that amino acid substitutions in its active sites can alter the stereochemistry or shape of its products[29,31]. We will use mutations (new and previously identified) that affect the position of deprotonation, intramolecular protein transfer, or carbocation stability (FIG. 8B). After installing these mutants into *E. COLI*, we will use GC/MS to search for new products (fragmentation tools such as MetFrag[40] or ACD/MS Fragmenter[41] will facilitate identification of novel compounds).

We will generate terpenoids that differ in size by using mutations that increase/decrease the volume of the active sites of ABS. Previous attempts to change the substrate specificities of terpene synthases[42,43] suggest that such mutations could enable enhanced activity on farnesyl pyrophosphate (FPP, C$_{15}$) and farnesylgeranyl pyrophosphate (FGPP, C$_{25}$). To synthesize FGPP, we will incorporate an FGPP synthase previously expressed in *E. COLI*[44].

We will isolate a subset of new terpenoids with particularly high titers by using flash chromatography and HPLC (a task for which feasibility has been established in several studies[28,31,45]), and we will use ITC to measure the free energy (AG°$_{bind}$), enthalpy (AH°$_{bind}$), and entropy (–TAS°$_{bind}$) of binding to PTP1B. Differences in AG°$_b$ind between ligands will reveal how structural changes affect the strength of binding; differences in AH°$_{bin}$d and –TAS°$_b$l$_{nd}$ will reveal their influence on binding geometry[46,47].

Figure 19A:
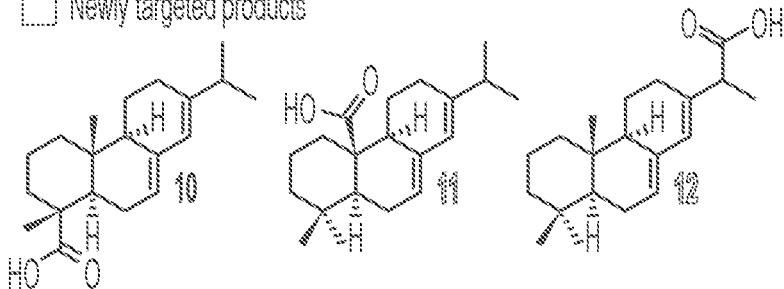
FIG. 19A-E illustrates exemplary terpenoids FIG. 19A carboxylated, FIG. 19B hydroxylated, FIG. 19C and halogenated diterpenoids.
Figure 19D:
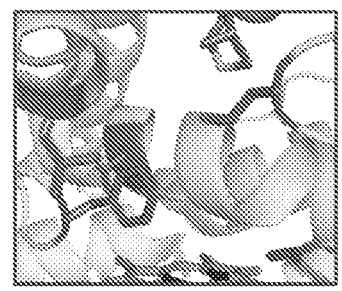
Figure 19B:
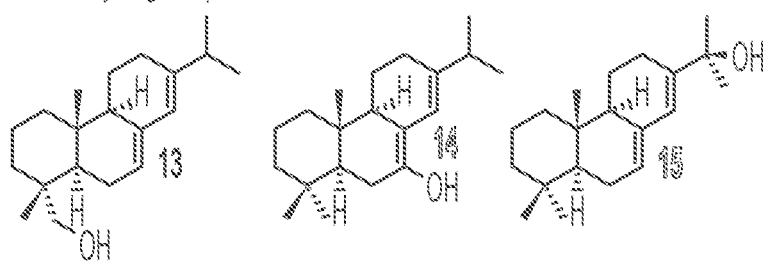
Figure 19C:
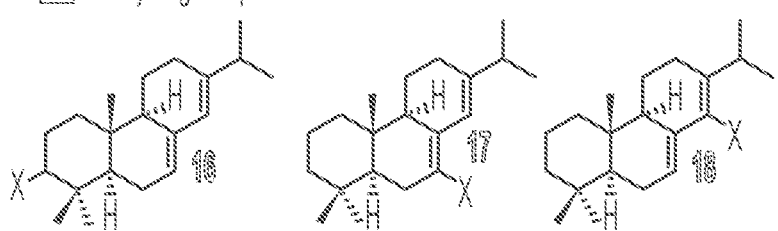

Hydroxylation and halogenation. For each of the three ligands selected in 6.1.2, we will use mutants of cytochrome P450 BM3 (P450$_b$m3) from *BACILLUS MEGATERIUM* and/or CYP720B4 (P450$_{72}$o) from *PICEA SITCHENSIS* to construct five variants with hydroxyl or carboxyl groups at different positions (FIGS. 19A and 19B). P450$_b$m3 can hydroxylate a wide range of substrates, including terpenoids[48]; P450$_{72}$o can carboxylate over 20 diterpenoids, including abietadiene[49]. Both enzymes can be expressed in *E. COLI*[44].

We will work with several sets of mutations: For P450$_{bm}$3, we will use (i) three (V78A, F87A, and A328L) that permit the stereoselective hydroxylation of sesquiterpenes and diterpenes[50], (ii) five (L75A, M177A, L181A, and L437A) that enable hydroxylation of alkaloids and steroids[51], and (iii) two (F87V and A82F) that permit carboxylation of heteroaromatics (FIG. 18D)[52]. For P450$_{72}$o, we will examine –10 similar mutations likely to alter the position of oxidation. We will, again, screen each mutant in *E. COLI*, isolate interesting products, and use ITC to analyze them.

Figure 19E:
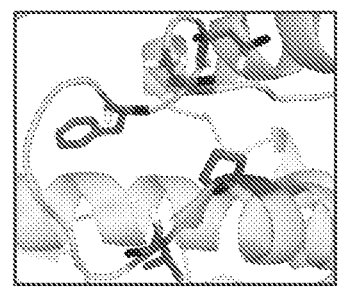
Figure 20:
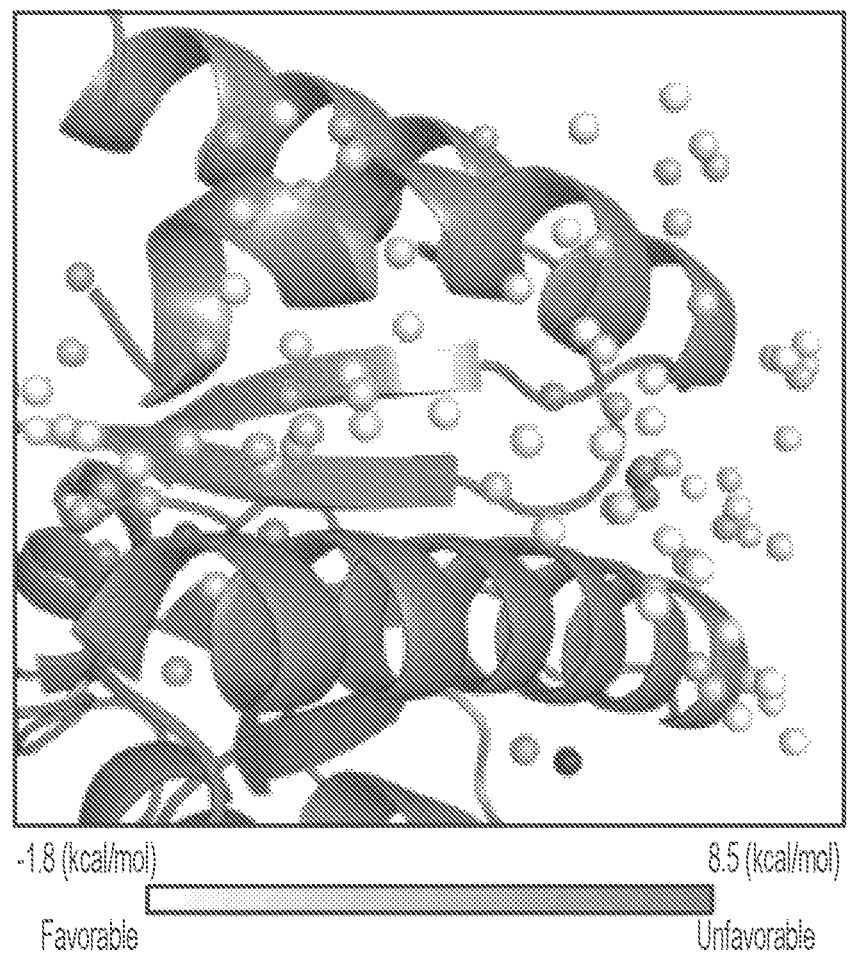
FIG. 20 illustrates an exemplary WaterMap analysis of UPPS. Colors of water molecules correspond to free energies, relative to bulk water.

For each of two high-affinity oxygenated ligands, we will construct six variants with bromide or iodide at different positions (FIG. 18C). These two halogens can engage in halogen bonds with oxygen, nitrogen, or sulfur acceptors in proteins[53], and can bind small nonpolar declivities on their surfaces[54]. The energetic contribution associated with both interactions tends to increase from Br to I[54,55] and, thus, lends itself to systematic analysis (i.e., a physical organic approach). To generate halogenated ligands, we will use mutants of tryptophan 6-halogenase (SttH) from *STREPTOMYCES TOXYTRICINI* and vanadium haloperoxidase (VHPO) from *ACARYOCHLORIS MARINA*. These enzymes can introduce halogens (chloride, bromide, or iodide) into sp$^2$-hybridized carbons of alkaloids or terpenoids (before or after cyclization)[56,57]. For each enzyme, we will examine several mutations known to change regioselectivity (e.g., L460F, P461E, and P452T for SttH[56]) and 5-10 mutations likely to change the orientation of bound FIG. 19 Examples: (FIG. 19A) carboxylated, (B) hydroxylated, ligands (FIG. 19E). We will, again, screen (FIG. 19C) and halogenated diterpenoids. (FIG. 19D-E) Residues each mutant in *E. COLI* and use ITC to targeted for mutagenesis in (FIG. 19D) P450$_{bm}$3 and (FIG. 19E) SttH.

IV. Evolving High-Affinity Terpenoid Inhibitors of PTP1B.

This section develops four high-throughput screens for rapidly evaluating the strength of PTP1B inhibitors, and it uses those methods, in conjunction with site-saturation and random mutagenesis, to evolve new inhibitors. The goal: a set of evolved inhibitors with particularly high affinities ($K_D$^1 uM) and/or unpredictable structures (i.e., structures inconsistent with rational design).

Biological selection. A selection method (i.e., a growth-coupled screen) in which the survival of *E. COLI* is linked to inhibitor potency will enable rapid screening of extremely large libraries of molecules ($10^{10}$)[66]. In this section, we develop such a method.

PTP1B catalyzes the dephosphorylation—and inactivation—of several cell surface receptors. We will use the tyrosine-containing regions of these receptors to build an operon that links inhibition of PTP1B to cell growth. This operon will require six components (FIG. 21A): (i) a substrate domain (the tyrosine-containing region of a receptor) tethered to a DNA-binding protein, (ii) a substrate recognition domain (a protein that binds the tyrosine-containing region after its phosphorylation) tethered to the co subunit of an RNA polymerase, (iii) a tyrosine kinase, (iv) PTP1B, (v) a gene for antibiotic resistance, and (vi) an operator for that gene. With this system, inhibitors of PTP1B will enable binding of the substrate and substrate recognition domains, recruitment of RNA polymerase to the DNA, and transcription of the gene for antibiotic resistance. Previous groups have used similar operons to evolve protein-protein binding partners; here, we take the additional steps of (i) using a protein-protein interaction mediated by enzymes (PTP1B and a kinase) and of (ii) screening that interaction in the presence of potential inhibitors of one of those enzymes.

Figure 21E:
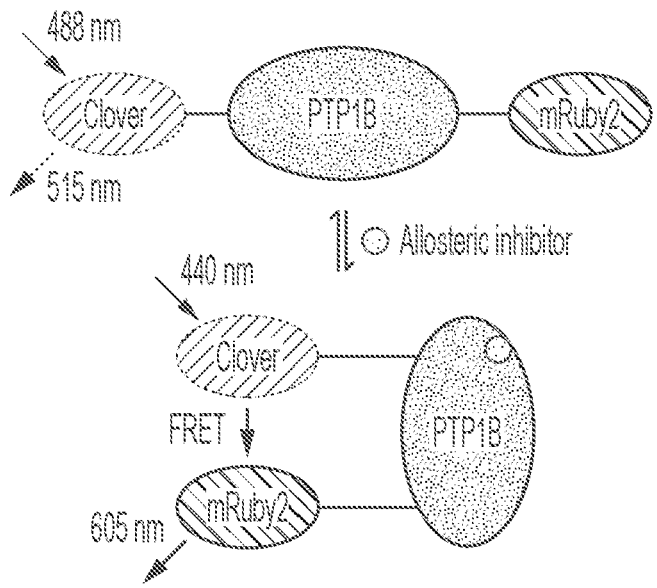
Figure 21E:
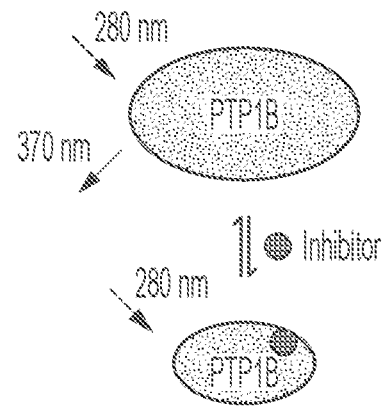
Figure 21E:
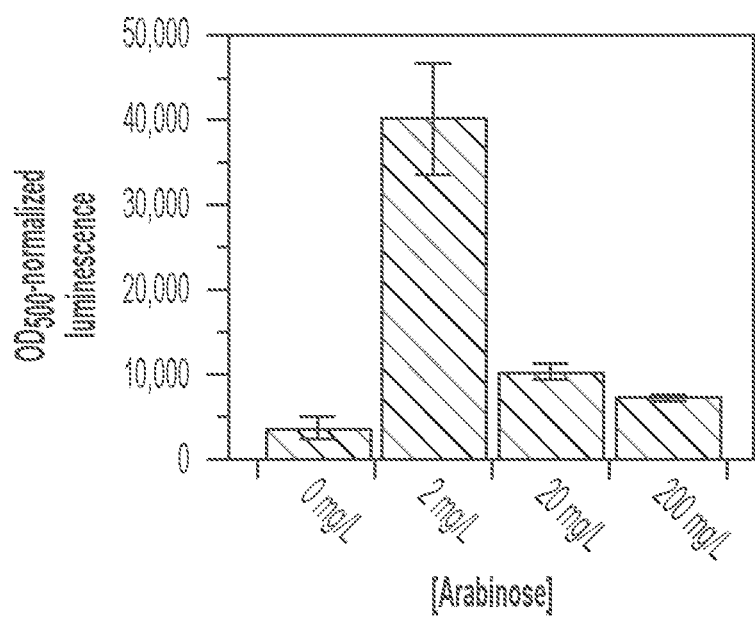
Figure 23A:
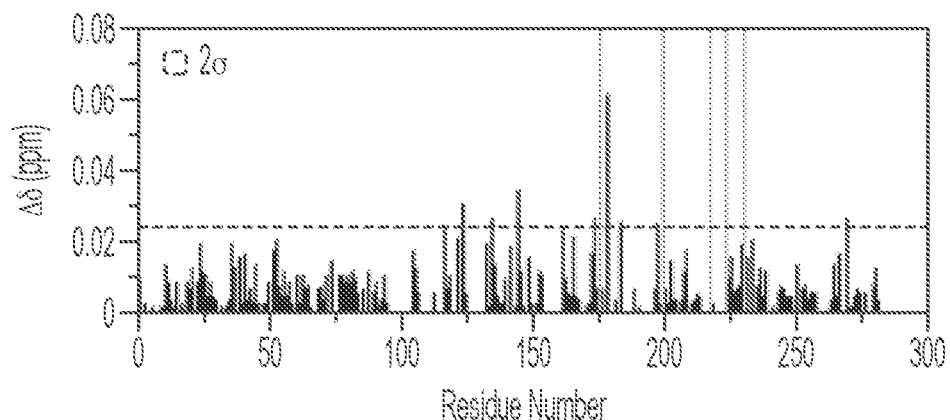
FIG. 23A-C illustrates an exemplary NMR analysis of PTP1B-AA association.
Figure 23B:
Figure 23C:
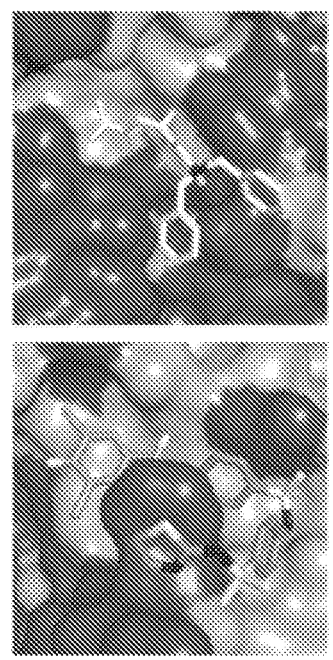
Figure 25A:
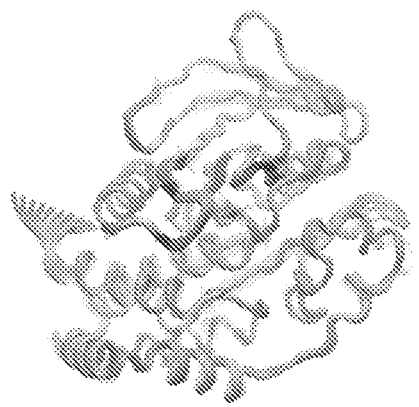
FIG. 25A-D illustrates exemplary computational analysis of AA binding.
Figure 25B:
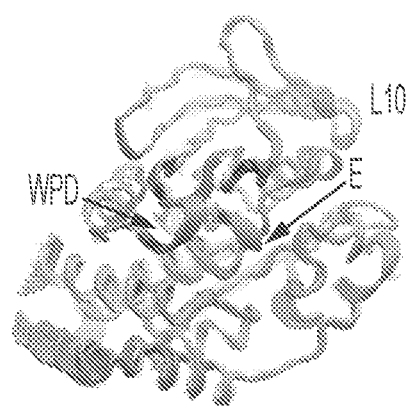
Figure 25C:
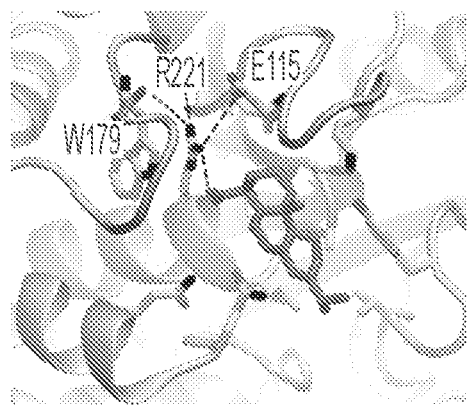
Figure 25D:
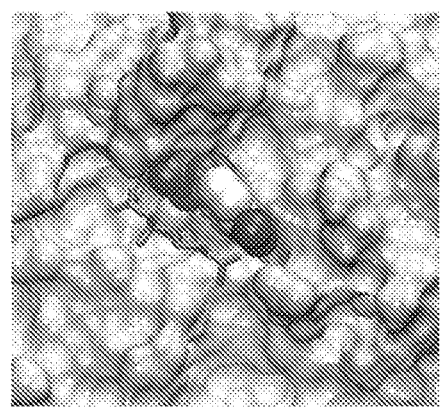
Figure 28A:
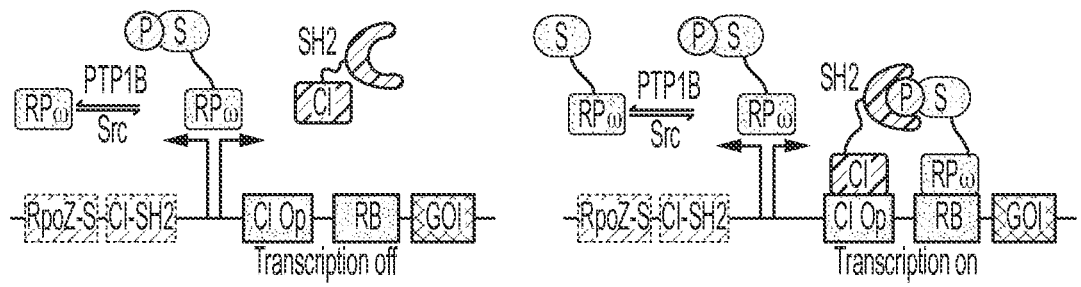
FIG. 28A-D illustrates and shows exemplary data using a Genetic operon linking PTP activity to the output of a gene of interest (GOI).
Figure 28B:
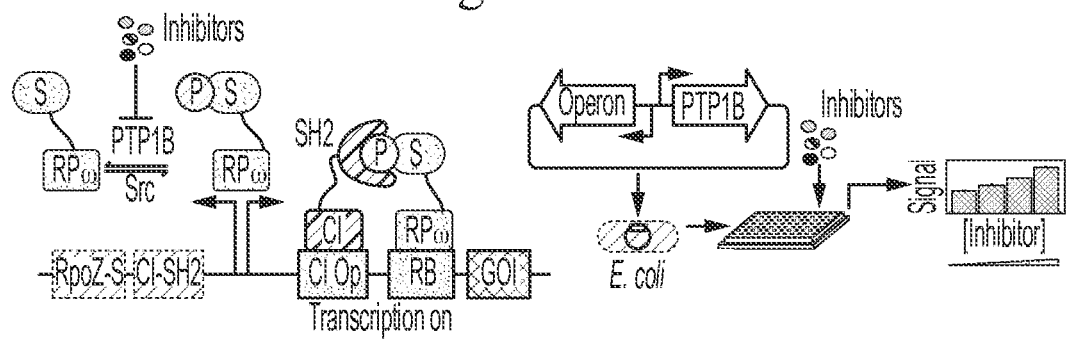
Figures 28C, 28D:
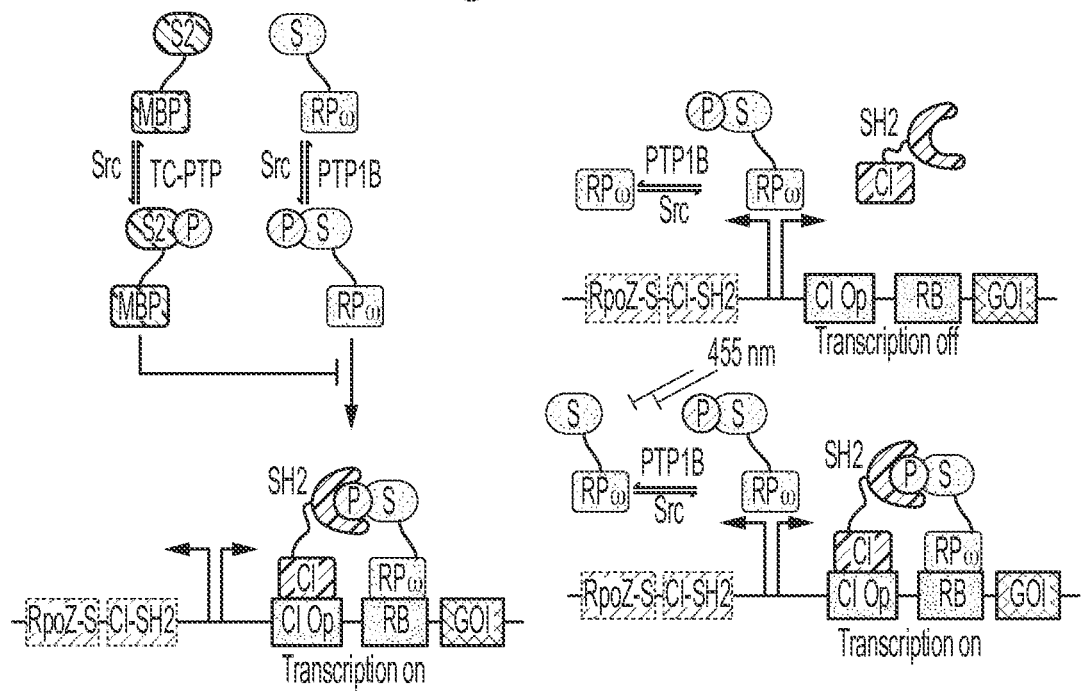
Figure 29A:
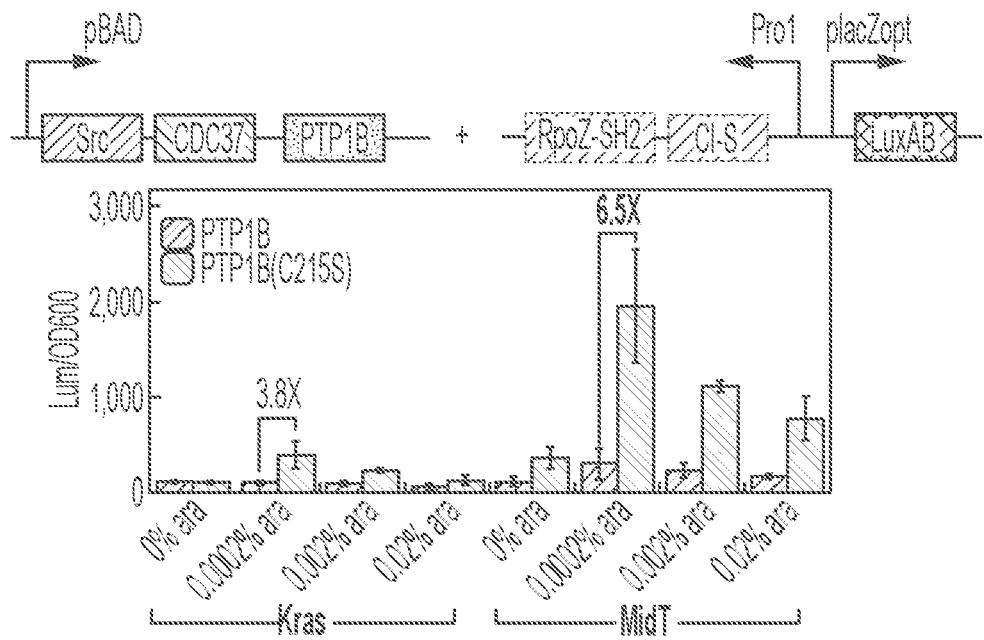
FIG. 29A-B shows exemplary Preliminary results showing phosphorylation-dependent expression of a GOI.
Figure 29B:
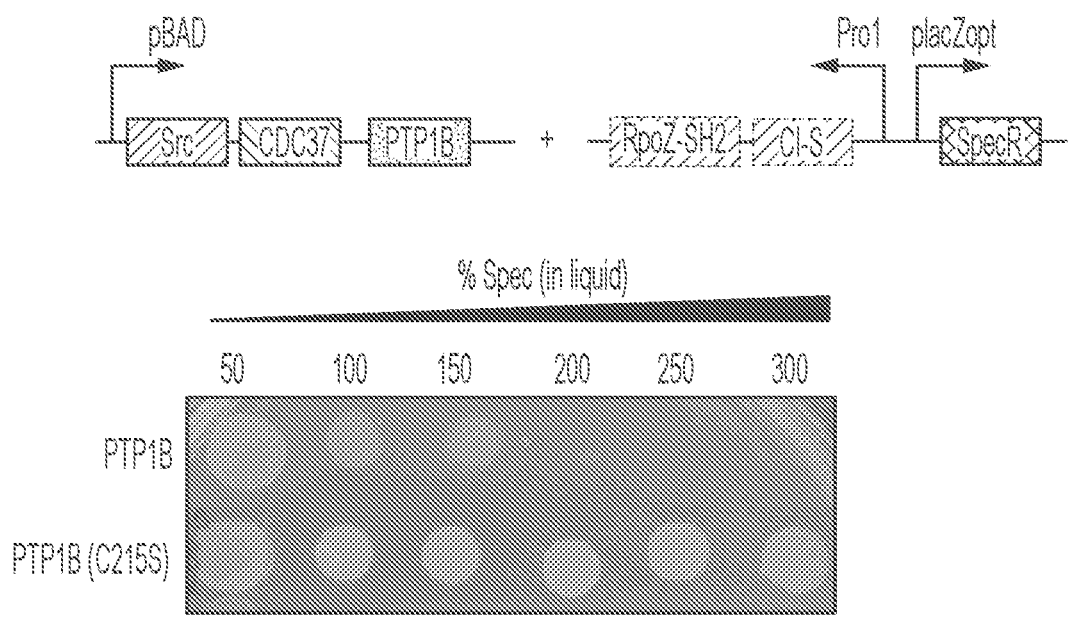
Figure 30A:
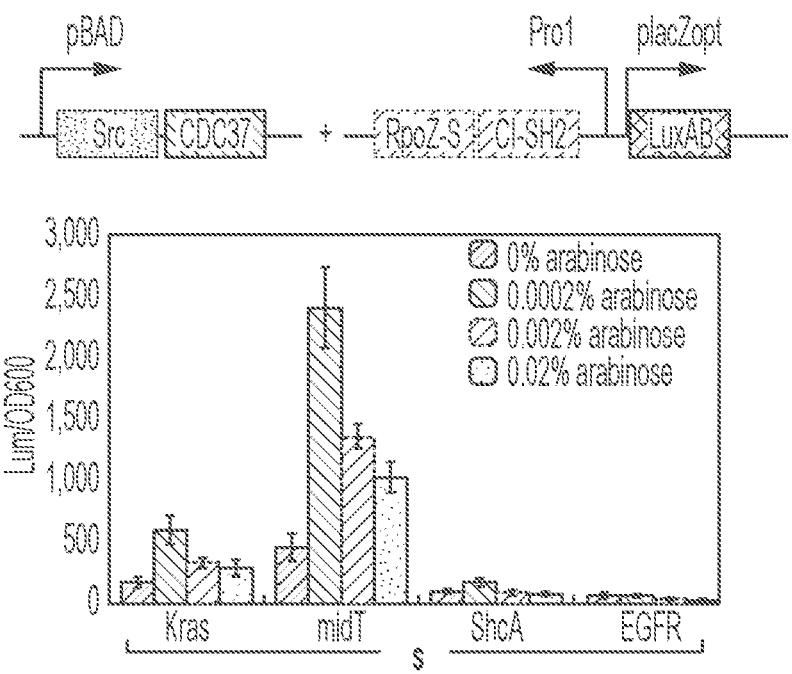
FIG. 30A-B illustrates Optimization of operon.
Figure 30B:
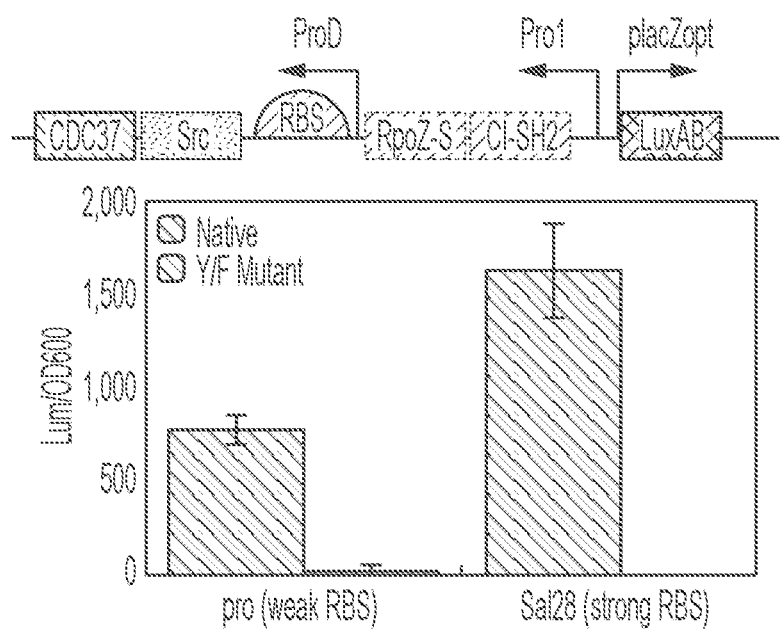
Figure 31A:
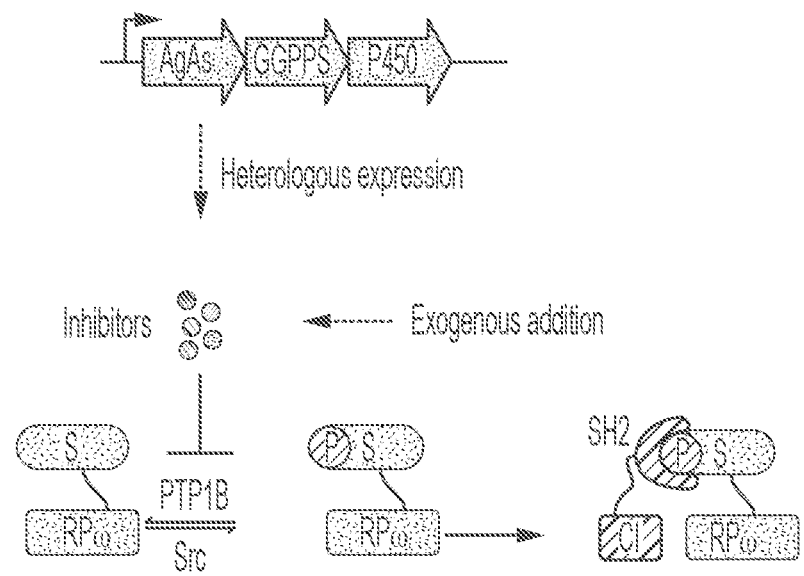
FIG. 31A-D illustrates Applications of operons.
Figure 31B:
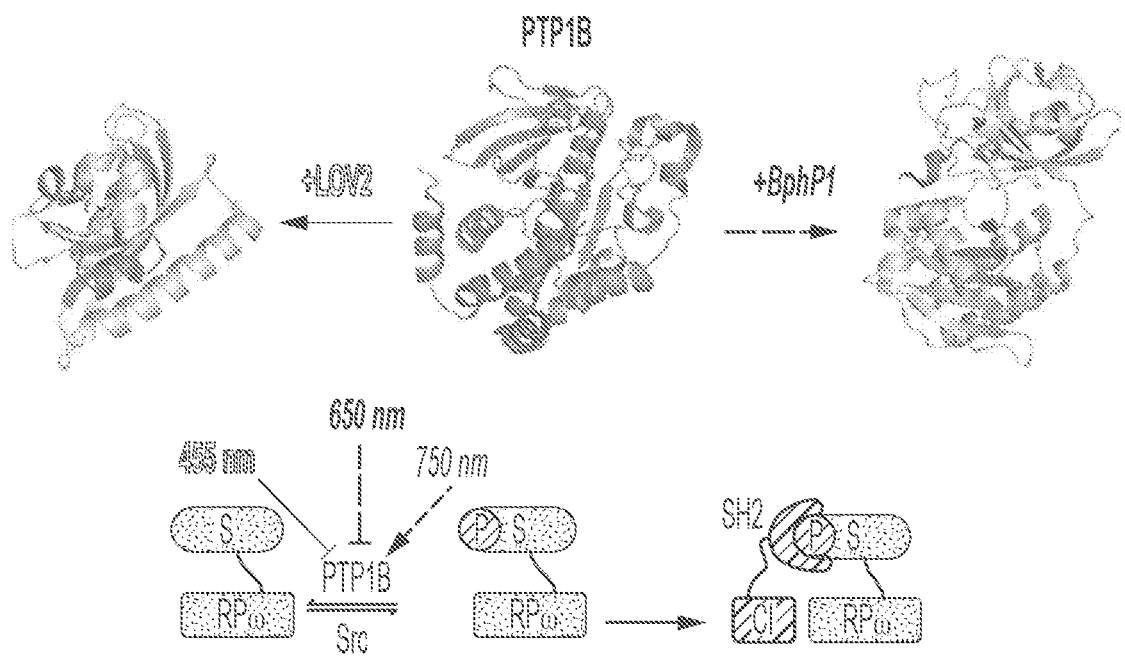
Figure 31C:
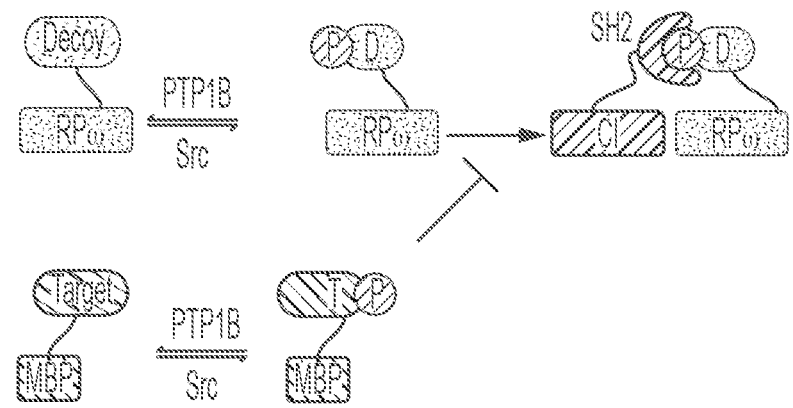
Figure 31D:
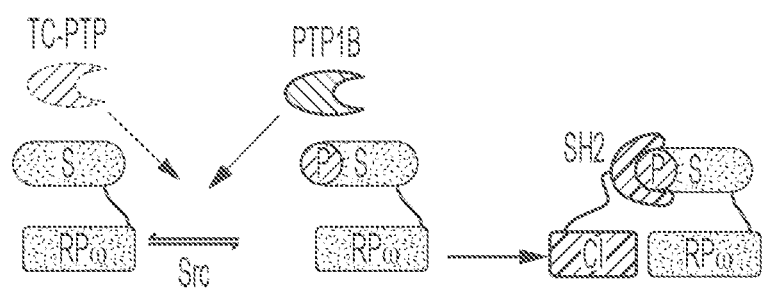
Figure 32A:
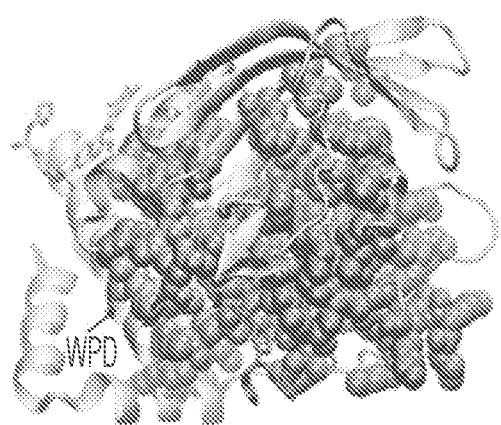
FIG. 32A-B presents exemplary evidence of an evolutionarily conserved allosteric network.
Figure 32B:
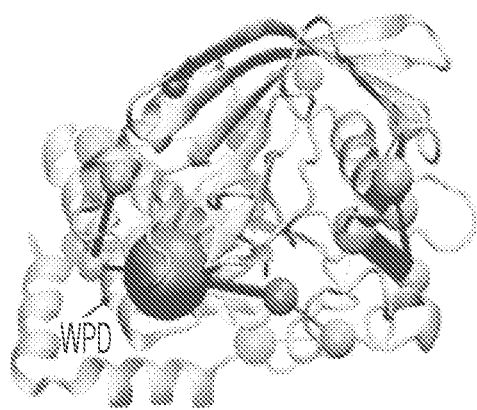

We will develop our operon by starting with a luminescence-based system, and we will add an antibiotic resistance gene as a final step. In our preliminary work with a system optimized by Liu et al.[67], we obtained a tenfold difference in Lux-based luminescence between a strain expressing two binding partners and a strain expressing one (FIG. 21E; arabinose induces expression of the second partner). We now plan to introduce—and test—different substrate domains, recognition domains, and kinases (eGFR and Src).

A FRET sensor for PTP1B activity. A high-throughput screen in which inhibition of PTP1B is linked to cell fluorescence will enable rapid screening via fluorescence-activated cell sorting (FACS). This technique tends to produce more false positives than selection and limits libraries to sizes of $10^7$-$10^8$, but it requires fewer heterologous genes[27,66].

For this strategy, we will make use of FRET (Forster resonance energy transfer) sensors commonly used to monitor kinase and phosphatase activity in mammalian cells[68,69]. These sensors consist of a kinase substrate domain, a short flexible linker, and a phosphorylation recognition domain—all sandwiched between two fluorescent proteins. Phosphorylation of the substrate domain causes it to bind to the recognition domain, inducing FRET between the two fluorescent proteins. In a PTP1B-compatible sensor, inhibitors of PTP1B will increase FRET (FIG. 21B). We have begun to develop such a sensor by trying different combinations of substrate domains, recognition domains, and kinases. (Note: FACS enables FRET-based screens[70,71]).

A FRET sensor for changes in the conformation of PTP1B. A FACS-based screen in which changes in cell fluorescence result from binding-induced changes in the conformation of PTP1B would be less generalizable than strategies 2 and 3 (which could be used for any kinase or phosphatase), but would require only one heterologous gene.

For this strategy, we will make use of a FRET experiment carried out by the Tonks Group[13]. These researchers sought to show that the binding of trodusquemine to PTP1B caused the protein to become more compact. To do so, they attached members of a FRET pair to each terminus of the PTP1B (FIG. 21C); upon protein-ligand association, an increase in FRET signal indicated that its termini approached one another. We hypothesize that this construct could be used as a sensor for identifying other molecules that bind to the allosteric site of PTP1B. We will begin by testing it with a variety of known inhibitors (a step the Tonks group did not take).

Binding-induced changes in the tryptophan fluorescence of PTP1B. A screen in which inhibition of PTP1B is linked to changes in tryptophan fluorescence (FIG. 21D) will enable rapid screening of moderately sized libraries ($10^3$-$10^4$)[27] in microtiter plates. Our use of binding-induced changes in tryptophan fluorescence is described in 5.6. In future work, we plan to extend this approach to other protein tyrosine phosphatases, many of which are allosteric and possess many tryptophans (e.g., SHP-2, a target for Noonan syndrome[72])

Mutagenesis. To use our high-throughput screens to evolve inhibitors of PTP1B, we will build libraries of mutated terpenoid pathways by using (i) site-saturation mutagenesis (SSM; we will target binary combinations of sites) and (ii) error-prone PCR (ep-PCR).

For SSM, we will identify "plastic" residues likely to accommodate useful mutations by developing functions similar to Eq. 1. This function scores residues based on their ability to accommodate mutations that influence the volume and hydration structure of an active site; S is a metric for the propensity of a residue to permit mutations, cr$^2$ is the variance in volume of $$s=4+RTW \quad (EQ\ 1)$$

similarly positioned residues in the active sites of other enzymes, A$^\wedge_W$ is the variance in hydrophilicity of those residues, and N$_V$ and N$_{HW}$ are normalization factors. In our preliminary analysis of ABS, we successfully used Eq. 1 (and structure/sequence information from Taxadiene, y-humulene, 5-selenine, and epi-isozizaene synthases) to identify residues for which mutations are known to yield new products (e.g., H348 of ABS)[31]. We note: Previous attempts to identify plastic residues have scanned each site near the bound substrate[73]; our approach will be unique in its inclusion of biophysical considerations from (i) our study of optimal ligand attributes (6.2.1) and (ii) our study of the types of mutations that bring them about (6.2.2).

For library construction, we will explore mutating our pathway (i) enzyme-by enzyme (e.g., ABS, then P450$_b$m3, and then VttH) or (ii) at random. The second approach could give us access to structures that might be difficult to find with conventional approaches to lead design.

To identify structure-activity relationships that enable the evolution of terpenoid inhibitors of arbitrary protein targets. This section develops a biophysical framework for using a crystal structure of a protein to identify enzymes capable of making inhibitors of that protein. The goal: the use of that framework to identify—and, then, test—enzymes capable of synthesizing new inhibitors of PTP1B and (separately) undecaprenyl diphosphate synthase (UPPS), a target for antibiotic-resistant bacterial infections.

Relationships between binding pockets. We will begin by determining how similarities in specific properties of binding pockets (e.g., volume, polarity, and shape) enable enzymes to synthesize, functionalize, and/or bind similar molecules. This effort will involve comparisons of the allosteric binding pocket of PTP1B with the binding pockets (i.e., active sites) of enzymes involved in inhibitor synthesis. For these comparisons, we will construct two matrices: matrix A in which each element (ay) represents the similarity of a specific property between binding pockets i and j ((0<aij<1, where 1 is highly similar) and matrix B in which each element (by) describes the ability of binding pockets i and j to bind similar molecules (0<by<1, where 1 represents identical binding specificities). The rank of the matrix formed by the product of these two matrices (AB) will suggest the number of independent variables (i.e., active site attributes) necessary to determine the functional compatibility of enzymes in a metabolic pathway; the eigenvalue will suggest the relative importance of the property under study (described by matrix A).

We will construct matrix A with PyMol- and MD-based analyses of protein crystal structures. We will construct matrix B by examining the binding of functionalized terpenoids and their precursors to each enzyme involved in terpenoid synthesis. Binding affinities for some of these ligand/protein combinations will be measured with ITC; most will be estimated with docking calculations (OEDocking[78]).

The result of this section will be an equation similar to Eq. 2, where J is a metric for an active site's ability to synthesize $$J = w_v V + w_p P + W i L + w_w W \qquad (Eq.\ 2)$$

terpenoids that bind a particular binding pocket V, P, L, and W represent specific properties of that active site (volume, polarity, longest diameter, and shortest diameter); and w's represent weighting factors. The final number of variables—and their respective weights—will be determined through the above analysis. In parameterizing the equation, we plan to examine different metrics for properties of binding pockets (e.g. shape) and to explore/develop different matrix manipulations.

Validation and Extension.

The identification of promising active site motifs for inhibitor synthesis will require a search of available protein structural data. We will perform such a search by using PROBIS (probis.nih.gov[79]), an alignment-based platform that uses a specified binding site to find similar binding sites on other proteins in the Protein Data Bank. PROBIS can identify similarly shaped binding pockets, even when the protein folds that surround those pockets are different (i.e., it detects similar constellations of amino acids).

To begin, we will use a PROBIS-based search to identify enzymes with active sites that have some level of structural similarity (we will explore different thresholds) to either (i) the allosteric binding site of PTP1B or (ii) the active sites of enzymes capable of synthesizing inhibitors of PTP1B. Using Eq. 2, we will select enzymes with the most favorable active sites and test them with our platform for inhibitor development).

We will assess the generalizability of our approach by attempting to construct inhibitors of UPPS, a protein known to bind terpenoids and polycyclic molecules[80]. Structure-based searches will use two starting points: (i) UPPS and (ii) mutants of ABS, P450$_b$m3, or similar enzymes that our biophysical analyses suggest might yield UPPS inhibitors. We will, again, select a subset of enzymes to test with our platform.

REFERENCES FOR SECTIONS

1. Koh, H.-L., Yau, W.-P., Ong, P.-S. & Hegde, A. Current trends in modern pharmaceutical analysis for drug discovery. Drug Discov. Today 8, 889-897 (2003).
2. Whitesides, G. M. & Krishnamurthy, V. M. Designing ligands to bind proteins. Q. Rev. Biophys. 38, 385-395 (2005).
3. Olsson, T. S. G., Williams, M. a., Pitt, W. R. & Ladbury, J. E. The Thermodynamics of Protein-Ligand Interaction and Solvation: Insights for Ligand Design. J. Mol. Biol. 384, 1002-1017 (2008).
4. Welsch, M. E., Snyder, S. A. & Stockwell, B. R. Privileged scaffolds for library design and drug discovery. Curr. Opin. Chem. Biol. 14, 347-361 (2010).
5. Gershenzon, J. & Dudareva, N. The function of terpene natural products in the natural world. Nat. Chem. Biol. 3, 408-414 (2007).
6. Chang, M. C. Y. & Keasling, J. D. Production of isprenoid pharmaceuticals by engineered microbes. Nat. Chem. Biol. 2, 674-681 (2006).
7. Johnson, T. O., Ermolieff, J. & Jirousek, M. R. Protein tyrosine phosphatase 1B inhibitors for diabetes. Nat. Rev. Drug Discov. 1, 696-709 (2002).
8. Koren, S. & Fantus, I. G. Inhibition of the protein tyrosine phosphatase PTP1B: potential therapy for obesity, insulin resistance and type-2 diabetes mellitus. Best Pract. Res. Clin. Endocrinol. Metab. 21, 621-640 (2007).
9. Soysal, S., Obermann, E. C, Gao, F., Oertli, D., Gillanders, W. E., Viehl, C. T. & Muenst, S. PTP1B expression is an independent positive prognostic factor in human breast cancer. Breast Cancer Res. Treat. 137, 637-644 (2013).
10. Tonks, N. K. & Muthuswamy, S. K. A Brake Becomes an Accelerator: PTP1B-A New Therapeutic Target for Breast Cancer. Cancer Cell 11, 214-216 (2007).
11. Lessard, L, Stuible, M. & Tremblay, M. L. The two faces of PTP1B in cancer. Biochim. Biophys. Acta—Proteins Proteomics 1804, 613-619 (2010).
12. Zhang, S. & Zhang, Z. Y. PTP1B as a drug target: recent developments in PTP1B inhibitor discovery. Drug Discov. Today 12, 373-381 (2007).
13. Krishnan, N., Koveal, D., Miller, D. H., Xue, B., Akshinthala, S. D., Kragelj, J., Jensen, M R., Gauss, C.-M., Page, R., Blackledge, M., Muthuswamy, S. K., Peti, W. & Tonks, N. K. Targeting the disordered C terminus of PTP1B with an allosteric inhibitor. Nat. Chem. Biol. 10, 558-566 (2014).
14. Sun, J. P., Fedorov, A. A., Lee, S. Y., Guo, X. L, Shen, K., Lawrence, D. S., Almo, S. C. & Zhang, Z. Y. Crystal structure of PTP1B complexed with a potent and selective bidentate inhibitor. J. Biol. Chem. 278, 12406-12414 (2003).
15. Wiesmann, C, Barr, K. J., Kung, J., Zhu, J., Erlanson, D. A., Shen, W., Fahr, B. J., Zhong M, Taylor, L., Randal, M., McDowell, R. S. & Hansen, S. K. Allosteric inhibition of protein tyrosine phosphatase 1B. Nat. Struct. Mol. Biol. 11, 730-737 (2004).
16. Krishnan, N. & Tonks, N. K. Anxious moments for the protein tyrosine phosphatase PTP1B. Trends Neurosci. 38, 462-465 (2015).

17. Hughes, J. P., Rees, S. S., Kalindjian, S. B. & Philpott, K. L. Principles of early drug discovery. Br. J. Pharmacol. 162, 1239-1249 (2011).
18. Kennedy, T. Managing the drug discovery/development interface. Drug Discov. Today 2, 436-444 (1997).
19. Snyder, P. W., Lockett, M. R., Moustakas, D. T. & Whitesides, G. M. Is it the shape of the cavity, or the shape of the water in the cavity? Eur. Phys. J. Spec. Top. 223, 853-891 (2014).
20. Klebe, G. Applying thermodynamic profiling in lead finding and optimization. Nat. Rev. Drug Discov. 14, 95-110 (2015).
21. Chang, M. C. Y. & Keasling, J. D. Production of isoprenoid pharmaceuticals by engineered microbes. Nat. Chem. Biol. 2, 674-681 (2006).
22. George, K. W., Alonso-Gutierrez, J., Keasling, J. D. & Lee, T. S. Isoprenoid Drugs, Biofuels, and Chemicals-Artemisinin, Farnesene, and Beyond. Adv Biochem Eng Biotechnol 148, 355-389 (2014).
23. Cragg, G. M. & Newman, D. J. Natural products: A continuing source of novel drug leads. Biochim. Biophys. Acta—Gen. Subj. 1830, 3670-3695 (2013).
24. Galanie, S., Thodey, K., Trenchard, I. J., Filsinger Interrante, M. & Smolke, C. D. Complete biosynthesis of opioids in yeast. Science (80-.). 349, 1095-1100 (2015).
25. Govindarajan, S., Recabarren, R. & Goldstein, R. a. Estimating the total number of protein folds. Proteins 35, 408-414 (1999).
26. Atanasov, A. G., Waltenberger, B., Pferschy-Wenzig, E. M., Linder, T., Wawrosch, C, Uhrin, P., Temml, V., Wang, L., Schwaiger, S., Heiss, E. H., Rollinger, J. M., Schuster, D., Breuss, J. M., Bochkov, V., Mihovilovic, M. D., Kopp, B., Bauer, R., Dirsch, V. M. & Stuppner, H. Discovery and resupply of pharmacologically active plant-derived natural products: A review. Biotechnol. Adv. 33, 1582-1614 (2015).
27. Lauchli, R., Rabe, K. S., Kalbarczyk, K. Z., Tata, A., Heel, T., Kitto, R. Z. & Arnold, F. H. High-throughput screening for terpene-synthase-cyclization activity and directed evolution of a terpene synthase. Angew. Chemie—Int. Ed. 52, 5571-5574 (2013).
28. Morrone, D., Lowry, L., Determan, M. K., Hershey, D. M., Xu, M. & Peters, R. J. Increasing diterpene yield with a modular metabolic engineering system in E. coli: Comparison of MEV and MEP isoprenoid precursor pathway engineering. Appl. Microbiol. Biotechnol. 85, 1893-1906 (2010).
29. Peters, R. J. & Croteau, R. B. Abietadiene synthase catalysis: mutational analysis of a prenyl diphosphate ionization-initiated cyclization and rearrangement. Proc. Natl. Acad. Sci. U.S.A 99, 580-584 (2002).
30. Wilderman, P. R. & Peters, R. J. A single residue switch converts abietadiene synthase into a pimaradiene specific cyclase. J. Am. Chem. Soc. 129, 15736-15737 (2007).
31. Criswell, J., Potter, K., Shephard, F., Beale, M. H. & Peters, R. J. A single residue change leads to a hydroxylated product from the class II diterpene cyclization catalyzed by abietadiene synthase. Org. Lett. 14, 5828-5831 (2012).
32. Fasan, R. Tuning P450 enzymes as oxidation catalysts. ACS Catal. 2, 647-666 (2012).
33. Hamberger, B. B., Ohnishi, T., Hamberger, B. B., Seguin, A. & Bohlmann, J. Evolution of diterpene metabolism: Sitka spruce CYP720B4 catalyzes multiple oxidations in resin acid biosynthesis of conifer defense against insects. Plant Physiol. 157, 1677-95 (2011).
34. Fujimori, D. G. & Walsh, C. T. What's new in enzymatic halogenations. Curr. Opin. Chem. Biol. 11, 553-560 (2007).
35. Martin, V. J. J., Pitera, D. J., Withers, S. T., Newman, J. D. & Keasling, J. D. Engineering a mevalonate pathway in Escherichia coli for production of terpenoid s. Nat. Biotechnol. 21, 796-802 (2003).
36. Zhang, F. & Keasling, J. Biosensors and their applications in microbial metabolic engineering. Trends Microbiol. 19, 323-329 (2011).
37. Ajikumar, P. K., Xiao, W.-H., Tyo, K. E. J., Wang, Y., Simeon, F., Leonard, E., Mucha, O., Phon, T. H., Pfeifer, B. & Stephanopoulos, G. Isoprenoid pathway optimization for Taxol precursor overproduction in Escherichia coli. Science 330, 70-74 (2010).
38. Dietrich, J. A., Yoshikuni, Y., Fisher, K. J., Woolard, F. X., Ockey, D., McPhee, D. J., Renninger, N. S., Chang, M. C. Y., Baker, D. & Keasling, J. D. A novel semi-biosynthetic route for artemisinin production using engineered substrate-promiscuous P450BM3. ACS Chem. Biol. 4, 261-267 (2009).
39. Zhang, K., El Damaty, S. & Fasan, R. P450 fingerprinting method for rapid discovery of terpene hydroxylating P450 catalysts with diversified regioselectivity. J. Am. Chem. Soc. 133,
40. Ruttkies, C, Schymanski, E. L, Wolf, S., Hollender, J. & Neumann, S. MetFrag relaunched: Incorporating strategies beyond in silico fragmentation. J. Cheminform. 8, (2016).
41. Pelander, A., Tyrkko, E. & Ojanpera, I. In silico methods for predicting metabolism and mass fragmentation applied to quetiapine in liquid chromatography/time-of-flight mass spectrometry urine drug screening. Rapid Commun. Mass Spectrom. 23, 506-514 2009.
42. Kampranis, S. C, Ioannidis, D., Purvis, A., Mahrez, W., Ninga, E., Katerelos, N. A., Anssour, S., Dunwell, J. M., Degenhardt, J., Makris, A. M., Goodenough, P. W. & Johnson, C. B. Rational conversion of substrate and product specificity in a Salvia monoterpene synthase: structural insights into the evolution of terpene synthase function. Plant Cell 19, 1994-2005 (2007).
43. Huang, Q., Williams, H. J., Roessner, C. A. & Scott, A. I. Sesquiterpenes produced by truncated taxadiene synthase. Tetrahedron Lett. 41, 9701-9704 (2000).
44. Tachibana, A., Yano, Y., Otani, S., Nomura, N., Sako, Y. & Taniguchi, M. Novel prenyltransferase gene encoding farnesylgeranyl diphosphate synthase from a hyperthermophilic archaeon, Aeropyrum pernix. Molecular evolution with alteration in product specificity. Eur. J. Biochem. 267, 321-328 (2000).
45. Jia, M., Potter, K. C. & Peters, R. J. Extreme promiscuity of a bacterial and a plant diterpene synthase enables combinatorial biosynthesis. Metab. Eng. 37, 24-34 (2016).
46. Fox, J. M., Kang, K. K., Sastry, M., Sherman, W., Sankaran, B., Zwart, P. H. & Whitesides, G. M. Water-Restructuring Mutations Can Reverse the Thermodynamic Signature of Ligand Binding to Human Carbonic Anhydrase. Angew. Chemie Int. Ed. 56, 3833-3837 (2017).
47. Krimmer, S. G., Betz, M., Heine, A. & Klebe, G. Methyl, ethyl, propyl, butyl: Futile but not for water, as the correlation of structure and thermodynamic signature shows in a congeneric series of thermolysin inhibitors. ChemMedChem 9, 833-846 (2014).

48. Jung, S. T., Lauchli, R. & Arnold, F. H. Cytochrome P450: Taming a wild type enzyme. Curr. Opin. Biotechnol. 22, 809-817 (2011).
49. Hamberger, B. B., Ohnishi, T., Hamberger, B. B., Seguin, A. & Bohlmann, J. Evolution of diterpene metabolism: Sitka spruce CYP720B4 catalyzes multiple oxidations in resin acid biosynthesis of conifer defense against insects. Plant Physiol. 157, 1677-95 (2011).
50. Seifert, A., Vomund, S., Grohmann, K., Kriening, S., Urlacher, V. B., Laschat, S. & Pleiss, J. Rational design of a minimal and highly enriched CYP102A1 mutant library with improved regio-, stereo- and chemoselectivity. ChemBioChem 10, 853-861 (2009).
51. Lewis, J. C, Mantovani, S. M., Fu, Y., Snow, C. D., Komor, R. S., Wong, C. H. & Arnold, F. H. Combinatorial alanine substitution enables rapid optimization of cytochrome P450BM3 for selective hydroxylation of large substrates. ChemBioChem 11, 2502-2505
52. Butler, C. F., Peet, C, Mason, A. E., Voice, M. W., Leys, D. & Munro, A. W. Key mutations alter the cytochrome P450 BM3 conformational landscape and remove inherent substrate bias. J. Biol. Chem. 288, 25387-25399 (2013).
53. Auffinger, P., Hays, F. a, Westhof, E. & Ho, P. S. Halogen bonds in biological molecules. Proc. Natl. Acad. Sci. U.S.A 101, 16789-16794 (2004).
54. Fox, J., Kang, K., Sherman, W., Heroux, A., Sastry, G., Baghbanzadeh, M., Lockett, M. & Whitesides, G. Interactions between Hofmeister anions and the binding pocket of a protein. J. Am. Chem. Soc. 137, 3859-3866 (2015).
55. Carter, M., Voth, A. R., Scholfield, M. R., Rummel, B., Sowers, L. C. & Ho, P. S. Enthalpy-entropy compensation in biomolecular halogen bonds measured in DNA junctions. Biochemistry 52, 4891-4903 (2013).
56. Shepherd, S. A., Menon, B. R. K., Fisk, H., Struck, A.-W., Levey, C, Leyes, D. & Micklefield, J. A Structure-Guided Switch in the Regioselectivity of a Tryptophan Halogenase. ChemBioChem 17, 821-824 (2016).
57. Carter-Franklin, J. N., Parrish, J. D., Tschirret-Guth, R. A., Little, R. D. & Butler, A. Vanadium haloperoxidase-catalyzed bromination and cyclization of terpenes. J. Am. Chem. Soc. 125, 3688-3689 (2003).
58. Li, R., Chou, W. K. W., Himmelberger, J. A., Litwin, K. M., Harris, G. G., Cane, D. E. & Christianson, D. W. Reprogramming the chemodiversity of terpenoid cyclization by remolding the active site contour of epi-isozizaene synthase. Biochemistry 53, 1155-1168 (2014).
59. Brown, S. & O'Connor, S. E. Halogenase Engineering for the Generation of New Natural Product Analogues. ChemBioChem 16, 2129-2135 (2015).
60. Steele, C. L., Crock, J., Bohlmann, J. & Croteau, R. Sesquiterpene Synthases from Grand Fir (*Abies grandis*). J. Biol. Chem. 273, 2078-2089 (1998).
61. Lu, Y. & Mei, L. Co-expression of P450 BM3 and glucose dehydrogenase by recombinant *Escherichia coli* and its application in an NADPH-dependent indigo production system. J. Ind. Microbiol. Biotechnol. 34, 247-253 (2007).
62. Tzeng, S.-R. & Kalodimos, C. G. Protein activity regulation by conformational entropy. Nature 488, 236-240 (2012).
63. Aramini, J. M., Vorobiev, S. M., Tuberty, L. M., Janjua, H., Campbell, E. T., Seetharaman, J., Su, M., Huang, Y. J., Acton, T. B., Xiao, R., Tong, L. & Montelione, G. T. The RAS-Binding Domain of Human BRAF Protein Serine/Threonine Kinase Exhibits Allosteric Conformational Changes upon Binding HRAS. Structure 23, 1382-1393 (2015).
64. Christianson, D. W. Structural biology and chemistry of the terpenoid cyclases. Chem. Rev. 106, 3412-3442 (2006).
65. O'Maille, P. E., Malone, A., Delias, N., Andes Hess, B., Smentek, L., Sheehan, I., Greenhagen, B. T., Chappell, J., Manning, G. & Noel, J. P. Quantitative exploration of the catalytic landscape separating divergent plant sesquiterpene synthases. Nat. Chem. Biol. 4, 617-623 (2008).
66. Packer, M. S. & Liu, D. R. Methods for the directed evolution of proteins. Nat. Rev. Genet. 16, 379-394 (2015).
67. Badran, A. H., Guzov, V. M., Huai, Q., Kemp, M. M., Vishwanath, P., Kain, W., Nance, A. M., Evdokimov, A., Moshiri, F., Turner, K. H., Wang, P., Malvar, T. & Liu, D. R. Continuous evolution of *Bacillus thuringiensis* toxins overcomes insect resistance. Nature 533, 58-63 (2016).
68. Ting, a Y., Kain, K. H., Klemke, R. L. & Tsien, R. Y. Genetically encoded fluorescent reporters of protein tyrosine kinase activities in living cells. Proc. Natl. Acad. Sci. U.S.A 98, 15003-15008 (2001).
69. Sato, M. & Umezawa, Y. in Cell Biol. Four-Volume Set 2, 325-328 (2006).
70. Dye, B. T. Flow cytometric analysis of CFP-YFP FRET as a marker for in vivo protein-protein interaction. Clin. Appl. Immunol. Rev. 5, 307-324 (2005).
71. Vereb, G., Nagy, P. & Szollosi, J. Flow cytometric FRET analysis of protein interaction. Methods Mol. Biol. 699, 371-92 (2011).
72. Chen, Y.-N. P., LaMarche, M. J., Chan, H. M., Fekkes, P., Garcia-Fortanet, J., Acker, M. G., Antonakos, B., Chen, C. H.-T., Chen, Z., Cooke, V. G., Dobson, J. R., Deng, Z., Fei, F., Firestone, B., Fodor, M., Fridrich, C, Gao, H., Grunenfelder, D., Hao, H.-X., Jacob, J., Ho, S., Hsiao, K., Kang, Z. B., Karki, R., Kato, M., Larrow, J., La Bonte, L. R., Lenoir, F., Liu, G., Liu, S., Majumdar, D., Meyer, M. J., Palermo, M., Perez, L., Pu, M., Price, E., Quinn, C, Shakya, S., Shultz, M. D., Slisz, J., Venkatesan, K., Wang, P., Warmuth, M., Williams, S., Yang, G., Yuan, J., Zhang, J.-H., Zhu, P., Ramsey, T., Keen, N. J., Sellers, W. R., Stams, T. & Fortin, P. D. Allosteric inhibition of SHP2 phosphatase inhibits cancers driven by receptor tyrosine kinases. Nature 535, 148-52 (2016).
73. Yoshikuni, Y., Ferrin, T. E. & Keasling, J. D. Designed divergent evolution of enzyme function. Nature 440, 1078-1082 (2006).
74. Gruet, A., Longhi, S. & Bignon, C. One-step generation of error-prone PCR libraries using Gateway® technology. Microb. Cell Fact. 11, 14 (2012).
75. Dietrich, J. A., McKee, A. E. & Keasling, J. D. High-Throughput Metabolic Engineering Advances in Small-Molecule Screening and Selection. Annu. Rev. Biochem. 79, 563-590 (2010).
76. Esvelt, K. M., Carlson, J. C. & Liu, D. R. A system for the continuous directed evolution of biomolecules. Nature 472, 499-503 (2011).
77. Feiler, C, Fisher, A. C, Boock, J. T., Marrichi, M. J., Wright, L., Schmidpeter, P. A. M., Blankenfeldt, W., Pavelka, M. & DeLisa, M. P. Directed Evolution of *Mycobacterium tuberculosis* (3-Lactamase Reveals Gatekeeper Residue That Regulates Antibiotic Resistance and Catalytic Efficiency. PLoS One 8, (2013).
78. Murphy, R. B., Repasky, M. P., Greenwood, J. R., Tubert-Brohman, I., Jerome, S., Annabhimoju, R., Boyles, N. A., Schmitz, C. D., Abel, R., Farid, R. &

Friesner, R. A. WScore: A flexible and accurate treatment of explicit water molecules in ligand-receptor docking. J. Med. Chem. acs.jmedchem.6b00131 (2016). doi:10.1021/acsjmedchem.6b00131

79. Konc, J., Miller, B. T., Stular, T., Lesnik, S., Woodcock, H. L., Brooks, B. R. & Janezic, D. ProBiS-CHARMMing: Web Interface for Prediction and Optimization of Ligands in Protein Binding Sites. J. Chem. Inf. Model. 55, 2308-2314 (2015).

80. Guo, R.-T., Cao, R., Liang, P.-H., Ko, T.-P., Chang, T.-H., Hudock, M. P., Jeng, W.-Y., Chen, C. K.-M., Zhang, Y., Song, Y., Kuo, C.-J., Yin, F., Oldfield, E. & Wang, A. H.-J. Bisphosphonates target multiple sites in both cis- and trans-prenyltransferases. Proc. Natl. Acad. Sci. U.S.A 104, 10022-10027 (2007).

81. Teng, K. H. & Liang, P. H. Structures, mechanisms and inhibitors of undecaprenyl diphosphate synthase: A cis-prenyltransferase for bacterial peptidoglycan biosynthesis. Bioorg. Chem. 43, 51-57 (2012).

82. Zhu, W., Zhang, Y., Sinko, W., Hensler, M. E., Olson, J., Molohon, K. J., Lindert, S., Cao, R, Li, K., Wang, K., Wang, Y., Liu, Y.-L, Sankovsky, A., de Oliveira, C. A. F., Mitchell, D. a, Nizet, V., McCammon, J. A. & Oldfield, E. Antibacterial drug leads targeting isoprenoid biosynthesis. Proc. Natl. Acad. Sci. U.S.A 110, 123-8 (2013).

83. Leonard, E., Ajikumar, P. K., Thayer, K., Xiao, W.-H., Mo, J. D., Tidor, B., Stephanopoulos, G. & Prather, K. L. J. Combining metabolic and protein engineering of a terpenoid biosynthetic pathway for overproduction and selectivity control. Proc. Natl. Acad. Sci. U.S.A 107, 13654-13659 (2010).

84. Ro, D.-K., Paradise, E. M., Ouellet, M., Fisher, K. J., Newman, K. L., Ndungu, J. M., Ho, K. A., Eachus, R. A., Ham, T. S., Kirby, J., Chang, M. C. Y., Withers, S. T., Shiba, Y., Sarpong R. & Keasling, J. D. Production of the antimalarial drug precursor artemisinic acid in engineered yeast. Nature 440, 940-943 (2006).

V. Specific Embodiments of Bacterial Systems for Identifying Small Molecules that Modulate the Activity of Enzymes.

As described herein, a strain of *Escherichia coli* was developed comprising both (i) a genetically encoded system (i.e., a "bacterial two-hybrid" or B2H system) that links cell survival to the modulation inhibition of a pathologically relevant enzyme from *Homo sapiens* (i.e., a drug target) and (ii) a pathway for metabolite biosynthesis. The genetically encoded system described herein contains more genetic elements than would traditionally constitute a single operon (e.g. it has more than one promoter), but it is sometimes referred to as an operon.

More specifically, as described herein, host organisms, e.g. *Escherichia (E.) coli*, were transformed with up to four plasmids, including a first plasmid (plasmid 1) an expression plasmid comprising a genetically encoded system that links the inhibition of a target enzyme to cell survival, wherein the target enzyme may be chosen for the purpose of identifying molecules that inhibit a specific target enzyme; a second plasmid (plasmid 2) an expression plasmid comprising an operon for expressing at least some of the genes necessary to synthesize products of a metabolic pathway, e.g. a mevalonate-dependent pathway for terpenoid biosynthesis derived from *Saccharomyces cerevisiae* for providing terpenoid product compounds; a third plasmid (plasmid 3) an expression plasmid comprising at least one additional gene, not present in plasmid (plasmid 2), e.g. a terpene synthase, such as ADS, GHS, ABS, or TXS, for providing desired products, e.g. terpenoid products, such that when the host bacterial expresses plasmids 1 and 2, desired products are not produced until the host bacterial expresses plasmid 3 for completing the pathway for desired compounds; and a fourth plasmid (plasmid 4) comprising additional genetic components specific to the strain of *E. coli*, e.g., the F-plasmid of 51030 (Addgene 105063).

Examples of plasmid 1 embodiments are shown in FIG. 33A, 33B, 33D, 33E, FIG. 34, FIG. 35, FIG. 40A, 40B, 40C, 40D, etc.

In some embodiments, a strain of *E. coli* used as a host for transformation possesses the ΔrpoZ mutation, which enable the system encoded by plasmid 1 to control the expression of a gene for antibiotic resistance.

In some embodiments, plasmids 2 and/or 3 constitute a pathway for terpenoid biosynthesis. In some embodiments, plasmids 2 and/or 3 constitute a pathway for alkaloid biosynthesis. In some embodiments, plasmids 2 and/or 3 constitute a pathway for polyketide biosynthesis.

In some embodiments, plasmid 3 further comprises a GGPPS gene in combination with either ABS or TXS. Examples of GGPPS genes provide substrates for terpene synthase genes, i.e. ABS, or TXS. In some embodiments, terpene synthase genes are wild-type genes. In some preferred embodiments, terpene synthase genes contain mutations for producing variants of terpenoid products, as described and shown herein. In some embodiments, plasmid 3 further comprises a gene for terpenoid functionalizing enzymes, e.g., cytochromes P450.

In some preferred embodiments, plasmid 1 is under control of constitutive promoters. Thus, in some preferred embodiments, at least some of the genes that are part of the operon in plasmid 1 are constitutively expressed. In some preferred embodiments, at least some of the genes that are part of the operon in plasmid 1 are expressed when contacted with an inducible compound, i.e. under control of an inducible promoter, such as a lacZ promoter turned on when in contact with X-gal.

In some preferred embodiments, plasmids 2 and 3 are under control of inducible promoters. Thus, in some preferred embodiments, at least some of, and in some cases the entire set of genes contained in a metabolic pathway operon in plasmid 2 are expressed when contacted with an inducible compound. In some preferred embodiments, some genes expressed in plasmid 3 are under inducible control.

In some preferred embodiments, plasmid 4 is under the control of constitutive promoters. Thus, in some embodiments, at least one gene in plasmid 4 is under control of a constitutive promoter. In some embodiments, at least one gene in plasmid 4 is under control of an inducible promoter.

In some preferred embodiments, a host bacterium undergoes at least 2 rounds of transformation, e.g. first to transform plasmids 1 and 2 simultaneously into a strain that already harbors plasmid 4 (e.g., a 51030 strain which already comprises this accessory plasmid), followed by transformation with plasmid 3. In some preferred embodiments, a host bacterium undergoes at least 3 rounds of transformation, e.g. first to transfect plasmid 1, then transfect plasmid 2, followed by transfection of plasmid 3.

In some preferred embodiments, each plasmid has an antibiotic resistance gene (or other type of selective gene) for identifying successfully transformed bacteria for that plasmid, i.e. antibiotic resistance genes may be different for each plasmid. Thus, when an antibiotic resistance gene is expressed, instead of a bacteria stopped from normal replication when in contact with the antibiotic, a bacteria has resistance so is able to replicate at normal or near normal rates.

Thus, as described herein, laboratory stains of *E. coli* were engineered to comprise up to three types of expression plasmids by first transfecting with plasmid 1, then selecting for transformants (growing colonies) on/in antibiotic containing media wherein nontransformants do not grow, then transfecting transformants with plasmid 2 and selecting for double transformants, e.g. media containing antibiotics for allowing the growth of double transformants, then transfecting double transformants with plasmid 3 and selecting for triple transformants, e.g. media containing antibiotics for allowing the growth of triple transformants. In one embodiment, triple transformants are grown in media containing an inducer(s) for the inducible plasmids (2 and 3) in combination with the three antibiotics for producing products having at least some inhibitory activity for the chosen enzyme of plasmid 1, made by the enzymes provided by the combination of enzymes expressed by plasmids 2 and 3.

Further, as described herein, laboratory stains of *E. coli* were engineered to comprise up to four types of expression plasmids by first transforming host cells with plasmids 1 and 2, simultaneously, into a strain that already harbors plasmid 4, then selecting for triple transformants (growing colonies) on/in antibiotic containing media wherein non-transformants do not grow, then further transforming successful triple transformants with plasmid 3 and selecting for quadruple transformants, e.g. media containing antibiotics that allow for the growth of quadruple transformants. In one embodiment, quadruple transformants are grown in media containing (i) an inducer(s) for the inducible plasmids (2 and 3), (ii) a metabolic precursor for metabolite biosynthesis, e.g., mevalonate, and (iii) five antibiotics (i.e., one for each plasmid and one under control of the genetically encoded system in plasmid 1) for producing products having at least some inhibitory activity on the chosen enzyme of plasmid 1, made by the combination of enzymes expressed by plasmids 2 and 3.

In some embodiments, a terpenoid operon pathway intended for insertion into or already within plasmid 2, may be altered by swapping in a different gene for terpene synthases (i.e., in each row of FIG. 36, the metabolic pathway differs in the identity of the gene for a terpene synthase; when ADS or TXS are present, GGPPS is also present).

In FIGS. 41A, 41B, 41C, and 41D, for examples, we mutate (rather than swap) a single gene of a metabolic pathway: e.g. induce at least one mutation in a gene encoding amorphadiene synthase. After doing so, we show that a metabolic pathway can be mutated to generate a library of pathways, and that these pathways can be screened to identify pathways that generate more potent inhibitors of PTP1B than the unmutated parent pathway.

To summarize, we provided a demonstration that (i) the B2H system (detection operon) and (ii) a metabolic pathway for terpenoid biosynthesis can be combined within a host organism to identify genes involved with production of small-molecules and evolve genes related to production of small-molecules that may be inhibitors that the microbial synthesis of PTP1B inhibitors.

In preferred embodiments, small-molecule products are derived from one general metabolic pathway (the mevalonate-dependent pathway for terpenoid biosynthesis from *Saccharomyces cerevisiae*), and one host organism (*Escherichia coli*). These small-molecule products produced as described herein, are contemplated for use as treatments of type 2 diabetes, obesity, and breast cancer, among other diseases.

Without being bound by theory, when a genetically encoded system for detecting the activity of a specified test enzyme is located within a host bacterium, a constitutive promoter expresses part A of the detection system (e.g. detection operon). So long as the phosphatase (or other test enzyme) expressed by part A is active, an expressed kinase enzyme, e.g. Src kinase, attaches a phosphate (P) group to the expressed second fusion protein comprising a substrate recognition domain (S) attached to a protein capable of recruiting RNA polymerase to DNA (e.g., the $RP_\omega$ subunit of RNA polymerase), and the phosphatase removes that phosphate group so that few molecules of phosphorylated fusion protein 2 stay bound to fusion protein 1 and, thus, few complexes between fusion proteins 2 and 1 form to initiate transcription of a gene of interest (GOI).

Thus, transcription of part B is off and the expression of a GOI is low, e.g. as observed when a GOI is a luminescent protein, so long as the placZ inducible promoter is not being induced. In this embodiment of an operon, the placZ inducible promoter is induced in order to allow the expression of a gene of interest in the absence of an inhibitor when not testing for inhibitor molecules.

However, in the presence of a small molecule that inhibits the phosphatase, a molecule either made endogenously from a metabolic pathway harbored by plasmids 2 and 3, or added to the growth media, then an excess of phosphorylated fusion protein 2 within the substrate binding region attaches to the substrate recognition domain of fusion protein 1 then when both are bound to the operator and the RB binding site then the GOI is expressed indicating the presence of a phosphatase inhibitor.

For practical purposes, it does not matter which fusion protein possesses a DNA-binding protein and which possesses a protein capable of recruiting RNA polymerase to DNA, so long as the DNA-binding protein constitutes part of one fusion protein and the protein that recruits RNA polymerase constitutes part of the other fusion protein, see FIG. 40, FIG. 10, for examples.

*E. coli* DH10B was used for molecular cloning and for preliminary analyses of terpenoid production; *E. coli* s1030' was used for luminescence studies and for experiments involving terpenoid-mediated selection (e.g., molecular evolution); and *E. coli* B121 was used for experiments involving the heterologous expression and subsequent purification of proteins. However, it is not intended to limit the host bacteria strain to these *E. coli* strains. Indeed, any bacteria strain that supports the expression of the operons, DNA sequences and plasmids as described herein may be used as a host bacteria strain.

In preferred embodiments, small molecule products are derived from one general metabolic pathway (the mevalonate-dependent pathway for terpenoid biosynthesis from *Saccharomyces cerevisiae*), and one host organism (*Escherichia coli*). These small molecule products produced as described herein, are contemplated for use as treatments of type 2 diabetes, obesity, and breast cancer, among other diseases.

A. Bacterial Two-Hybrid (B2H) Systems (Operons) for the Identification of Microbially Synthesizable Inhibitors of PTP1B.

In one embodiment, an application of the B2H system to the evolution of genes that enable the microbial synthesis of molecules that (i) inhibit PRI B and (ii) may be identified (i.e., structurally characterized) with standard analytical methods. In brief, the B2H system links the inactivation of PIM B to the expression of a gene for antibiotic resistance. Accordingly, when a strain of *E. coli* (or other host bacterium) harbors both (i) the 132E1 system and (ii) a metabolic pathway for terpenoid biosynthesis, it will survive in the presence of antibiotics when it produces terpenoids that inhibit PTP1B.

A bacterial two-hybrid (B2H) system as described herein comprises one embodiment of an operon as described herein. Data displayed on left side of the plot in FIG. 33D (i.e., p130cas [also called. Kras] and NUT substrates) is the same data displayed in FIG. 29A with the addition of providing more details of the B2H system in light of development.

We propose to use directed evolution to evolve new inhibitors; that is, we will manually introduce mutations into specific genes (or sets of genes) within a metabolic pathway to generate a library of metabolic pathways that can be screened alongside the B2H system. FIG. 41A describes a general approach to introduce mutations; Example C provides a very specific approach represented by FIG. 41A. To screen our library, we transform it into B2H-containing cells, and we grow them on plates containing various concentrations of spectinomycin; colonies that form on plates with high concentrations of spectinomycin contain a pathway capable of generating molecules that activate the B2H system (i.e., inhibit PTP1B). This pathway will not naturally evolve on its own. We can, thus, remove it from the first host cell, and transform it into another strain of E. coli to make high concentrations of inhibitors, Embodiments of the system described herein enables the rapid identification of drug leads that can be readily synthesized in microbial hosts. It allows for a simultaneous solutions to two problems encountered during pharmaceutical development that are often examined separately 1) the identification of leads and 2) subsequent synthesis of those leads identified in 1).

Systems described herein have at least five uses:
1. Enables the identification of genes for proteins that generate inhibitors of the drug target. In brief, when the pathway for terpenoid biosynthesis generates target-inhibiting molecules, the cell survives at high antibiotic concentrations. By swapping out genes for terpene synthesizing and/or functionalizing enzymes, we can identify genes for enzymes that build such inhibitors.
2. Enables the construction of novel—and, perhaps, unnatural—inhibitors. By mutating the pathway for terpenoid biosynthesis, we can generate pathways that confer survival at high antibiotic concentrations. These pathways contain mutated (i.e., unnatural) genes and, thus, can generate inhibitor molecules not found in Nature.
3. Enables the construction of inhibitors that overcome drug resistance. Briefly, after building a strain that generates a target-inhibiting molecule, we can carry out two steps: (i) We can mutate the drug target until it becomes resistant to that inhibitor. (ii) We can mutate the metabolic pathway until it generates an inhibitor of the mutated drug target. In this way, we can both (i) predict drug-resistance mutations and (ii) address those mutations by generating new inhibitors that overcome them.
4. Enables the construction of inhibitors of protein tyrosine kinases. Using a selection strategy similar to that described in 3.ii, we can mutate a metabolic pathway until it generates an inhibitor of Src kinase.

B. A Genetically Encoded System that Links the Inhibition of a Protein Tyrosine Phosphatase to Cell Survival.

In one preferred embodiment, a genetically encoded system was developed and used, as described herein, for detecting the presence of a small-molecule inhibitor of the catalytic domain of a chosen enzyme, e.g. a drug target enzyme, while allowing the survival of a host cell in the presence of a selective growth media. In other words, when the genetically encoded system is part of an expression plasmid in E. coli.

In one embodiment, an exemplary drug target enzyme was chosen, e.g. protein tyrosine phosphatase enzyme, protein tyrosine phosphatase 1B (PTP1B), In one embodiment, the genetically encoded system is part of an expression plasmid. In one embodiment, the sensing operon is operably linked to a constitutive promoter for expression in E. coli.

FIG. 33A-E illustrates an embodiment of a genetically encoded system that links the activity of an enzyme to the expression of a gene of interest (GOI). Error bars in FIG. 33B-E denote standard deviation with n=3 biological replicates.

Figure 33A:
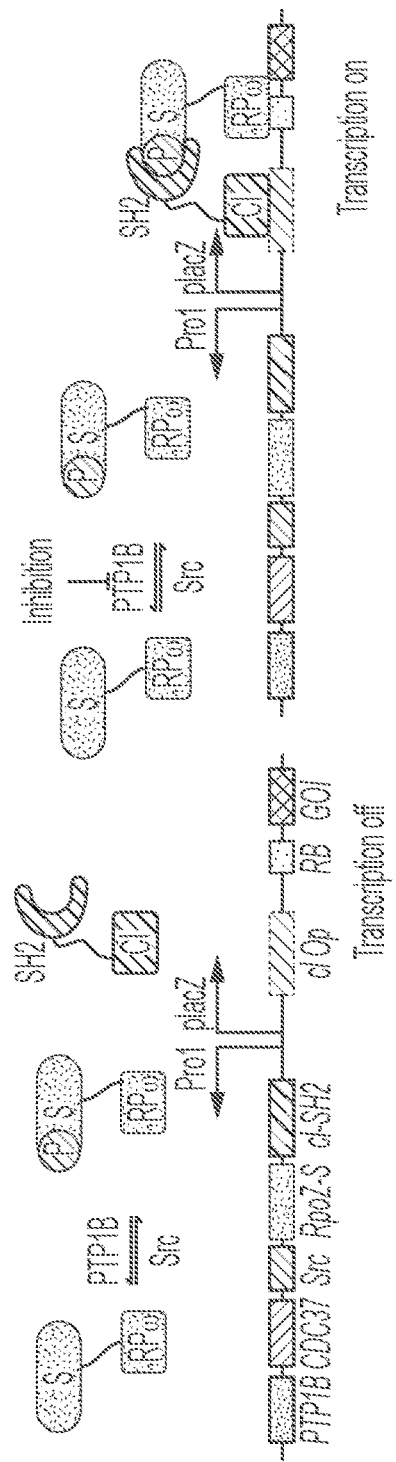
FIG. 33A-E illustrates an embodiment of a genetically encoded system that links the activity of an enzyme to the expression of a gene of interest (GOI). Error bars in FIG. 33B-E denote standard deviation with n=3 biological replicates.
Figure 33B:
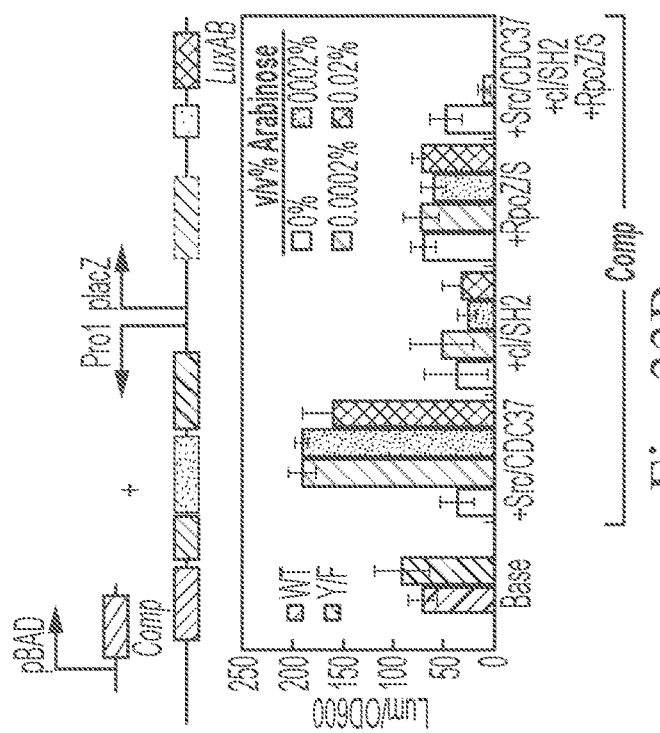
Figure 33C:
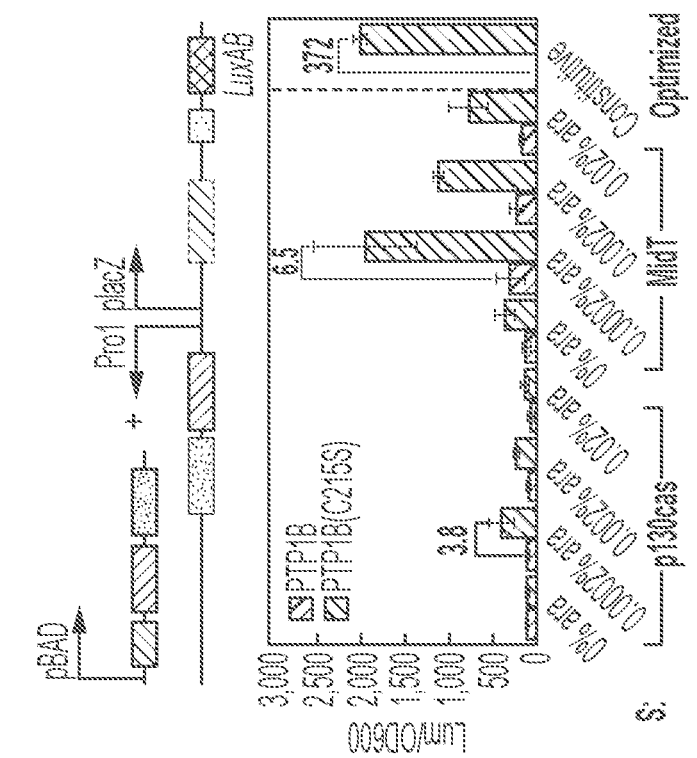
Figure 33D:
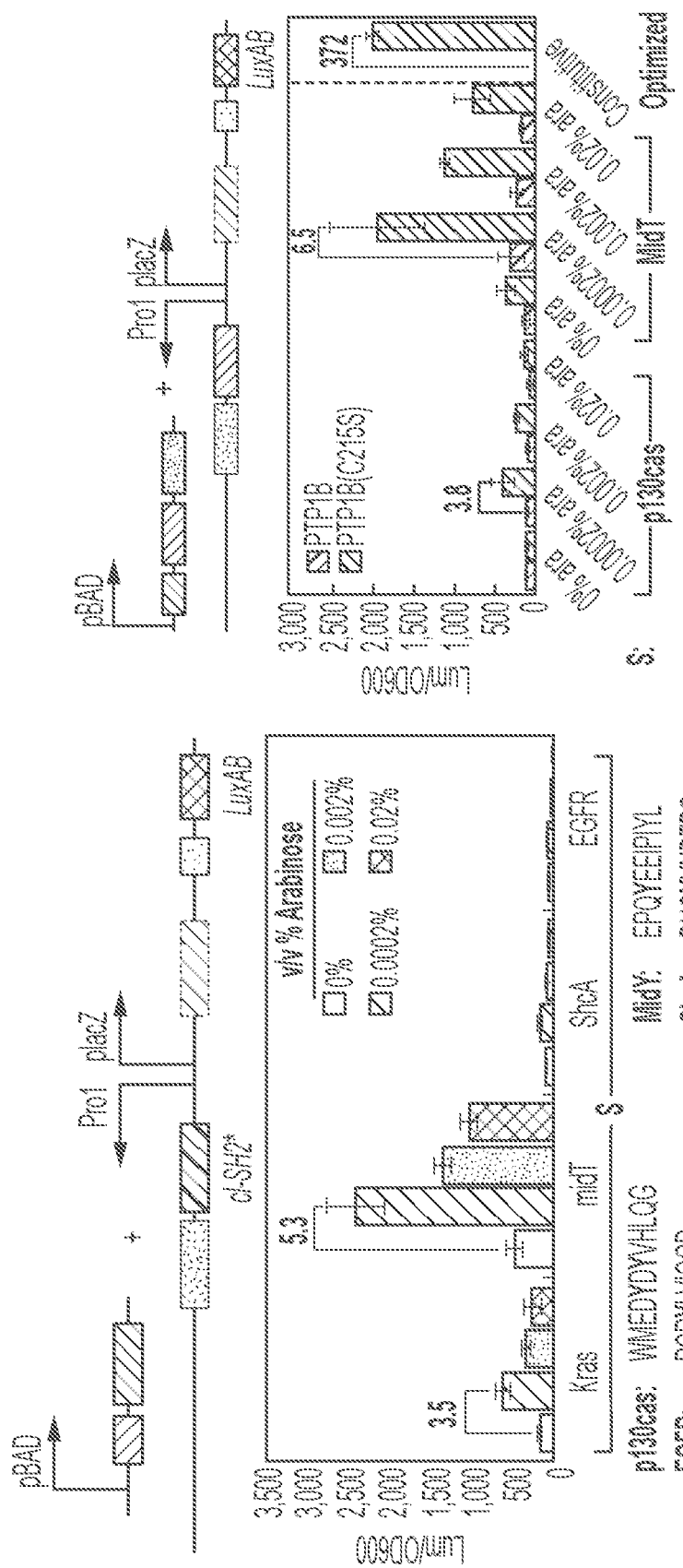
Figure 33E:
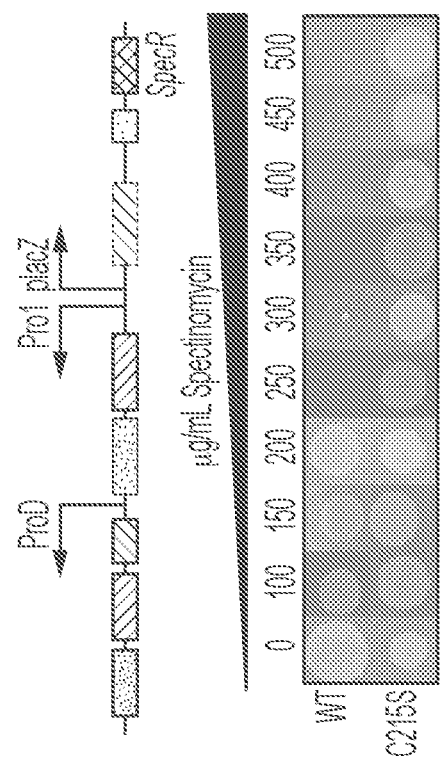

FIG. 33A illustrates an embodiment of a bacterial two-hybrid system that detects phosphorylation-dependent protein-protein interactions. Components include (i) a substrate domain fused to the omega subunit of RNA polymerase (yellow), (ii) an SH2 domain fused to the 434 phage cI repressor (light blue), (iii) an operator for 434cI (dark green), (iv) a binding site for RNA polymerase (purple), (v) Src kinase, and (vi) PTP1B. Src-catalyzed phosphorylation of the substrate domain enables a substrate-SH2 interaction that activates transcription of a gene of interest (GOI, black). PTP1B-catalyzed dephosphorylation of the substrate domain prevents that interaction; inhibition of PTP1B re-enables it. FIG. 33B refers to an embodiment of the two-hybrid system from FIG. 33A that (i) lacks PTP1B and (ii) contains luxAB as the GOI. We used an inducible plasmid to increase expression of specific components; overexpression of Src enhanced luminescence. FIG. 33C refers to an embodiment of the two-hybrid system from FIG. 33A that (i) lacks both PTP1B and Src and (ii) includes a "superbinder" SH2 domain (SH2*, i.e., an SH2 domain with mutations that enhance its affinity for phosphopeptides), a variable substrate domain, and LuxAB as the GOI. We used an inducible plasmid to increase expression of Src; luminescence increased most prominently for p130cas and MidT, suggesting that Src acts on both substrate domains. FIG. 33D refers to an embodiment of a two-hybrid system from FIG. 33C with one of two substrates: p130cas or MidT. We used a second plasmid to overexpress either (i) Src and PTP1B or (ii) Src and an inactive variant of PTP1B (C215S). The difference in luminescence between systems containing PTP1B or PTP1B (C215S) was greatest for MidT, suggesting that PTP1B acts on this substrate. Right: An optimized version of the two-hybrid system (with bb030 as the RBS for PTP1B) appears for reference. FIG. 33E displays the results of an exemplary growth-coupled assay performed using an optimized B2H including SH2*, a midT substrate, optimized promoters and ribosome binding sites (bb034 for PTP1B), and SpecR as the GOI. This system is illustrated at the top of the figure. Exemplary growth results demonstrate that inactivation of PTP1B enables strain of E. coli harboring this system to survive at high concentrations of spectinomycin (>250 µg/ml).

1. Sequential Optimization of a Two-Hybrid System with LuxAB as the GM.

Phase 1: We examined two different promoters for Src in a system that lacked PTP1B. Phase 2: We examined two different ribosome binding sites (RBSs) for Src in a system that lacked PTP1B. Phase 3: We examined two different RBSs for PTP1B in a complete system. Note: In phases 1 and 2, the operon contains wild-type (WT) or non-phosphorylate-able (mutant, Y/F) versions of the substrate domain. In phase 3, the operon contains wild-type (WT) or catalytically inactive (mutant, C215S) version so PTP1B. See, FIG. 34.

Figure 34:
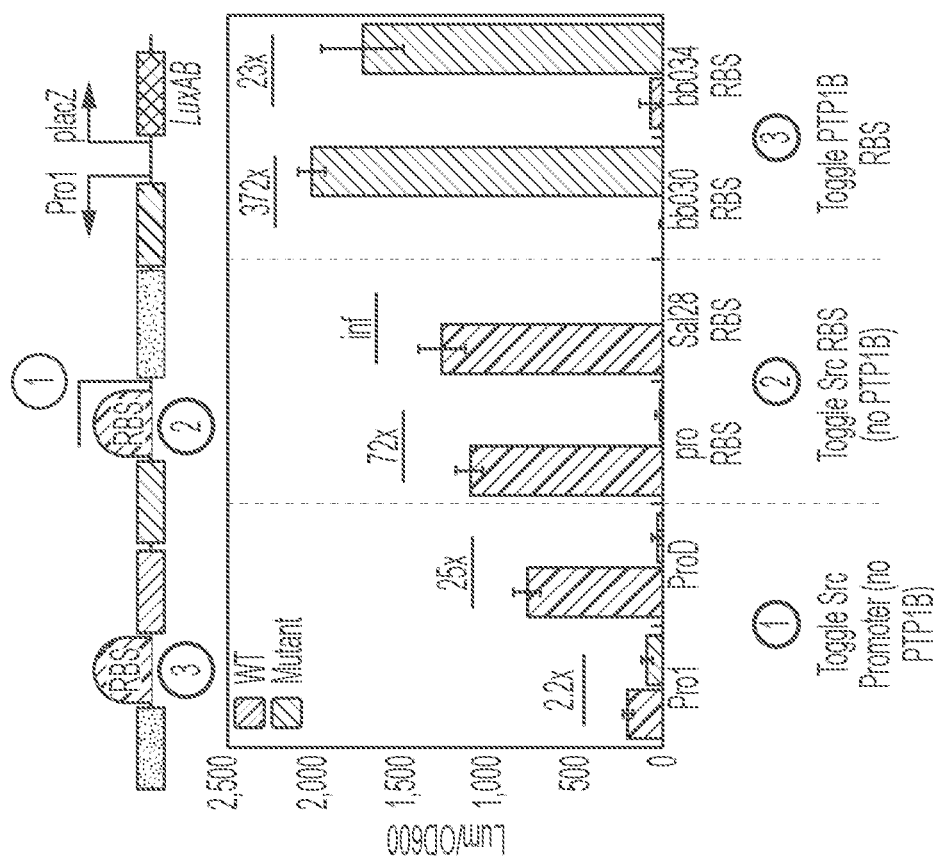
FIG. 34 illustrates exemplary experiments used to optimized the B2H system depicted in FIG. 33.

FIG. 34 illustrates exemplary experiments used to optimize the B2H system depicted in FIG. 33.

2. Comparing RB Sites.

We grew strains of *E. coli* harboring versions of the bacterial two-hybrid that contained different RBSs for PTP1B (bb034 or bb030) on various concentrations of spectinomycin (left to right) and plated them on various concentrations of spectinomycin (top to bottom). We used bb034 for one embodiment of an "optimized" two-hybrid system shown in FIG. 33E. See, FIG. 35.

Figure 35:
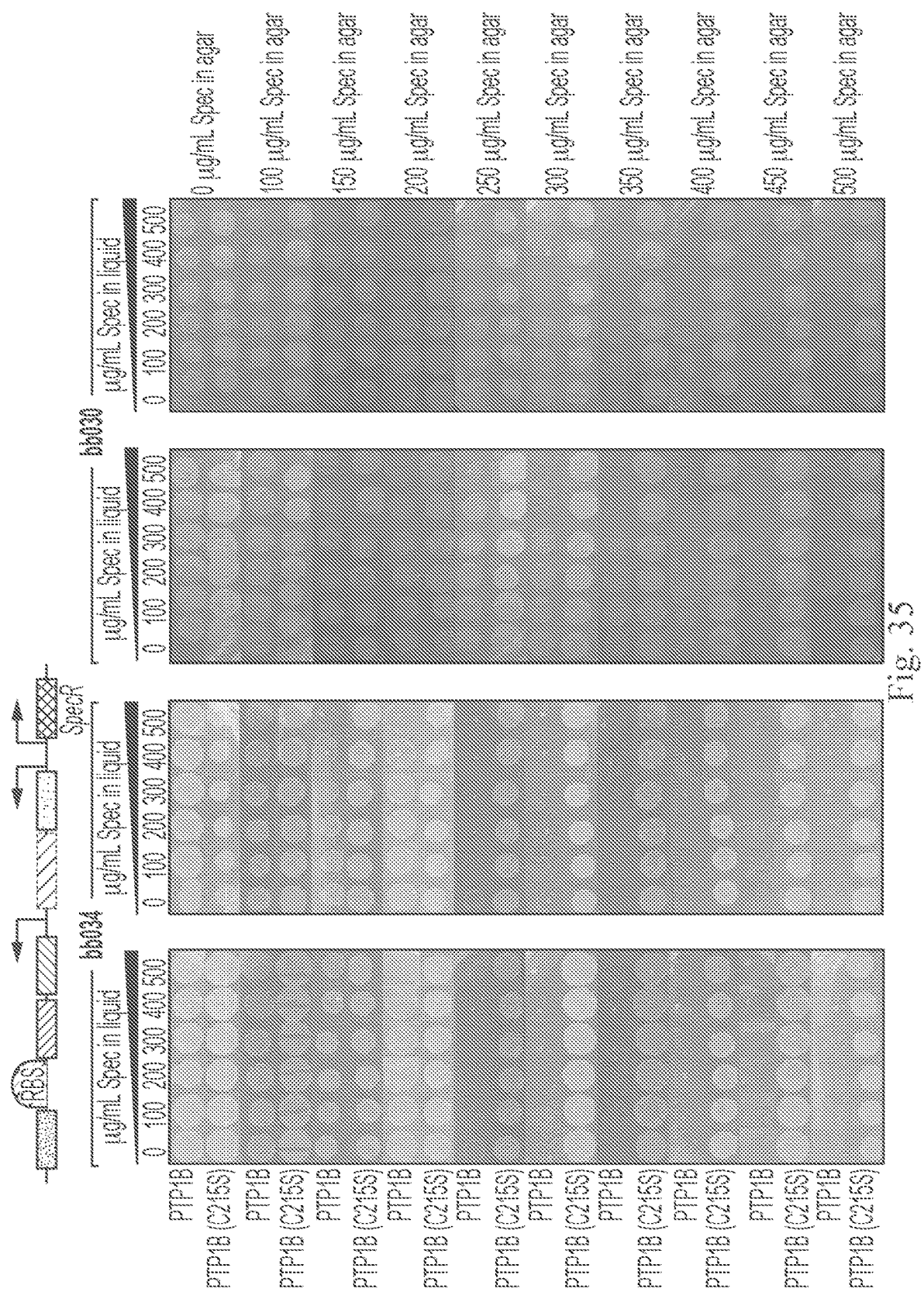
FIG. 35 illustrates exemplary experiments used to optimize the B2H system depicted in FIG. 33 for growth-coupled assays.

FIG. 35 FIG. 3 illustrates exemplary experiments used to optimize the B2H system depicted in FIG. 33 for growth-coupled assays.

Rice, P., Longden, L. & Bleasby, A. EMBOSS: The European Molecular Biology Open Software Suite. *Trends Genet.* 16, 276-277 (2000).

C. Biosynthesis of PTP1B-Inhibiting Terpenoids Enables Cell Survival.

When pTS contains ADS or GHS, it does not contain GGPPS; when pTS contains ABS or TXS, it also contains GGPPS; ABS$_{D404A/D621A}$ refers to a catalytically inactive variant of ABS; and B2H* contains PTP1B (C215S). ADS and, marginally, ABS enabled survival in the presence of spectinomycin, a result suggestive of the ability of these to terpene synthases to generate inhibitors of PTP1B.

Figure 36A:
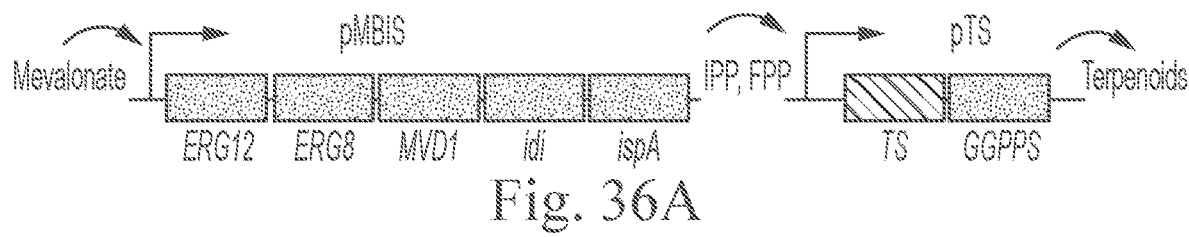
FIG. 36A-C depicts an exemplary metabolic pathway for the biosynthesis of terpenoids.
Figure 36B:
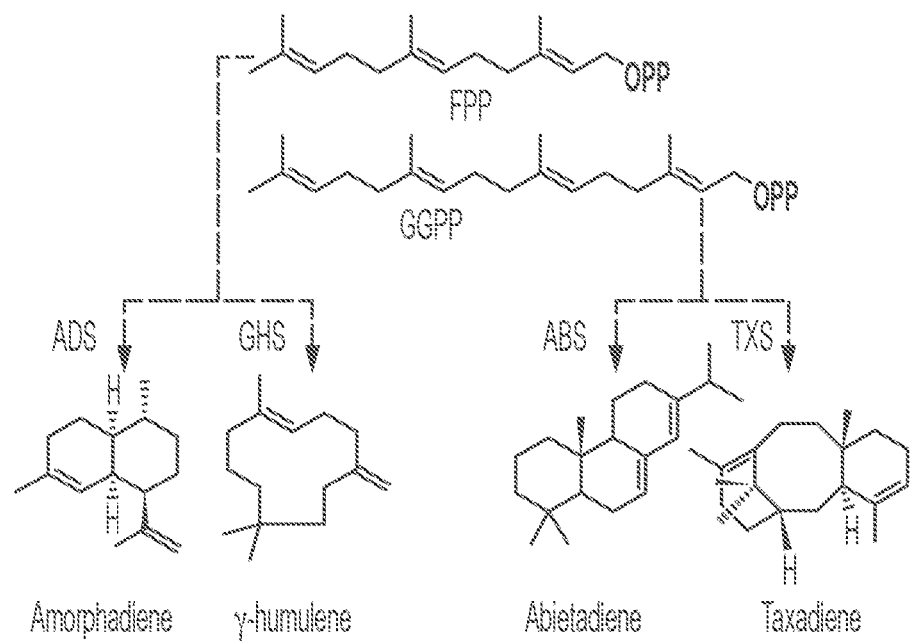
Figure 36C:
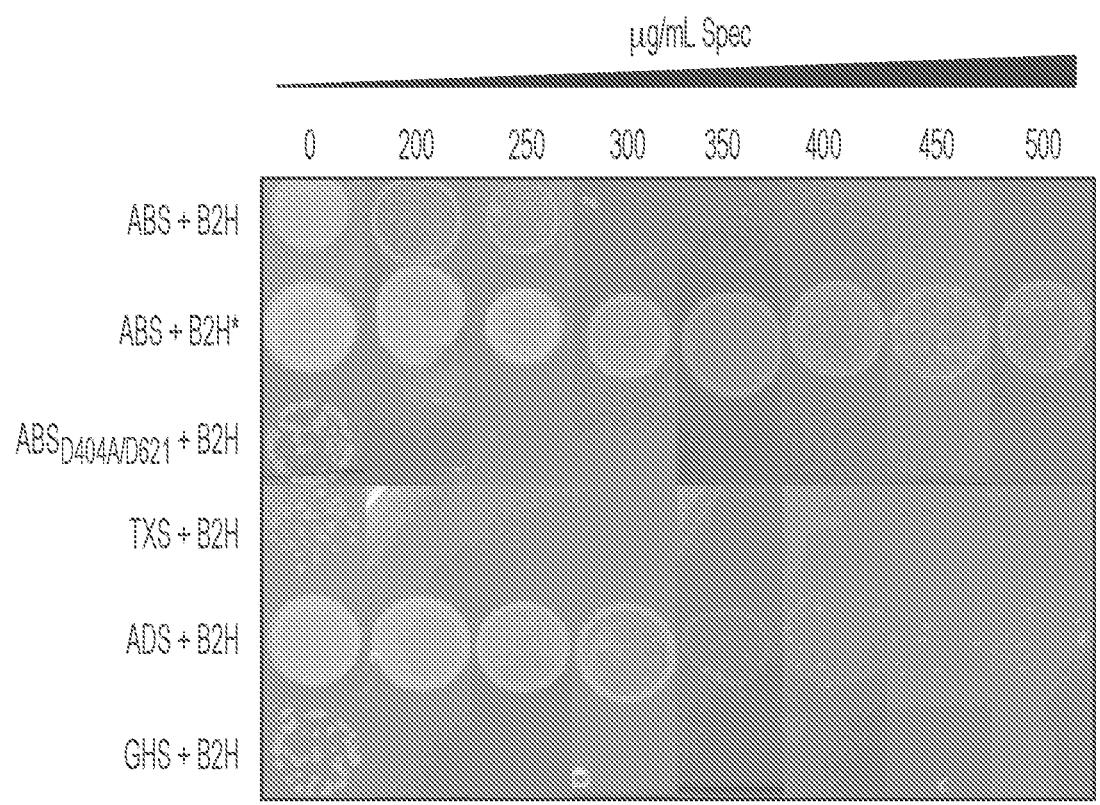

FIG. 36A-C FIG. 4 shows an illustration of an operon (FIG. 36A) used for providing exemplary results during biosynthesis of PTP1B-inhibiting terpenoids FIG. 36B enabling cell survival FIG. 36C.

FIG. 36A-C FIG. 4 depicts an exemplary metabolic pathway for the biosynthesis of terpenoids.

FIG. 36A depicts a plasmid-borne pathway for terpenoid biosynthesis: (i) pMBIS, which harbors the mevalonate-dependent isoprenoid pathway of *S. cerevisiae*, converts mevalonate to isopentyl pyrophosphate (IPP) and farnesyl pyrophosphate (FPP). (ii) pTS, which encodes a terpene synthase (TS) and, when necessary, a geranylgeranyl diphosphate synthase (GPPS), converts IPP and FPP to sesquiterpenes and/or diterpenes.

FIG. 36B depicts exemplary terpene synthases: amorphadiene synthase (ADS) from *Artemisia annua*, γ-humulene synthase (GHS) from *Abies grandis*, abietadiene synthase (ABS) from *Abies grandis*, and taxadiene synthase (TXS) from *Taxus brevifolia*.

FIG. 36C shows the results of an exemplary growth-coupled assay of strain of *E. coli* that contains both (i) an embodiment of the optimized bacterial two-hybrid (B2H) system (i.e., the B2H system from FIG. 33E) and (ii) an embodiment of a pathway for terpenoid biosynthesis (i.e., the pathway from FIG. 35A).

Briefly, we grew strains of *E. coli* that harbored (i) the same pathway for producing linear isoprenoid precursors and (ii) a different plasmid encoding a terpene synthase (pTS). The pTS plasmid contained on of the following: (i) amorphadiene synthase (ADS) from *Artemisia annua*, (ii) γ-humulene synthase (GHS) from *Abies grandis*, (iii) abietadiene synthase (ABS) from *Abies grandis* in operable combination with a geranylgeranyl diphosphate synthase (GGPPS, (iv) taxadiene synthase (TXS) from *Taxus brevifolia* in operable combination with a GGPPS, (v) a inactive variant of ABS (i.e., ABS$_{XX}$, which corresponds to ABS$_{D404A/D621A}$), or (vi) the L450Y mutant of GHS. After growing these strains, we compared the ability of their products to inhibit PTP1B by carrying out the following steps: (i) We used a hexane overlay to extract hydrophobic products (e.g., terpene-like products) from each culture, we then dried the products in a rotary evaporator, we dissolved the dried extract in dimethyl sulfoxide (DMSO), and we measured PTP1B-catalyzed hydrolysis of p-nitrophenyl phosphate (pNPP) in the presence and absence of extract-containing DMSO. We note: The L450Y mutant of GHS was included in our analysis because the wild-type form of GHS does not permit B2H-mediated growth in the presence of an antibiotic, but our preliminary data indicate that the L450Y mutant of GHS does permit such growth. Accordingly, we hypothesized that this mutant produced a molecule that is a stronger inhibitor of PTP1B than the molecules generated by wild-type GHS. See, FIG. 37A-C Demonstration of differential inhibition by structurally distinct terpenoids.

Figure 37A:
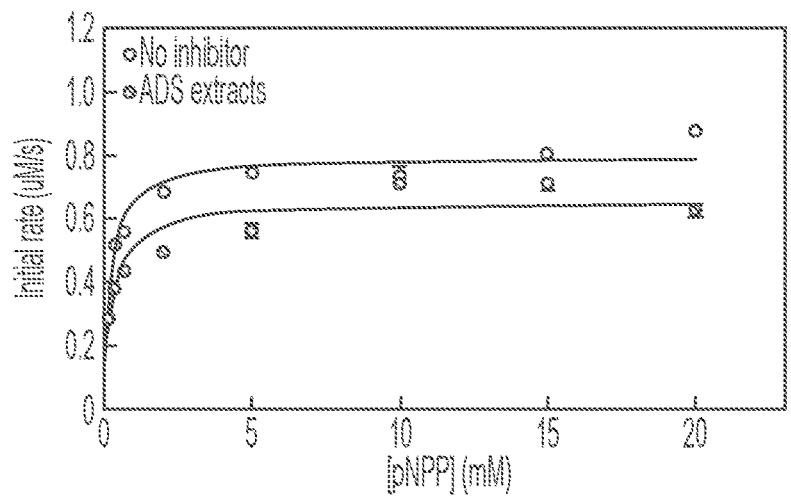
FIG. 37A-C provides an exemplary analysis of the inhibitory effects of terpenoids generated by different strains of E. coli.
Figure 37B:
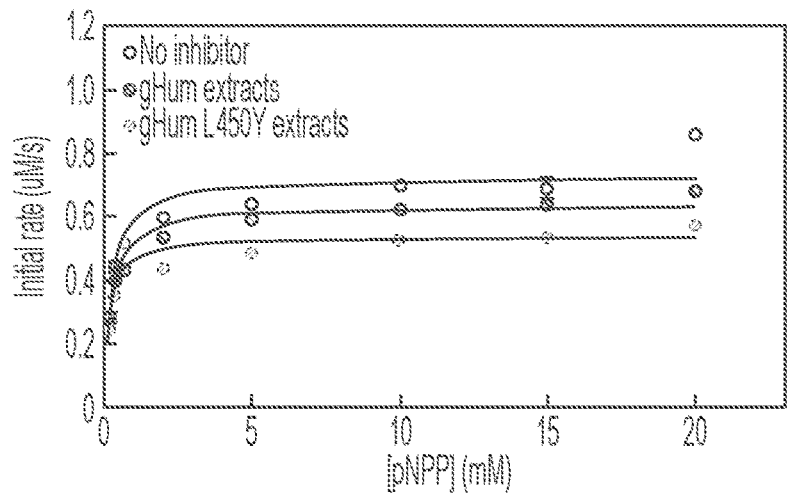
Figure 37C:
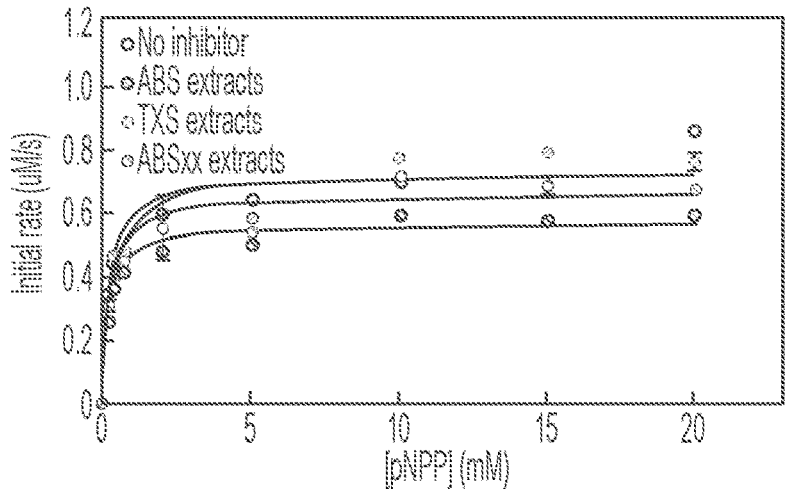

In examining FIG. 37A-C, we observed a trend: Extracts from strains containing terpene synthases that confer resistance to high concentrations of antibiotic (see FIG. 36) where ADS and GHS$_{L450Y}$ were more inhibitory than extracts from strains that did not confer resistance, e.g., TXS and ABS$_{xx}$. We note: strains containing ADS and GHS also included the optimized bacterial two-hybrid (B2H) system, but selection was not performed in the experiments used to product terpenoids for the experiments described by these figures.

FIG. 37A-C provides an exemplary analysis of the inhibitory effects of terpenoids generated by different strains of *E. coli*.

FIG. 37A depicts the results of our analysis of the inhibitory effect of DMSO containing (i) no inhibitor and (ii) extracted compounds from the culture broth of the ADS-containing strain. FIG. 37B depicts the results of our analysis of the inhibitory effect of DMSO containing (i) extracted compounds from the culture broth of the GHS-containing strain (gHUM) or (ii) extracted compounds from the culture broth of the strain including the L450Y mutant of GHS. FIG. 37C depicts the results of our analysis of the inhibitory effect of DMSO containing (i) no inhibitor, (ii) extracted compounds from the culture broth of the ABS-containing strain, (iii) extracted compounds from the culture broth of the TXS-containing strain, and (iv) extracted compounds from the culture broth of the train strain containing a catalytically inactive variant of ABS.

Briefly, we grew strains of *E. coli* containing both (i) the optimized bacterial two-hybrid system and (ii) a terpenoid pathway with mutants γ-humulene synthase (GHS; 1 mutant/cell) on varying concentrations of spectinomycin. Above: product profiles of strains with GHS mutants that conferred survival at high antibiotic concentrations. See, FIG. 38.

Figure 38:
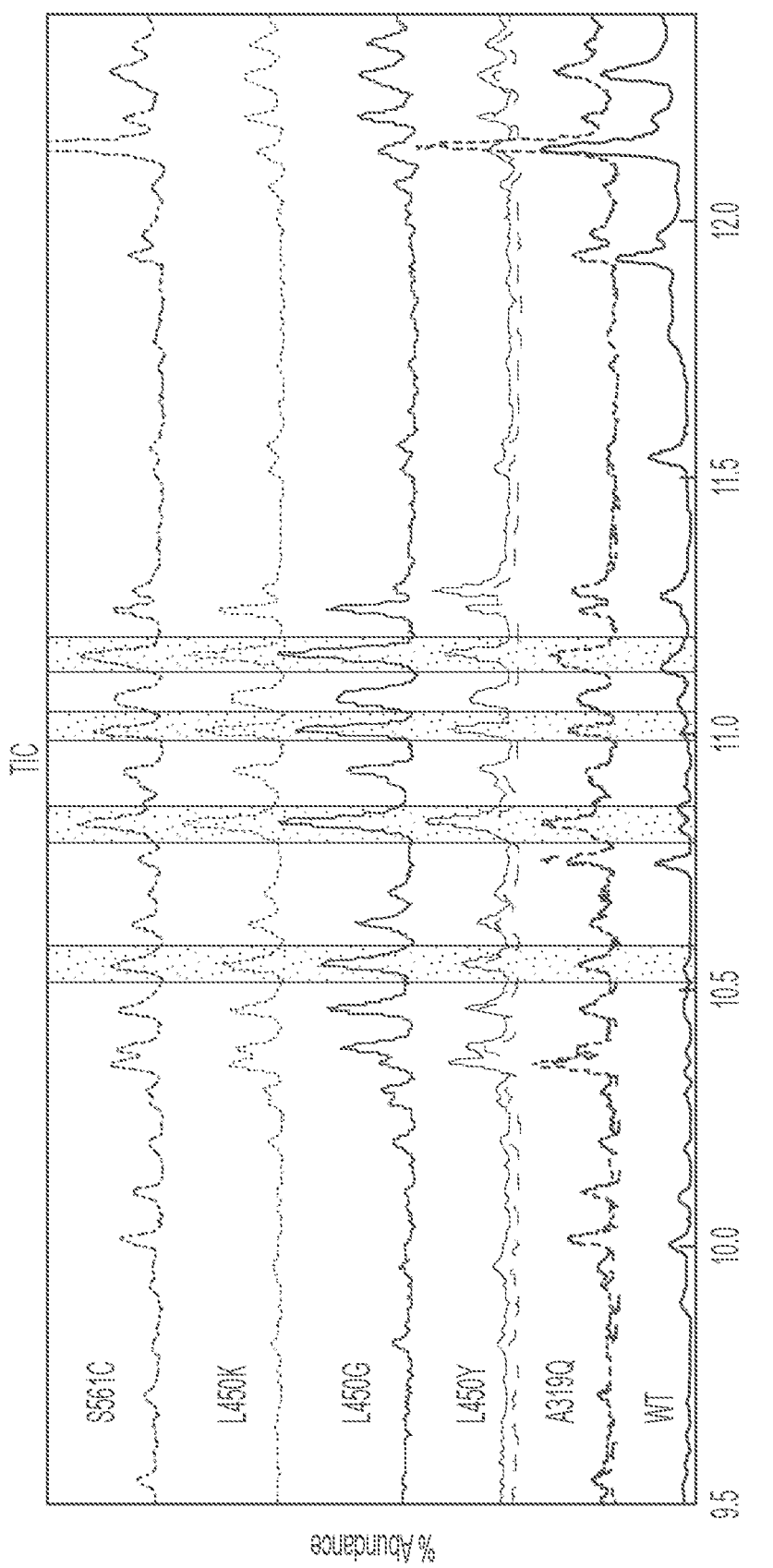
FIG. 38 shows exemplary analysis of the product profiles of mutants of GHS that enabled growth in the presence of spectinomcyin.

FIG. 38 shows exemplary analysis of the product profiles of mutants of GHS that enabled growth in the presence of spectinomcyin.

In brief, we constructed versions of the bacterial two-hybrid system that include SH2*, the midT substrate, optimized promoters and ribosome binding sites, SpecR, and alternative PTPs: the catalytic domain of PTPN6 (e.g., SHP-1) and PTP1B$_{405}$ (the full-length version of PTP1B). Note: these systems are identical to the B2H system depicted in FIG. 33E, except they possess only one of the following PTP genes: PTP1B (as in FIG. 33E), PTPN6 (different from FIG. 33E), or full-length PTP1B. Inactivation of the catalytic domain of both PTPN6 and the full-length PTP1B enabled strains of *E. coli* harboring corresponding operons to survive at high concentrations of spectinomycin (>400

μg/ml). To extend our operon to other PTPs, we plan on modifying the substrate, SH2, and/or kinase domains. See, FIG. 39.

Figure 39:
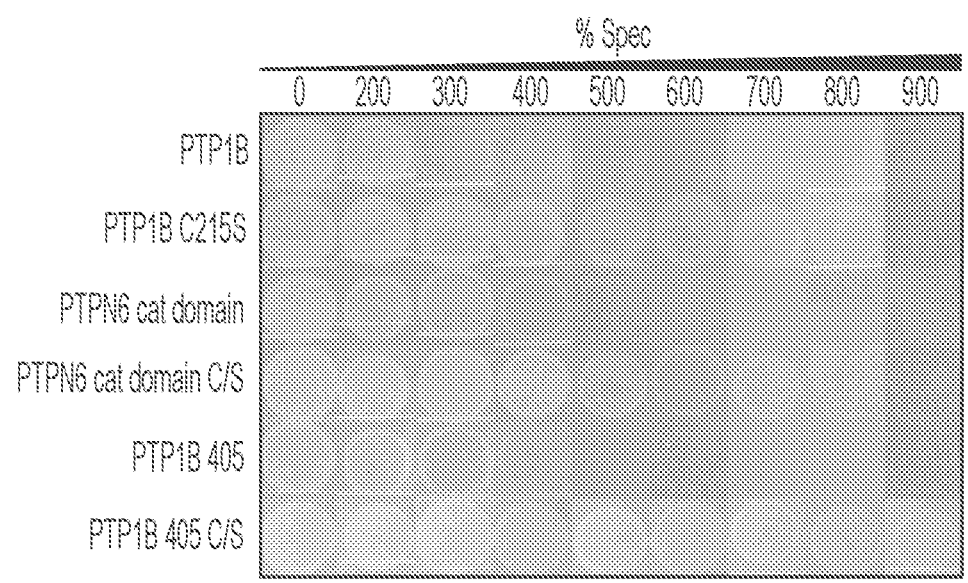
FIG. 39 shows an analysis of an exemplary B2H systems that link the inhibition of other PTPs to cell survival.

FIG. 39 An analysis of exemplary B2H systems that link the inhibition of other PTPs to cell survival.

We also generated versions of the bacterial two-hybrid system that include SH2*, the midT substrate, optimized promoters and ribosome binding sites, SpecR, and alternative PTPs: the catalytic domain of PTPN6 (e.g., SHP-1) and PTP1B$_{405}$ (the full-length version of PTP1B). Inactivation of the catalytic domain of PTPN6 and the full-length PTP1B enabled strains of E. coli harboring corresponding operons to survive at high concentrations of spectinomycin (>400 μg/ml). To extend our operon to other PTPs, we plan on modifying the substrate, SH2, and/or kinase domains.

FIG. 40A-E depicts exemplary embodiments of genetically encoded systems that link the activity of an enzyme to the expression of a gene of interest, and the application of those embodiments to (i) the prediction of resistance mutations, (ii) the construction of inhibitors that combat resistance mutations, and (ii) the evolution of inhibitors of kinases.

Figures 40D, 40E:
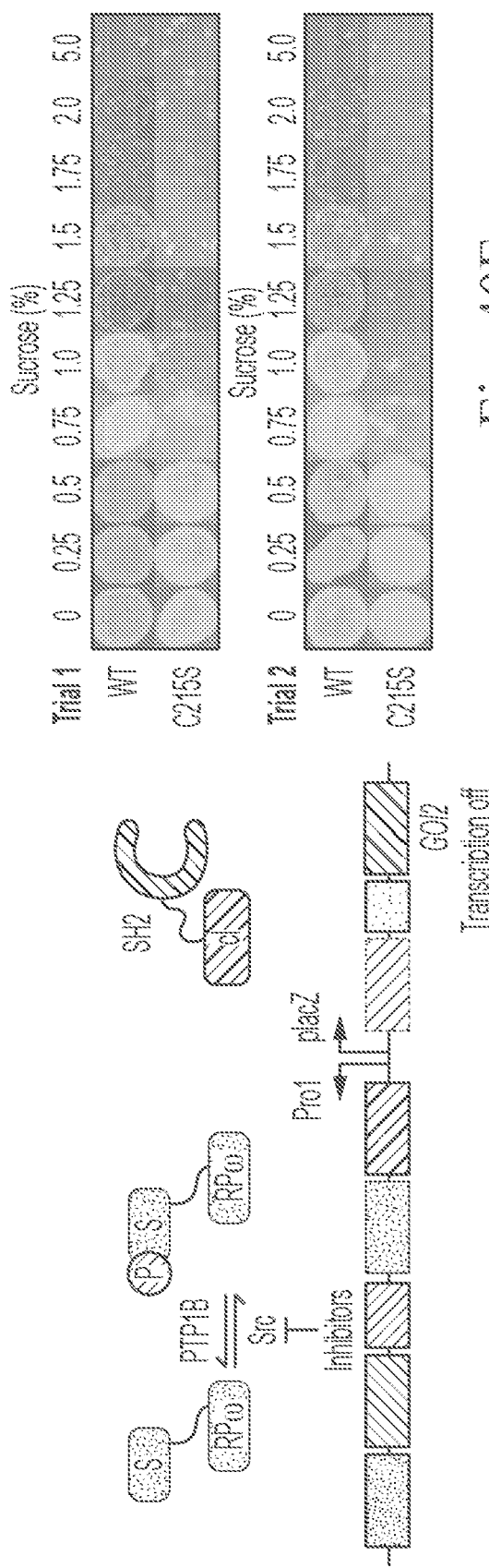

FIG. 40A depicts an exemplary first step in examining potential resistance mutations. By evolving a metabolic pathway to produce molecules that inhibit a known drug target (e.g., PTP1B); these molecules will permit expression of a gene of interest (GOI) that confers survival in the presence of a selection pressure (e.g., the presence of spectinomycin, an antibiotic). FIG. 40B depicts an exemplary second step in examining potential resistance mutations. In a second strain of E. coli, we will replace the original gene of interest with a second (GOI2) that confers conditional toxicity (e.g., SacB, which converts sucrose to levan, a toxic product); we will evolve the drug target to become resistant to the endogenous inhibitors, while still retaining its activity. This mutant will prevent expression of the toxic gene. FIG. 40C depicts an exemplary third step in combating resistance mutations. In a third strain of E. coli, we will evolve a metabolic pathway that produces molecules that inhibit the mutated drug target. In this way, we will both predict—and, through our second evolved pathway, address—mutations that might cause resistance to terpenoid-based drugs. We note: FIG. 40A-40C describe the use of our genetically encoded system to evolve inhibitors, but the steps 2 and 3 could be used to predict mutations that permit resistance to endogenously supplied inhibitors and, subsequently, to identify new endogenously supplied inhibitors that might combat that resistance. FIG. 40D depicts an exemplary genetically encoded system that detects inhibitors of an Src kinase. In brief, Src activity enables expression of a toxic gene (GOI2); inhibition of Src, in turn, would confer survival.

One embodiment of a configuration of the B2H architecture that enables survival when PTP1B is active, that is, when the activity of Src kinase is successfully canceled out. in the absence of PTP1B, this configuration could be used to evolve inhibitors of Src kinase; such an inhibitor would act similarly to PTP1B by preventing the phosphorylation of the substrate domain (as shown in FIG. 40E), Src kinase is a validated drug target; tyrosine kinases are targets of over 40 FDA-approved drugs.

FIG. 40E demonstrates one embodiment of a roof of principle for the B2H system describe in FIG. 40B. The system shown here includes two GOIs: SpecR and SacB. Expression of the GOIs confers survival in the presence of spectinomycin; expression of the GOIs causes toxicity in the presence of sucrose. The images depict the results of a growth-coupled assay performed on a strain of E. coli in the presence of various concentrations of sucrose. The strain harboring an active form of PTP1B (WT) grows better at high sucrose concentrations that the strain harboring an inactive form of PTP1B (C215S).

FIG. 41A depicts an exemplary strategy for the evolution of inhibitors of PTP1B.

FIG. 41A depicts an exemplary structural analysis used to identify targets for mutagenesis in the active sites of terpene synthases. It shows an alignment of the class I active site of ABS (gray, PDB entry 3s9v) and TXS (blue, PDB entry 3p5r) with the locations of sites targeted for site-saturation mutagenesis (SSM) highlighted on ABS (red). A substrate analogue (yellow) of TXS appears for reference. FIG. 41B depicts an exemplary strategy for introducing diversity into libraries of metabolic pathways: An iterative combination of SSM of key sites on a terpene synthase (as in a), error-prone PCR (ePCR) of the entire terpene synthase gene, SSM of key sites on a terpene-functionalizing enzyme (e.g., P450), and ePCR of the entire terpene-functionalizing enzyme. FIG. 41C depicts an exemplary quantification the total terpenoids present in DMSO samples with extracts of various TS-containing strains. In brief, we performed site-saturation mutagenesis of six sites on ADS (analogous to the sites shown in a); we plated the SSM library on agar plates containing different concentrations of spectinomycin; we picked colonies that grew on a plate containing a high concentration (800 μg/ml) of spectinomycin and used each colony to inoculate a separate culture; we used a hexane overlay to extract the terpenoids secreted into each culture broth; we dried the hexane extract in a rotary evaporator and re-suspended the solid in DMSO; and we used a GC-MS to quantify the total amount of terpenoids present in the DMSO.

"ADS WT", "ADS F514E", "ADS F370L", "ADS G400A", "ADS G439A", and "ADS G4001," describe mixtures of molecules generated by strains of E. coli harboring mutants of amorphadiene synthase (ADS): The labels describe the mutant: "G439A" corresponds to a mutant of abietadiene synthase in which glycine 439 has been mutated to alanine, and so on. In future work, we plan on (i) purifying different terpenoids from these mixtures, (ii) assessing their inhibitory effect on PTP1B in vitro, (iii) assaying their inhibitory effect on other PTPs (notably TC-PTP and PTPN11) in vitro, and (iv) assaying their influence on mammalian cells. See, FIG. 41D.

FIG. 41D depicts an exemplary analysis of the inhibitory effect of various extracts on PTP1B. In brief, the figure shows initial rates of PTP1B-catalyzed hydrolysis of p-nitrophenyl phosphate (pNPP) in the presence of terpenoids quantified in FIG. 41C. Two mutants of ADS (G439A and G400L) generate particularly potent inhibitors of PTP1B.

Figure 42:
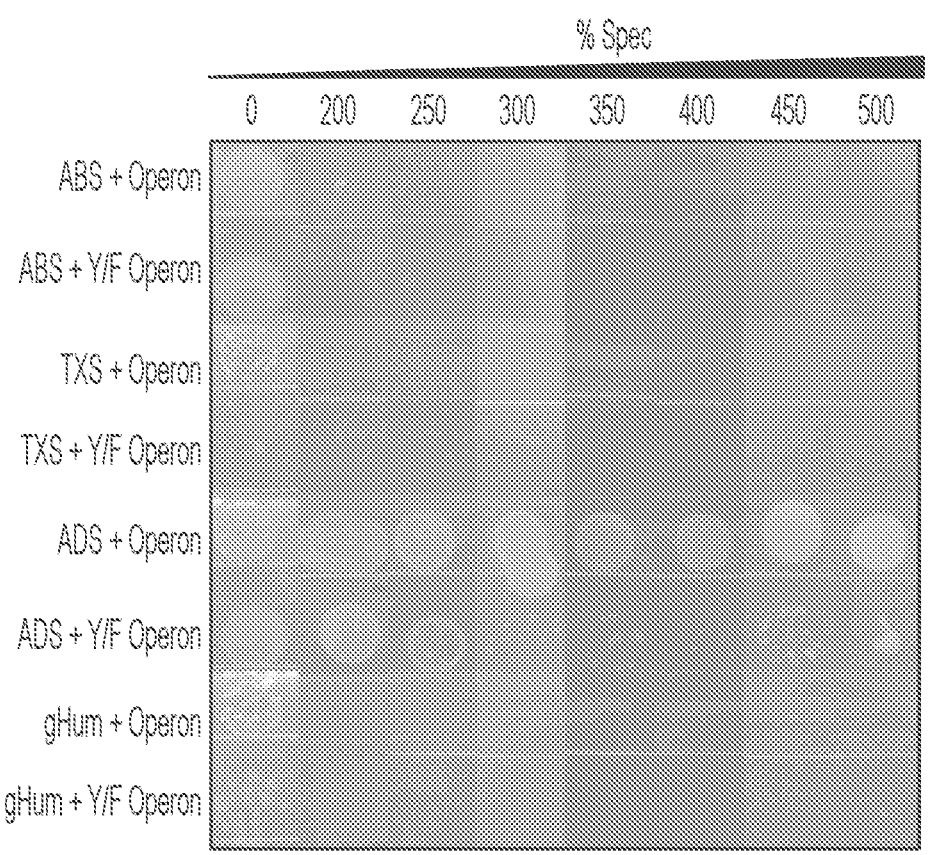
FIG. 42 depicts an exemplary analysis of the link between B2H activation and cell survival. An exemplary strain of E. coli that contains both (i) the optimized bacterial two-hybrid (B2H) system (FIG. 33E) and (ii) the terpenoid pathway depicted in FIG. 36A. Note: pTS includes GGPPS only when ABS or TXS are present; the "Y/F" operon corresponds to a B2H system in which the substrate domain cannot be phosphorylated. Survival at high concentrations of spectinomycin requires activation of the B2H system (i.e., phosphorylation of the substrate domain, a process facilitated by inhibition of PTP1B).

FIG. 42 depicts an exemplary analysis of the link between B2H activation and cell survival. An exemplary strain of E. coli that contains both (i) the optimized bacterial two-hybrid (B2H) system (FIG. 33E) and (ii) the terpenoid pathway depicted in FIG. 36A. Note: pTS includes GGPPS only when ABS or TXS are present; the "Y/F" operon corresponds to a B2H system in which the substrate domain cannot be phosphorylated. Survival at high concentrations of spectinomycin requires activation of the B2H system (i.e., phosphorylation of the substrate domain, a process facilitated by inhibition of PTP1B).

Figure 43:
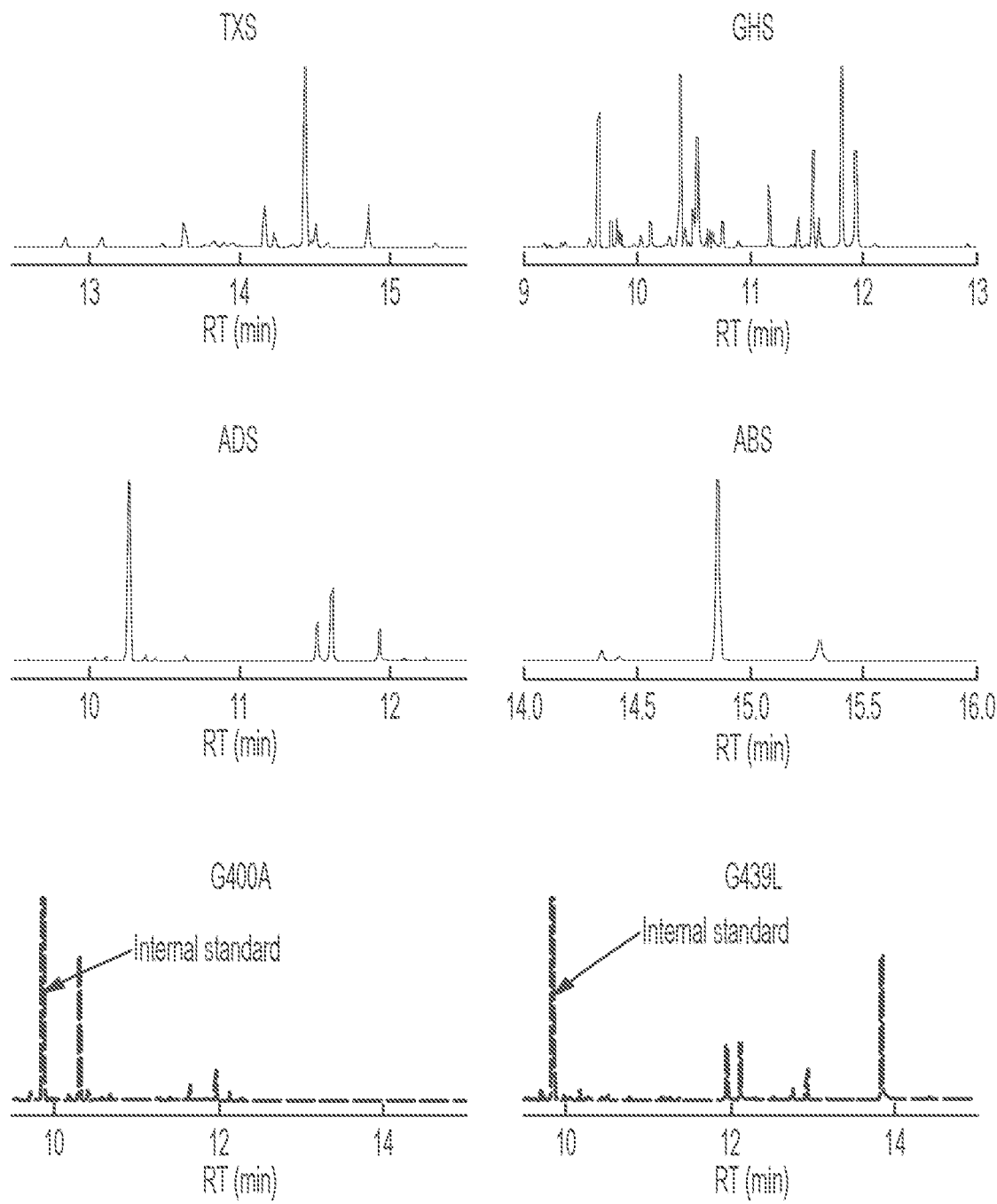
FIG. 43 provides exemplary product profiles of strains of E. coli harboring various terpene synthases. For this figure, the strain of E. coli harbored (i) the optimized B2H system (FIG. 33E) and (ii) the terpenoid pathway (FIG. 36A). The pathways corresponding to each profile differ only in the composition of the pTS plasmid, which contains TXS (taxadiene synthase from Taxus brevifolia and a geranylgeranyl diphosphate synthase from Taxus Canadensis); GHS (γ-humulene synthase from Abies grandis); ADS (amorphadiene synthase from Artemisia annua); ABS (abietadiene synthase from Abies grandis and a geranylgeranyl diphosphate synthase from Taxus Canadensis); G400A (the G400A mutant of amorphadiene synthase from Artemisia annua); and G439L (the G439L mutant of amorphadiene synthase from Artemisia annua). Note that the two mutants of ADS yield different product profiles than the wild-type enzyme (ADS); our results indicate that products generated by these two mutants are more inhibitory than those generated by the wild-type enzyme (FIG. 41E).

FIG. 43 provides exemplary product profiles of strains of E. coli harboring various terpene synthases. For this figure, the strain of E. coli harbored (i) the optimized B2H system (FIG. 33E) and (ii) the terpenoid pathway (FIG. 36A). The pathways corresponding to each profile differ only in the composition of the pTS plasmid, which contains TXS (taxadiene synthase from *Taxus brevifolia* and a geranylgeranyl diphosphate synthase from *Taxus Canadensis*); GHS (γ-humulene synthase from *Abies grandis*); ADS (amorphadiene synthase from *Artemisia annua*); ABS (abietadiene synthase from *Abies grandis* and a geranylgeranyl diphosphate synthase from *Taxus Canadensis*); G400A (the G400A mutant of amorphadiene synthase from *Artemisia annua*); and G439L (the G439L mutant of amorphadiene synthase from *Artemisia annua*). Note that the two mutants of ADS yield different product profiles than the wild-type enzyme (ADS); our results indicate that products generated by these two mutants are more inhibitory than those generated by the wild-type enzyme (FIG. 41E).

D. Identification of Sites for Site Saturation Mutagenesis (SSM).

The active sites of terpene synthases and cytochrome P450s contain constellations of amino acids that guide catalysis in two ways: (i) They control the conformation space available to reacting substrates, and (ii) they alter the organization of water that surrounds substrates[8-10]. We identified "plastic" residues likely to modulate these attributes in the class I active sites of terpene synthase by carrying out the following steps: (i) We aligned the crystal structure of ABS with the crystal structure of TXS. (ii) We selected all residues within 8 angstroms of the substrate analog (2-fluoro-geranylgeranyl diphosphate) of the class I active site of TXS, and we identified a subset of sites that differed between ABS and TXS. (iii) We aligned the sequences of ABS, $$S = \frac{\sigma_V^2}{n_v} + \frac{\sigma_{HW}^2}{n_{HW}}$$

GHS, delta-selenine synthase (DSS), and epi-isozizaene synthase (EIS). (iv) We used Eq. S1 to score each site based on its variability in size and hydrophilicity across the five enzymes analyzed. In this equation, $\sigma_v^z$ is the variance in volume, $\sigma_{HW}^z$ is the variance in Hopp-Woods index, and $n_v$ and $n_{HW}$ are normalization factors (based on the highest variances measured in this study). (v) We ranked each site according to S and selected the six highest-scoring sites. We note: For this analysis, we chose ABS and TXS because they are structurally similar enzymes (i.e., both possess α, β, and γ domains) with crystal structures; we chose GHS, DSS, and EIS because they have been shown to exhibit mutation-responsive product profiles.

FIG. 44A-D provides exemplary structural and sequence-based evidence that supports the extension the B2H system to other protein tyrosine phosphatases (PTPs).

Figure 1E:
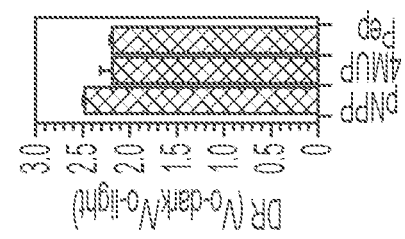
Figure 1D:
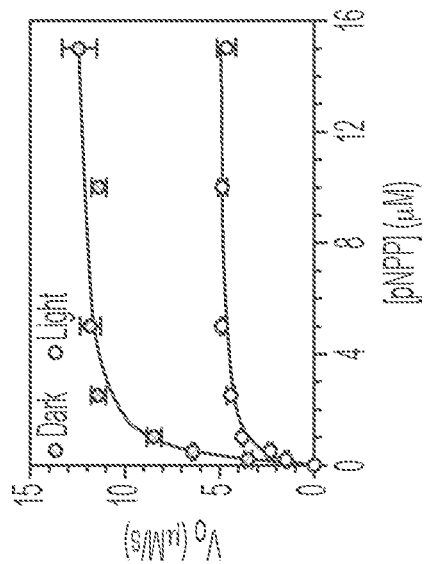
Figure 1G:
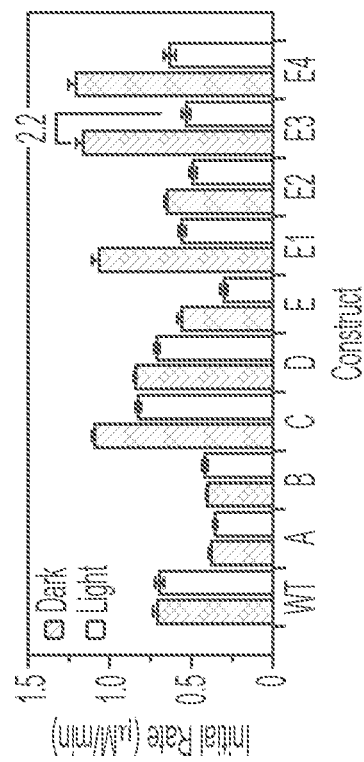
Figures 44A, 44B:
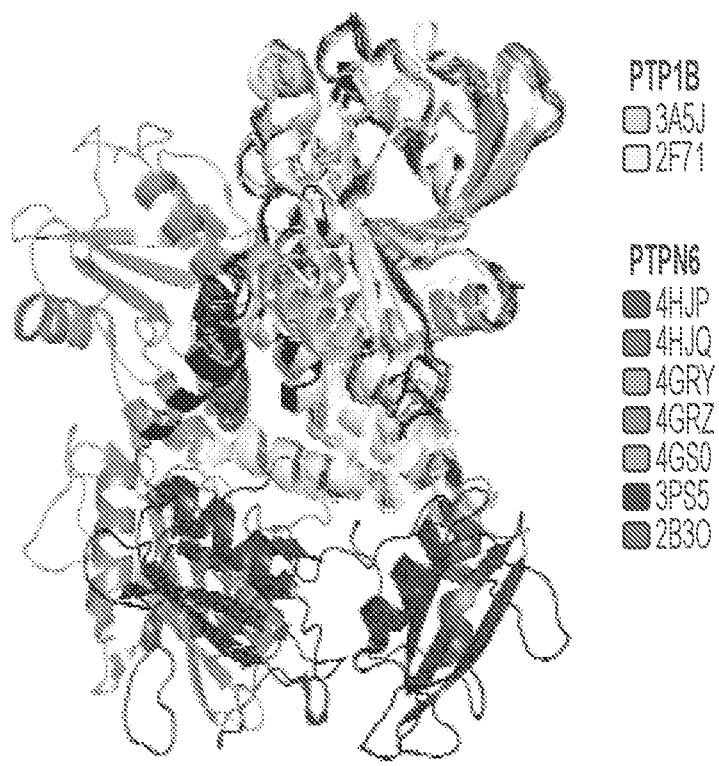

FIG. 44A provides an exemplary structural alignment PTP1B and PTPN6, two PTPs that are compatible with the B2H system (see FIGS. 1e and 7 of Update A for evidence of compatibility). We used the align function of PyMol to align each structure of PTPN6 with either (i) the ligand-free (3A5J) or (ii) ligand-bound (2F71) structure of the catalytic domain of PTP1B. The align function carries out a sequence alignment followed by a structural superposition and, thus, effectively aligns the catalytic domains of both proteins. FIG. 44B provides an exemplary structural comparison of PTP1B and PTPN6; the root-mean-square deviations (RMSD) of aligned structures of PTP1B and PTPN6 range from 0.75 to 0.94 Å. FIG. 44C proves an exemplary sequence alignment of the catalytic domains of PTP1B (SEQ ID NO: 3) and PTPN6 (SEQ ID NO: 4) (EMBOSS Needle[1]). FIG. 44D provides an exemplary sequence comparison of the catalytic domains of PTP1B and TPPN6. The sequences share 34.1% sequence identity and 53.5% sequence similarity. In summary, the results of this figure indicate that our B2H system can be readily extended to PTPs that possess catalytic domains that are (i) structurally similar to the catalytic domain of PTP1B (here, we define structural similarity as two structures that when aligned, have with an RMSD of ≤0.94 Å RMSD with the framework similar to the one used by the align function of PyMol) and/or (ii) sequence similar to the catalytic domain of PTP1B (here, we define sequence similarity as ≥34% sequence identity or ≥53.5% sequence similarity as defined by the EMBOSS Needle algorithm).

To identify "plastic" residues capable of adjusting the activity of P450$_{BM3}$, we carried out an approach similar to that described above: (i) We used the mutant database[11] (http://www.MuteinDB org) to identify the 25 most commonly mutated sites in functional variants of P450$_{BM3}$. (ii) We used Eq. 51 to score each site based on its variability in size and hydrophobicity across different mutants. (iii) We ranked each site according to S and selected the 7 highest-scoring sites. Site S1024 scored highly based on S but was omitted due to its location on the P450 reductase domain.

E. Exemplary Purification of Products.

See section relating to flash chromatography and HPLC[1-3].

F. Exemplary Concentration Range for Testing Products.

We plan on incubating mammalian cells with 1-400 µM of inhibitors; we will assess the biochemical influence of those inhibitors by using the assays described below.

G. Exemplary Cell-Based Assays.

We will characterize the biological activity of newly developed inhibitors in at least two ways:

1. We will assay the influence of inhibitors on insulin receptor phosphorylation. In brief, we will expose HepG2, Hela, Hek393t, MCF-7, and/or Cho-hIR cells to insulin shock in the presence and absence of inhibitors, and we will use a western blot and/or an enzyme-linked immunosorbent assay (ELISA) to measure the influence of the inhibitors on insulin receptor phosphorylation. In some embodiments we may use cell-permeable inhibitors of PTP1B to enhance insulin receptor phosphorylation.

2. We will examine the morphological and/or growth effects inhibitors identified in a system described herein on cellular models of HER2(+) and TN breast cancer.

In brief, we will examine the relevance of inhibitors to HER2(+) breast cancer by evaluating their ability to inhibit the migration of BT474 and SKBR3 cells, which are HER2(+), but not MCF-7 and MDA-MB-231 cells, which are HER2(−). We will examine the relevance of inhibitors to triple negative breast cancer, in turn, by carrying out viability and proliferation assays on panels of TN cell lines (e.g., ATCC TCP-1002). All cell lines are available from the ATCC (ATCC.org) and have been used previously to characterize potential therapeutics for HER2(+) and TN subtypes[4,5].

It is not meant to limit a pathway to terpenoid synthesis. Indeed, an alkaloid biosynthesis pathway is contemplated for use to identify, An exemplary pathway for alkaloid biosynthesis consists of three modules (Nakagawa, A. et al. A bacterial platform for fermentative production of plant alkaloids. Nat. Commun. (2011). doi:10.1038/ncomms1327, herein incorporated by reference) (i) the first enables the overexpression of our enzymes for L-tyrosine overproduction: TKT, PEPS, fbr- DAHPS, and fbr-CM/PDH; (ii) the second enables the expression of three enzymes necessary for the construction of dopamine and 3,4-DHPAA: TYR, DODC, and MAO; and (iii) the third enable the expression of four enzymes for the construction of (S) reticuline from 3,4-DHPAA and dopamine: NCS, 6OMT, CNMT, and 4'OMT. Enzymes are as follows: TKT, transketolase (tktA, GenBank accession number X68025); PEPS, phosphoenolpyruvate (PEP) synthetase (ppsA, GenBank accession number X59381); fbr-DAHPS, feedback-inhibition resistant 3-deoxy-D-arabino-heptulosonate-7-phosphate synthase (aroGfbr, GenBank accession number J01591); fbr-CM/PDH, feedback-inhibition resistant chorismate mutase/prephenate dehydrogenase (tyrAfbr, GenBank accession number M10431); TYR, tyrosinase of *Streptomyces castaneoglobisporus* (ScTYR containing tyrosinase and its adaptor protein, ORF378, GenBank accession numbers AY254101 and AY254102); DODC, DOPA decarboxylase of *Pseudomonas putida* (GenBank accession number AE015451); MAO, monoamine oxidase of *Micrococcus luteus* (GenBank accession number AB010716); NCS, norcoclaurine synthetase of *C. japonica* (GenBank accession number AB267399); 6OMT, norcoclaurine 6-O-methyltransferase of *C. japonica* (GenBank accession number D29811); CNMT, coclaurine-N-methyltransferase of Coptis *japonica* (GenBank accession number AB061863); 4'OMT, 3'-hydroxy-N-methylcodaurine 4'-O-methyltransferase of *C. japonica* (GenBank accession number D29812). We note; these three modules may be encoded by two plasmids.

REFERENCES FOR SECTION V, HEREIN INCORPORATED BY REFERENCE IN THEIR ENTIRETY

1. Jia, M., Potter, K. C. & Peters, R. J. Extreme promiscuity of a bacterial and a plant diterpene synthase enables combinatorial biosynthesis. *Metab. Eng.* 37, 24-34 (2016).
2. Criswell, J., Potter, K., Shephard, F., Beale, M. H. & Peters, R. J. A single residue change leads to a hydroxylated product from the class II diterpene cyclization catalyzed by abietadiene synthase. *Org. Lett.* 14, 5828-5831 (2012).
3. Morrone, D. et al. Increasing diterpene yield with a modular metabolic engineering system in *E. coli*: Comparison of MEV and MEP isoprenoid precursor pathway engineering. *Appl. Microbiol. Biotechnol.* 85, 1893-1906 (2010).
4. Dagliyan, O. et al. Engineering extrinsic disorder to control protein activity in living cells. *Science (80-.).* 354, 1441-1444 (2016).
5. Lehmann, B. D. et al. Identification of human triple-negative breast cancer subtypes and preclinical models for selection of targeted therapies. *J. Clin. Invest.* (2011). doi:10.1172/JCI45014
6. Dempke, W. C. M., Uciechowski, P., Fenchel, K. & Chevassut, T. Targeting SHP-1, 2 and SHIP Pathways: A novel strategy for cancer treatment? *Oncology (Switzerland)* (2018). doi:10.1159/000490106
7 Nakagawa, A. et al. A bacterial platform for fermentative production of plant alkaloids. *Nat. Commun.* (2011). doi:10.1038/ncomms1327
8. Christianson, D. W. Structural biology and chemistry of the terpenoid cyclases. *Chem. Rev.* 106, 3412-3442 (2006).
9. Fasan, R. Tuning P450 enzymes as oxidation catalysts. *ACS Catalysis* 2, 647-666 (2012).
10. Jung, S. T., Lauchli, R. & Arnold, F. H. Cytochrome P450: Taming a wild type enzyme. *Current Opinion in Biotechnology* 22, 809-817 (2011).
11. Braun, A. et al. MuteinDB: The mutein database linking substrates, products and enzymatic reactions directly with genetic variants of enzymes. *Database* (2012). doi: 10.1093/database/bas028

VI. Evolving Optogenetic Actuators: Photoswitchable Constructs.

A. Optical Control with Red and Infrared Light.

Contemporary efforts for using light to control enzyme activity have relied on at least two optogenetic actuators: LOV2, which has terminal helices that are destabilized by blue light (~450 nm)[2,18,48], and Dronpa, which switches from a dimer to a monomer in response to green light (~500 nm)[19]. Unfortunately, blue and green light suffer from problems of phototoxicity, penetration depth, and spectral similarity that limit their use in signaling studies[21]. Thus, in one embodiment, photoswitchable enzymes stimulated by red or infrared light are contemplated for development. These wavelengths have lower phototoxicities and greater penetration depths than blue and green light[20,21], and will permit multi-color actuation alongside blue or green light.

B. An Operon to Evolve Photoswitchable Constructs.

Figure 3A:
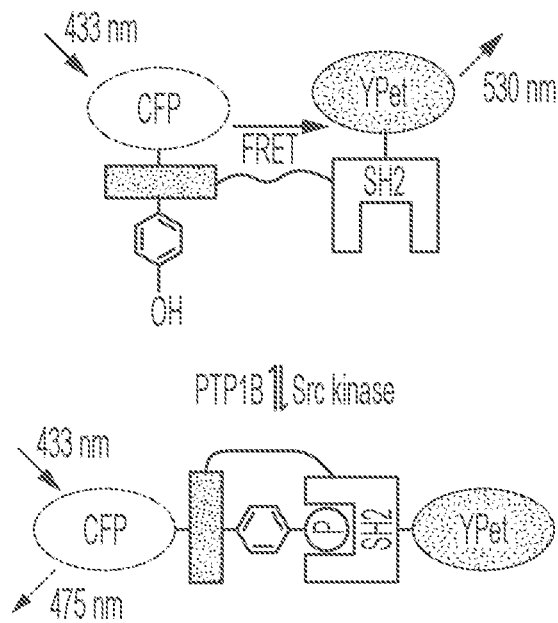
FIG. 3A-D demonstrates exemplary Fluorescence-based Biosensors having PTP1B activity.
Figure 3B:
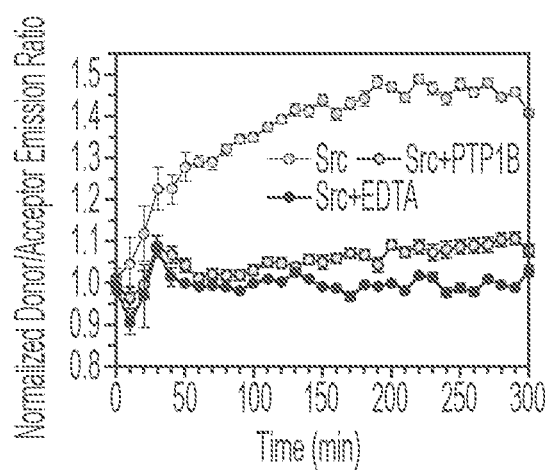
Figure 3C:
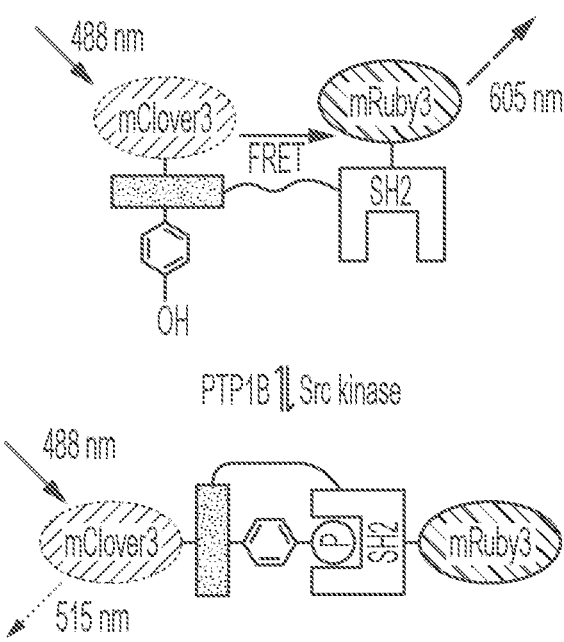
Figure 3D:
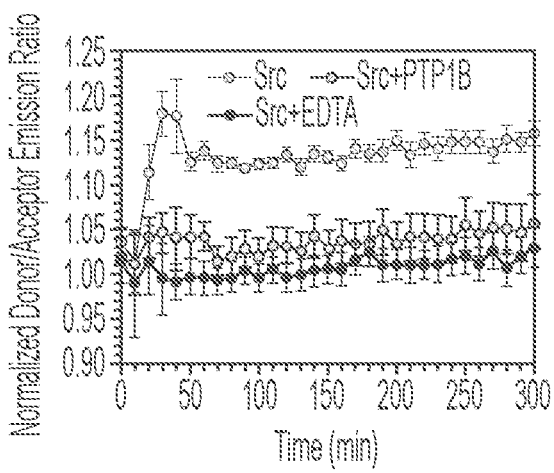
Figure 4A:
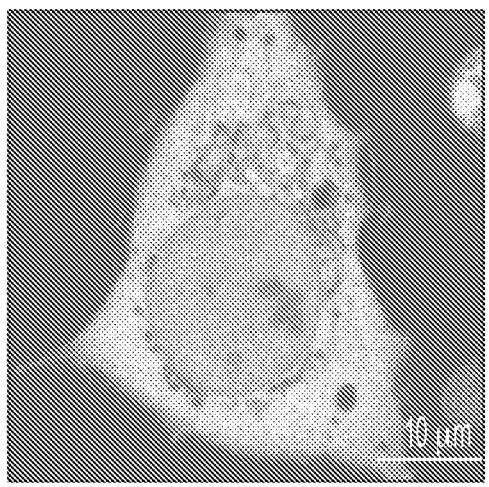
FIG. 4A-H demonstrates exemplary Evidence of phosphatase activity within living cells using photoconstructs and fluorescent tags.
Figure 4B:
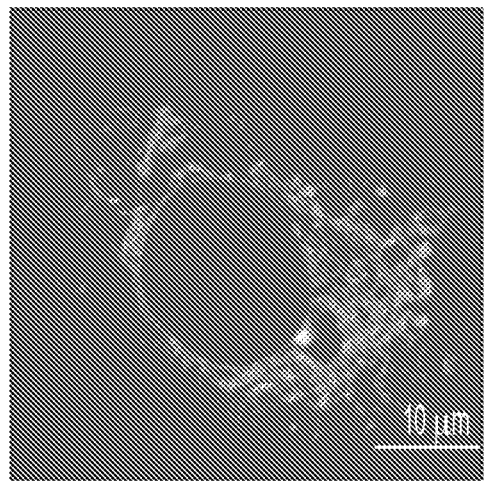
Figure 4C:
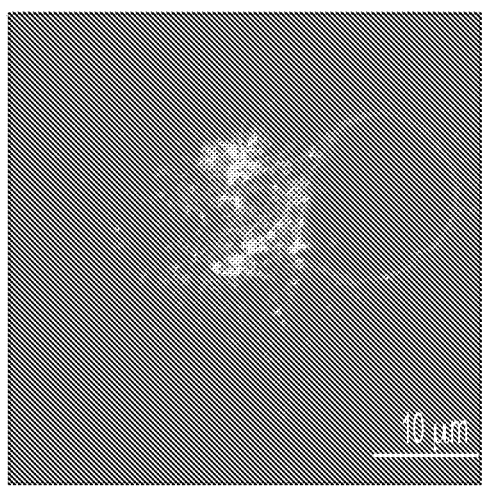
Figure 4D:
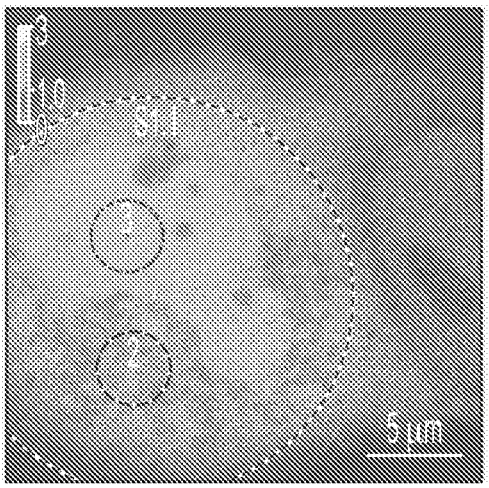
Figure 4E:
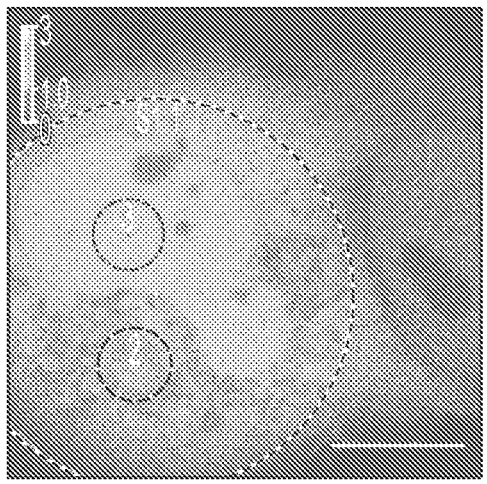
Figure 4F:
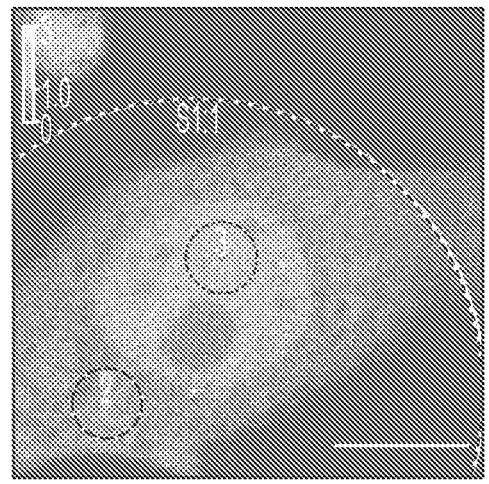
Figure 4G:
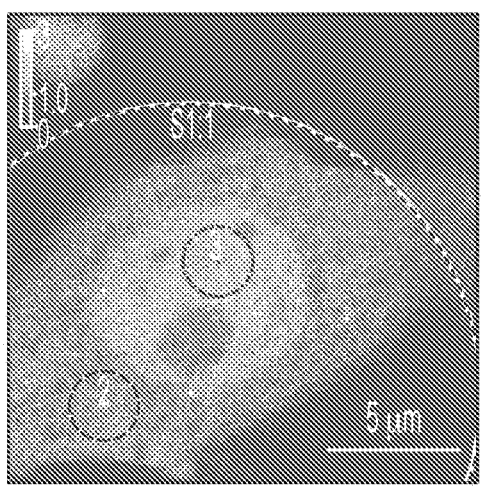
Figure 4H:
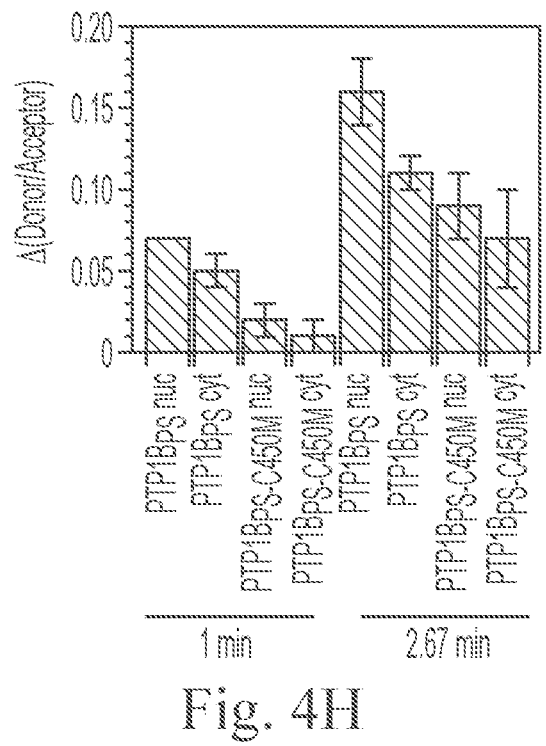

In one embodiment, an operon that links the activity of PTP1B to cell growth is contemplated. In brief, this operon is based on the following control strategy (some additional details in FIG. 10): A kinase stimulates the binding of two proteins, which in turn, promote transcription of an essential gene; PTP1B suppresses the binding of these two proteins and, thus, inhibits transcription. This operon allows cells in possession of photoswitchable variants of PTP1B to grow faster in the presence of one light source than in the present of another (e.g., 750 nm vs. 650 nm). The difference in growth rates enables the identification of functional chimeras. Initial experiments with an operon based on Lux-based luminescence (based on a system developed by Liu and colleagues[53]) show a 20-fold difference in luminescence between a strain expressing two model binding partners and a strain expressing one (FIG. 3E). We will continue to develop this operon by adding a protein-protein interaction that is modulated by a PTP and PTK (see below).

This operon allows cells in possession of photoswitchable variants of PTP1B to grow faster in the presence of one light source than in the present of another (e.g., 750 nm vs. 650 nm). The difference in growth rates enables the identification of functional chimeras. Initial experiments with an operon based on Lux-based luminescence (based on a system developed by Liu and colleagues 53) show a 20-fold difference in luminescence between a strain expressing two model binding partners and a strain expressing one (FIG. 3E). We will continue to develop this operon by adding a protein-protein interaction that is modulated by a PTP and PTK.

FRET sensors. We will use Forster resonance energy transfer (FRET) to monitor the activity of PTP1B in living cells. Our preliminary sensor exhibits a 20% reduction in FRET signal when treated with Src kinase (FIG. 3F). Previous imaging studies indicate that a 20% change in FRET is sufficient to monitor intracellular kinase activity54"56. To enhance spatial resolution in imaging studies, we will attempt to optimize our sensor further (and use it to measure the activity of PTP1B in vitro).

1. To Evolve Phosphatases and Kinases Modulated by Red and Infrared Light.

This section uses directed evolution to build enzymes that can be turned "on" and "off" with red and infrared light. We will know that we are successful when we have (i) built a genetic operon that links the activity of PTP1B to antibiotic resistance, (ii) A used that operon to build a PTP1B-phytochrome chimera that exhibits a three- to ten-fold change in activity in response to red and infrared light, and (iii) built similar phytochrome chimeras of STEP and PTK6.

Hypothesis. Phytochrome proteins exhibit global conformational changes when exposed to red and infrared light[27, 28], but to date, have eluded rational integration into photoswitchable enzymes. We hypothesize that a genetic operon that links PTP or PTK activity to cell growth will enable the evolution of PTP- or PTK-phytochrome chimeras stimulated by red or infrared light.

Experimental approach: We will build an operon that links PTP1B inhibition to antibiotic resistance, and we will use that operon to evolve photoswitchable PTP1B-phytochrome chimeras. This effort will involve (i) the construction a library of PTP1B-phytochrome chimeras that differ in linker composition and/or linker length, (ii) the use of our operon to screen that library for functional mutants, (iii) a kinetic and biostructural characterization of the most photoswitchable mutants, and (iv) the extension of this approach to STEP and PTK6. This effort has two major goals: a variant of PTP1B modulated by red and/or infrared light, and a general approach for using directed evolution to extend optical control to new enzymes and different wavelengths of light.

2. Development of a Synthetic Operon for Evolving PTP1B-Phytochrome Chimeras.

We will build a variant of PTP1B that can be modulated by red and infrared light by attaching its C-terminal a-helix to the N-terminal a-helix of bacterial phytochrome protein 1 (BphP1) from *Rhodopseudomonas palustris* (FIG. 9); this protein undergoes a reversible conformational change when exposed to 650 nm and 750 nm light. Phytochromes such as BphP1 are valuable for photocontrol because they can be actively toggled between conformations (i.e., turned "on" and "off"). Their structures, however, are not compatible with cage-based actuation (they do not undergo large-scale "unwinding"); they have, thus, been overlooked in previous efforts to develop photoswitchable enzymes.

We will evolve photoswitchable PTP1B-BphP1 chimeras by using a genetic operon that links PTP1B activity to antibiotic resistance. This operon will consist of six components (FIG. 10A-B): (i) a PTP1B substrate domain tethered to a DNA-binding protein, (ii) a substrate recognition domain (i.e., a substrate homology 2 domain, or SH2) tethered to the subunit of an RNA polymerase, (iii) an Src kinase (a kinase capable of phosphorylating a wide range of substrates), (iv) PTP1B (or a potentially photoswitchable variant of PTP1B), (v) a gene for antibiotic resistance, and (vi) an operator for that gene.

With this system, light-induced inactivation of PTP1B will enable transcription of the gene for antibiotic resistance. Previous groups have used similar operons to evolve protein-protein binding partners (our system is based on an operon used by Liu et al. to evolve insecticidal proteins[53]); here, we take the additional (new) steps of (i) using a protein-protein interaction mediated by enzymes (phosphatases and kinases) and (ii) screening that interaction in the presence and absence of light.

We have begun to develop our operon by using a Lux-based luminescence as an output. Preliminary results show that model protein-protein binding partners can elicit a 20-fold change in luminescence (FIG. 3E). We plan to swap out these binding partners with substrate and SH2 domains, and test the new system alongside simultaneously expressed PTP1B and Src kinase (which have some complementary activities, and can be expressed in *E. coli*[68,69]).

Figure 5B:
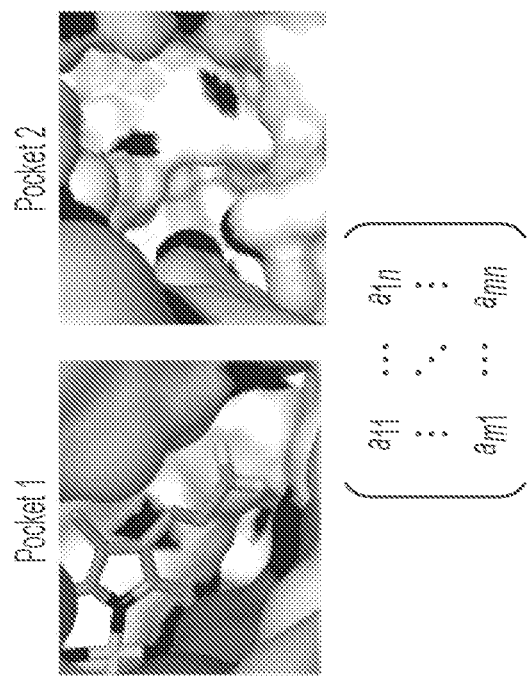
FIG. 5A-C illustrates embodiments of drug discovery.
Figure 5C:
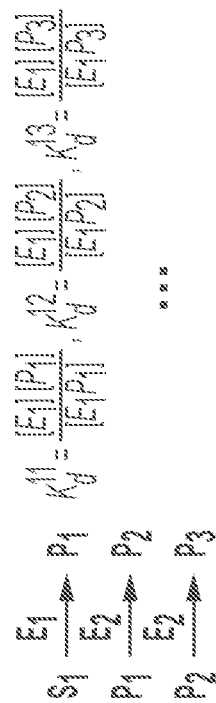
Figure 5A:
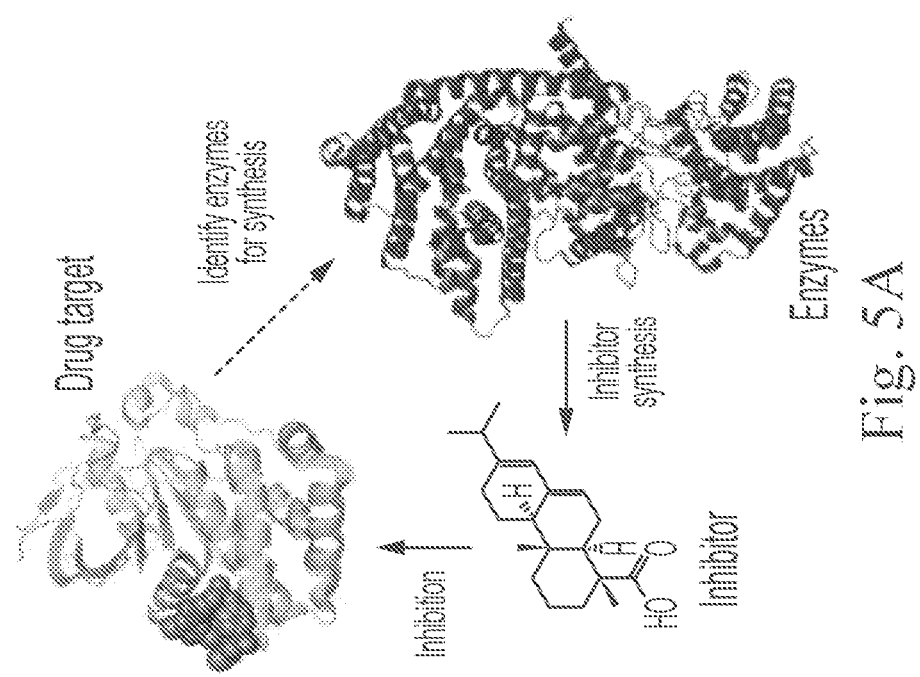

Advantages of using operons expressing photosensitive phosphatases includes but is not limited to enabling high-throughput screens of mutants of photoswitchable enzymes and provides a method for screening the libraries of enzymes that they motivate, see, FIG. 5A for example. In contrast, have shown that mutagenesis a photoswitchable enzyme can adjust (i.e., improve) its dynamic range (i.e., ratio of dark-state activity to light-state activity); while some published studies, such as WO2011002977. Genetically Encoded Photomanipulation Of Protein And Peptide Activity. Published Jan. 6, 2011, have proposed, but not shown, that mutagenesis of protein light switches might enable spectral tuning of photoswitchable enzymes. WO2011002977, provides a list of sites that could be mutated to modify the flavin-binding pocket of LOV2 to accept flavins that absorb light at alternative wavelengths. However, their construct is described as a LOV2 domain of *Avena sativa* (oat) phototropin 1 (404-546), including the C-terminal helical extension J alpha where Ja unwinds instead of the A alpha helix described herein. Nonetheless, there is no available method for carrying out high-throughput screens of mutants with modified binding pockets for which the invention described herein provides a platform for doing so. Further, in contrast to WO2013016693. "Near-infrared light-activated proteins." Publication Date Jan. 31, 2013, inventions described herein provide a platform for screening potentially improved/modified variants of photoswitchable proteins, such as a plant phototropin 1 LOV2.

Additionally, methods for screening the libraries of enzymes enable the detection of (i) molecules or (ii) photoswitchable domains that change the activity of any enzyme that, in turn, can modulate the affinity, or outcome associated with, a protein-protein interaction: protein tyrosine phosphatase (PTPs) and protein tyrosine kinases (PTKs) are demonstrated. Moreover, proteases are contemplated as proteins to add to this system.

C. Directed Evolution.

We will build libraries of PTP1B-BphP1 chimeras by pairing overlap extension PCR (oePCR) with error-prone PCR (epPCR). Specifically, we will use oePCR to build chimeras that differ in linker length (here, we define the linker as the ~20 residue region comprised of the C-terminal a-helix of PTP1B and the N-terminal a-helix of BphP1), and we will use epPCR to vary linker composition. Depending on the results of this initial library, we may extend error-prone PCR into the BphP1 gene, but we will not mutate PTP1B beyond its C-terminal a-helix.

Figure 11B:
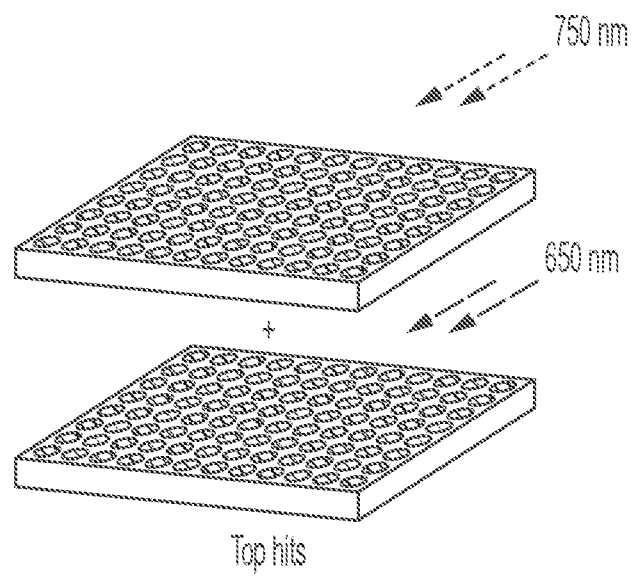

In the presence of a small amount of antibiotic (i.e. an amount that impedes the growth of *E. coli*), our genetic operon will cause cells that contain functional PTP1B-BphP1 chimeras to exhibit different growth rates under red and infrared light. We will exploit these differences to identify cells that harbor photoswitchable constructs. In brief, we will (i) generate two replicate plates of cell colonies, (ii) grow one under red light and one under infrared light (FIG. 11A), and (iii) select a subset of colonies (top hits) that show differential growth. We will further characterize our top hits by growing them in small-scale liquid cultures (e.g., 96-well plates with ~1 ml/well; FIG. 11B) under red and infrared light, and by sequencing the PTP1B-BphP1 genes of colonies that show the greatest different in growth rates.

We will attempt to build enzyme-phytochrome chimeras of STEP and PTK6 by pursuing two strategies: (i) We will replace PTP1B in our final PTP1B-BphP1 chimera with STEP or PTK6; this strategy will allow us to assess the modularity of our final design, (ii) We will use our operon-based approach to evolve functional STEP-BphP1 and PTK6-BphP1 chimeras; this strategy will allow us to assess the generalizability of our approach to evolution.

Operons for evolving STEP-BphP1 and PTK6-BphP1 chimeras will closely resemble the PTP IB-specific operon. For STEP, we will use a STEP-specific substrate and SH2 domain (Src kinase, which has a broad substrate specificity, is likely to have complementary activities on a subset of STEP substrates); for PTK6, we will use a recognition process that is inhibited—not activated—by phosphorylation (here, we can use PTP1B$_{WT}$ as the complementary enzyme).

D. Extension of Approach.

We will attempt to build enzyme-phytochrome chimeras of STEP and PTK6 by pursuing two strategies: (i) We will replace PTP1B in our final PTP1B-BphP1 chimera with STEP or PTK6; this strategy will allow us to assess the modularity of our final design, (ii) We will use our operon-based approach to evolve functional STEP-BphP1 and PTK6-BphP1 chimeras; this strategy will allow us to assess the generalizability of our approach to evolution.

Operons for evolving STEP-BphP1 and PTK6-BphP1 chimeras will closely resemble the PTP IB-specific operon. For STEP, we will use a STEP-specific substrate and SH2 domain (Src kinase, which has a broad substrate specificity, is likely to have complementary activities on a subset of STEP substrates); for PTK6, we will use a recognition process that is inhibited—not activated—by phosphorylation (here, we can use PTP1BWT as the complementary enzyme)

F. Exemplary Contemplated Characterization: Biophysical Characterization of Enzyme-Phytochrome Chimeras.

We will examine the structural basis of photocontrol in the most photo switchable chimeras by using a subset of crystallographic and kinetic analyses. X-ray crystal structures will show how BphP1 affects the structures of PTP1B, STEP, and PTK6. Kinetic studies will show how BphP1 affects substrate specificity and binding affinity (or more specifically, Km, which is affected by binding affinity).

TABLE 1

Exemplary Promoters.

| Name | DNA Sequence | SEQ ID NO.# |
|---|---|---|
| Pro1 | TTCTAGAGCACAGCTAACACCACGTCGTCCCTATCTGCTGCCCTAGGTCTA TGAGTGGTTGCTGGATAACTTTACGGGCATGCATAAGGCTCGGTATCTATA TTCAGGGAGACCACAACGGTTTCCCTCTACAAATAATTTTGTTTAACTTTT ACTAGAG | SEQ ID NO. 25 |
| ProD | GCACAGCTAACACCACGTCGTCCCTATCTGCTGCCCTAGGTCTATGAGTGG TTGCTGGATAACTTTACGGGCATGCATAAGGCTCGTATAATATATTCAGGG AGACCACAACGGTTTCCCTCTACAAATAATTTTGTTTAACTTTTACTAGAG | SEQ ID NO. 26 |
| pBAD | AGAAACCAATTGTCCATATTGCATCAGACATTGCCGTCACTGCGTCTTTTA CTGGCTCTTCTCGCTAACCAAACCGGTAACCCCGCTTATTAAAAGCATTCT GTAACAAAGCGGGACCAAAGCCATGACAAAAACGCGTAACAAAAGTGTC TATAATCACGGCAGAAAAGTCCACATTGATTATTTGCACGGCGTCACACTT TGCTATGCCATAGCATTTTTATCCATAAGATTAGCGGATCCTACCTGACGC TTTTTATCGCAACTCTCTACTGTTTCTCCATACCCGTTTTTTGGGCTAGC | SEQ ID NO. 27 |
| pLacZOpt (cI operate bolded) | ACAAGAAAGTTTGTTCATTAGGCACCCCGGGCTTTACTCGTAAAGCTTCC GGCGCGTATGTTGTGTCGACCG | SEQ ID No. 28 |
| pTrc | CGACTGCACGGTGCACCAATGCTTCTGGCGTCAGGCAGCCATCGGAAGCT GTGGTATGGCTGTGCAGGTCGTAAATCACTGCATAATTCGTGTCGCTCAAG GCGCACTCCCGTTCTGGATAATGTTTTTTGCGCCGACATCATAACGGTTCT GGCAAATATTCTGAAATGAGCTGTTGACAATTAATCATCCGGCTCGTATAA TGTGTGGAATTGTGAGCGGATAACAATTTCACACAGGAAACAG | SEQ ID No. 29 |
| T7 | CCTATAGTGAGTCGTATTA | SEQ ID No. 30 |

TABLE 2

Exemplary Ribosome Binding Sites.

| Name | DNA Sequence | SEQ ID NO. # |
|---|---|---|
| proRBS | TTAAAGAGGAGAAAGGTC | SEQ ID NO. 31 |
| Sal28 RBS | CGAAAAAAAGTAAGGCGGTAATCC | SEQ ID NO. 32 |
| bb034 RBS | TGCAGAAAGAGGAGAAATACTAG | SEQ ID NO. 33 |
| bb030 | ATTAAAGAGGAGAAATACTAG | SEQ ID No. 34 |
| RBS for GOI in B2H | GTGCAGTAAGGAGGAAAAAAAA | SEQ ID No. 35 |
| bbAH | GCTAGCTTTAAGAAGGAGATATACC | SEQ ID No. 36 |

TABLE 3

Exemplary Protein Sequences (includes truncations).

| Name | Amino Acid Sequence | SEQ ID NO.# |
| --- | --- | --- |
| RpoZ (linker bolded) | MARVTVQDAVEKIGNRFDLVLVAARRARQMQVGGKDPLVPEENDKTTV IALREIEEGLINNQILDVRERQEQQEQEAAELQAVTAIAEGRRAAA | SEQ ID NO. 37 |
| cI (linker bolded) | MSISSRVKSKRIQLGLNQAELAQKVGTTQQSIEQLENGKTKRPRFLPELAS ALGVSVDWLLNGTSDSNVRFVGHVEPKGKYPLISMVRARSWCEACEPYD IKDIDEWYDSDVNLLGNGFWLKVEGDSMTSPVGQSIPEGHMVLVDTGRE PVNGSLVVAKLTDANEATFKKLVIDGGQKYLKGLNPSWPMTPINGNCKII GVVVEARVKFVDYKDDDDK | SEQ ID NO. 38 |
| SH2 | WYFGKITRRESERLLLNPENPRGTFLVRESETVKGAYALSVSDFDNAKGL NVKHYLIRKLDSGGFYITSRTQFSSLQQLVAYYSKHADGLCHRLTNVC | SEQ ID NO. 39 |
| Kras Substrate | WMEDYDYVHLQG | SEQ ID NO. 40 |
| MidT Substrate | EPQYEEIPIYL | SEQ ID NO. 41 |
| ShcA Substrate | DHQYYNDFPG | SEQ ID NO. 42 |
| EGFR Substrate | PQRYLVIQGD | SEQ ID NO. 43 |
| Src | MSKPQTQGLAKDAWEIPRESLRLEVKLGQGCFGEVWMGTWNGTTRVAI KTLKPGTMSPEAFLQEAQVMKKLRHEKLVQLYAVVSEEPIYIVTEYMSKG SLLDFLKGETGKYLRLPQLVDMAAQIASGMAYVERMNYVHRDLRAANIL VGENLVCKVADFGLARLIEDNEYTARQGAKFPIKWTAPEAALYGRFTIKS DVWSFGILLTELTTKGRVPYPGMVNREVLDQVERGYRMPCPPECPESLHD LMCQCWRKEPEERPTFEYLQAFLEDYFTSTEPQYQPGENL | SEQ ID NO. 44 |
| CDC37 | MVDYSVWDHIEVSDDEDETHPNIDTASLFRWRHQARVERMEQFQKEKEE LDRGCRECKRKVAECQRKLKELEVAEGGKAELERLQAEAQQLRKEERSW EQKLEEMRKKEKSMPWNVDTLSKDGFSKSMVNTKPEKTEEDSEEVREQK HKTFVEKYEKQIKHFGMLRRWDDSQKYLSDNVHLVCEETANYLVIWCID LEVEEKCALMEQVAHQTIVMQFILELAKSLKVDPRACFRQFFTKIKTADR QYMEGFNDELEAFKERVRGRAKLRIEKAMKEYEEEERKKRLGPGGLDPV EVYESLPEELQKCFDVKDVQMLQDAISKMDPTDAKYHMQRCIDSGLWVP NSKASEAKEGEEAGPGDPLLEAVPKTGDEKDVSV | SEQ ID NO. 45 |
| PTP1B | MEMEKEFEQIDKSGSWAAIYQDIRHEASDFPCRVAKLPKNKNRNRYRDV SPFDHSRIKLHQEDNDYINASLIKMEEAQRSYILTQGPLPNTCGHFWEMV WEQKSRGVVMLNRVMEKGSLKCAQYWPQKEEKEMIFEDTNLKLTLISED IKSYYTVRQLELENLTTQETREILHFHYTTWPDFGVPESPASFLNFLFKVRE SGSLSPEHGPVVHSSAGIGRSGTFCLADTCLLLMDKRKDPSSVDIKKVLL EMRKFRMGLIQTADQLRFSYLAVIEGAKFIMGDSSVQDQWKELSHEDLEP PPEHIPPPPRPPKRILEPHN | SEQ ID NO. 46 |
| MBP | MKIEEGKLVIWINGDKGYNGLAEVGKKFEKDTGIKVTVEHPDKLEEKFP QVAATGDGPDIIFWAHDRFGGYAQSGLLAEITPDKAFQDKLYPFTWDA VRYNGKLIAYPIAVEALSLIYNKDLLPNPPKTWEEIPALDKELKAKGKS ALMFNLQEPYFTWPLIAADGGYAFKYENGKYDIKDVGVDNAGAKAGL TFLVDLIKNKHMNADTDYSIAEAAFNKGETAMTINGPWAWSNIDTSKV NYGVTVLPTFKGQPSKPFVGVLSAGINAASPNKELAKEFLENYLLTDEG LEAVNKDKPLGAVALKSYEEELAKDPRIAATMENAQKGEIMPNIPQMS AFWYAVRTAVINAASGRQTVDEALKDAQTRITK | SEQ ID NO. 47 |
| LuxAB | MKFGNFLLTYQPPQFSQTEVMKRLVKLGRISEECGFDTVWLLEHHFTEF GLLGNPYVAAAYLLGATKKLNVGTAAIVLPTAHPVRQLEDVNLLDQM SKGRFRFGICRGLYNKDFRVFGTDMNNSRALAECWYGLIKNGMTEGYM EADNEHIKFHKVKVNPAAYSRGGAPVYVVAESASTTEWAAQFGLPMIL SWIINTNEKKAQLELYNEVAQEYGHDIHNIDHCLSYITSVDHDSIKAKEIC RKFLGHWYDSYVNATTIFDDSDQTRGYDFNKGQWRDFVLKGHKDTNRR IDYSYEINPVGTPQECIDIIQKDIDATGISNICCGFEANGTVDEIIASMKLFQ SDVMPFLKEKQRSLLYYGGGGSGGGGSGGGGSGGGGSKFGLFFLNFINS TTVQEQSIVRMQEITEYVDKLNFEQILVYENHFSDNGVVGAPLTVSGFLL GLTEKIKIGSLNHIITTHHPVRIAEEEACLLDQLSEGRFILGFSDCEKKDEMH FFNRPVEYQQQLFEECYEIIINDALTTGYCNPDNDFYSFPKISVNPHAYTPG GPRKYVTATSHHIVEWAAKKGIPLIFKWDDSNDVRYEYAERYKAVADKY DVDLSEIDHQLMILVNYNEDSNKAKQETRAFISDYVLEMHPNENFENKLE EIIIAENAVGNYTECITAAKLAIEKCGAKSVLLSFEPMNDLMSQKNVINIV DDNIKKYHTEYT | SEQ ID NO. 48 |

TABLE 3-continued

Exemplary Protein Sequences (includes truncations).

| Name | Amino Acid Sequence | SEQ ID NO.# |
| --- | --- | --- |
| SpecR | MREAVIAEVSTQLSEVVGVIERHLEPTLLAVHLYGSAVDGGLKPHSDIDL LVTVTVRLDETTRRALINDLLETSASPGESEILRAVEVTIVVHDDIIPWRY PAKRELQFGEWQRNDILAGIFEPATIDIDLAILLTKAREHSVALVGPAAE ELFDPVPEQDLFEALNETLTLWNSPPDWAGDERNVVLTLSRIWYSAVTG KIAPKDVAADWAMERLPAQYQPVILEARQAYLGQEEDRLASRADQLEE FVHYVKGEITKVVGK | SEQ ID NO. 49 |
| AgAs | MVKREFPPGFWKDDLIDSLTSSHKVAASDEKRIETLISEIKNMFRCMGY GETNPSAYDTAWVARIPAVDGSDNPHFPETVEWILQNQLKDGSWGEG FYFLAYDRILATLACIITLTLWRTGETQVQKGIEFFRTQAGKMEDEADSH RPSGFEIVFPAMLKEAKILGLDLPYDLPFLKQIIEKREAKLKRIPTDVLYA LPTTLLYSLEGLQEIVDWQKIMKLQSKDGSFLSSPASTAAVFMRTGNKKC LDFLNFVLKKFGNHVPCHYPLDLFERLWAVDTVERLGIDRHFKEEIKEAL DYVYSHWDERGIGWARENPVPDIDDTAMGLRILRLHGYNVSSDVLKTFR DENGEFFCFLGQTQRGVTDMLNVNRCSHVSFPGETIMEEAKLCTERYLRN ALENVDAFDKWAPKKNIRGEVEYALKYPWHKSMPRLEARSYIENYGPDD VWLGKTVYMMPYISNEKYLELAKLDFNKVQSIHQTELQDLRRWWKSSGF TDLNFTRERVTEIYFSPASFIFEPEFSKCREVYTKTSNFTVILDDLYDAHGSL DDLKLFTESVKRWDLSLVDQMPQQMKICFVGFYNTFNDIAKEGRERQGR DVLGYIQNVWKVQLEAYTKEAEWSEAKYVPSFNEYIENASVSIALGTVVL ISALFTGEVLTDEVLSKIDRESRFLQLMGLTGRLVNDTKTYQAERGQGEV ASAIQCYMKDHPKISEEEALQHVYSVMENALEELNREFVNNKIPDIYKRL VFETARIMQLFYMQGDGLTLSHDMEIKEHVKNCLFQPVA | SEQ ID NO. 50 |
| GGPPS | MFDFNEYMKSKAVAVDAALDKAIPLEYPEKIHESMRYSLLAGGKRVRPA LCIAACELVGGSQDLAMPTACAMEMIHTMSLIHDDLPCMDNDDFRRGKP TNHKVFGEDTAVLAGDALLSFAFEHIAVATSKTVPSDRTLRVISELGKTIG SQGLVGGQVVDITSEGDANVDLKTLEWIHIHKTAVLLECSVVSGGILGGA TEDEIARIRRYARCVGLLFQVVDDILDVTKSSEELGKTAGKDLLTDKATYP KLMGLEKAKEFAAELATRAKEELSSFDQIKAAPLLGLADYIAFRQN | SEQ ID NO. 51 |
| P450 | MTIKEMPQPKTFGELKNLPLLNTDKPVQALMKIADELGEIFKFEAPGRVIR YLSSQRLIKEACDESRFDKNLSQALKFVRDFAGDGLFTSWTHEKNWKKA HNILLPSFSQQAMKGYHAMMVDIAVQLVQKWERLNADEHIEVPEDMTRL TLDTIGLCGFNYRFNSFYRDQPHPFITSMVRALDEAMNKLQRANPDDPAY DENKRQFQEDIKVMNDLVDKIIADRKASGEQSDDLLTHMLNGKDPETGEP LDDENIRYQIITFLIAGHETTSGLLSFALYFLVKNPHVLQKAAEEAARVLV DPVPSYKQVKQLKYVGMVLNEALRLWPTAPAFSLYAKEDTVLGGEYPLE KGDELMVLIPQLHRDKTIWGDDVEEFRPERFENPSAIPQHAFKPFGNGQR ACIGQQFALHEATLVLGMMLKHFDFEDHTNYELDIKETLTLKPEGFVVKA KSKKIPLGGIPSPSTEQSAKKVRKKAENAHNTPLLVLYGSNMGTAEGTAR DLADIAMSKGFAPQVATLDSHAGNLPREGAVLIVTASYNGHPPDNAKQF VDWLDQASADEVKGVRYSVFGCGDKNWATTYQKVPAFIDETLAAKGAE NIADRGEADASDDFEGTYEEWREHMWSDVAAYFNLDIENSEDNKSTLSL QFVDSAADMPLAKMHGAFSTNVVASKELQQPGSARSTRHLEIELPKEASY QEGDHLGVIPRNYEGIVNRVTARFGLDASQQIRLEAEEEKLAHLPLAKTVS VEELLQYVELQDPVTRTQLRAMAAKTVCPPHKVELEALLEKQAYKEQVL AKRLTMLELLEKYPACEMKFSEFIALLPSIRPRYYSISSSPRVDEKQASITVS VVSGEAWSGYGEYKGIASNYLAELQEGDTITCFISTPQSEFTLPKDPETPLI MVGPGTGVAPFRGFVQARKQLKEQGQSLGEAHLYFGCRSPHEDYLYQEE LENAQSEGIITLHTAFSRMPNQPKTYVQHVMEQDGKKLIELLDQGAHFYI CGDGSQMAPAVEATLMKSYADVHQVSEADARLWLQQLEEKGRYAKDV WAG | SEQ ID NO. 52 |
| LOV2 | AATLERIEKNFVITDPRLPDNPIIFASDSFLQLTEYSREEILGRNCRFLQGPET DRATVRKIRDAIDNQTEVTVQLINYTKSGKKFWNLFHLQPMRDQKGDVQ YFIGVQLDGTEHVRDAAEREGVMLIKKTAENIDEAAKEL | SEQ ID NO. 53 |
| BphP1 | MASVAGHASGSPAFGTADLSNCEREEIHLAGSIQPHGALLVVSEPDHRIIQ ASANAAEFLNLGSVLGVPLAEIDGDLLIKILPHLDPTAEGMPVAVRCRIGN PSTEYDGLMHRPPEGGLIIELERAGPPIDLSGTLAPALERIRTAGSLRALCD DTALLFQQCTGYDRVMVYRFDEQGHGEVFSERHVPGLESYFGNRYPSSDI PQMARRLYERQRVRVLVDVSYQPVPLEPRLSPLTGRDLDMSGCFLRSMSP IHLQYLKNMGVRATLVVSLVVGGKLWGLVACHHYLPRFMHFELRAICEL LAEAIATRITALESFAQSQSELFVQRLEQRMIEAITREGDWRAAIFDTSQSIL QPLHAAGCALVYEDQIRTIGDVPSTQDVREIAGWLDRQPRAAVTSTASLG LDVPELAHLTRMSGVVAAPISDHRGEFLMWFRPERVHTVTWGGDPKKP FTMGDTPADLSPRRSFAKWHQVVEGTSDPWTAADLAAARTIGQTVADIV LQFRAVRTLIAREQYEQFSSQVHASMQPVLITDAEGRILLMNDSFRDMLP AGSPSAVHLDDLAGFFVESNDFLRNVAELIDHGRGWRGEVLLRGAGNRP LPLAVRADPVTREDQSLGFVLIFSDATDRRTADAARTRFQEGILASARPG VRLDSKSDLLHEKLLSALVENAQLAALEITYGVETGRIAELLEGVRQSML RTAEVLGHLVQHAARTAGSDSSNGSQNKKEFDSAGSAGSAGTS | SEQ ID NO. 54 |

TABLE 3-continued

Exemplary Protein Sequences (includes truncations).

| Name | Amino Acid Sequence | SEQ ID NO.# |
|---|---|---|
| TC-PTP | MGMPTTIEREFEELDTQRRWQPLYLEIRNESHDYPHRVAKFPENRNRNRY RDVSPYDHSRVKLQNAENDYINASLVDIEEAQRSYILTQGPLPNTCCHFW LMVWQQKTKAVVMLNRIVEKESVKCAQYWPTDDQEMLFKETGFSVKLL SEDVKSYYTVHLLQLENINSGETRTISHFHYTTWPDFGVPESPASFLNFLFK VRESGSLNPDHGPAVIHCSAGIGRSGTFSLVDTCLVLMEKGDDINIKQVLL NMRKYRMGLIQTPDQLRFSYMAIIEGAKCIKGDSSIQKRWKELS | SEQ ID No. 55 |
| PTP1B$_{1-435}$ | MEMEKEFEQIDKSGSWAAIYQDIRHEASDFPCRVAKLPKNKNRNRYRDV SPFDHSRIKLHQEDNDYINASLIKMEEAQRSYILTQGPLPNTCGHFWEMV WEQKSRGVVMLNRVMEKGSLKCAQYWPQKEEKEMIFEDTNLKLTLISED IKSYYTVRQLELENLTTQETREILHFHYTTWPDFGVPESPASFLNFLFKVRE SGSLSPEHGPVVVHCSAGIGRSGTFCLADTCLLLMDKRKDPSSVDIKKVLL EMRKFRMGLIQTADQLRFSYLAVIEGAKFIMGDSSVQDQWKELSHEDLEP PPEHIPPPPRPPKRILEPHNGKCREFFPNHQWVKEETQEDKDCPIKEEKGSP LNAAPYGIESMSQDTEVRSRVVGGSLRGAQAASPAKGEPSLPEKDEDHAL SYWKPFLVNMCVATVLTAGAYLCYRFLFNSNT | SEQ ID No. 56 |
| SacB | MNIKKFAKQATVLTFTTALLAGGATQAFAKETNQKPYKETYGISHITRHD MLQIPEQQKNEKYQVPEFDSSTIKNISSAKGLDVWDSWPLQNADGTVAN YHGYHIVFALAGDPKNADDTSIYMFYQKVGETSIDSWKNAGRVFKDSDK FDANDSILKDQTQEWSGSATFTSDGKIRLFYTDFSGKHYGKQTLTTAQVN VSASDSSLNINGVEDYKSIFDGDGKTYQNVQQFIDEGNYSSGDNHTLRDP HYVEDKGHKYLVFEANTGTEDGYQEESLFNKAYYGKSTSFFRQESQKL LQSDKKRTAELANGALGMIELNDDYTLKKVMKPLIASNTVTDEIERANVF KMNGKWYLFTDSRGSKMTIDGITSNDIYMLGYVSNSLTGPYKPLNKTGL VLKMDLDPNDVTFTYSHFAVPQAKGNNVVITSYMTNRGFYADKQSTFAP SFLLNIKGKKTSVVKDSILEQGQLTVNK | SEQ ID No. 57 |
| GalK | MSLKEKTQSLFANAFGYPATHTIQAPGRVNLIGEHTDYNDGFVLPCAIDY QTVISCAPRDDRKVRVMAADYENQLDEFSLDAPIVAHENYQWANYVRG VVKHLQLRNNSFGGVDMVISGNVPQGAGLSSSASLEVAVGTVLQQLYHL PLDGAQIALNGQEAENQFVGCNCGIMDQLISALGKKDHALLIDCRSLGTK AVSMPKGVAVVIINSNFKRTLVGSEYNTRREQCETGARFFQQPALRDVTIE EFNAVAHELDPIVAKRVRHILTENARTVEAASALEQGDLKRMGELMAES HASMRDDFEITVPQIDTLVEIVKAVIGDKGGVRMTGGGFGGCIVALIPEEL VPAVQQAVAEQYEAKTGIKETFYVCKPSQGAGQC | SEQ ID No. 58 |
| GHS | MAQISESVSPSTDLKSTESSITSNRHGNMWEDDRIQSLNSPYGAPAYQERS EKLIEEIKLLFLSDMDDSCNDSDRDLIKRLEIVDTVECLGIDRHFQPEIKLAL DYVYRCWNERGIGEGSRDSLKKDLNATALGFRALRLHRYNVSSGVLENF RDDNGQFFCGSTVEEEGAEAYNKHVRCMLSLSRASNILFPGEKVMEEAK AFTTNYLKKVLAGREATHVDESLLGEVKYALEFPWHCSVQRWEARSFIEI FGQIDSELKSNLSKKMLELAKLDFNILQCTHQKELQIISRWFADSSIASLNF YRKCYVEFYFWMAAAISEPEFSGSRVAFTKIAILMTMLDDLYDTHGTLDQ LKIFTEGVRRWDVSLVEGLPDFMKIAFEFWLKTSNELIAEAVKAQGQDMA AYIRKNAWERYLEAYLQDAEWIATGHVPTFDEYLNNGTPNTGMCVLNLI PLLLMGEHLPIDILEQIFLPSRFHHLIELASRLVDDARDFQAEKDHGDLSCIE CYLKDHPESTVEDALNHVNGLLGNCLLEMNWKFLKKQDSVPLSCKKYSF HVLARSIQFMYNQGDGFSISNKVIKDQVQKVLIVPVPI* | SEQ ID No. 59 |
| ADS | MALTEEKPIRPIANFPPSIWGDQFLIYEKQVEQGVEQIVNDLKKEVRQLLK EALDIPMKHANLLKLIDEIQRLGIPYHFEREIDHALQCIYETYGDNWNGDR SSLWFRLMRKQGYYVTCDVFNNYKDKNGAFKQSLANDVEGLLELYEAT SMRVPGEIILEDALGFTRSRLSIMTKDAFSTNPALFTEIQRALKQPLWKRLP RIEAAQYIPFYQQQDSHNKTLLLKLAKLEFNLLQSLHKEELSHVCKWWKAF DIKKNAPCLRDRIVECYFWGLGSGYEPQYSRARVFFTKAVAVITLIDDTYD AYGTYEELKIFTEAVERWSITCLDTLPEYMKPIYKLFMDTYTEMEEFLAKE GRTDLFNCGKEFVKEFVRNLMVEAKWANEGHIPTTEEHDPVVIITGGANL LTTTCYLGMSDIFTKESVEWAVSAPPLFRYSGILGRRLNDLMTHKAEQER KHSSSSLESYMKEYNVNEEYAQTLIYKEVEDVWKDINREYLTTKNIPRPLL MAVIYLCQFLEVQYAGKDNFTRMGDEYKHLIKSLLVYPMSI* | SEQ ID No. 60 |
| TXS | MSSSTGTSKVVSETSSTIVDDIPRLSANYHGDLWHHNVIQTLETPFRESSTY QERADELVVKIKDMFNALGDGDISPSAYDTAWVARLATISSDGSEKPRFP QALNWVFNNQLQDGSWGIESHFSLCDRLLNTTNSVIALSVWKTGHSQVQ QGAEFIAENLRLLNEEDELSPDFQIIFPALLQKAKALGINLPYDLPFIKYLST TREARLTDVSAAADNIPANMLNALEGLEEVIDWNKIMRFQSKDGSFLSSP ASTACVLMNTGDEKCFTFLNNLLDKFGGCVPCMYSIDLLERLSLVDNIEH LGIGRHFKQEIKGALDYVYRHWSERGIGWGRDSLVPDLNTTALGLRTLR MHGYNVSSDVLNNFKDENGRFFSSAGQTHVELRSVVNLFRASDLAFPDE RAMDDARKFAEPYLREALATKISTNTKLFKEIEYVVEYPWHMSIPRLEAR SYIDSYDDNYVWQRKTLYRMPSLSNSKCLELAKLDFNIVQSLHQEELKLL TRWWKESGMADINFTRHRVAEVYFSSATFEPEYSATRIAFTKIGCLQVLFD DMADIFATLDELKSFTEGVKRWDTSLLHEIPECMQTCFKVWFKLMEEVN NDVVKVQGRDMLAHIRKPWELYFNCYVQEREWLEAGYIPTFEEYLKTYA | SEQ ID No. 61 |

TABLE 3-continued

Exemplary Protein Sequences (includes truncations).

| Name | Amino Acid Sequence | SEQ ID NO.# |
|------|---------------------|-------------|
| | ISVGLGPCTLQPILLMGELVKDDVVEKVHYPSNMFELVSLSWRLTNDTKT<br>YQAEKARGQQASGIACYMKDNPGATEEDAIKHICRVVDRALKEASFEYF<br>KPSNDIPMGCKSFIFNLRLCVQIFYKFIDGYGIANEEIKDYIRKVYIDPIQV* | |
| TC-PTP | MPTTIEREFEELDTQRRWQPLYLEIRNESHDYPHRVAKFPENRNRNRYRD<br>VSPYDHSRVKLQNAENDYINASLVDIEEAQRSYILTQGPLPNTCCHFWLM<br>VWQQKTKAVVMLNRIVEKESVKCAQYWPTDDQEMLFKETGFSVKLLSE<br>DVKSYYTVHLLQLENINSGETRTISHFHYTTWPDFGVPESPASFLNFLFKV<br>RESGSLNPDHGPAVIHCSAGIGRSGTFSLVDTCLVLMEKGDDINIKQVLLN<br>MRKYRMGLIQTPDQLRFSYMAIIEGAKCIKGDSSIQKRWKELSKEDLSPAF<br>DHSPNKIMTEKYNGNR | SEQ ID No. 62 |
| PTPN5 | MSSGVDLGTENLYFQSMSRVLQAEELHEKALDPFLLQAEFFEIPMNFVDP<br>KEYDIPGLVRKNRYKTILPNPHSRVCLTSPDPDDPLSSYINANYIRGYGGEE<br>KVYIATQGPIVSTVADFWRMVWQEHTPIIVMITNIEEMNEKCTEYWPEEQ<br>VAYDGVEITVQKVIHTEDYRLRLISLKSGTEERGLKHYWFTSWPDQKTPD<br>RAPPLLHLVREVEEAAQQEGPHCAPIIVHCSAGIGRTGCFIATSICCQQLRQ<br>EGVVDILKTTCQLRQDRGGMIQTCEQYQFVHHVMSLYEKQLSHQS* | SEQ ID No. 63 |
| PTPN6 | MVRWFHRDLSGLDAETLLKGRGVHGSFLARPSRKNQGDFSLSVRVGDQV<br>THIRIQNSGDFYDLYGGEKFATLTELVEYYTQQQGVVQDRDGTIIHLKYPL<br>NCSDPTSERWYHGHMSGGQAETLLQAKGEPWTFLVRESLSQPGDFVLSV<br>LSDQPKAGPGSPLRVTHIKVMCEGGRYTVGGLETFDSLTDLVEHFKKTGI<br>EEASGAFVYLRQPYYATRVNAADIENRVLELNKKQESEDTAKAGFWEEF<br>ESLQKQEVKNLHQRLEGQRPENKGKNRYKNILPFDHSRVILQGRDSNIPGS<br>DYINANYIKNQLLGPDENAKTYIASQGCLEATVNDFWQMAWQENSRVIV<br>MTTREVEKGRNKCVPYWPEVGMQRAYGPYSVTNCGEHDTTEYKLRTLQ<br>VSPLDNGDLIREIWHYQYLSWPDHGVPSEPGGVLSFLDQINQRQESLPHA<br>GPIIVHCSAGIGRTGTIIVIDMLMENISTKGLDCDIDIQKTIQMVRAQRSGM<br>VQTEAYKFIYVAIAQFIETTKKKLEVLQSQKGQESEYGNITYPPAMKNA<br>HAKASRTSSKHKEDVYENLHTKNKREEKVKKQRSADKEKSKGSLKRK* | SEQ ID No. 64 |
| PTPN11 | MTSRRWFHPNITGVEAENLLLTRGVDGSFLARPSKSNPGDFTLSVRRNGA<br>VTHIKIQNTGDYYDLYGGEKFATLAELVQYYMEHHGQLKEKNGDVIELK<br>YPLNCADPTSERWFHGHLSGKEAEKLLTEKGKHGSFLVRESQSHPGDFVL<br>SVRTGDDKGESNDGKSKVTHVMIRCQELKYDVGGGERFDSLTDLVEHYK<br>KNPMVETLGTVLQLKQPLNTTRINAAEIESRVRELSKLAETTDKVKQGFW<br>EEFETLQQQECKLLYSRKEGQRQENKNRYKNILPFDHTRVVLHDGDP<br>NEPVSDYINANIIMPEFETKCNNSKPKKSYIATQGCLQNTVNDFWRMVFQ<br>ENSRVIVMTTKEVERGKSKCVKYWPDEYALKEYGVMRVRNVKESAAHD<br>YTLRELKLSKVGQGNTERTVWQYHFRTWPDHGVPSDPGGVLDFLEEVHH<br>KQESIMDAGPVVVHCSAGIGRTGTFIVIDILIDIIREKGVDCDIDVPKTIQMV<br>RSQRSGMVQTEAYRFIYMAVQHYIETLQRRIEEEQKSKRKGHEYTNIKY<br>SLADQTSGDQSPLPPCTPTPPCAEMREDSARVYENVGLMQQQKSFR* | SEQ ID No. 65 |
| PTN12 | MEQVEILRKFIQRVQAMKSPDHNGEDNFARDFMRLRRLSTKYRTEKIYPT<br>ATGEKEENVKKNRYKDILPFDHSRVKLTLKTPSQDSDYINANFIKGVYGP<br>KAYVATQGPLANTVIDFWRMVWEYNVVIIVMACREFEMGRKKCERYWP<br>LYGEDPITFAPFKISCEDEQARTDYFIRTLLLEFQNESRRLYQFHYVNWPD<br>HDVPSSFDSILDMISLMRKYQEHEDVPICIHCSAGCGRTGAICAIDYTWNL<br>LKAGKIPEEFNVFNLIQEMRTQRHSAVQTKEQYELVHRAIAQLFEKQLQL<br>YEIHGAQKIADGVNEINTENMVSSIEPEKQDSPPPKPPRTRSCLVEGDAKEE<br>ILQPPEPHPVPPILTSPPSAFPTVTTVWQDNDRYHPKPVLQWFHQNNIQQT<br>STETIVNQQNFQGKMNQQLNR | SEQ ID No. 66 |
| PTPN22 | MDQREILQKFLDEAQSKKITKEEFANEFLKLKRQSTKYKADKTYPTTVAE<br>KPKNIKKNRYKDILPYDSRVELSLITSDEDSSYINANFIKGVYGPKAYIAT<br>QGPLSTTLLDFWRMIWEYSVLIIVMACMEYEMGKKKCERYWAEPGEMQ<br>LEFGPFSVSCEAEKRKSDYIIRTLKVKFNSETRTTYQFHYKNWPDHDVPSSI<br>DPILELIWDVRCYQEDDSVPICIHCSAGCGRTGVICAIDYTWMLLKDGIIPE<br>NFSVFSLIREMRTQRPSLVQTQEQYELVYNAVLELFKRQMDVIRD | SEQ ID No. 67 |
| sfGFP | MRKGEELFTGVVPILVELDGDVNGHKFSVRGEGEGDATNGKLTLKFICTT<br>GKLPVPWPTLVTTLTYGVQCFARYPDHMKQHDFFKSAMPEGYVQERTIS<br>FKDDGTYKTRAEVKFEGDTLVNRIELKGIDFKEDGNILGHKLEYNFNSHN<br>VYITADKQKNGIKANFKIRHNVEDGSVQLADHYQQNTPIGDGPVLLPDNH<br>YLSTQSVLSKDPNEKRDHMVLLEFVTAAGITHGMDELYK* | SEQ ID No. 68 |
| mClover | MHHHHHHVSKGEELFTGVVPILVELDGDVNGHKFSVRGEGEGDATNGKL<br>TLKFICTTGKLPVPWPTLVTTFGYGVACFSRYPDHMKQHDFFKSAMPEGY<br>VQERTISFKDDGTYKTRAEVKFEGDTLVNRIELKGIDFKEDGNILGHKLEY<br>NFNSHNVYITADKQKNGIKANFKIRHNVEDGSVQLADHYQQNTPIGDGPV<br>LLPDNHYLSHQSALSKDPNEKRDHMVLLEFVTAAGITHGMDELYK | SEQ ID No. 69 |

TABLE 4

Exemplary Terminators.

| Name | DNA Sequence | SEQ ID No. # |
|---|---|---|
| T7 | ATCCGGATATAGTTCCTCCTTTCAGCAAAAAACCCCTCAAGACCCGTTTAGAGG CCCCAAGGGGTTATGCTAGTTATTGCTCAGCGGTGGCAGCAGCCAACTCAGCTT CCTTTCGGGCTTTGTTAGCAG | SEQ ID No. 70 |
| rrnB T1/T2 | GGCTGTTTTGGCGGATGAGAGAAGATTTTCAGCCTGATACAGATTAAATCAGAA CGCAGAAGCGGTCTGATAAAACAGAATTTGCCTGGCGGCAGTAGCGCGGTGGT CCCACCTGACCCCATGCCGAACTCAGAAGTGAAACGCCGTAGCGCCGATGGTA GTGTGGGGTCACCCCATGCGAGAGTAGGGAACTGCCAGGCATCAAATAAAACG AAAGGCTCAGTCGAAAGACTGGGCCTTTCGTTTTATCTGTTGTTTGTCGGTGAA CGCTCTCCTGAGTAGGACAAATCCGCCGGGAGCGGATTTGAACGTTGCGAAGC AACGGCCCGGAGGGTGGCGGGCAGGACGCCCGCCATAAACTGCCAGGCATCAA ATTAAGCAGAAGGCCATCCTGACGGATGGCCTTTTTGCGTTTCTACAAACTCT | SEQ ID No. 71 |
| TrrnB | TGCCTGGCGGCAGTAGCGCGGTGGTCCCACCTGACCCCATGCCGAACTCAGAA GTGAAACGCCGTAGCGCCGATGGTAGTGTGGGGTCTCCCCATGCGAGAGTAGG GAACTGCCAGGCATCAAATAAAACGAAAGGCTCAGTCGAAAGACTGGGCCTTT | SEQ ID No. 72 |

TABLE 5

Exemplary DNA Sequences (includes truncations):

| Comp. | Organism | DNA Sequence | SEQ ID No. # |
|---|---|---|---|
| Src | H. sapiens | ATGGGCTCCAAGCCGCAGACTCAGGGCCTGGCCAAGGATGCCTGGGA GATCCCTCGGGAGTCGCTGCGGCTGGAGGTCAAGCTGGGCCAGGGCT GCTTTGGCGAGGTGTGGATGGGGACCTGGAACGGTACCACCAGGGTG GCCATCAAAACCCTGAAGCCTGGCACGATGTCTCCAGAGGCCTTCCTG CAGGAGGCCCAGGTCATGAAGAAGCTGAGGCATGAGAAGCTGGTGCA GTTGTATGCTGTGGTTTCAGAGGAGCCCATTTACATCGTCACGGAGTA CATGAGCAAGGGGAGTTTGCTGGACTTTCTCAAGGGGGAGACAGGCA AGTACCTGCGGCTGCCTCAGCTGGTGGACATGGCTGCTCAGATCGCCT CAGGCATGGCGTACGTGGAGCGGATGAACTACGTCCACCGGGACCTTC GTGCAGCCAACATCCTGGTGGGAGAGAACCTGGTGTGCAAAGTGGCC GACTTTGGGCTGGCTCGGCTCATTGAAGACAATGAGTACACGGCGCGG CAAGGTGCCAAATTCCCCATCAAGTGGACGGCTCCAGAAGCTGCCCTC TATGGCCGCTTCACCATCAAGTCGGACGTGTGGTCCTTCGGGATCCTG CTGACTGAGCTCACCACAAAGGGACGGGTGCCCTACCCTGGGATGGTG AACCGCGAGGTGCTGGACCAGGTGGAGCGGGGCTACCGGATGCCCTG CCCGCCGGAGTGTCCCGAGTCCCTGCACGACCTCATGTGCCAGTGCTG GCGGAAGGAGCCTGAGGAGCGGCCCACCTTCGAGTACCTGCAGGCCT TCCTGGAGGACTACTTCACGTCCACCGAGCCCCAGTACCAGCCCGGGG AGAACCTCTAA | SEQ ID No. 73 |
| CDC37 | H. sapiens | ATGGTGGACTACAGCGTGTGGGACCACATTGAGGTGTCTGATGATGAA GACGAGACGCACCCCAACATCGACACGGCCAGTCTCTTCCGCTGGCGG CATCAGGCCCGGGTGGAACGCATGGAGCAGTTCCAGAAGGAGAAGGA GGAACTGGACAGGGGCTGCCGCGAGTGCAAGCGCAAGGTGGCCGAGT GCCAGAGGAAACTGAAGGAGCTGGAGGTGGCCGAGGGCGGCAAGGC AGAGCTGGAGCGCCTGCAGGCCGAGGCACAGCAGCTGCGCAAGGAGG AGCGGAGCTGGGAGCAGAAGCTGGAGGAGATGCGCAAGAAGGAGAA GAGCATGCCCTGGAACGTGGACACGCTCAGCAAAGACGGCTTCAGCA AGAGCATGGTAAATACCAAGCCCGAGAAGACGGAGGAGGACTCAGAG GAGGTGAGGGAGCAGAAACACAAGACCTTCGTGGAAAAATACGAGAA ACAGATCAAGCACTTTGGCATGCTTCGCCGCTGGGATGACAGCCAAAA GTACCTGTCAGACAACGTCCACCTGGTGTGCGAGGAGACAGCCAATTA CCTGGTCATTTGGTGCATTGACCTAGAGGTGGAGGAGAAATGTGCACT CATGGAGCAGGTGGCCCACCAGACAATCGTCATGCAATTTATCCTGGA GCTGGCCAAGAGCCTAAAGGTGGACCCCCGGGCCTGCTTCCGGCAGTT CTTCACTAAGATTAAGACAGCCGATCGCCAGTACATGGAGGGCTTCAA CGACGAGCTGGAAGCCTTCAAGGAGCGTGTGCGGGGCCGTGCCAAGC TGCGCATCGAGAAGGCCATGAAGGAGTACGAGGAGGAGGAGCGCAA GAAGCGGCTCGGCCCCGGCGGCCTGGACCCCGTCGAGGTCTACGAGTC CCTCCCTGAGGAACTCCAGAAGTGCTTCGATGTGAAGGACGTGCAGAT GCTGCAGGACGCCATCAGCAAGATGGACCCCACCGACGCAAAGTACC ACATGCAGCGCTGCATTGACTCTGGCCTCTGGGTCCCCAACTCTAAGG CCAGCGAGGCCAAGGAGGGAGAGGAGGCAGGTCCTGGGGACCCATTA CTGGAAGCTGTTCCCAAGACGGGCGATGAGAAGGATGTCAGTGTGTA A | SEQ ID No. 74 |

TABLE 5-continued

Exemplary DNA Sequences (includes truncations):

| Comp. | Organism | DNA Sequence | SEQ ID No. # |
|---|---|---|---|
| PTP1B$_{1-435}$ | H. sapiens | ATGGAGATGGAAAAGGAGTTCGAGCAGATCGACAAGTCCGGGAGCTG<br>GGCGGCCATTTACCAGGATATCCGACATGAAGCCAGTGACTTCCCATG<br>TAGAGTGGCCAAGCTTCCTAAGAACAAAAACCGAAATAGGTACAGAG<br>ACGTCAGTCCCTTTGACCATAGTCGGATTAAACTACATCAAGAAGATA<br>ATGACTATATCAACGCTAGTTTGATAAAAATGGAAGAAGCCCAAAGG<br>AGTTACATTCTTACCCAGGGCCCTTTGCCTAACACATGCGGTCACTTTT<br>GGGAGATGGTGTGGGAGCAGAAAAGCAGGGGTGTCGTCATGCTCAAC<br>AGAGTGATGGAGAAAGGTTCGTTAAAATGCGCACAATACTGGCCACA<br>AAAAGAAGAAAAGAGATGATCTTTGAAGACACAAATTTGAAATTAA<br>CATTGATCTCTGAAGATATCAAGTCATATTATACAGTGCGACAGCTAG<br>AATTGGAAAACCTTACAACCCAAGAAACTCGAGAGATCTTACATTTCC<br>ACTATACCACATGGCCTGACTTTGGAGTCCCTGAATCACCAGCCTCAT<br>TCTTGAACTTTCTTTTCAAAGTCCGAGAGTCAGGGTCACTCAGCCCGG<br>AGCACGGGCCCGTTGTGGTGCACTGCAGTGCAGGCATCGGCAGGTCTG<br>GAACCTTCTGTCTGGCTGATACCTGCCTCTTGCTGATGGACAAGAGGA<br>AAGACCCTTCTTCCGTTGATATCAAGAAAGTGCTGTTAGAAATGAGGA<br>AGTTTCGGATGGGGCTGATCCAGACAGCCGACCAGCTGCGCTTCTCCT<br>ACCTGGCTGTGATCGAAGGTGCCAAATTCATCATGGGGGACTCTTCCG<br>TGCAGGATCAGTGGAAGGAGCTTTCCCACGAGGACCTGGAGCCCCCA<br>CCCGAGCATATCCCCCCACCTCCCCGGCCACCCAAACGAATCCTGGAG<br>CCACACAATGGGAAATGCAGGGAGTTCTTCCCAAATCACCAGTGGGTG<br>AAGGAAGAGACCCAGGAGGATAAAGACTGCCCCATCAAGGAAGAAA<br>AAGGAAGCCCCTTAAATGCCGCACCCTACGGCATCGAAAGCATGAGT<br>CAAGACACTGAAGTTAGAAGTCGGGTCGTGGGGGGAAGTCTTCGAGG<br>TGCCCAGGCTGCCTCCCCAGCCAAAGGGGAGCCGTCACTGCCCGAGA<br>AGGACGAGGACCATGCACTGAGTTACTGGAAGCCCTTCCTGGTCAACA<br>TGTGCGTGGCTACGGTCCTCACGGCCGGCGCTTACCTCTGCTACAGGT<br>TCCTGTTCAACAGCAACACATAG | SEQ ID No. 75 |
| LuxAB | Bacterial | ATGAAATTTGGAAACTTTTTGCTTACATACCAACCTCCCCAATTTTCCC<br>AAACAGAGGTAATGAAACGTTTGGTTAAATTAGGTCGCATCTCTGAGG<br>AGTGTGGTTTTGATACCGTATGGTTACTGGAGCATCATTTCACGGAGTT<br>TGGTTTGCTTGGTAACCCTTATGTCGCTGCTGCATATTTACTTGGCGCG<br>ACTAAAAAATTGAATGTAGGAACTGCCGCTATTGTTCTTCCCACAGCC<br>CATCCAGTACGCCAACTTGAAGATGTGAATTTATTGGATCAAATGTCA<br>AAAGGACGATTTCGGTTTGGTATTTGCCGAGGGCTTTACAACAAGGAC<br>TTTCGCGTATTCGGCACAGATATGAATAACAGTCGCGCCTTAGCGGAA<br>TGCTGGTACGGGCTGATAAAGAATGGCATGACAGAGGGATATATGGA<br>AGCTGATAATGAACATATCAAGTTCCATAAGGTAAAAGTAAACCCCGC<br>GGCGTATAGCAGAGGTGGCGCACCGGTTTATGTGGTGGCTGAATCAGC<br>TTCGACGACTGAGTGGGCTGCTCAATTTGGCCTACCGATGATATTAAG<br>TTGGATTATAAATACTAACGAAAAGAAAGCACAACTTGAGCTTTATAA<br>TGAAGTGGCTCAAGAATATGGGCACGATATTCATAATATCGACCATTG<br>CTTATCATATATAACATCTGTAGATCATGACTCAATTAAAGCGAAAGA<br>GATTTGCCGGAAATTTCTGGGGCATTGGTATGATTCTTATGTGAATGCT<br>ACGACTATTTTTGATGATTCAGACCAAACAAGAGGTTATGATTTCAAT<br>AAAGGGCAGTGGCGTGACTTTGTATTAAAAGGACATAAAGATACTAA<br>TCGCCGTATTGATTACAGTTACGAAATCAATCCCGTGGGAACGCCGCA<br>GGAATGTATTGACATAATTCAAAAAGACATTGATGCTACAGGAATATC<br>AAATATTTGTTGTGGATTTGAAGCTAATGGAACAGTAGACGAAATTAT<br>TGCTTCCATGAAGCTCTTCCAGTCTGATGTCATGCCATTTCTTAAAGAA<br>AAACAACGTTCGCTATTATATTATTAA | SEQ ID No. 76 |
| LuxB | V. fischeri | ATGAGCAAATTTGGATTGTTCTTCCTTAACTTCATCAATTCAACAACTG<br>TTCAAGAACAGAGTATAGTTCGCATGCAGGAAATAACGGAGTATGTTG<br>ATAAGTTGAATTTTGAACAGATTTTAGTGTATGAAATCATTTTTCAGA<br>TAATGGTGTTGTCGGCGCTCCTCTGACTGTTTCTGGTTTTCTGCTCGGT<br>TTAACAGAGAAATTAAAATTGGTTCATTAAATCACATCATTACAACT<br>CATCATCCTGTCCGCATAGCGGAGGAAGCTTGCTTATTGGATCAGTTA<br>AGTGAAGGGAGATTATTTTAGGGTTTAGTGATTGCGAAAAAAAGAT<br>GAAATGCATTTTTTTAATCGCCCGGTTGAATATCAACAGCAACTATTTG<br>AAGAGTGTTATGAAATCATTAACGATGCTTTAACAACAGGCTATTGTA<br>ATCCAGATAACGATTTTTATAGCTTCCCTAAAATATCTGTAAATCCCCA<br>TGCTTATACGCCAGGCGGACCTCGGAAATATGTAACAGCAACCAGTCA<br>TCATATTGTTGAGTGGGCGGCCAAAAAAGGTATTCCTCTCATCTTTAA<br>GTGGGATGATTCTAATGATGTTAGATATGAATATGCTGAAAGATATAA<br>AGCCGTTGCGGATAAATATGACGTTGACCTATCAGAGATAGACCATCA<br>GTTAATGATATTAGTTAACTATAACGAAGATAGTAATAAAGCTAAACA<br>AGAAACGCGTCATTTATTAGTGATTATGTTCTTGAAATGCACCCTAA<br>TGAAAATTTCGAAAATAAACTTGAAGAAATAATTGCAGAAAACGCTG<br>TCGGAAATTATACGGAGTGTATAACTGCGGCTAAGTTGGCAATTGAAA<br>AGTGTGGTGCGAAAAGTGTATTGCTGTCCTTTGAACCAATGAATGATT<br>TGATGAGCCAAAAAAATGTAATCAATATTGTTGATGATAATATTAAGA<br>AGTACCACACGGAATATACCTAA | SEQ ID No. 77 |

TABLE 5-continued

Exemplary DNA Sequences (includes truncations):

| Comp. | Organism | DNA Sequence | SEQ ID No. # |
|---|---|---|---|
| RpoZ | *Escherichia coli* | ATGGCACGCGTAACTGTTCAGGACGCTGTAGAGAAAATTGGTAACCGT<br>TTTGACCTGGTACTGGTCGCCGCGCGTCGCGCTCGTCAGATGCAGGTA<br>GGCGGAAAGGATCCGCTGGTACCGGAAGAAAACGATAAAACCACTGT<br>AATCGCGCTGCGCGAAATCGAAGAAGGTCTGATCAACAACCAGATCC<br>TCGACGTTCGCGAACGCCAGGAACAGCAAGAGCAGGAAGCCGCTGAA<br>TTACAAGCCGTTACCGCTATTGCTGAAGGTCGTCGTTAA | SEQ ID No. 78 |
| cI | Lambda bacterio-phage | ATGAGTATCAGCAGCAGGGTAAAAAGCAAAAGAATTCAGCTTGGACT<br>TAACCAGGCTGAACTTGCTCAAAAGGTGGGGACTACCCAGCAGTCTAT<br>AGAGCAGCTCGAAAACGGTAAAATAAGCGACCACGCTTTTTTACCAG<br>AACTTGCGTCAGCTCTTGGCGTAAGTGTTGACTGGCTGCTCAATGGCA<br>CCTCTGATTCGAATGTTAGATTTGTTGGGCACGTTGAGCCCAAAGGGA<br>AATATCCATTGATTAGCATGGTTAGAGCTCGTTCGTGGTGTGAAGCTT<br>GTGAACCCTACGATATCAAGGACATTGATGAATGGTATGACAGTGACG<br>TTAACTTATTAGGCAATGGATTCTGGCTGAAGGTTGAAGGTGATTCCA<br>TGACCTCACCTGTAGGTCAAAGCATCCCTGAAGGTCATATGGTGTTAG<br>TAGATACTGGACGGGAGCCAGTGAATGGAAGCTTGTTGTAGCCAAA<br>CTGACTGACGCGAACGAAGCAACATTCAAGAAACTGGTCATAGATGG<br>CGGTCAGAAGTACCTGAAAGGCCTGAATCCTTCATGGCCTATGACTCC<br>TATCAACGGAAACTGCAAGATTATCGGTGTTGTCGTGGAAGCGAGGGT<br>AAAATTCGTAGACTAA | SEQ ID No. 79 |
| SH2 | Rous sarcoma virus | ATGTGGTATTTTGGGAAGATCACTCGTCGGGAGTCCGAGCGGCTGCTG<br>CTCAACCCCGAAAACCCCGGGGAACCTTCTTGGTCCGGGAGAGCGA<br>GACGGTAAAAGGTGCCTATGCCCTCTCCGTTTCTGACTTTGACAACGC<br>CAAGGGGCTCAATGTGAAACACTACCTGATCCGCAAGCTGGACAGCG<br>GCGGCTTCTACATCACCTCACGCACACAGTTCAGCAGCCTGCAGCAGC<br>TGGTGGCCTACTACTCCAAACATGCTGATGGCTTGTGCCACCGCCTGA<br>CCAACGTCTGCTAA | SEQ ID No. 80 |
| MBP | E. coli | ATGAAAATCGAAGAAGGTAAACTGGTAATCTGGATTAACGGCGATAA<br>AGGCTATAACGGTCTCGCTGAAGTCGGTAAGAAATTCGAGAAAGATA<br>CCGGAATTAAAGTCACCGTTGAGCATCCGGATAAACTGGAAGAGAAA<br>TTCCCACAGGTTGCGGCAACTGGCGATGGCCCTGACATTATCTTCTGG<br>GCACACGACCGCTTTGGTGGCTACGCTCAATCGGCCTGTTGGCTGAA<br>ATCACCCCGGACAAAGCGTTCCAGGACAAGCTGTATCCGTTTACCTGG<br>GATGCCGTACGTTACAACGGCAAGCTGATTGCTTACCCGATCGCTGTT<br>GAAGCGTTATCGCTGATTTATAACAAAGATCTGCTGCCGAACCCGCCA<br>AAAACCTGGGAAGAGATCCCGGCGCTGGATAAAGAACTGAAAGCGAA<br>AGGTAAGAGCGCGCTGATGTTCAACCTGCAAGAACCGTACTTCACCTG<br>GCCGCTGATTGCTGCTGACGGGGGTTATGCGTTCAAGTATGAAAACGG<br>CAAGTACGACATTAAAGACGTGGGCGTGGATAACGCTGGCGCGAAAG<br>CGGGTCTGACCTTCCTGGTTGACCTGATTAAAAACAAACACATGAATG<br>CAGACACCGATTACTCCATCGCAGAAGCTGCCTTTAATAAAGGCGAAA<br>CAGCGATGACCATCAACGGCCCGTGGGCATGGTCCAACATCGACACC<br>AGCAAAGTGAATTATGGTGTAACGGTACTGCCGACCTTCAAGGGTCAA<br>CCATCCAAACCGTTCGTTGGCGTGCTGAGCGCAGGTATTAACGCCGCC<br>AGTCCGAACAAAGAGCTGGCGAAAGAGTTCCTCGAAAACTATCTGCT<br>GACTGATGAAGGTCTGGAAGCGGTTAATAAAGACAAACCGCTGGGTG<br>CCGTAGCGCTGAAGTCTTACGAGGAAGAGTTGGCGAAAGATCCACGT<br>ATTGCCGCCACCATGGAAAACGCCCAGAAAGGTGAAATCATGCCGAA<br>CATCCCGCAGATGTCCGCTTTCTGGTATGCCGTGCGTACTGCGGTGATC<br>AACGCCGCCAGCGGTCGTCAGACTGTCGATGAAGCCCTGAAAGACGC<br>GCAGACTCGTATCACCAAGTAA | SEQ ID No. 81 |
| p130cas (or Kras) substrate | H. sapiens | TGGATGGAGGACTATGACTACGTCCACCTACAGGGG | SEQ ID No. 82 |
| MidT substrate | Hamster polyoma virus | GAACCGCAGTATGAAGAAATTCCGATTTATCTG | SEQ ID No. 83 |
| EGFR substrate | H. sapiens | CCGCAGCGCTATCTGGTGATTCAGGGCGAT | SEQ ID No. 84 |
| ShcA substrate | H. sapiens | GATCATCAGTATTATAACGATTTTCCGGGC | SEQ ID No. 85 |

TABLE 5-continued

Exemplary DNA Sequences (includes truncations):

| Comp. | Organism | DNA Sequence | SEQ ID No. # |
|---|---|---|---|
| MBIS | S. cerevisiae (from pMBIS Addgene#: 17817) | ATGTCATTACCGTTCTTAACTTCTGCACCGGGAAAGGTTATTATTTTTG GTGAACACTCTGCTGTGTACAACAAGCCTGCCGTCGCTGCTAGTGTGT CTGCGTTGAGAACCTACCTGCTAATAAGCGAGTCATCTGCACCAGATA CTATTGAATTGGACTTCCCGGACATTAGCTTTAATCATAAGTGGTCCAT CAATGATTTCAATGCCATCACCGAGGATCAAGTAAACTCCCAAAAATT GGCCAAGGCTCAACAAGCCACCGATGGCTTGTCTCAGGAACTCGTTAG TCTTTTGGATCCGTTGTTAGCTCAACTATCCGAATCCTTCCACTACCAT GCAGCGTTTTGTTTCCTGTATATGTTTGTTTGCCTATGCCCCCATGCCA AGAATATTAAGTTTTCTTTAAAGTCTACTTTACCCATCGGTGCTGGGTT GGGCTCAAGCGCCTCTATTTCTGTATCACTGGCCTTAGCTATGGCCTAC TTGGGGGGTTAATAGGATCTAATGACTTGGAAAAGCTGTCAGAAAA CGATAAGCATATAGTGAATCAATGGGCCTTCATAGGTGAAAAGTGTAT TCACGGTACCCCTTCAGGAATAGATAACGCTGTGGCCACTTATGGTAA TGCCCTGCTATTTGAAAAAGACTCACATAATGGAACAATAAACACAAA CAATTTTAAGTTCTTAGATGATTTCCCAGCCATTCCAATGATCCTAACC TATACTAGAATTCCAAGGTCTACAAAAGATCTTGTTGCTCGCGTTCGT GTGTTGGTCACCGAGAAATTTCCTGAAGTTATGAAGCCAATTCTAGAT GCCATGGGTGAATGTGCCCTACAAGGCTTAGAGATCATGACTAAGTTA AGTAAATGTAAAGGCACCGATGACGAGGCTGTAGAAACTAATAATGA ACTGTATGAACAACTATTGGAATTGATAAGAATAAATCATGGACTGCT TGTCTCAATCGGTGTTTCTCATCCTGGATTAGAACTTATTAAAAATCTG AGCGATGATTTGAGAATTGGCTCCACAAAACTTACCGGTGCTGGTGGC GGCGGTTGCTCTTTGACTTTGTTACGAAGAGACATTACTCAAGAGCAA ATTGACAGCTTCAAAAAGAAATTGCAAGATGATTTTAGTTACGAGACA TTTGAAACAGACTTGGGTGGGACTGCTGCTGTTTGTTAAGCGCAAAA AATTTGAATAAAGATCTTAAAATCAAATCCCTAGTATTCCAATTATTTG AAAATAAAACTACCACAAAGCAACAAATTGACGATCTATTATTGCCAG GAAACACGAATTTTCCATGGACTTCATAGGAGGCAGATCAAATGTCA GAGTTGAGAGCCTTCAGTGCCCCAGGGAAAGCGTTACTAGCTGGTGGA TATTTAGTTTTAGATACAAAATATGAAGCATTTGTAGTCGGATTATCG GCAAGAATGCATGCTGTAGCCCATCCTTACGTTCATTGCAAGGGTCT GATAAGTTTGAAGTGCGTGTGAAAAGTAAACAATTTAAAGATGGGGA GTGGCTGTACCATATAAGTCCTAAAAGTGGCTTCATTCCTGTTTCGATA GGCGGATCTAAGAACCCTTTCATTGAAAAAGTTATCGCTAACGTATTT AGCTACTTTAAACCTAACATGGACGACTACTGCAATAGAAACTTGTTC GTTATTGATATTTTCTCTGATGATGCCTACCATTCTCAGGAGGATAGCG TTACCGAACATCGTGGCAACAGAAGATTGAGTTTTCATTCGCACAGAA TTGAAGAAGTTCCCAAAACAGGGCTGGGCTCCTCGGCAGGTTTAGTCA CAGTTTTAACTACAGCTTTGGCCTCCTTTTTTGTATCGGACCTGGAAAA TAATGTAGACAAATATAGAGAAGTTATTCATAATTTAGCACAAGTTGC TCATTGTCAAGCTCAGGGTAAAATTGGAAGCGGGTTTGATGTAGCGGC GGCAGCATATGGATCTATCAGATATAGAAGATTCCCACCCGCATTAAT CTCTAATTTGCCAGATATTGGAAGTGCTACTTACGGCAGTAAACTGGC GCATTTGGTTGATGAAGAAGACTGGAATATTACGATTAAAAGTAACCA TTTACCTTCGGGATTAACTTTATGGATGGGCGATATTAAGAATGGTTC AGAAACAGTAAAACTGGTCCAGAAGGTAAAAAATTGGTATGATTCGC ATATGCCAGAAAGCTTGAAAATATATACAGAACTCGATCATGCAAATT CTAGATTTATGATGGACTATCTAAACTAGATCGCTTACACGAGACTC ATGACGATTACAGCGATCAGATATTTGAGTCTCTTGAGAGGAATGACT GTACCTGTCAAAAGTATCCTGAAATCACAGAAGTTAGAGATGCAGTTG CCACAATTAGACGTTCCTTTAGAAAAATAACTAAAGAATCTGGTGCCG ATATCGAACCTCCCGTACAAACTAGCTTATTGGATGATTGCCAGACCT TAAAAGGAGTTCTTACTTGCTTAATACCTGGTGCTGGTGGTTATGACG CCATTGCAGTGATTACTAAGCAAGATGTTGATCTTAGGGCTCAAACCG CTAATGACAAAAGATTTTCTAAGGTTCAATGGCTGGATGTAACTCAGG CTGACTGGGGTGTTAGGAAAGAAAAAGATCCGGAAACTTATCTTGATA AATAGGAGGTAATACTCATGACCGTTTACACAGCATCCGTTACCGCAC CCGTCAACATCGCAACCCTTAAGTATTGGGGAAAAGGGACACGAAG TTGAATCTGCCCACCAATTCGTCCATATCAGTGACTTTATCGCAAGATG ACCTCAGAACGTTGACCTCTGCGGCTACTGCACCTGAGTTTGAACGCG ACACTTTGTGGTTAAATGGAGAACCACACAGCATCGACAATGAAAGA ACTCAAAATTGTCTGCGCGACCTACGCCAATTAAGAAAGGAAATGGA ATCGAAGGACGCCTCATTGCCCACATTATCTCAATGGAAACTCCACAT TGTCTCCGAAAATAACTTTCCTACAGCAGCTGGTTTAGCTTCCTCCGCT GCTGGCTTTGCTGCATTGGTCTCTGCAATTGCTAAGTTATACCAATTAC CACAGTCAACTTCAGAAATATCTAGAATAGCAAGAAAGGGGTCTGGTT CAGCTTGTAGATCGTTGTTTGGCGGATACGTGGCCTGGGAAATGGGAA AAGCTGAAGATGGTCATGATTCCATGGCAGTACAAATCGCAGACAGCT CTGACTGGCCTCAGATGAAAGCTTTGCCTAGTTGTCAGCGATATTA AAAAGGATGTGAGTTCCACTCAGGGTATGCAATTGACCGTGGCAACCT CCGAACTATTTAAAGAAGAATTGAACATGTCGTACCAAAGAGATTTG AAGTCATGCGTAAAGCCATTGTTGAAAAAGATTTCGCCACCTTTGCAA AGGAAACAATGATGGATTCCAACTCTTTCCATGCCACATGTTTGGACT CTTTCCCTCCAATATTCTACATGAATGACACTTCCAAGCGTATCATCAG | SEQ ID No. 86 |

TABLE 5-continued

Exemplary DNA Sequences (includes truncations):

| Comp. | Organism | DNA Sequence | SEQ ID No. # |
|---|---|---|---|
| | | TTGGTGCCACACCATTAATCAGTTTTACGGAGAAACAATCGTTGCATA CACGTTTGATGCAGGTCCAAATGCTGTGTTGTACTCTTAGCTGAAAA TGAGTCGAAACTCTTTGCATTTATCTATAAATTGTTTGGCTCTGTTCCT GGATGGGACAAGAAATTTACTACTGAGCAGCTTGAGGCTTTCAACCAT CAATTTGAATCATCTAACTTTACTGCACGTGAATTGGATCTTGAGTTGC AAAAGGATGTTGCCAGAGTGATTTTAACTCAAGTCGGTTCAGGCCCAC AAGAAACAAACGAATCTTTGATTGACGCAAAGACTGGTCTACCAAAG GAATAACTGCAGCCCGGGAGGAGGATTACTATATGCAAACGGAACAC GTCATTTTATTGAATGCACAGGGAGTTCCCACGGGTACGCTGGAAAAG TATGCCGCACACACGGCAGACACCCGCTTACATCTCGCGTTCTCCAGT TGGCTGTTTAATGCCAAAGGACAATTATTAGTTACCCGCCGCGCACTG AGCAAAAAGCATGGCCTGGCGTGTGGACTAACTCGGTTTGTGGGCAC CCACAACTGGGAGAAAGCAACGAAGACGCAGTGATCCGCCGTTGCCG TTATGAGCTTGGCGTGGAAATTACGCCTCCTGAATCTATCTATCCTGAC TTTCGCTACCGCGCCACCGATCCGAGTGGCATTGTGGAAAATGAAGTG TGTCCGGTATTTGCCGCACGCACCACTAGTGCGTTACAGATCAATGAT GATGAAGTGATGGATTATCAATGGTGTGATTTAGCAGATGTATTACAC GGTATTGATGCCACGCCGTGGGCGTTCAGTCCGTGGATGGTGATGCAG GCGACAAATCGCGAAGCCAGAAAACGATTATCTGCATTTACCCAGCTT AAATAACCCGGGGGATCCACTAGTTCTAGAGCGGCCGCCACCGCGGA GGAGGAATGAGTAATGGACTTTCCGCAGCAACTCGAAGCCTGCGTTAA GCAGGCCAACCAGGCGCTGAGCCGTTTTATCGCCCCACTGCCCTTTCA GAACACTCCCGTGGTCGAAACCATGCAGTATGGCGCATTATTAGGTGG TAAGCGCCTGCGACCTTTCCTGGTTTATGCCACCGGTCATATGTTCGGC GTTAGCACAAACACGCTGGACGCACCCGCTGCCGCCGTTGAGTGTATC CACGCTTACTCATTAATTCATGATGATTTACCGGCAATGGATGATGAC GATCTGCGTCGCGGTTTGCCAACCTGCCATGTGAAGTTTGGCGAAGCA AACGCGATTCTCGCTGGCGACGCTTTACAAACGCTGGCGTTCTCGATT TTAAGCGATGCCGATATGCCGGAAGTGTCGGACCGCGACAGAATTTCG ATGATTTCTGAACTGGCGAGCGCCAGTGGTATTGCCGGAATGTGCGGT GGTCAGGCATTAGATTTAGACGCGGAAGGCAAACACGTACCTCTGGA CGCGCTTGAGCGTATTCATCGTCATAAAACCGGCGCATTGATTCGCGC CGCCGTTCGCCTTGGTGCATTAAGCGCCGGAGATAAAGGACGTCGTGC TCTGCCGGTACTCGACAAGTATGCAGAGAGCATCGGCCTTGCCTTCCA GGTTCAGGATGACATCCTGGATGTGGTGGGAGATACTGCAACGTTGGG AAAACGCCAGGGTGCCGACCAGCAACTTGGTAAAAGTACCTACCCTG CACTTCTGGGTCTTGAGCAAGCCCGGAAGAAAGCCCGGGATCTGATCG ACGATGCCCGTCAGTCGCTGAAACAACTGGCTGAACAGTCACTCGATA CCTCGGCACTGGAAGCGCTAGCGGACTACATCATCCAGCGTAATAAAT AA | |
| ADS | Artemisia annua | GCCCTGACCGAAGAGAAACCGATCCGCCCGATCGCTAACTTCCCGCCG TCTATCTGGGGTGACCAGTTCCTGATCTACGAAAAGCAGGTTGAGCAG GGTGTTGAACAGATCGTAAACGACCTGAAGAAAGAAGTTCGTCAGCT GCTGAAAGAAGCTCTGGACATCCCGATGAAACACGCTAACCTGTTGAA GCTGATCGACGAGATCCAGCGTCTGGGTATCCCGTACCACTTCGAACG CGAAATCGACCACGCACTGCAGTGCATCTACGAAACCTACGGCGACA ACTGGAACGGCGACCGTTCTTCTCTGTGGTTTCGTCTGATGCGTAAAC AGGGCTACTACGTTACCTGTGACGTTTTTAACAACTACAAGGACAAGA ACGGTGCTTTCAAACAGTCTCTGGCTAACGACGTTGAAGGCCTGCTGG AACTGTACGAAGCGACCTCCATGCGTGTACCGGGTGAAATCATCCTGG AGGACGCGCTGGGTTTCACCCGTTCTCGTCTGTCCATTATGACTAAAG ACGCTTTCTCTACTAACCCGGCTCTGTTCACCGAAATCCAGCGTGCTCT GAAACAGCCGCTGTGGAAACGTCTGCCGCGTATCGAAGCAGCACAGT ACATTCCGTTTTACCAGCAGCAGGACTCTCACAACAAGACCCTGCTGA AACTGGCTAAGCTGGAATTCAACCTGCTGCAGTCTCTGCACAAAGAAG AACTGTCTCACGTTTGTAAGTGGTGGAAGGCATTTGACATCAAGAAAA ACGCGCCGTGCCTGCGTGACCGTATCGTTGAATGTTACTTCTGGGGTCT GGGTTCTGGTTATGAACCACAGTACTCCCGTGCACGTGTGTTCTTCACT AAAGCTGTAGCTGTTATCACCCTGATCGATGACACTTACGATGCTTAC GGCACCTACGAAGAACTGAAGATCTTTACTGAAGCTGTAGAACGCTGG TCTATCACTTGCCTGGACACTCTGCCGGAGTACATGAAACCGATCTAC AAACTGTTCATGGATACCTACACCGAAATGGAGGAATTCCTGGCAAAA GAAGGCCGTACCGACCTGTTCAACTGCGGTAAAGAGTTTGTTAAAGAA TTCGTACGTAACCTGATGGTTGAAGCTAAATGGGCTAACGAAGGCCAT ATCCCGACTACCGAAGAACATGACCCGGTTGTTATCATCACCGGCGGT GCAAACCTGCTGACCACCACTTGCTATCTGGGTATGTCCGACATCTTTA CCAAGGAATCTGTTGAATGGGCTGTTTCTGCACCGCCGCTGTTCCGTTA CTCCGGTATTCTGGGTCGTCGTCTGAACGACCTGATGACCCACAAAGC AGAGCAGGAACGTAAACACTCTTCCTCCTCTCTGGAATCCTACATGAA GGAATATAACGTTAACGAGGAGTACGCACAGACTCTGATCTATAAAG AAGTTGAAGACGTATGGAAAGACATCAACCGTGAATACCTGACTACT AAAAACATCCCCGCGCCCGCTGCTGATGGCAGTAATCTACCTGTGCCAG | SEQ ID No. 87 |

TABLE 5-continued

Exemplary DNA Sequences (includes truncations):

| Comp. | Organism | DNA Sequence | SEQ ID No. # |
|---|---|---|---|
| | | TTCCTGGAAGTACAGTACGCTGGTAAAGATAACTTCACTCGCATGGGC<br>GACGAATACAAACACCTGATCAAATCCCTGCTGGTTTACCCGATGTCC<br>ATCTGA | |
| GHS | Abies grandis | ATGGCTCAAATCAGCGAATCAGTGTCTCCAAGCACCGACCTTAAAAGC<br>ACGGAATCTTCTATTACCAGCAACCGCCACGGTAACATGTGGGAAGAT<br>GACCGCATTCAGAGCTTAAACAGCCCATATGGCGCACCCGCTTATCAG<br>GAACGTAGCGAAAAATTGATTGAAGAAATTAAGCTCCTGTTTCTGTCC<br>GATATGGACGATAGTTGCAATGATTCGGATCGCGACTTGATCAAACGC<br>CTGGAGATCGTAGATACGGTTGAGTGTCTGGGCATTGATCGTCATTTC<br>CAACCTGAAATTAAGCTGGCGCTGGATTACGTGTACCGTTGCTGGAAT<br>GAGCGTGGCATCGGAGAAGGTAGCCGTGATAGCTTAAAAAAGGACCT<br>GAATGCGACCGCCTTGGGCTTTCGGGCTTTACGCTTACACCGTTATAAT<br>GTAAGCTCAGGAGTGCTGGAGAACTTCCGTGATGACAATGGTCAATTC<br>TTTTGCGGTTCTACTGTGGAGGAGGAAGGCGCGGAGGCCTACAATAAA<br>CATGTACGTTGCATGCTGTCCCTGTCCCGCGCTTCCAATATTTTATTCC<br>CGGGCGAGAAAGTGATGGAAGAAGCGAAGGCGTTTACGACCAACTAT<br>CTTAAGAAAGTCCTGGCGGGTCGTGAAGCAACTCATGTCGACGAGAGT<br>CTCCTTGGAGAGGTCAAGTATGCACTAGAATTTCCGTGGCATTGTTCC<br>GTGCAGCGCTGGGAGGCACGTTCTTTTATCGAAATTTTCGGTCAGATT<br>GATAGTGAACTGAAAAGCAACCTCTCTAAAAAAATGCTCGAACTCGC<br>AAAACTTGATTTTAACATACTCCAGTGTACGCATCAAAAAGAGCTCCA<br>GATCATTAGTCGATGGTTCGCCGATTCAAGTATCGCAAGTCTGAACTT<br>TTACCGTAAATGCTATGTGGAATTTTACTTCTGGATGGCCGCGGCAATT<br>TCAGAACCAGAATTTAGTGGCTCTCGCGTGGCATTCACTAAAATTGCG<br>ATCTTGATGACAATGTTAGATGACTTATACGACACGCATGGGACGCTG<br>GATCAATTGAAAATATTTACCGAAGGTGTGCGCAGGTGGGACGTGTCG<br>CTGGTGGAGGGCCTGCCGGATTTCATGAAAATTGCCTTTGAGTTCTGG<br>TTAAAGACCTCCAACGAACTGATTGCGGAGGCGGTTAAGGCCCAAGG<br>CCAGGATATGGCGGCCTATATCCGCAAAAACGCTTGGGAACGCTATCT<br>GGAAGCGTATTTGCAGGATGCCGAATGGATCGCCACCGGTCACGTTCC<br>GACATTCGATGAATATCTGAACAATGGCACCCCCAACACCGGTATGTG<br>TGTACTTAATCTGATCCCGTTGCTGCTTATGGGCGAACACTTGCCGATC<br>GATATTCTTGAACAGATCTTTCTGCCGAGCCGGTTCCACCATCTGATTG<br>AACTGGCTAGCCGACTGGTCGATGATGCGAGAGATTTTCAAGCCGAAA<br>AAGATCATGGTGATTTATCCTGCATCGAATGCTACCTGAAAGACCATC<br>CGGAATCAACAGTTGAAGACGCCCTGAATCACGTCAACGGCCTGCTGG<br>GGAATTGTTTGCTGGAAATGAATTGGAAATTTCTGAAAAAACAGGACT<br>CGGTACCTCTGTCGTGTAAAAAATACTCATTCCACGTCCTGGCGCGGT<br>CGATTCAGTTTATGTATAACCAGGGGGACGGGTTTTCGATTTCGAACA<br>AAGTTATTAAAGACCAGGTCCAGAAAGTTCTAATCGTTCCGGTTCCTA<br>TATAA | SEQ ID No. 88 |
| ABS | Abies grandis | TGAAACGAGAATTTCCTCCAGGATTTTGGAAGGATGATCTTATCGATT<br>CTCTAACGTCATCTCACAAGGTTGCAGCATCAGACGAGAAGCGTATCG<br>AGACATTAATATCCGAGATTAAGAATATGTTTAGATGTATGGGCTATG<br>GCGAAACGAATCCCTCTGCATATGACACTGCTTGGGTAGCAAGGATTC<br>CAGCAGTTGATGGCTCTGACAACCCTCACTTTCCTGAGACGGTTGAAT<br>GGATTCTTCAAAATCAGTTGAAAGATGGGTCTTGGGGTGAAGGATTCT<br>ACTTCTTGGCATATGACAGAATACTGGCTACACTTGCATGTATTATTAC<br>CCTTACCCTCTGGCGTACTGGGGAGACACAAGTACAGAAAGGTATTGA<br>ATTCTTCAGGACACAAGCTGGAAAGATGGAAGATGAAGCTGATAGTC<br>ATAGGCCAAGTGGATTTGAAATAGTATTTCCTGCAATGCTAAAGGAAG<br>CTAAAATCTTAGGCTTGGATCTGCCTTACGATTTGCCATTCCTGAAACA<br>AATCATCGAAAAGCGGGAGGCTAAGCTTAAAAGGATTCCC<br>ACTGATGTTCTCTATGCCCTTCCAACAACGTTATTGTATTCTTTGGAAG<br>GTTTACAAGAAATAGTAGACTGGCAGAAAATAATGAAACTTCAATCC<br>AAGGATGGATCATTTCTCAGCTCTCCGGCATCTACAGCGGCTGTATTC<br>ATGCGTACAGGGAACAAAAAGTGCTTGGATTTCTTGAACTTTGTCTTG<br>AAGAAATTCGGAAACCATGTGCCTTGTCACTATCCGCTTGATCTATTTG<br>AACGTTTGTGGGCGGTTGATACAGTTGAGCGGCTAGGTATCGATCGTC<br>ATTTCAAAGAGGAGATCAAGGAAGCATTGGATTATGTTTACAGCCATT<br>GGGACGAAAGAGGCATTGGATGGGCGAGAGAGAATCCTGTTCCTGAT<br>ATTGATGATACAGCCATGGGCCTTCGAATCTTGAGATTACATGGATAC<br>AATGTATCCTCAGATGTTTTAAAAACATTTAGAGATGAGAATGGGGAG<br>TTCTTTTGCTTCTTGGGTCAAACACAGAGAGGAGTTACAGACATGTTA<br>AACGTCAATCGTTGTTCACATGTTTCATTTCCGGGAGAAACGATCATG<br>GAAGAAGCAAAACTCTGTACCGAAAGGTATCTGAGGAATGCTCTGGA<br>AAATGTGGATGCCTTTGACAAATGGGCTTTTAAAAAGAATATTCGGGG<br>AGAGGTAGAGTATGCACTCAAATATCCCTGGCATAAGAGTATGCCAA<br>GGTTGGAGGCTAGAAGCTATATTGAAAACTATGGGCCAGATGATGTGT<br>GGCTTGGAAAAACTGTATATATGATGCCATACATTTCGAATGAAAAGT<br>ATTTAGAACTAGCGAAACTGGACTTCAATAAGGTGCAGTCTATACACC<br>AAACAGAGCTTCAAGATCTTCGAAGGTGGTGGAAATCATCCGGTTTCA | SEQ ID No. 89 |

TABLE 5-continued

Exemplary DNA Sequences (includes truncations):

| Comp. | Organism | DNA Sequence | SEQ ID No. # |
|---|---|---|---|
| | | CGGATCTGAATTTCACTCGTGAGCGTGTGACGGAAATATATTTCTCAC<br>CGGCATCCTTTATCTTTGAGCCCGAGTTTTCTAAGTGCAGAGAGGTTTA<br>TACAAAAACTTCCAATTTCACTGTTATTTTAGATGATCTTTATGACGCC<br>CATGGATCTTTAGACGATCTTAAGTTGTTCACAGAATCAGTCAAAAGA<br>TGGGATCTATCACTAGTGGACCAAATGCCACAACAAATGAAAATATGT<br>TTTGTGGGTTTCTACAATACTTTTAATGATATAGCAAAAGAAGGACGT<br>GAGAGGCAAGGGCGCGATGTGCTAGGCTACATTCAAAATGTTTGGAA<br>AGTCCAACTTGAAGCTTACACGAAAGAAGCAGAATGGTCTGAAGCTA<br>AATATGTGCCATCCTTCAATGAATACATAGAGAATGCGAGTGTGTCAA<br>TAGCATTGGGAACAGTCGTTCTCATTAGTGCTCTTTTCACTGGGGAGGT<br>TCTTACAGATGAAGTACTCTCCAAAATTGATCGCGAATCTAGATTTCTT<br>CAACTCATGGGCTTAACAGGGCGTTTGGTGAATGACACCAAAACTTAT<br>CAGGCAGAGAGAGGTCAAGGTGAGGTGGCTTCTGCCATACAATGTTAT<br>ATGAAGGACCATCCTAAAATCTCTGAAGAAGAAGCTCTACAACATGTC<br>TATAGTGTCATGGAAAATGCCCTCGAAGAGTTGAATAGGGAGTTTGTG<br>AATAACAAAATACCGGATATTTACAAAAGACTGGTTTTTGAAACTGCA<br>AGAATAATGCAACTCTTTTATATGCAAGGGGATGGTTTGACACTATCA<br>CATGGATATGGAAATTAAAGAGCATGTCAAAAATTGCCTCTTCCAACCA<br>GTTGCC | |
| TXS | Taxus brevifola | ATGAGCAGCAGCACTGGCACTAGCAAGGTGGTTTCCGAGACTTCCAGT<br>ACCATTGTGGATGATATCCCTCGACTCTCCGCCAATTATCATGGCGATC<br>TGTGGCACCACAATGTTATACAAACTCTGGAGACACCGTTTCGTGAGA<br>GTTCTACTTACCAAGAACGGGCAGATGAGCTGGTTGTGAAAATTAAAG<br>ATATGTTCAATGCGCTCGGAGACGGAGATATCAGTCCGTCTGCATACG<br>ACACTGCGTGGGTGGCGAGGCTGGCGACCATTCCTCTGATGGATCTG<br>AGAAGCCACGGTTTCCTCAGGCCCTCAACTGGGTTTTCAACAACCAGC<br>TCCAGGATGGATCGTGGGGTATCGAATCGCACTTTAGTTTATGCGATC<br>GATTGCTTAACACGACCAATTCTGTTATCGCCCTCTCGGTTTGGAAAAC<br>AGGGCACAGCCAAGTACAACAAGGTGCTGAGTTTATTGCAGAGAATC<br>TAAGATTACTCAATGAGGAAGATGAGTTGTCCCCGGATTTCCAAATAA<br>TCTTTCCTGCTCTGCTGCAAAAGGCAAAGCGTTGGGGATCAATCTTC<br>CTTACGATCTTCCATTTATCAAATATTTGTCGACAACACGGGAAGCCA<br>GGCTTACAGATGTTTCTGCGGCAGCAGACAATATTCCAGCCAACATGT<br>TGAATGCGTTGGAAGGACTCGAGGAAGTTATTGACTGGAACAAGATT<br>ATGAGGTTTCAAAGTAAAGATGGATCTTTCCTGAGCTCCCCTGCCTCC<br>ACTGCCTGTGTACTGATGAATACAGGGGACGAAAAATGTTTCACTTTT<br>CTCAACAATCTGCTCGACAAATTCGGCGGCTGCGTGCCCTGTATGTAT<br>TCCATCGATCTGCTGGAACGCCTTTCGCTGGTTGATAACATTGAGCATC<br>TCGGAATCGGTCGCCATTTCAAACAAGAAATCAAAGGAGCTCTTGATT<br>ATGTCTACAGACATTGGAGTGAAAGGGGCATCGGTTGGGGCAGAGAC<br>AGCCTTGTTCCAGATCTCAACACCACAGCCCTCGGCCTGCGAACTCTT<br>CGCATGCACGGATACAATGTTTCTTCAGACGTTTTGAATAATTTCAAA<br>GATGAAAACGGGCGGTTCTTCTCCTCTGCGGGCCAAACCCATGTCGAA<br>TTGAAGAAGCGTGGTGAATCTTTTCAGAGCTTCCGACCTTGCATTTCCTG<br>ACGAAAGAGCTATGGACGATGCTAGAAAATTTGCAGAACCATATCTTA<br>GAGAGGCACTTGCAACGAAAATCTCAACCAATACAAAACTATTCAAA<br>GAGATTGAGTACGTGGTGGAGTACCCTTGGCACATGAGTATCCCACGC<br>TTAGAAGCCAGAAGTTATATTGATTCATATGACGACAATTATGTATGG<br>CAGAGGAAGACTCTATATAGAATGCCATCTTTGAGTAATTCAAAATGT<br>TTAGAATTGGCAAAATTGGACTTCAATATCGTACAATCTTTGCATCAA<br>GAGGAGTTGAAGCTTCTAACAAGATGGTGGAAGGAATCCGGCATGGC<br>AGATATAAATTTCACTCGACACCGAGTGGCGGAGGTTTATTTTTCATC<br>AGCTACATTTGAACCCGAATATTCTGCCACTAGAATTGCCTTCACAAA<br>AATTGGTTGTTTACAAGTCCTTTTTGATGATATGGCTGACATCTTTGCA<br>ACACTAGATGAATTGAAAAGTTTCACTGAGGGAGTAAAGAGATGGGA<br>TACATCTTTGCTACATGAGATTCCAGAGTGTATGCAAACTTGCTTTAAA<br>GTTTGGTTCAAATTAATGGAAGAAGTAAATAATGATGTGGTTAAGGTA<br>CAAGGACGTGACATGCTCGCTCACATAAGAAAACCCTGGGAGTTGTAC<br>TTCAATTGTTATGTACAAGAAAGGGAGTGGCTTGAAGCCGGGTATATA<br>CCAACTTTTGAAGAGTACTTAAAGACTTATGCTATATCAGTAGGCCTT<br>GGACCGTGTACCCTACAACCAATACTACTAATGGGTGAGCTTGTGAAA<br>GATGATGTTGTTGAGAAAGTGCACTATCCCTCAAATATGTTTGAGCTT<br>GTATCCTTGAGCTGGCGACTAACAAACGACACCAAAACATATCAGGCT<br>GAAAAGGCTCGAGGACAACAAGCCTCAGGCATGACATGCTATATGAA<br>GGATAATCCAGGAGCAACTGAGGAAGATGCCATTAAGCACATATGTC<br>GTGTTGTTGATCGGGCCTTGAAAGAAGCAAGCTTTGAATATTTCAAAC<br>CATCCAATGATATCCCAATGGGTTGCAAGTCCTTTATTTTTAACCTTAG<br>ATTGTGTGTCCAAATCTTTTACAAGTTTATAGATGGGTACGGAATCGC<br>CAATGAGGAGATTAA | SEQ ID No. 90 |

TABLE 5-continued

Exemplary DNA Sequences (includes truncations):

| Comp. | Organism | DNA Sequence | SEQ ID No. # |
|---|---|---|---|
| GGPPS | *Taxus Canadensis* | GGACTATATAAGAAAAGTTTATATTGATCCAATTCAAGTATGA ATGTTTGATTTCAATGAATATATGAAAAGTAAGGCTGTTGCGGTAGAC GCGGCTCTGGATAAAGCGATTCCGCTGGAATATCCCGAGAAGATTCAC GAATCGATGCGCTACTCCCTGTTAGCAGGAGGGAAACGCGTTCGTCCG GCATTATGCATCGCGGCCTGTGAACTCGTCGGCGGTTCACAGGACTTA GCAATGCCAACTGCTTGCGCAATGGAAATGATTCACACAATGAGCCTG ATTCATGATGATTTGCCTTGCATGGACAACGATGACTTTCGGCGCGGT AAACCTACTAATCATAAGGTTTTTGGCGAAGATACTGCAGTGCTGGCG GGCGATGCGCTGCTGTCGTTTGCCTTCGAACATATCGCCGTCGCGACC TCGAAAACCGTCCCGTCGGACCGTACGCTTCGCGTGATTTCCGAGCTG GGAAAGACCATCGGCTCTCAAGGACTCGTGGGTGGTCAGGTAGTTGAT ATCACGTCTGAGGGTGACGCGAACGTGGACCTGAAAACCCTGGAGTG GATCCATATTCACAAAACGGCCGTGCTGCTGGAATGTAGCGTGGTGTC AGGGGGGATCTTGGGGGCGCCACGGAGGATGAAATCGCGCGTATTC GTCGTTATGCCCGCTGTGTTGGACTGTTATTTCAGGTGGTGGATGACAT CCTGGATGTCACAAAATCCAGCGAAGAGCTTGGCAAGACCGCGGGCA AAGACCTTCTGACGGATAAGGCTACATACCCGAAATTGATGGGCTTGG AGAAAGCCAAGGAGTTCGCAGCTGAACTTGCCACGCGGGCGAAGGAA GAACTCTCTTCTTTCGATCAAATCAAAGCCGCGCCACTGCTGGGCCTC GCCGATTACATTGCGTTTCGTCAGAACTGA | SEQ ID No. 91 |
| P450<sub>BM3</sub> | *Bacillus megaterium* | ATGACAATTAAAGAAATGCCTCAGCCAAAAACGTTTGGAGAGCTTAA AAATTTACCGTTATTAAACACAGATAAACCGGTTCAAGCTTTGATGAA AATTGCGGATGAATTAGGAGAAATCTTTAAATTCGAGGCGCCTGGTCG TGTAACGCGCTACTTATCAAGTCAGCGTCTAATTAAAGAAGCATGCGA TGAATCACGCTTTGATAAAAACTTAAGTCAAGCGCTTAAATTTGTACG TGATTTTGCAGGAGACGGGTTATTTACAAGCTGGACGCATGAAAAAA TTGGAAAAAAGCGCATAATATCTTACTTCCAAGCTTCAGTCAGCAGGC AATGAAAGGCTATCATGCGATGATGGTCGATATCGCCGTGCAGCTTGT TCAAAAGTGGGAGCGTCTAAATGCAGATGAGCATATTGAAGTACCGG AAGACATGACACGTTTAACGCTTGATACAATTGGTCTTTGCGGCTTTA ACTATCGCTTTAACAGCTTTTACCGAGATCAGCCTCATCCATTTATTAC AAGTATGGTCCGTGCACTGGATGAAGCAATGAACAAGCTGCAGCGAG CAAATCCAGACGACCCAGCTTATGATGAAAACAAGCGCCAGTTTCAA GAAGATATCAAGGTGATGAACGACCTAGTAGATAAAATTATTGCAGA TCGCAAAGCAAGCGGTGAACAAAGCGATGATTTATTAACGCATATGCT AAACGGAAAAGATCCAGAAACGGGTGAGCCGCTTGATGACGAGAACA TTCGCTATCAAATTATTACATTCTTAATTGCGGGACACGAAACAACAA GTGGTCTTTTATCATTTGCGCTGTATTTCTTAGTGAAAAATCCACATGT ATTACAAAAAGCAGCAGAAGAAGCAGCACGAGTTCTAGTAGATCCTG TTCCAAGCTACAAACAAGTCAAACAGCTTAAATATGTCGGCATGGTCT TAAACGAAGCGCTGCGCTTATGGCCAACTGCTCCTGCGTTTTCCCTATA TGCAAAAGAAGATACGGTGCTTGGAGGAGAATATCCTTTAGAAAAAG GCGACGAACTAATGGTTCTGATTCCTCAGCTTCACCGTGATAAAACA TTTTGGGGAGACGATGTGGAAGAGTTCCGTCCAGAGCGTTTTGAAAATC CAAGTGCGATTCCGCAGCATGCGTTTAAACCGTTTGGAAACGGTCAGC GTGCCGTGTATCGGTCAGCAGTTCGCTCTTCATGAAGCAACGCTGGTAC TTGGTATGATGCTAAAACACTTTGACTTTGAAGATCATACAAACTACG AGCTGGATATTAAAGAAACTTTAACGTTAAAACCTGAAGGCTTTGTGG TAAAAGCAAATCGAAAAAATTCCGCTTGGCGGTATTCCTTCACCTA GCACTGAACAGTCTGCTAAAAAAGTACGCAAAAAGGCAGAAAACGCT CATAATACGCCGCTGCTTGTGCTATACGGTTCAAATATGGGAACAGCT GAAGGAACGGCGCGTGATTAGCAGATATTGCAATGAGCAAAGGATT TGCACCGCAGGTCGCAACGCTTGATTCACACGCCGGAAATCTTCCGCG CGAAGGAGCTGTATTAATTGTAACGGCGTCTTATAACGGTCATCCGCC TGATAACGCAAAGCAATTTGTCGACTGGTTAGACCAAGCGTCTGCTGA TGAAGTAAAAGGCGTTCGCTACTCCGTATTTGGATGCGGCGATAAAAA CTGGGCTACTACGTATCAAAAAGTGCCTGCTTTTATCGATGAAACGCT TGCCGCTAAAGGGCAGAAAACATCGCTGACCGCGGTGAAGCAGATG CAAGCGACGACTTTGAAGGCACATATGAAGAATGGCGTGAACATATG TGGAGTGACGTAGCAGCCTACTTTAACCTCGACATTGAAAACAGTGAA GATAATAAATCTACTCTTTCACTTCAATTTGTCGACAGCGCCGCGGAT ATGCCGCTTGCGAAAATGCACGGTGCGTTTTCAACGAACGTCGTAGCA AGCAAAGAACTTCAACAGCCAGGCAGTGCACGAAGCACGCGACATCT TGAAATTGAACTTCCAAAAGAAGCTTCTTATCAAGAAGGAGATCATTT AGGTGTTATTCCTCGCAACTATGAAGGAATAGTAAACCGTGTAACAGC AAGGTTCGGCCTAGATGCATCACAGCAAATCCGTCTGGAAGCAGAAG AAGAAAAATTAGCTCATTTGCCACTCGCTAAAACAGTATCCGTAGAAG AGCTTCTGCAATACGTGGAGCTTCAAGATCCTGTTACGCGCACGCAGG TTCGCGCAATGGCTGCTAAAACGGTCTGCCCGCCGCATAAAGTAGAGC TTGAAGCCTTGCTTGAAAAGCAAGCCTACAAAGAACAAGTGCTGGCA AAACGTTTAACAATGCTTGAACTGCTTGAAAATACCGGCGTGTGAA ATGAAATTCAGCGAATTTATCGCCCTTCTGCCAAGCATACGCCCGCGC TATTACTCGATTTCTTCATCACCTCGTGTCGATGAAAAACAAGCAAGC | SEQ ID No. 92 |

TABLE 5-continued

Exemplary DNA Sequences (includes truncations):

| Comp. | Organism | DNA Sequence | SEQ ID No. # |
|---|---|---|---|
| | | ATCACGGTCAGCGTTGTCTCAGGAGAAGCGTGGAGCGGATATGGAGA<br>ATATAAAGGAATTGCGTCGAACTATCTTGCCGAGCTGCAAGAAGGAG<br>ATACGATTACGTGCTTTATTTCCACACCGCAGTCAGAATTTACGCTGCC<br>AAAAGACCCTGAAACGCCGCTTATCATGGTCGGACCGGGAACAGGCG<br>TCGCGCCGTTTAGAGGCTTTGTGCAGGCGCGCAAACAGCTAAAAGAAC<br>AAGGACAGTCACTTGGAGAAGCACATTTATACTTCGGCTGCCGTTCAC<br>CTCATGAAGACTATCTGTATCAAGAAGAGCTTGAAAACGCCCAAAGC<br>GAAGGCATCATTACGCTTCATACCGCTTTTTCTCGCATGCCAAATCAGC<br>CGAAAACATACGTTCAGCACGTAATGGAACAAGACGGCAAGAAATTG<br>ATTGAACTTCTTGATCAAGGAGCGCACTTCTATATTTGCGGAGACGGA<br>AGCCAAATGGCACCTGCCGTTGAAGCAACGCTTATGAAAAGCTATGCT<br>GACGTTCACCAAGTGAGTGAAGCAGACGCTCGCTTATGGCTGCAGCAG<br>CTAGAAGAAAAAGGCCGATACGCAAAAGACGTGTGGGCTGGGTAA | |
| SpecR | Bacterial | ATGAGGGAAGCGGTTGATCGCCGAAGTATCGACTCAACTATCAGAGGT<br>AGTTGGCGTCATCGAGCGCCATCTCGAACCGACGTTGCTGGCCGTACA<br>TTTGTACGGCTCCGCAGTGGATGGCGGCCTGAAGCCACACAGTGATAT<br>TGATTTGCTGGTTACGGTGACCGTAAGGCTTGATGAAACAACGCGGCG<br>AGCTTTGATCAACGACCTTTTGGAAACTTCGGCTTCCCCTGGAGAGAG<br>CGAGATTCTCCGCGCTGTAGAAGTCACCATTGTTGTGCACGACGACAT<br>CATTCCGTGGCGTTATCCAGCTAAGCGCGAACTGCAATTTGGAGAATG<br>GCAGCGCAATGACATTCTTGCAGGTATCTTCGAGCCAGCCACGATCGA<br>CATTGATCTGGCTATCTTGCTGACAAAAGCAAGAGAACATAGCGTTGC<br>CTTGGTAGGTCCAGCGGCGGAGGAACTCTTTGATCCGGTTCCTGAACA<br>GGATCTATTTGAGGCGCTAAATGAAACCTTAACGCTATGGAACTCGCC<br>GCCCGACTGGGCTGGCGATGAGCGAAATGTAGTGCTTACGTTGTCCCG<br>CATTTGGTACAGCGCAGTAACCGGCAAATCGCGCCGAAGGATGTC<br>CTGCCGACTGGGCAATGGAGCGCCTGCCGGCCCAGTATCAGCCCGTCA<br>TACTTGAAGCTAGACAGGCTTATCTTGGACAAGAAGAAGATCGCTTGG<br>CCTCGCGCGCAGATCAGTTGGAAGAATTTGTCCACTACGTGAAAGGCG<br>AGATCACCAAGGTAGTCGGCAAA | SEQ ID No. 93 |
| LOV2 | Avena sativa | TTGGCTACTACACTTGAACGTATTGAGAAGAACTTTGTCATTACTGAC<br>CCAAGGTTGCCAGATAATCCCATTATATTCGCGTCCGATAGTTTCTTGC<br>AGTTGACAGAATATAGCCGTGAAGAAATTTTGGGAAGAAACTGCAGG<br>TTTCTACAAGGTCCTGAAACTGATCGCGCGACAGTGAGAAAAATTAGA<br>GATGCCATAGATAACCAAACAGAGGTCACTGTTCAGCTGATTAATTAT<br>ACAAAGAGTGGTAAAAAGTTCTGGAACCTCTTTCACTTGCAGCCTATG<br>CGAGATCAGAAGGGAGATGTCCAGTACTTTATTGGGGTTCAGTTGGAT<br>GGAACTGAGCATGTCCGAGATGCTGCCGAGAGAGAGGGAGTCATGCT<br>GATTAAGAAAACTGCAGAAAATATTGATGAGGCGGCAAAAGAACTTC<br>CA | SEQ ID No. 94 |
| BphP1 | Rhodo-<br>pseudomonas<br>palustris | ATGGCTAGCGTGGCAGGTCATGCCTCTGGCAGCCCCGCATTCGGGACC<br>GCCGATCTTTCGAATTGCGAACGTGAAGAGATCCACCTCGCCGGCTCG<br>ATCCAGCCGCATGGCGCGCTTCTGGTCGTCAGCGAGCCGGATCATCGC<br>ATCATCCAGGCCAGCGCCAACGCCGCGGAATTTCTGAATCTCGGAAGC<br>GTGCTCGGCGTTCCGCTCGCCGAGATCGACGGCGATCTGTTGATCAAG<br>ATCCTGCCGCATCTCGATCCCACCGCCGAAGGCATGCCGGTCGCGGTG<br>CGCTGCCGGATCGGCAATCCCTCCACGGAGTACGACGGTCTGATGCAT<br>CGGCCTCCGGAAGGCGGGCTGATCATCGAGCTCGAACGTGCCGGCCC<br>GCCGATCGATCTGTCCGGCACGCTGGCGCCGGCGCTGGAGCGGATCCG<br>CACGGCGGGCTCGCTGCGCGCGCTGTGCGATGACACCGCGCTGCTGTT<br>TCAGCAGTGCACCGGCTACGACCGGGTGATGGTGTATCGCTTCGACGA<br>GCAGGGCCACGGCGAAGTGTTCTCCGAGCGCCACGTGCCCGGGCTCG<br>AATCCTATTTCGGCAACCGCTATCCGTCGTCGGACATTCCGCAGATGG<br>CGCGGCGGCTGTACGAGCGGCAGCGCGTCCGCGTGCTGGTCGACGTCA<br>GCTATCAGCCGGTGCCGCTGGAGCCGCGGCTGTCGCCGCTGACCGGGC<br>GCGATCTCGACATGTCGGGCTGCTTCCTGCGCTCGATGTCGCCGATCC<br>ATCTGCAGTACCTGAAGAACATGGGCGTGCGCGCCACCCTGGTGGTGT<br>CGCTGGTGGTCGGCGGCAAGCTGTGGGGCCTGGTTGCCTGTCATCATT<br>ATCTGCCGCGCTTCATGCATTTCGAGCTGCGGGCGATCTGCGAACTGC<br>TCGCCGAAGCGATCGCGACGCGGATCACCGCGCTTGAGAGCTTCGCGC<br>AGAGCCAGTCGGAGCTGTTCGTGCAGCGGCTCGAACAGCGCATGATC<br>GAAGCGATTACCCGTGAAGGCGATTGGCGCGCAGCGATTTTCGACACC<br>AGCCAATCGATCCTGCAGCCGCTGCACGCCGCCGGTTGCGCGCTGGTG<br>TACGAAGACCAGATCAGGACCATCGGCGACGTGCCTTCCACGCAGGA<br>TGTGCGCGAGATCGCCGGGTGGCTCGATCGCCAGCCGCGCGCGGCGGT<br>GACCTCGACCGCGTCGCTCGGTCTCGACGTGCCGGAGCTCGCATCT<br>GACGCGGATGGCGAGCGGCGTGGTCGCGGCGCCGATTTCGGATCATC<br>GCGGCGAGTTTCTGATGTGGTTCCGCCCCGAGCGCGTCCACACCGTTA<br>CCTGGGGCGGCGATCCGAAGAAGCCGTTCACGATGGGCGATACACCG<br>GCGGATCTGTCGCCGCGGCGCTCCTTCGCCAAATGGCATCAGGTTGTC<br>GAAGGCACGTCCGATCCGTGGACGGCCGCCGATCTCGCCGCGGCTCGC |  SEQ ID No. 95 |

TABLE 5-continued

Exemplary DNA Sequences (includes truncations):

| Comp. | Organism | DNA Sequence | SEQ ID No. # |
|---|---|---|---|
| | | ACCATCGGTCAGACCGTCGCCGACATCGTGCTGCAATTCCGCGCGGTG<br>CGGACACTGATCGCCCGCGAACAGTACGAACAGTTTTCGTCCCAGGTG<br>CACGCTTCGATGCAGCCGGTGCTGATCACCGACGCCGAAGGCCGCATC<br>CTGCTGATGAACGACTCGTTCCGCGACATGTTGCCGGCGGGTTCGCCA<br>TCCGCCGTCCATCTCGACGATCTCGCCGGGTTCTTCGTCGAATCGAAC<br>GATTTCCTGCGCAACGTCGCCGAACTGATCGATCACGGCCGCGGGTGG<br>CGCGGCGAAGTTCTGCTGCGCGGCGCAGGCAACCGCCCGTTGCCGCTG<br>GCAGTGCGCGCCGATCCGGTGACGCGCACGGAGGACCAGTCGCTCGG<br>CTTCGTGCTGATCTTCAGCGACGCTACCGATCGTCGCACCGCAGATGC<br>CGCACGCACGCGTTTCCAGGAAGGCATTCTTGCCAGCGCACGTCCCGG<br>CGTGCGGCTCGACTCCAAGTCCGACCTGTTGCACGAGAAGCTGCTGTC<br>CGCGCTGGTCGAGAACGCGCAGCTTGCCGCATTGGAAATCACTTACGG<br>CGTCGAGACCGGACGCATCGCCGAGCTGCTCGAAGGCGTCCGCCAGTC<br>GATGCTGCGCACCGCCGAAGTGCTCGGCCATCTGGTGCAGCACGCGGC<br>GCGCACGGCCGGCAGCGACAGCTCGAGCAATGGCTCGCAGAACAAGA<br>AGGAATTCGATAGTGCTGGTAGTGCTGGTAGTGCTGGTACTAGT | |
| PTP1B$_{1-435}$ | H.<br>Sapiens | ATGGAGATGGAAAAGGAGTTCGAGCAGATCGACAAGTCCGGGAGCTG<br>GGCCGGCCATTTACCAGGATATCCGACATGAAGCCAGTGACTTCCCATG<br>TAGAGTGGCCAAGCTTCCTAAGAACAAAAACCGAAATAGGTACAGAG<br>ACGTCAGTCCCTTTGACCATAGTCGGATTAAACTACATCAAGAAGATA<br>ATGACTATATCAACGCTAGTTTGATAAAAATGGAAGAAGCCCAAAGG<br>AGTTACATTCTTACCCAGGGCCCTTTGCCTAACACATGCGGTCACTTTT<br>GGGAGATGGTGTGGGAGCAGAAAAGCAGGGGTGTCGTCATGCTCAAC<br>AGAGTGATGGAGAAAGGTTCGTTAAAATGCGCACAATACTGGCCACA<br>AAAAGAAGAAAAGAGATGATCTTTGAAGACACAAATTTGAAATTAA<br>CATTGATCTCTGAAGATATCAAGTCATATTATACAGTGCAGCTAG<br>AATTGGAAAACCTTACAACCCAAGAAACTCGAGAGATCTTACATTTCC<br>ACTATACCACATGGCCTGACTTTGGAGTCCCTGAATCACCAGCCTCAT<br>TCTTGAACTTTCTTTTCAAAGTCCGAGAGTCAGGGTCACTCAGCCCGG<br>AGCACGGGCCCGTTGTGGTGCACTGCAGTGCAGGCATCGGCAGGTCTG<br>GAACCTTCTGTCTGGCTGATACCTGCCTCTTGCTGATGGACAAGAGGA<br>AAGACCCTTCTTCCGTTGATATCAAGAAAGTGCTGTTAGAAATGAGGA<br>AGTTTCGGATGGGGCTGATCCAGACAGCCGACCAGCTGCGCTTCTCCT<br>ACCTGGCTGTGATCGAAGGTGCCAAATTCATCATGGGGGACTCTTCCG<br>TGCAGGATCAGTGGAAGGAGCTTTCCCACGAGGACCTGGAGCCCCA<br>CCCGAGCATATCCCCCCACCTCCCCGGCCACCCAAACGAATCCTGGAG<br>CCACACAATGGGAAATGCAGGGAGTTCTTCCCAAATCACCAGTGGGTG<br>AAGGAAGAGACCCAGGAGGATAAAGACTGCCCCATCAAGGAAGAAA<br>AAGGAAGCCCCTTAAATGCCGCACCCTACGGCATCGAAAGCATGAGT<br>CAAGACACTGAAGTTAGAAGTCGGGTCGTGGGGGGAAGTCTTCGAGG<br>TGCCCAGGCTGCCTCCCCAGCCAAAGGGGAGCCGTCACTGCCCGAGA<br>AGGACGAGGACCATGCACTGAGTTACTGGAAGCCCTTCCTGGTCAACA<br>TGTGCGTGGCTACGGTCCTCACGGCCGGCGCTTACCTCTGCTACAGGT<br>TCCTGTTCAACAGCAACACATAG | SEQ ID No. 96 |
| TC-<br>PTP<br>(full) | H.<br>Sapiens | ATGCCCACCACCATCGAGCGGGAGTTCGAAGAGTTGGATACTCAGCGT<br>CGCTGGCAGCCGCTGCTACTTGGAAATTCGAAATGAGTCCCATGACTAT<br>CCTCATAGAGTGGCCAAGTTTCCAGAAAACAGAAATCGAAACAGATA<br>CAGAGATGTAAGCCCATATGATCACAGTCGTGTTAAACTGCAAAATGC<br>TGAGAATGATTATATTAATGCCAGTTTAGTTGACATAGAAGAGGCACA<br>AAGGAGTTACATCTTAACACAGGGTCCACTTCCTAACACATGCTGCCA<br>TTTCTGGCTTATGGTTTGGCAGCAGAAGACCAAAGCAGTTGTCATGCT<br>GAACCGCATTGTGGAGAAAGAATCGGTTAAATGTGCACAGTACTGGC<br>CAACAGATGACCAAGAGATGCTGTTTAAAGAAACAGGATTCAGTGTG<br>AAGCTCTTGTCAGAAGATGTGAAGTCGTATTATACAGTACATCTACTA<br>CAATTAGAAAATATCAATAGTGGTGAAACCAGAACAATATCTCACTTT<br>CATTATACTACCTGGCCAGATTTTGGAGTCCCTGAATCACCAGCTTCAT<br>TTCTCAATTTCTTGTTTAAAGTGAGAGAATCTGGCTCCTTGAACCCTGA<br>CCATGGGCCTGCGGTGATCCACTGTAGTGCAGGCATTGGGCGCTCTGG<br>CACCTTCTCTCTGGTAGACACTTGTCTTGTTTTGATGGAAAAGGGAGAT<br>GATATTAACATAAAACAAGTGTTACTGAACATGAGAAAATACCGAAT<br>GGGTCTTATTCAGACCCCAGATCAACTGAGATTCTCATACATGGCTAT<br>AATAGAAGGAGCAAAATGTATAAAGGGAGATTCTAGTATACAGAAAC<br>GATGGAAAGAACTTTCTAAGGAAGACTTATCTCCTGCCTTTGATCATT<br>CACCAAACAAAATAATGACTGAAAAATACAATGGGAACAGA | SEQ ID No. 97 |
| PTPN5 | H. sapiens | ATGTCTTCTGGTGTAGATCTGGGTACCGAGAACCTGTACTTCCAATCC<br>ATGTCCCGTGTCCTCCAAGCAGAAGAGCTTCATGAAAAGGCCCTGGAC<br>CCTTTCCTGCTGCAGGCGGAATTCTTTGAAATCCCCATGAACTTTGTGG<br>ATCCGAAAGAGTACGACATCCCTGGGCTGGTGCGAAGAACCGGTAC<br>AAAACCATACTTCCCAACCCTCACAGCAGAGTGTGTCTGACCTCACCA<br>GACCCTGACGACCCTCTGAGTTCCTACATCAATGCCAACTACATCCGG<br>GGCTATGGTGGGGAGGAGAAGGTGTACATCGCCACTCAGGGACCCAT | SEQ ID No. 98 |

TABLE 5-continued

Exemplary DNA Sequences (includes truncations):

| Comp. | Organism | DNA Sequence | SEQ ID No. # |
|---|---|---|---|
| | | CGTCAGCACGGTCGCCGACTTCTGGCGCATGGTGTGGCAGGAGCACAC GCCCATCATTGTCATGATCACCAACATCGAGGAGATGAACGAGAAAT GCACCGAGTATTGGCCGGAGGAGCAGGTGGCGTACGACGGTGTTGAG ATCACTGTGCAGAAAGTCATTCACACGGAGGATTACCGGCTGCGACTC ATCTCCCTCAAGAGTGGGACTGAGGAGCGAGGCCTGAAGCATTACTG GTTCACATCCTGGCCCGACCAGAAGACCCCAGACCGGGCCCCCCCACT CCTGCACCTGGTGCGGGAGGTGGAGGAGGCAGCCCAGCAGGAGGGGC CCCACTGTGCCCCCATCATCGTCCACTGCAGTGCAGGGATTGGGAGGA CCGGCTGCTTCATTGCCACCAGCATCTGCTGCCAGCAGCTGCGGCAGG AGGGTGTAGTGGACATCCTGAAGACCACGTGCCAGCTCCGTCAGGAC AGGGGCGGCATGATCCAGACATGCGAGCAGTACCAGTTTGTGCACCA CGTCATGAGCCTCTACGAAAAGCAGCTGTCCCACCAGTCCTGA | |
| PTPN6 | H. sapiens | ATGGTGAGGTGGTTTCACCGAGACCTCAGTGGGCTGGATGCAGAGACC CTGCTCAAGGGCCGAGGTGTCCACGGTAGCTTCCTGGCTCGGCCCAGT CGCAAGAACCAGGGTGACTTCTCGCTCTCCGTCAGGGTGGGGGATCAG GTGACCCATATTCGGATCCAGAACTCAGGGGATTTCTATGACCTGTAT GGAGGGGAGAAGTTTGCGACTCTGACAGAGCTGGTGGAGTACTACAC TCAGCAGCAGGGTGTGGTGCAGGACCGCGACGGCACCATCATCCACCT CAAGTACCCGCTGAACTGCTCCGATCCCACTAGTGAGAGGTGGTACCA TGGCCACATGTCTGGCGGGCAGGCAGAGACGCTGCTGCAGGCCAAGG GCGAGCCCTGGACGTTTCTTGTGCGTGAGAGCCTCAGCCAGCCTGGAG ACTTCGTGCTTTCTGTGCTCAGTGACCAGCCCAAGGCTGGCCCAGGCT CCCCGCTCAGGGTCACCCACATCAAGGTCATGTGCGAGGGTGGACGCT ACACAGTGGGTGGTTTGGAGACCTTCGACAGCCTCACGGACCTGGTGG AGCATTTCAAGAAGACGGGGATTGAGGAGGCCTCAGGCGCCTTTGTCT ACCTGCGGCAGCCGTACTATGCCACGAGGGTGAATGCGGCTGACATTG AGAACCGAGTGTTGGAACTGAACAAGAAGCAGGAGTCCGAGGATACA GCCAAGGCTGGCTTCTGGGAGGAGTTTGAGAGTTTGCAGAAGCAGGA GGTGAAGAACTTGCACCAGCGTCTGGAAGGGCAACGGCCAGAGAACA AGGGCAAGAACCGCTACAAGAACATTCTCCCCTTTGACCACAGCCGAG TGATCCTGCAGGGACGGGACAGTAACATCCCCGGGTCCGACTACATCA ATGCCAACTACATCAAGAACCAGCTGCTAGGCCCTGATGAGAACGCTA AGACCTACATCGCCAGCCAGGGCTGTCTGGAGGCCACGGTCAATGACT TCTGGCAGATGGCGTGGCAGGAGAACAGCCGTGTCATCGTCATGACCA CCCGAGAGGTGGAGAAAGGCCGGAACAAATGCGTCCCATACTGGCCC GAGGTGGGCATGCAGCGTGCTTATGGGCCCTACTCTGTGACCAACTGC GGGGAGCATGACACAACCGAATACAAACTCCGTACCTTACAGGTCTCC CCGCTGGACAATGGAGACCTGATTCGGGAGATCTGGCATTACCAGTAC CTGAGCTGGCCCGACCATGGGGTCCCCAGTGAGCCTGGGGGTGTCCTC AGCTTCCTGGACCAGATCAACCAGCGGCAGGAAAGTCTGCCTCACGCA GGGCCCATCATCGTGCACTGCAGCGCCGGCATCGGCCGCACAGGCACC ATCATTGTCATCGACATGCTCATGGAGAACATCTCCACCAAGGGCCTG GACTGTGACATTGACATCCAGAAGACCATCCAGATGGTGCGGGCGCA GCGCTCGGGCATGGTGCAGACGGAGGCGCAGTACAAGTTCATCTACGT GGCCATCGCCCAGTTCATTGAAACCACTAAGAAGAAGCTGGAGGTCCT GCAGTCGCAGAAGGGCCAGGAGTCGGAGTACGGGAACATCACCTATC CCCCAGCCATGAAGAATGCCCATGCCAAGGCCTCCCGCACCTCGTCCA AACACAAGGAGGATGTGTATGAGAACCTGCACACTAAGAACAAGAGG GAGGAGAAAGTGAAGAAGCAGCGGTCAGCAGACAAGGAGAAGAGCA AGGGTTCCCTCAAGAGGAAGTGA | SEQ ID No. 99 |
| PTPN11 | H. sapiens | ATGACATCGCGGAGATGGTTTCACCCAAATATCACTGGTGTGGAGGCA GAAAACCTACTGTTGACAAGAGGAGTTGATGGCAGTTTTTTGGCAAGG CCTAGTAAAAGTAACCCTGGAGACTTCACACTTTCCGTTAGAAGAAAT GGAGCTGTCACCCACATCAAGATTCAGAACACTGGTGATTACTATGAC CTGTATGGAGGGGAGAAATTTGCCACTTTGGCTGAGTTGGTCCAGTAT TACATGGAACATCACGGGCAATTAAAAGAGAAGAATGGAGATGTCAT TGAGCTTAAATATCCTCTGAACTGTGCAGATCCTACCTCTGAAAGGTG GTTTCATGGACATCTCTCTGGGAAAGAAGCAGAGAAATTATTAACTGA AAAAGGAAAACATGGTAGTTTTCTTGTACGAGAGAGCCAGAGCCACC CTGGAGATTTTGTTCTTTCTGTGCGCACTGGTGATGACAAAGGGGAGA GCAATGACGGCAAGTCTAAAGTGACCCATGTTATGATTCGCTGTCAGG AACTGAAATACGACGTTGGTGGAGGAGAACGGTTTGATTCTTTGACAG ATCTTGTGGAACATTATAAGAAGAATCCTATGGTGGAAACATTGGGTA CAGTACTACAACTCAAGCAGCCCCTTAACACGACTCGTATAAATGCTG CTGAAATAGAAAGCAGAGTTCGAGAACTAAGCAAATTAGCTGAGACC ACAGATAAAGTCAAACAAGGCTTTTGGGAAGAATTTGAGACACTACA ACAACAGGAGTGCAAACTTCTCTACAGCCGAAAAGAGGGTCAAAGGC AAGAAAACAAAAACAAAAATAGATATAAAAACATCCTGCCCTTTGAT CATACCAGGGTTGTCCTACACGATGGTGATCCCAATGAGCCTGTTTCA GATTACATCAATGCAAATATCATCATGCCTGAATTTGAAACCAAGTGC AACAATTCAAAGCCCAAAAAGAGTTACATTGCCACACAAGGCTGCCT GCAAAACACGGTGAATGACTTTTGGCGGATGGTGTTCCAAGAAAACTC | SEQ ID No. 100 |

TABLE 5-continued

Exemplary DNA Sequences (includes truncations):

| Comp. | Organism | DNA Sequence | SEQ ID No. # |
|---|---|---|---|
| | | CCGAGTGATTGTCATGACAACGAAAGAAGTGGAGAGAGGAAAGAGTA<br>AATGTGTCAAATACTGGCCTGATGAGTATGCTCTAAAAGAATATGGCG<br>TCATGCGTGTTAGGAACGTCAAAGAAAGCGCCGCTCATGACTATACGC<br>TAAGAGAACTTAAACTTTCAAAGGTTGGACAAGGGAATACGGAGAGA<br>ACGGTCTGGCAATACCACTTTCGGACCTGGCCGGACCACGGCGTGCCC<br>AGCGACCCTGGGGCGTGCTGGACTTCCTGGAGGAGGTGCACCATAA<br>GCAGGAGAGCATCATGGATGCAGGGCCGGTCGTGGTGCACTGCAGTG<br>CTGGAATTGGCCGGACAGGGACGTTCATTGTGATTGATATTCTTATTG<br>ACATCATCAGAGAGAAAGGTGTTGACTGCGATATTGACGTTCCCAAA<br>CCATCCAGATGGTGCGGTCTCAGAGGTCAGGGATGGTCCAGACAGAA<br>GCACAGTACCGATTTATCTATATGGCGGTCCAGCATTATATTGAAACA<br>CTACAGCGCAGGATTGAAGAAGAGCAGAAAAGCAAGAGGAAAGGGC<br>ACGAATATACAATATTAAGTATTCTCTAGCGGACCAGACGAGTGGAG<br>ATCAGAGCCCTCTCCCGCCTTGTACTCCAACGCCACCCTGTGCAGAAA<br>TGAGAGAAGACAGTGCTAGAGTCTATGAAAACGTGGGCCTGATGCAA<br>CAGCAGAAAAGTTTCAGATGA | |
| PTPN12 | H. sapiens | ATGGAGCAAGTGGAGATCCTGAGGAAATTCATCCAGAGGGTCCAGGC<br>CATGAAGAGTCCTGACCACAATGGGGAGGACAACTTCGCCGAGGACT<br>TCATGCGGTTAAGAAGATTGTCTACCAAATATAGAACAGAAAAGATAT<br>ATCCCACAGCCACTGGAGAAAAAGAAGAAAATGTTAAAAAGAACAGA<br>TACAAGGACATACTGCCATTTGATCACAGCCGAGTTAAATTGACATTA<br>AAGACTCCTTCACAAGATTCAGACTATATCAATGCAAATTTTATAAAG<br>GGCGTCTATGGGCCAAAAGCATATGTAGCAACTCAAGGACCTTTAGCA<br>AATACAGTAATAGATTTTTGGAGGATGGTATGGGAGTATAATGTTGTG<br>ATCATTGTAATGGCCTGCCGAGAATTTGAGATGGGAAGGAAAAAATG<br>TGAGCGCTATTGGCCTTTGTATGGAGAAGACCCCATAACGTTTGCACC<br>ATTTAAAATTTCTTGTGAGGATGAACAAGCAAGAACAGACTACTTCAT<br>CAGGACACTCTTACTTGAATTTCAAAATGAATCTCGTAGGCTGTATCA<br>GTTTCATTATGTGAACTGGCCAGACCATGATGTTCCTTCATCATTTGAT<br>TCTATTCTGGACATGATAAGCTTAATGAGGAAATATCAAGAACATGAA<br>GATGTTCCTATTTGTATTCATTGCAGTGCAGGCTGTGGAAGAACAGGT<br>GCCATTTGTGCCATAGATTATACGTGGAATTTACTAAAAGCTGGGAAA<br>ATACCAGAGGAATTTAATGTATTTAATTTAATACAAGAAATGAGAACA<br>CAAAGGCATTCTGCAGTACAAACAAAGGAGCAATATGAACTTGTTCAT<br>AGAGCTATTGCCCAACTGTTTGAAAAACAGCTACAACTATATGAAATT<br>CATGGAGCTCAGAAAATTGCTGATGGAGTGAATGAAATTAACACTGA<br>AAACATGGTCAGCTCCATAGAGCCTGAAAAACAAGATTCTCCTCCTCC<br>AAAACCACCAAGGACCCGCAGTTGCCTTGTTGAAGGGATGCTAAAG<br>AAGAAATACTGCAGCCACCGGAACCTCATCCAGTGCCACCCATCTTGA<br>CACCTTCTCCCCCTTCAGCTTTTCCAACAGTCACTACTGTGTGGCAGGA<br>CAATGATAGATACCATCCAAAGCCAGTGTTGCAATGGTTTCATCAGAA<br>CAACATTCAGCAGACCTCAACAGAAACTATAGTAAATCAACAGAACTT<br>CCAGGGAAAAATGAATCAACAATTGAACAGA | SEQ ID No. 101 |
| PTPN22 | H. sapiens | ATGGACCAAAGAGAAATTCTGCAGAAGTTCCTGGATGAGGCCCAAAG<br>CAAGAAAATTACTAAAGAGGAGTTTGCCAATGAATTTCTGAAGCTGAA<br>AAGGCAATCTACCAAGTACAAGGCAGACAAAACCTATCCTACAACTG<br>TGGCTGAGAAGCCCAAGAATATCAAGAAAACAGATATAAGGATATT<br>TTGCCCTATGATTATAGCCGGGTAGAACTATCCCTGATAACCTCTGAT<br>GAGGATTCCAGCTACATCAATGCCAACTTCATTAAGGGAGTTTATGGA<br>CCCAAGGCTTATATTGCCACCCAGGGTCCTTTATCTACAACCCTCCTGG<br>ACTTCTGGAGGATGATTTGGGAATATAGTGTCCTTATCATTGTTATGGC<br>ATGCATGGAGTATGAAATGGGAAGAAAAAGTGTGAGCGCTACTGGG<br>CTGAGCCAGGAGAGATGCAGCTGGAATTTGGCCCTTTCTCTGTATCCT<br>GTGAAGCTGAAAAAAGGAAATCTGATTATATAATCAGGACTCTAAAA<br>GTTAAGTTCAATAGTGAAACTCGAACTATCTACCAGTTTCATTACAAG<br>AATTGGCCAGACCATGATGTACCTTCATCTATAGACCCTATTCTTGAGC<br>TCATCTGGGATGTACGTTGTTACCAAGAGGATGACAGTGTTCCCATAT<br>GCATTCACTGCAGTGCTGGCTGTGAAGGACTGGTGTTATTTGTGCTA<br>TTGATTACATGGATGTTGCTAAAAGATGGGATAATTCCTGAGAACT<br>TCAGTGTTTTCAGTTTGATCCGGGAAATGCGGACACAGAGGCCTTCAT<br>TAGTTCAAACGCAGGAACAATATGAACTGGTCTACAATGCTGTATTAG<br>AACTATTTAAGAGACAGATGGATGTTATCAGAGATAA | SEQ ID No. 102 |
| GalK | Escherichia coli | ATGAGTCTGAAAGAAAAAACACAATCTCTGTTTGCCAACGCATTTGGC<br>TACCCTGCCACTCACACCATTCAGGCGCCTGGCCGCGTGAATTTGATT<br>GGTGAACACACCGACTACAACGACGGTTTCGTTCTGCCCTGCGCGATT<br>GATTATCAAACCGTGATCAGTTGTGCACCACGCGATGACCGTAAAGTT<br>CGCGTGATGGCAGCCGATTATGAAAATCAGCTCGACGAGTTTTCCCTC<br>GATGCGCCCATTGTCGCACATGAAAACTATCAATGGGCTAACTACGTT<br>CGTGGCGTGGTGAAACATCTGCAACTGCGTAACAACAGCTTCGGCGGC<br>GTGGACATGGTGATCAGCGGCAATGTGCCGCAGGGTGCCGGGTTAAG<br>TTCTTCCGCTTCACTGGAAGTCGCGGTCGGAACCGTATTGCAGCAGCT | SEQ ID No. 103 |

TABLE 5-continued

Exemplary DNA Sequences (includes truncations):

| Comp. | Organism | DNA Sequence | SEQ ID No. # |
|---|---|---|---|
| | | TTATCATCTGCCGCTGGACGGCGCACAAATCGCGCTTAACGGTCAGGA AGCAGAAAACCAGTTTGTAGGCTGTAACTGCGGGATCATGGATCAGCT AATTTCCGCGCTCGGCAAGAAAGATCATGCCTTGCTGATCGATTGCCG CTCACTGGGGACCAAAGCAGTTTCCATGCCCAAAGGTGTGGCTGTCGT CATCATCAACAGTAACTTCAAACGTACCCTGGTTGGCAGCGAATACAA CACCCGTCGTGAACAGTGCGAAACCGGTGCGCGTTTCTTCCAGCAGCC AGCCCTGCGTGATGTCACCATTGAAGAGTTCAACGCTGTTGCGCATGA ACTGGACCCGATCGTGGCAAAACGCGTGCGTCATATACTGACTGAAAA CGCCCGCACCGTTGAAGCTGCCAGCGCGCTGGAGCAAGGCGACCTGA AACGTATGGGCGAGTTGATGGCGGAGTCTCATGCCTCTATGCGCGATG ATTTCGAAATCACCGTGCCGCAAATTGACACTCTGGTAGAAATCGTCA AAGCTGTGATTGGCGACAAAGGTGGCGTACGCATGACCGGCGGCGGA TTTGGCGGCTGTATCGTCGCGCTGATCCCGGAAGAGCTGGTGCCTGCC GTACAGCAAGCTGTCGCTGAACAATATGAAGCAAAAACAGGTATTAA AGAGACTTTTTACGTTTGTAAACCATCACAAGGAGCAGGACAGTGCTG A | |
| SacB | Bacillus subtilis | ATGAACATCAAAAAGTTTGCAAAACAAGCAACAGTATTAACCTTTACT ACCGCACTGCTGGCAGGAGGCGCAACTCAAGCGTTTGCGAAAGAAAC GAACCAAAAGCCATATAAGGAAACATACGGCATTTCCCATATTACACG CCATGATATGCTGCAAATCCCTGAACAGCAAAAAAATGAAAAATATC AAGTTCCTGAATTCGATTCGTCCACAATTAAAAATATCTCTTCTGCAAA AGGCCTGGACGTTTGGGACAGCTGGCCATTACAAAACGCTGACGGCA CTGTCGCAAACTATCACGGCTACCACATCGTCTTTGCATTAGCCGGAG ATCCTAAAAATGCGGATGACACATCGATTTACATGTTCTATCAAAAAG TCGGCGAAACTTCTATTGACAGCTGGAAAAACGCTGGCCGCGTCTTTA AAGACAGCGACAAATTCGATGCAAATGATTCTATCCTAAAAGACCAA ACACAAGAATGGTCAGGTTCAGCCACATTTACATCTGACGGAAAAATC CGTTTATTCTACACTGATTTCTCCGGTAAACATTACGGCAAACAAACA CTGACAACTGCACAAGTTAACGTATCAGCATCAGACAGCTCTTTGAAC ATCAACGGTGTAGAGGATTATAAATCAATCTTTGACGGTGACGGAAAA ACGTATCAAAATGTACAGCAGTTCATCGATGAAGGCAACTACAGCTCA GGCGACAACCATACGCTGAGAGATCCTCACTACGTAGAAGATAAAGG CCACAAATACTTAGTATTTGAAGCAAACACTGGAACTGAAGATGGCTA CCAAGGCGAAGAATCTTTATTTAACAAAGCATACTATGGCAAAAGCAC ATCATTCTTCCGTCAAGAAAGTCAAAAACTTCTGCAAAGCGATAAAAA ACGCACGGCTGAGTTAGCAAACGGCGCTCTCGGTATGATTGAGCTAAA CGATGATTACACACTGAAAAAAGTGATGAAACCGCTGATTGCATCTAA CACAGTAACAGATGAAATTGAACGCGCGAACGTCTTTAAAATGAACG GCAAATGGTACCTGTTCACTGACTCCCGCGGATCAAAAATGACGATTG ACGGCATTACGTCTAACGATATTTACATGCTTGGTTATGTTTCTAATTC TTTAACTGGCCCATACAAGCCGCTGAACAAAACTGGCCTTGTGTTAAA AATGGATCTTGATCCTAACGATGTAACCTTTACTTACTCACACTTCGCT GTACCTCAAGCGAAAGGAAACAATGTCGTGATTACAAGCTATATGAC AAACAGAGGATTCTACGCAGACAAACAATCAACGTTTGCGCCAAGCTT CCTGCTGAACATCAAAGGCAAGAAAACATCTGTTGTCAAAGACAGCA TCCTTGAACAAGGACAATTAACAGTTAACAAATAA | SEQ ID No. 104 |

Abbreviations

PTP IB, protein tyrosine phosphatase IB; TC-PTP, T-cell protein tyrosine phosphatase; SHP2, protein tyrosine phosphatase non-receptor type 11; BBR, 3-(3,5-Dibromo-4-hydroxy-benzoyl)-2-ethyl-benzofuran-6-sulfonicacid-(4-(thiazol-2-ylsulfamyl)-phenyl)-amide; TCS401, 2-[(Carboxycarbonyl)amino]-4,5,6,7-tetrahydro-thieno[2,3-c]pyridine-3-carboxylic acid hydrochloride; AA, abietic acid; SCA, statistical coupling analysis. $PTP1B_{1-435}$, protein tyrosine phosphatase 1B (full-length); SacB, levansucrase; GHS, γ-humulene synthase; ADS, amorphadiene synthase; ABS (or AgAs), abietadiene synthase; TXS, taxadiene synthase, PTPNS, protein tyrosine phosphatase non-receptor type 5; PTPN6, protein tyrosine phosphatase non-receptor type 6; PTPN11, protein tyrosine phosphatase non-receptor type 11; PTPN12, protein tyrosine phosphatase non-receptor type 12; PPTN22, protein tyrosine phosphatase non-receptor type 22; RpoZ, omega subunit of RNA polymerase; cI (or cI434), cI repressor protein from lambda phage; Kras (or p130cas), p130cas phosphotyrosine substrate; MidT, phosphotyrosine substrate from hamster polyoma virus; EGFR substrate, phosphotyrosine substrate from epidermal growth factor receptor; Src, Src kinase; CDC37, Hsp90 co-chaperone Cdc37; MBP, maltose-binding protein; LuxAB, bacterial luciferase modules A and B; SpecR, spectinomycin resistance gene; GGPPS, geranylgeranyl diphosphate synthase; P450 (or $P450_{BM3}$) Cytochrome P450; LOV2, light-oxygen-voltage domain 2 from phototropin 1; BphP1, bacterial phytochrome; Galk, galatokinase.

EXAMPLES

The following examples are offered to illustrate various embodiments of the invention, but should not be viewed as limiting the scope of the invention.

Statistical Analysis of Kinetic Models. We evaluated four kinetic models of inhibition as described previously (19). In brief, we used an F-test to compare a two-parameter mixed model to several single-parameter models, and we used Akaike's Information Criterion (AIC, or Ai) to compare the single-parameter models to one another. Mixed models with p<0.05 are superior to all single-parameter models, and single-parameter models with Aj >10 are inferior to the reference (i.e., "best fit") model.

Exemplary Estimation of IC50. We estimated the half maximal inhibitory concentration (IC50) of BBR by using kinetic models to estimate the concentration of inhibitor required to reduce initial rates of PTP-catalyzed hydrolysis of 20 mM of pNPP by 50%, and we used the MATLAB function "nlparci" to determine the confidence intervals on those estimates (19).

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in medicine, molecular biology, cell biology, genetics, statistics or related fields are intended to be within the scope of the following claims.

The invention claimed is:

1. A system, comprising;
    a first region of DNA that encodes:
      (i) a first fusion protein, wherein the first fusion protein comprises a substrate recognition domain coupled to a DNA-binding protein;
      (ii) a second fusion protein, wherein the second fusion protein comprises a substrate domain coupled to a subunit of RNA polymerase;
      (iii) a protein kinase; and
      (iv) a protein phosphatase; and
    a second region of DNA that encodes:
      (i) an operator for the DNA-binding protein;
      (ii) a binding site for the RNA polymerase operatively coupled to the operator for the DNA-binding protein, wherein the subunit of the RNA polymerase is configured to recruit the RNA polymerase to the binding site; and
      (iii) a reporter gene encoding a reporter protein, wherein transcription of the reporter gene is initiated upon (1) binding the DNA-binding protein to the operator and (2) binding the RNA polymerase to the RNA polymerase binding site.

2. The system of claim 1, wherein the substrate recognition domain comprises a substrate homology 2 (SH2) domain.

3. The system of claim 1, wherein the DNA-binding protein comprises a 434 phage cI repressor.

4. The system of claim 1, wherein the substrate domain comprises a peptide substrate of the protein kinase and the protein phosphatase.

5. The system of claim 1, wherein the subunit of the RNA polymerase comprises the omega subunit of RNA polymerase ($RP_\omega$).

6. The system of claim 1, wherein the protein kinase comprises a Src kinase.

7. The system of claim 1, wherein the first region of DNA further encodes a molecular chaperone.

8. The system of claim 7, wherein the molecular chaperone comprises:
    the Hsp90 co-chaperone from *H. sapiens*; or
    CDC37.

9. The system of claim 1, wherein the operator comprises a 434 phage cI operator.

10. The system of claim 1, wherein the reporter protein comprises an antibiotic resistance protein.

11. The system of claim 10, wherein the antibiotic resistance protein comprises an enzyme configured to inactivate an antibiotic protein.

12. The system of claim 1, wherein the protein phosphatase comprises protein tyrosine phosphatase 1B.

13. The system of claim 1, wherein the first fusion protein and the second fusion protein are under the control of a first promoter, and the protein kinase and the protein phosphatase are under the control of the second promoter.

14. The system of claim 1, wherein the operator and the binding site for the RNA polymerase are under control of a promoter, wherein the promoter is an inducible promoter.

15. The system of claim 1, further comprising:
   an isoprenoid pathway DNA sequence encoding one or more components of an isoprenoid pathway; and
   a synthase DNA sequence encoding a synthase enzyme.

16. The system of claim 15, further comprising a cell, wherein the cell comprises the first region of the DNA, the second region of the DNA and the synthase DNA sequence.

17. The system of claim 15, wherein the synthase enzyme comprises a terpene synthase enzyme.

18. The system of claim 16, wherein the cell is a bacterial cell.

19. The system of claim 16, wherein expression of the reporter protein in the bacterial cell is indicative that the bacterial cell further comprises a protein phosphatase inhibitor.

20. The system of claim 1, further comprising a protein phosphatase inhibitor configured to inhibit activity of the protein phosphatase, thereby inducing expression of the reporter protein.

* * * * *